US008871728B2

(12) United States Patent
Oyelere et al.

(10) Patent No.: US 8,871,728 B2
(45) Date of Patent: *Oct. 28, 2014

(54) NON-PEPTIDE MACROCYCLIC HISTONE DEACETYLESE (HDAC) INHIBITORS AND METHODS OF MAKING AND USING THEREOF

(75) Inventors: Adegboyega Oyelere, Marietta, GA (US); Subhasish Tapadar, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/481,043

(22) Filed: May 25, 2012

(65) Prior Publication Data

US 2012/0329741 A1 Dec. 27, 2012

Related U.S. Application Data

(63) Continuation-in-part of application No. 12/643,633, filed on Dec. 21, 2009, now Pat. No. 8,188,054, which is a continuation-in-part of application No. PCT/US2008/068787, filed on Jun. 30, 2008.

(60) Provisional application No. 60/947,036, filed on Jun. 29, 2007.

(51) Int. Cl.
*A61K 31/70* (2006.01)
*C07H 17/08* (2006.01)
*C07H 17/00* (2006.01)

(52) U.S. Cl.
CPC ............... *C07H 17/08* (2013.01); *C07H 17/00* (2013.01)
USPC ............................... 514/29; 536/7.2; 536/7.4

(58) Field of Classification Search
CPC ........................................................ C07H 17/08
USPC ............................................ 514/29; 536/7.4
See application file for complete search history.

(56) References Cited

U.S. PATENT DOCUMENTS

| 3,725,385 | A | 4/1973 | Freiberg |
|---|---|---|---|
| 5,631,355 | A | 5/1997 | Asaka |
| 6,054,435 | A | 4/2000 | Or |
| 6,579,986 | B2 | 6/2003 | Allen |
| 7,091,187 | B2 | 8/2006 | Mercep |
| 7,335,753 | B2 | 2/2008 | Wang |
| 2004/0097434 | A1 | 5/2004 | Mercep |
| 2007/0149463 | A1 | 6/2007 | Oyelere |

FOREIGN PATENT DOCUMENTS

| WO | 2004043984 | 5/2004 |
|---|---|---|
| WO | 2007072179 | 6/2007 |

OTHER PUBLICATIONS

Grozinger and Schreiber, "Deacetylase enzymes: biological functions and the use of small-molecule inhibitors,", Chem. Biol., 9(1):3-16 (2002).

Haggarty, et al., "Domain-selective small-molecule inhibitor of histone deacetylase 6 (HDAC6)-mediated tubulin deacetylation.", Proc. Natl. Acad. Sci, USA, 100(8):4389-4394 (2003).
Kashimura, et al., "The synthesis and antibacterial activity of tetracyclic macrolides.", J. Antibiot., 56(12)1062-1065 (2003).
Kelly, et al., "Histone deacetylase inhibitors: from target to clinical trials.", Expert. Opin. lnvestig. Drugs, 11(12):1695-1713 (2002).
Meinke, et al., "Histone deacetylase: a target for antiproliferative and antiprotozoal agents.", Curr. Med. Chem., 8(2):211-235 (2001).
Miller, "Histone deacetylase inhibitors.", J. Med. Chem., 46(24):5097-5116 (2003).
Monneret, "Histone deacetylase inhibitors", Eur. J. of Med. Chem., 40(1):1-13 (2005).
Morimoto, et al., "Chemical modification of erythromycins. II. Synthesis and antibacterial activity of O-alkyl derivatives of erythromycin A." , J. Antibiot., 43 (3):286-294 (1990).
Rosato and Grant, "Histone deacetylase inhibitors in clinical development" , Expert Opin, Invest. Drugs, 13(1):21-38 (2004).
Wong, et al., "Structural biasing elements for in-cell histone deacetylase paralog selectivity." , J. Am. Chem. Soc., 125(19):5586-5587 (2003).

*Primary Examiner* — Elli Peselev
(74) *Attorney, Agent, or Firm* — Pabst Patent Group LLP

(57) ABSTRACT

Compounds of Formula I or II, and methods of making and using thereof, are described herein.

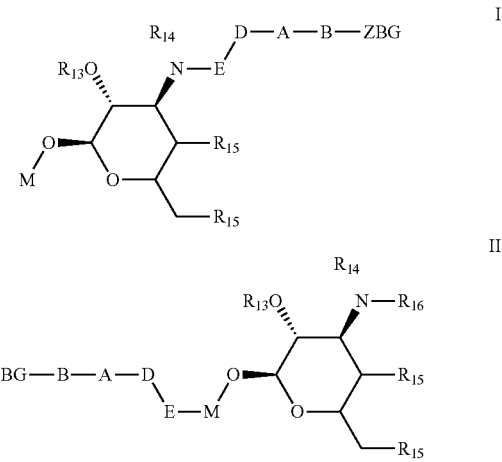

M represents a macrolide subunit,
E is a $C_{1-6}$ group, optionally containing one or more heteroatoms,
D is an alkyl or aryl group,
A is a linking group connected to D,
B is an alkyl, alkylaryl or alkylheteroaryl spacer group,
ZBG is a Zinc Binding Group,
$R_1$, $R_2$ and $R_4$ are independently are selected from hydrogen, a C1-6 alkyl group, a $C_{2-6}$ alkenyl group, a $C_{2-6}$ alkynyl group, a $C_{1-6}$ alkanoate group, a $C_{2-6}$ carbamate group, a $C_{2-6}$ carbonate group, a $C_{2-6}$ carbamate group, or a $C_{2-6}$ thiocarbamate group,
$R_3$ is hydrogen or —$OR_5$,
$R_5$ is selected from a group consisting of Hydrogen, a $C_{1-6}$ alkyl group, a $C_{2-6}$ alkenyl group, a $C_{2-6}$ alkynyl group, $C_{1-6}$ alkanoate group, $C_{2-6}$ carbamate group, $C_{2-6}$ carbonate group, $C_{2-6}$ carbamate group, or $C_{2-6}$ thiocarbamate group.

17 Claims, No Drawings

NON-PEPTIDE MACROCYCLIC HISTONE DEACETYLESE (HDAC) INHIBITORS AND METHODS OF MAKING AND USING THEREOF

CROSS-REFERENCE TO RELATED APPLICATIONS

This application is a continuation-in-part of U.S. Ser. No. 12/643,633 filed Dec. 21, 2009, now U.S. Pat. No. 8,188,054, issued May 9, 2012, which is a continuation-in-part of PCT/US2008/068787 filed Jun. 30, 2008, which claims priority to U.S. Ser. No. 60/947,036 filed Jun. 29, 2007.

FIELD OF THE INVENTION

The present invention generally relates to non-peptide macrocyclic histone deacetylase (HDAC) inhibitors and methods of making and using thereof.

BACKGROUND OF THE INVENTION

Histone deacetylases (HDACs) and histone acetyltransferases (HATs) are two functionally opposing enzymes which tightly regulate chromatin structure and function by maintaining the equilibrium between the acetylated- and deacetylated-states of nucleosomal histones. Aberrations in intracellular histone acetylation-deacetylation equilibrium have been linked to the repression of a subset of genes resulting in excessive proliferation and are implicated in a number of malignant diseases (Jenuwein, T.; Allis, C. D., *Science* 293, 1074-1080 (2001); Marks, P.; Rifkind, R. A.; Richon, V. M.; Breslow, R.; Miller, T.; Kelly, W. K., *Nat. Rev. Cancer,* 1, 194-202 (2001)). HDACs function as part of multiprotein complexes that catalyze the removal of acetyl groups from the ε-amino groups of specific lysine residues located near the N-termini of nucleosomal core histones (Grozinger, C. M.; Schreiber, S. L., *Chem. Biol.* 9, 3-16 (2002)). HDAC-catalyzed deacetylation results in positively charged, hypoacetylated histones which bind tightly to the phosphate backbone of DNA, thus inducing gene-specific repression of transcription. Inhibition of HDAC function results in the weakening of the bond between histones and DNA, thus increasing DNA accessibility and gene transcription.

Eighteen distinct human HDACs have been identified to date. They are classified into three major families based on their homology to three *Saccharomyces cerevisiae* HDACs: RPD3, HDA1, and SIR2. Class I includes HDACs 1, 2, 3 and 8. Class II includes HDACs 4, 5, 6, 7, 9, 10 and 11. The third class of HDACs is the sirtuins, which are homologically distinct from all the currently known HDACs. HDAC inhibition by small molecules has been observed for the natural product (R)-trichostatin A which induced cell differentiation of murine erythroleukemia cells and hyperacetylation of histone proteins at nanomolar concentrations. Suberoylanilide hydroxamic acid (SAHA) has also been identified as a HDAC inhibitor.

Inhibition of HDACs is an emerging therapeutic strategy in cancer therapy. HDAC inhibitors have demonstrated ability to arrest proliferation of nearly all transformed cell types, including epithelial (melanoma, lung, breast, pancreas, ovary, prostate, colon and bladder) and hematological (lymphoma, leukemia and multiple myeloma) tumors (Kelly, W. K; O'Connor, O. A.; Marks, P. A., *Expert. Opin. Investig. Drugs,* 11, 1695-1713 (2002)). Additionally, HDAC inhibitors have demonstrated other biological activity including anti-inflammatory, anti-arthritic, anti-infective, anti-malarial, cytoprotective, neuroprotective, chemopreventive and/or cognitive enhancing effects.

All HDAC inhibitors so far reported typically fit a three-motif pharmacophoric model namely, a zinc-binding group (ZBG), a hydrophobic linker and a recognition cap-group (Miller, T. A.; Witter, D. J.; Belvedere, S., *J. Med Chem.,* 46, 5097-5116 (2003)). Structural modifications of the ZBG yielding hydroxamate isosteres such as benzamide, α-ketoesters, electrophilic ketones, mercaptoamide and phosphonates have been reported. The cap-group may present opportunities to discover more potent and/or selective HDAC inhibitors. Toward this end, recent work by Schreiber and co-workers has led to the identification of cap group-modified agents that display differential inhibition against specific HDAC sub-types (Wong, J.; Hong, R.; Schreiber, S., *J. Am. Chem. Soc.* 125, 5586-5587 (2003); Haggarty, S. J.; Koeller, K. M.; Wong, J. C.; Grozinger, C. M.; Schreiber, S. L., *Proc. Natl. Acad. Sci. USA,* 100, 4389-4394 (2003)).

Cyclic-peptide moieties are the most complex of all HDAC inhibitor cap-groups and present an opportunity for the modulation of the biological activities of HDAC inhibitors. The macrocycle group is made up of hydrophobic amino acids and the prominent difference among the members of this class is in the amino acid side-chain substitution on the ring. Mechanistically, cyclic-peptide HDAC inhibitors can be divided into two classes: (i) reversible HDAC inhibitors and (ii) irreversible HDAC inhibitors, due to the alkylative modification of HDAC enzyme by the epoxy-ketone moiety on their side-chain. HDAC inhibitory activity and selectivity can vary significantly by changing the side-chain of each amino acid and/or the pattern of the combination of amino acid chirality.

Although cyclic-peptide HDAC inhibitors may possess potent HDAC inhibitory activity, their broad application in specific therapies, such as cancer therapy, currently remains largely unproven. The absence of clinically effective cyclic-peptide HDAC inhibitors may be in part due to development problems characteristic of large peptides, particularly poor oral bioavailability. In fact, the overall in vivo efficacy of cyclic-peptide HDAC inhibitors is complicated by their membrane penetration ability. HDAC inhibitory potency has been noted to increase with increase in the hydrophobicity of the macrocyclic ring (Meinke, P. T.; Liberator, P., *Curr. Med. Chem.,* 8, 211-235 (2001)). Unfortunately, SAR studies for this class of compounds have been impaired largely because most macrocyclic HDAC inhibitors known to date contain peptide macrocycles. In addition to retaining the pharmacologically disadvantaged peptidyl-backbone, they offer only limited opportunity for side-chain modifications.

To date, several other structurally distinct small molecule HDAC inhibitors have been reported including hydroxamates, benzamides, short-chain fatty acids, electrophilic ketones and cyclic-peptides (Miller, T. A.; Witter, D. J.; Belvedere, S., *J. Med. Chem.* 46, 5097-5116 (2003); Rosato, R. R.; Grant, S., *Expert Opin. Invest. Drugs,* 13, 21-38 (2004); Monneret, C., *Eur. J. of Med. Chem.,* 40, 1-13 (2005); Yoo, C. B.; Jones, P. A., *Nature Reviews Drug Discovery,* 5, 37-50 (2006)). Most of these agents have been shown to non-selectively inhibit the deacetylase activity of class I/II HDAC enzymes. The HDAC inhibitor SAHA has been approved by the FDA for the treatment of cutaneous T cell lymphoma. However, a large number of the identified HDAC inhibitors have elicited only limited in vivo antitumor activities and have not progressed beyond preclinical characterizations.

Therefore, there is a need to develop new HDAC inhibitors with improved efficacy, and better pharmacokinetic properties for use as therapeutic agents, such as anti-cancer agents and anti-parasitic agents.

It is therefore an object of the invention to provide non-peptide macrocyclic HDAC inhibitors having improved efficacy and methods of making and using thereof.

SUMMARY OF THE INVENTION

Compounds of Formula I and II, and methods of making and using thereof, are described herein.

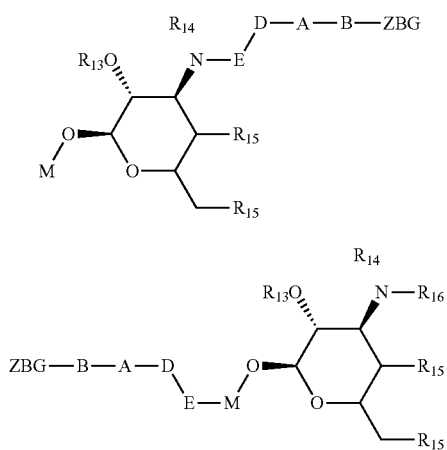

wherein M represents a macrolide subunit,

E is a substituted or unsubstituted $C_{1-6}$ group, optionally containing one or more heteroatoms, wherein the carbon atoms and/or heteroatoms are in a linear and/or cyclic arrangement, D is a substituted or unsubstituted alkyl, substituted or unsubstituted heteroalkyl, substituted or unsubstituted aryl, substituted or unsubstituted heteroaryl group, A is a linking group connected to D, B is an alkyl, heteroalkyl, alkylaryl or alkylheteroaryl spacer group, ZBG is a Zinc Binding Group, $R_{13}$ is selected from hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group, $R_{14}$ and $R_{16}$ is selected from hydrogen, hydroxyl, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group, $R_{15}$ is hydrogen or —$OR_{17}$, $R_{17}$ is selected from a group consisting of hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group.

The macrolide subunit can be attached to the pyran moiety at multiple locations on the macrolide subunit. In one embodiment, the compound contains the macrolide M9, M27, M28, M29, or M30 in Table 2, z is 1, n is 1, D is an aryl group, such as a phenyl group, A is a 1,2,3-triazolyl group, B is an alkyl group having from 5-8 carbons, and ZBG is a hydroxamate group.

The compounds can be administered as the free acid or base, or as a pharmaceutically acceptable salt, prodrug, or solvate. The compounds can be formulated with a pharmaceutically acceptable carrier and, optionally one or more pharmaceutically acceptable excipients, for enteral, parenteral, or topical administration. The compounds can be formulated for immediate release and/or controlled release. Examples of controlled release formulations include sustained release, delayed release, pulsatile release, and combinations thereof.

The compounds may be useful as anti-cancer agents, anti-inflammatory agents, anti-infective agents, anti-parasitic agents, such as anti-malarial agents and antileishmanial agents, cytoprotective agents, chemopreventive agents, prokinetic agents, and/or cognitive enhancing agents. The presence of the macrolide group may allow for the targeted delivery of the HDAC inhibitor in view on the ability of macrolides to accumulate in specific tissues.

DETAILED DESCRIPTION OF THE INVENTION

I. Definitions

"Macrolide", as used herein, includes, but is not limited to, multi-member lactonic ring molecules, wherein "member" refers to the carbon atoms and heteroatoms in the ring, and "multi" is a number greater than about 10, preferably from 10 to about 20, more preferably 12-, 14-, 15-, 16-, 17- or 18-member lactonic rings. Suitable macrolides include, but are not limited to, azithromycin and its derivatives; clarithromycin and its derivatives; erythromycin and its derivatives; bridged bicyclic macrolides, such as EDP-420 and its derivatives; dirithromycin and its derivatives, 9-dihydro-9-deoxo-9a-aza-9a-homoerythrornycin and its derivatives; HMR 3004 and its derivatives, HMR 3647 and its derivatives; HMR 3787 and its derivatives; josamycin and its derivatives; erythromycylamine and its derivatives; ABT 773 and its derivatives; TE 802 and its derivatives; flurithromycin and its derivatives; tylosin and its derivatives; tilmicosin and its derivatives; oleandomycin and its derivatives; desmycosin and its derivatives; CP-163505 and its derivatives; EDP-420 and its derivatives; roxithromycin and its derivatives; miocamycin and its derivatives; rokitamycin and derivatives thereof, such as ketolides (e.g., 3-ketone), lactams (e.g., 8a- or 9a-lactams) and derivatives lacking one or more sugar moieties.

"Aryl", as used herein, refers to 5-12-membered, preferably 5-, 6- and 7-membered aromatic, heterocyclic, fused aromatic, fused heterocyclic, biaromatic, or bihetereocyclic ring systems, optionally substituted, for example, by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "Ar" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, (uranyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Zinc binding group" or "ZBG", as used herein, refers to a moiety or moieties capable of inhibiting the activity of zinc metalloenzymes including, but not limited to, HDAC and matrix metalloproteinase (MMP) activity. Suitable examples include, but are not limited to, hydroxamates, N-formyl hydroxylamine (or retro-hydroxamate), carboxylates, thiols, dithiols, trithiocarbonates, thioesters, benzamide, keto groups, mercaptoacetamides, 2-ketoamides, epoxides, epoxyketones, trifluoromethyl ketones, hydroxypyridinones, such as 2-hydroxy and 3-hydroxypyridinones, pyrones, hydroxylpyridinethiones, such as 3-hydroxy-2-methylpyridine-4-thione, and thiopyrones.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., C1-C30 for straight chain, C3-C30 for branched chain), preferably 20 or fewer, more preferably 10 or fewer, most preferably 6 or less. Likewise, preferred cycloalkyls have from 3-10 carbon atoms in their ring structure, and more preferably have 5, 6 or 7 carbons in the ring structure. "Heteroalkyl", as used herein, refers to an alkyl group containing one or more heteroatoms, such as O, S, or N.

"Alkoxycarbonyl", as used herein, refers to a substituent having the following chemical formula:

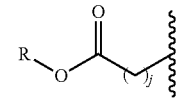

wherein R is a linear, branched, or cyclic alkyl group, wherein j is from about 1 to about 12, "Alkoxycarbamido", as used herein, refers to a substituent having the following chemical formula:

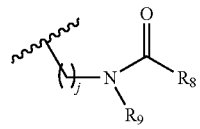

wherein $R_8$ is alkoxy and $R_9$ is hydrogen, alkoxy-alkyl, or alkanoyl, and j is from about 1 to about 12.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, (C$_{1-4}$)alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, (uranyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The terms "alkenyl" and "alkynyl" refer to unsaturated aliphatic groups analogous in length and possible substitution to the alkyls described above, but that contain at least one double or triple bond respectively.

The terms ortho, meta and para apply to 1,2-, 1,3- and 1,4-disubstituted benzenes, respectively. For example, the names 1,2-dimethylbenzene and ortho-dimethylbenzene are synonymous.

"Substituted", as used herein, means that the functional group contains one or more substituents including, but not limited to, hydroxyl, halogen, nitro, aldehyde, ketone, carboxylic acid, ester, ether, amino, alkyl amino, dialkyl amino, amide, thiol, thioether, thione, sulfate, phosphate, and combinations thereof.

"Pharmaceutically acceptable salt", as used herein, refer to derivatives of the compounds defined by Formula I and II wherein the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the compounds can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Prodrug", as used herein, refers to a pharmacological substance (drug) which is administered in an inactive (or significantly less active) form. Once administered, the prodrug is metabolized in the body (in vivo) into the active compound.

"Solvate", as used herein, refers to a compound which is formed by the interaction of molecules of a solute with molecules of a solvent.

"Reverse ester", as used herein, refers to the interchange of the positions of the oxygen and carbon groups in a series of structurally related compounds "Reverse amide", as used herein, refers to the interchange of the positions of the nitrogen and carbon groups in a series of structurally related compounds.

II. Compounds

Compounds of Formula I or II, and methods of making and using thereof, are described herein.

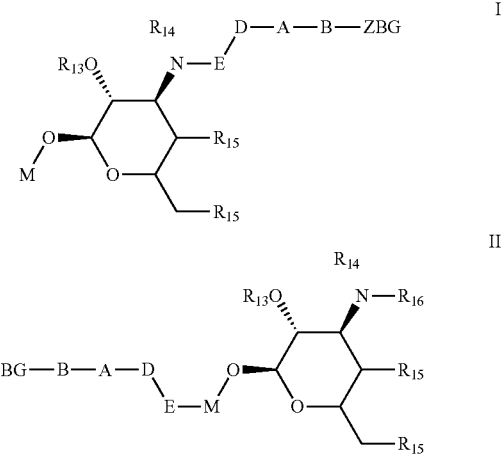

wherein M represents a macrolide subunit,

E is a substituted or unsubstituted $C_{1-6}$ group, optionally containing one or more heteroatoms, wherein the carbon atoms and/or heteroatoms are in a linear and/or cyclic arrangement, D is a substituted or unsubstituted alkyl, substituted or unsubstituted heteroalkyl, substituted or unsubstituted aryl, substituted or unsubstituted heteroaryl group, A is a linking group connected to D, B is an alkyl, heteroalkyl, alkylaryl or alkylheteroaryl spacer group, ZBG is a Zinc Binding Group, $R_{13}$ is selected from hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group, $R_{14}$ and $R_{16}$ is selected from hydrogen, hydroxyl, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group, $R_{15}$ is hydrogen or —$OR_{17}$, $R_{17}$ is selected from a group consisting of hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group.

Examples of the linking group A include, but are not limited to, amide, reverse amide, ester, reverse ester, alkoxyl, sulfonyl, sulfonyl, sulfonyl, sulfonamido, ketone, $sp^3$ hybridized carbon, $sp^2$ hybridized carbon, sp hybridized carbon, 5 or 6 membered heterocyclic rings including but not limiting to 1,2,3-triazolyl, 1,2,4-triazolyl, 1-tetrazolyl, 1-indolyl, 1-indazolyl, 2-isoindolyl, 7-oxo-2-isoimdolyl, 1-pirinyl, 3-isothiazolyl, 4-isothiazolyl and 5-isothiazolyl, 1,3,4,-oxadiazole, 4-oxo-2-thiazolinyl or 5-methyl-1,3,4-thiadiazol-2-yl, thiazoledione, 1,2,3,4-thiatriazole, 1,2,4-dithiazolone, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazolyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl 4-pyrazolyl, 5-pyrazolyl, 2-oxazolyl, 4-oxazolyl, 4-oxo-2-oxazolyl, 5-oxazolyl, 4,5-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole. benzisoxazole, 2-furanyl, 3-furanyl, 2-thienyl, 3-thienyl, 2-pyrrolyl, pyrrolyl, 3-pyrrolyl, 3-isopyrrolyl, 4-isopyrrolyl, 5-isopyrrolyl, 1,2,3-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,3-thiadiazol-5-yl, 3-oxo-1,2,3-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl. Each of these moieties may be substituted as appropriate.

B is a substituted or unsubstituted alkyl, alkylaryl or alkylheteroaryl spacer group. Suitable alkyl spacer group chain length ranges from about $C_4$ to about $C_{12}$, optionally substituted by one or more double and/or triple bonds. The total number of atoms in the alkylaryl and alkylheteroaryl groups is from about 6 to about 50, preferably from about 6 to about 30, more preferably from about 6 to about 20, most preferably from about 6 to about 10.

M is a macrolide subunit. Suitable macrolide subunits include, but are not limited to, multi-member lactonic ring molecules, wherein "member" refers to the carbon atoms or heteroatoms in the ring, and "multi" is a number greater than about 10, preferably from 10 to about 20, more preferably 12-, 14-, 15-, 16, 17-, or 18-member lactonic rings. Exemplary macrolides include, but are not limited to, azithromycin and its derivatives; clarithromycin and its derivatives; erythromycin and its derivatives; bridged bicyclic macrolides, such as EDP-420 and its derivatives; dirithromycin and its derivatives, 9-dihydro-9-deoxo-9a-aza-9a-homoerythromycin and its derivatives; HMR 3004 and its derivatives, HMR 3647 and its derivatives; HMR 3787 and its derivatives; josamycin and its derivatives; erythromycylamine and its derivatives; ABT 773 and its derivatives; TE 802 and its derivatives; flurithromycin and its derivatives; tylosin and its derivatives; tilmicosin and its derivatives; oleandomycin and its derivatives; desmycosin and its derivatives; CP-163505 and its derivatives; EDP-420 and its derivatives; roxithromycin and its derivatives; miocamycin and its derivatives; rokitamycin and derivatives thereof, such as ketolides (e.g., 3-ketone), lactams (e.g., 8a- or 9a-lactams) and derivatives lacking one or more sugar moieties.

In one embodiment, the macrolide M has the formula:

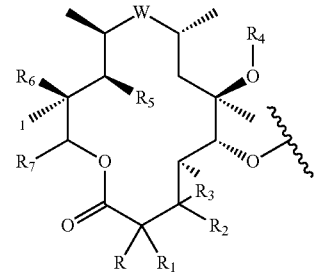

as described in U.S. Patent Application Publication No. 2007/0149463, which is incorporated herein by reference, wherein W is selected from —C(O)—, —C(=NOR$_{11}$)—, —CH(—OR$_{11}$)—, —NR$_{11}$CH$_2$—, —CH$_2$NR$_{11}$—, —CH(NR$_{11}$R$_{11}$)—, —C(=NNR$_{11}$R$_{11}$)—, —NR$_{11}$C(O)—, —C(O)NR$_{11}$—, and —C(=NR$_{11}$)—;

R is selected from the group consisting of H and $C_{1-6}$ alkyl;

$R_1$ is selected from the group H, halogen, —NR$_{11}$R$_{11}$, NR$_{11}$C(O)R$_{11}$, —OR$_{11}$, —OC(O)R$_{11}$, —OC(O)OR$_{11}$, —OC(O)NR$_{11}$R$_{11}$, —OC$_{1-6}$alcyl-R$_{12}$, —OC(O)C$_{1-6}$ alkyl-R$_{12}$, —OC(O)OC$_{1-6}$ alkyl-R$_{12}$, —OC(O)NR$_{11}$C$_{1-6}$ alkyl-R$_{12}$, $C_{1-6}$ alkyl, $C_{1-6}$ alkenyl, $C_{1-6}$ alkynyl, optionally is substituted with one or more $R_{12}$ groups;

$R_2$ is H;

$R_3$ is selected from H, —OR$_{11}$, —OC$_{1-6}$ alkyl-R$_{12}$, —OC(O)R$_{11}$, —OC(O)C$_{1-6}$ alkyl-R$_{12}$, —OC(O)OR$_{11}$, —OC(O)OC$_{1-6}$ alkyl-R$_{12}$, —OC(O)NR$_{11}$R$_{11}$, —OC(O)NR$_{11}$C$_{1-6}$ alkyl-R$_{12}$; alternatively, $R_3$ is a pyran ring which can be substituted as defined above in Formulae I and II;

$R_4$ is selected from H, R$_{11}$, —C(O)R$_{11}$, —C(O)OR$_{11}$, —C(O)NR$_{11}$R$_{11}$, —C$_{1-6}$ alkyl-T-R$_{11}$, —C$_{2-6}$ alkenyl-T-R$_{11}$, and —C$_{2-6}$ alkynyl-T-R$_{11}$; alternatively $R_3$ and $R_4$ taken together form

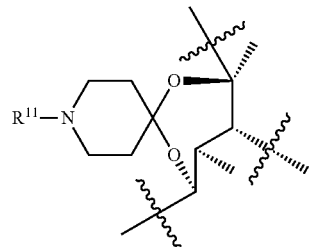

T is selected from —C(O)—, —C(O)O—, —C(O)NR$_{11}$—, —C(=NR$_{11}$)—, —C—(=NR$_{11}$)O—, —C(=NR$_{11}$)NR$_{11}$—, g) —OC(O)—, —OC(O)O—, —OC(O)NR$_{11}$—, —NR$_{11}$C(O)—, —NR$_{11}$C(O)O—, —NR$_{11}$C(O)NR$_{11}$—, —NR$_{11}$C(=NR$_{11}$)NR$_{11}$—, and —S(O)$_p$—, wherein p 0-2;

R$_5$ is selected from R$_{11}$, —OR$_{11}$, —NR$_{11}$R$_{11}$, —OC$_{1-6}$ alkyl-R$_{12}$, —C(O)R$_{11}$, —C(O)C$_{1-6}$ alkyl-R$_{12}$, —OC(O)R$_{11}$, —OC(O)G$_{1-6}$ alkyl-R$_{12}$, —OC(O)OR$_{11}$, —OC(O)OC$_{1-6}$ alkyl-R$_{12}$, —OC(O)NR$_{11}$R$_{11}$, —OC(O)NR$_{11}$C$_{1-6}$ alkyl-R$_{12}$, —C(O)C$_{2-6}$ alkenyl-R$_{12}$, and —C(O)C$_{2-6}$ alkynyl-R$_{12}$;

alternatively, R$_4$ and R$_5$ taken together with the atoms to which they are bonded, form:

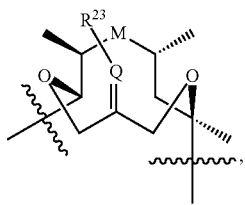

wherein, Q is CH or N, and R$_{23}$ is —OR$_{11}$ or R$_{11}$;

R$_6$ is selected from —OR$_{11}$, alkoxy-R$_{12}$, —C(O)R$_{11}$, —OC(O)R$_{11}$, —OC(O)OR$_{11}$, —OC(O)NR$_{11}$R$_{11}$, NR$_{11}$R$_{11}$;

alternatively, R$_5$ and R$_6$ taken together with the atoms to which they are attached form a 5-membered ring by attachment to each other through a linker selected from —OC(R$_{12}$)$_2$O—, —OC(O)O—, —OC(O)NR$_{11}$—, d) —NR$_{11}$C(O)O—, —OC(O)NOR$_{11}$—, —NOR$_{11}$C(O)O—, —OC(O)NNR$_{11}$R$_{11}$—, —NNR$_{11}$R$_{11}$C(O)O—, —OC(O)C(R$_{12}$)$_2$—, —C(R$_{12}$)$_2$C(O)O—, —OC(S)O—, —OC(S)NR$_{11}$—, —NR$_{11}$C(S)O—, n) —OC(S)NOR$_{11}$—, —NOR$_{11}$C(S)O—, —OC(S)NNR$_{11}$R$_{11}$—, —NNR$_{11}$R$_{11}$C(S)O—, —OC(S)C(R$_{12}$)$_2$—, —C(R$_{12}$)$_2$C(S)O—;

alternatively, W, R$_5$, and R$_6$ taken together with the atoms to which they are attached form:

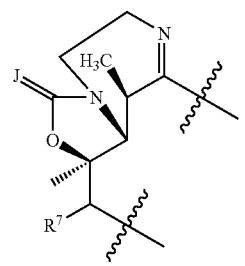

wherein J is selected from the group consisting of O, S, and NR$_{11}$;

R$_{6'}$ is selected from H, unsubstituted or substituted C$_{1-4}$ alkyl, C$_{2-4}$ alkenyl, which can be further substituted with C$_{1-2}$ alkyl or one or more halogens, C$_{2-4}$ alkynyl, which can be further substituted with C$_{1-2}$ alicyl or one or more halogens, aryl or heteroaryl, which can be further substituted with C$_{1-2}$ alkyl or one or more halogens, —C(O)H, —COOH, —CN, —COOR$_{11}$, —C(O)NR$_{11}$R$_{11}$, —C(O)R$_{11}$, —C(O)SR$_{11}$;

alternatively R$_6$ and R$_{6'}$ taken together with the atom to which they are attached to form an epoxide, a carbonyl, an olefin, or a substituted olefin, or a C$_3$-C$_7$ carbocyclic, carbonate, or carbamate, wherein the nitrogen of the carbamate can be further substituted with a C$_1$-C$_6$ alkyl;

R$_7$ is selected from C$_{1-6}$ alkyl, C$_{2-6}$ alkenyl, and C$_{2-6}$ alkynyl, optionally is substituted with one or more R$_{12}$ groups;

R$_{11}$, for each occurrence, is selected from H, C$_{1-6}$ alkyl, C$_{2-6}$ alkenyl, C$_{2-6}$ alkynyl, C$_{6-10}$ saturated, unsaturated, or aromatic carbocycle, 3-12 membered saturated, unsaturated, or aromatic heterocycle containing one or more heteroatoms selected from nitrogen, oxygen, and sulfur, —C(O)—C$_{1-6}$ alkyl, —C(O)—C$_{2-6}$ alkenyl, —C(O)—C$_{2-6}$ alkynyl, —C(O)—C$_{6-10}$ saturated, unsaturated or aromatic carbocycle, —C(O)-3-12 membered saturated, unsaturated, or aromatic heterocycle containing one or more heteroatoms selected from nitrogen, oxygen, and sulfur, —C(O)O—C$_{1-6}$ allyl, —C(O)O—C$_{2-6}$ alkenyl, —C(O)O—C$_{2-6}$ alkynyl, —C(O)O—C$_{6-10}$ saturated, unsaturated, or aromatic carbocycle, —C(O)O-3-12 membered saturated, unsaturated, or aromatic heterocycle containing one or more heteroatoms selected from the group consisting of nitrogen, oxygen, and sulfur, and —C(O)NR$_{13}$R$_{13}$, optionally is substituted with one or more R$_{12}$ groups, R$_{12}$ is selected from R$_{14}$, C$_{1-8}$ alkyl, C$_{2-8}$ alkenyl, C$_{2-8}$ alkynyl, C$_{3-12}$ saturated, unsaturated, or aromatic carbocycle, 3-12 membered saturated, unsaturated, or aromatic heterocycle containing one or more heteroatoms selected from nitrogen, oxygen, and sulfur, optionally substituted with one or more substituents.

Exemplary macrolides are shown in Tables 1 and 2.

TABLE 1

Macrolide Subunits

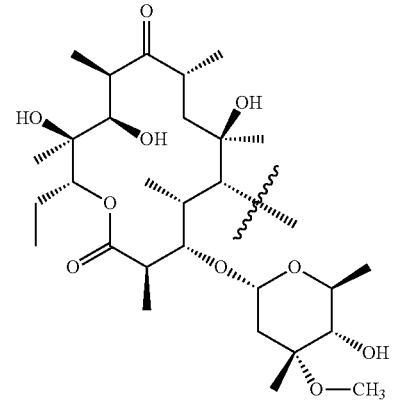 [SMILES: CC[C@H]1OC(=O)[C@H](C)[C@@H](O[C@H]2C[C@@](C)(OC)[C@@H](O)[C@H](C)O2)[C@H](C)[C@@H](C)[C@](C)(O)C[C@@H](C)C(=O)[C@H](C)[C@@H](O)[C@]1(C)O]

M1

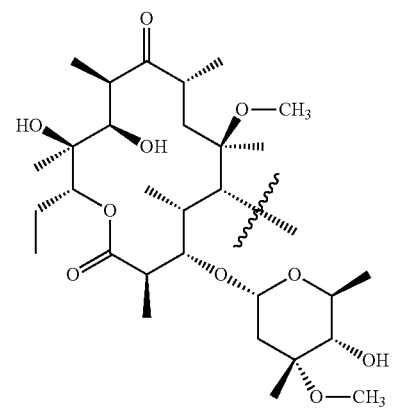 [SMILES: CC[C@H]1OC(=O)[C@H](C)[C@@H](O[C@H]2C[C@@](C)(OC)[C@@H](O)[C@H](C)O2)[C@H](C)[C@@H](C)[C@](C)(OC)C[C@@H](C)C(=O)[C@H](C)[C@@H](O)[C@]1(C)O]

M2

TABLE 1-continued
Macrolide Subunits
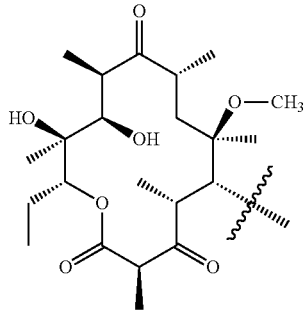 [SMILES: CC[C@H]1OC(=O)[C@H](C)C(=O)[C@H](C)[C@@H](C)[C@](C)(OC)C[C@@H](C)C(=O)[C@H](C)[C@@H](O)[C@]1(C)O]
M3
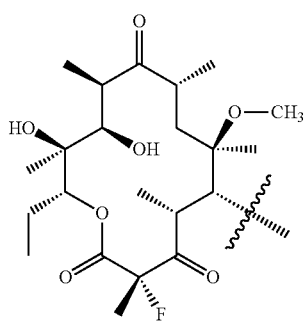 [SMILES: CC[C@H]1OC(=O)[C@@](C)(F)C(=O)[C@H](C)[C@@H](C)[C@](C)(OC)C[C@@H](C)C(=O)[C@H](C)[C@@H](O)[C@]1(C)O]
M4
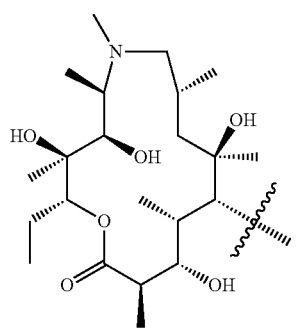 [SMILES: CC[C@H]1OC(=O)[C@H](C)[C@@H](O)[C@H](C)[C@@H](C)[C@](C)(O)C[C@@H](C)CN(C)[C@H](C)[C@@H](O)[C@]1(C)O]
M5
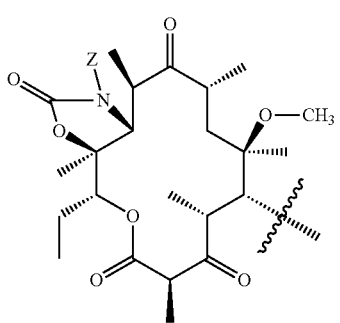
M6
TABLE 1-continued
Macrolide Subunits
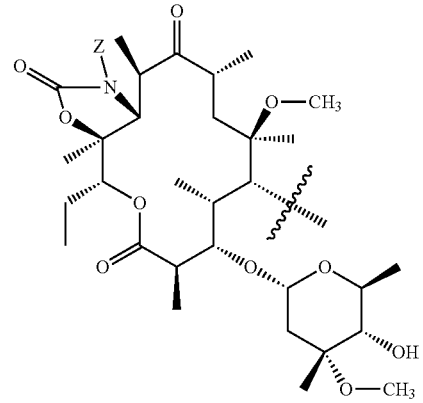
M7
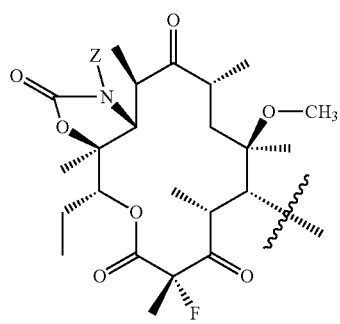
M8
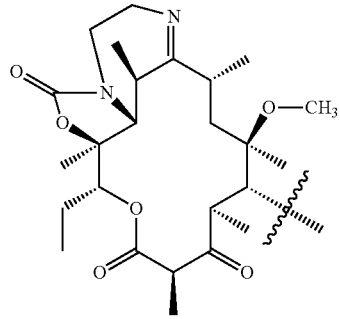 [SMILES: CC[C@H]1OC(=O)[C@H](C)C(=O)[C@H](C)[C@@H](C)[C@](C)(OC)C[C@@H](C)C2=NCCN3C(=O)O[C@@]1(C)[C@H]3[C@H]2C]
M9
M10

TABLE 1-continued
Macrolide Subunits
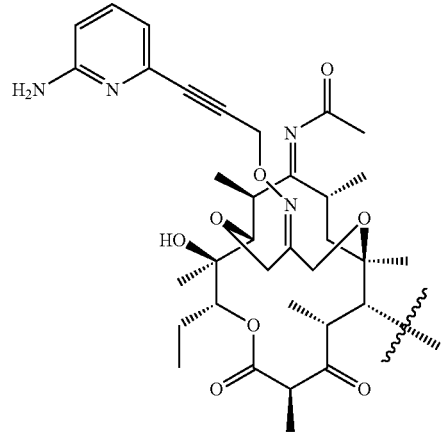 [SMILES: CC[C@H]1OC(=O)[C@H](C)C(=O)[C@H](C)[C@@H](C)[C@@]2(C)C[C@@H](C)/C(=N\C(C)=O)[C@H](C)[C@@H](OC/C(=N\OCC#Cc3cccc(N)n3)CO2)[C@]1(C)O]
M11
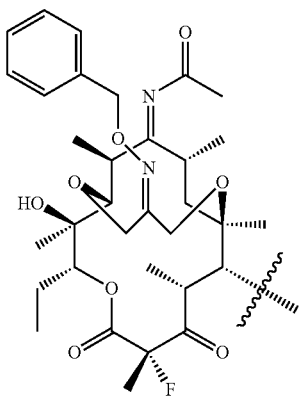
M14
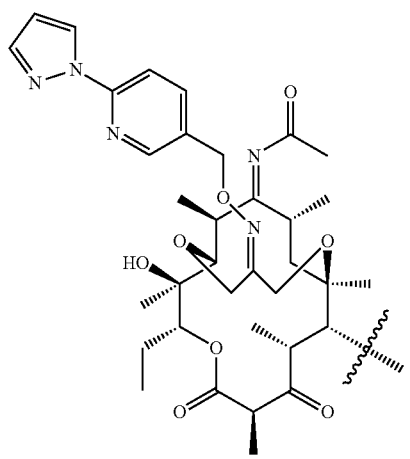 [SMILES: CC[C@H]1OC(=O)[C@H](C)C(=O)[C@H](C)[C@@H](C)[C@@]2(C)C[C@@H](C)/C(=N\C(C)=O)[C@H](C)[C@@H](OC/C(=N\OCc3ccc(-n4cccn4)nc3)CO2)[C@]1(C)O]
M12
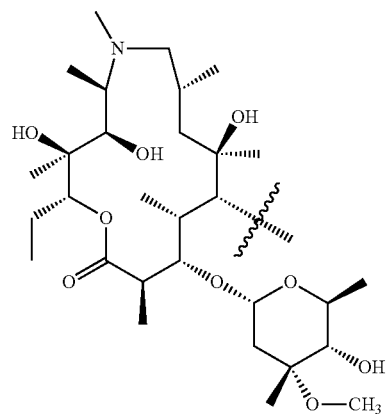
M15
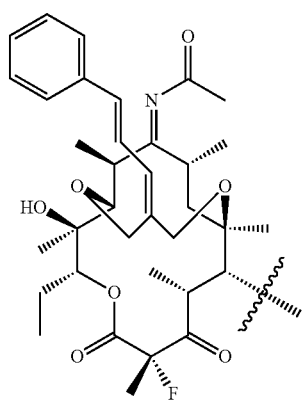 [SMILES: CC[C@H]1OC(=O)[C@@](C)(F)C(=O)[C@H](C)[C@@H](C)[C@@]2(C)C[C@@H](C)/C(=N\C(C)=O)[C@H](C)[C@@H](OC/C(=C\C=C\c3ccccc3)CO2)[C@]1(C)O]
M13
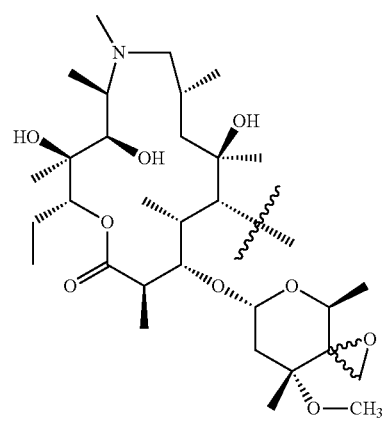
M16

TABLE 1-continued
Macrolide Subunits
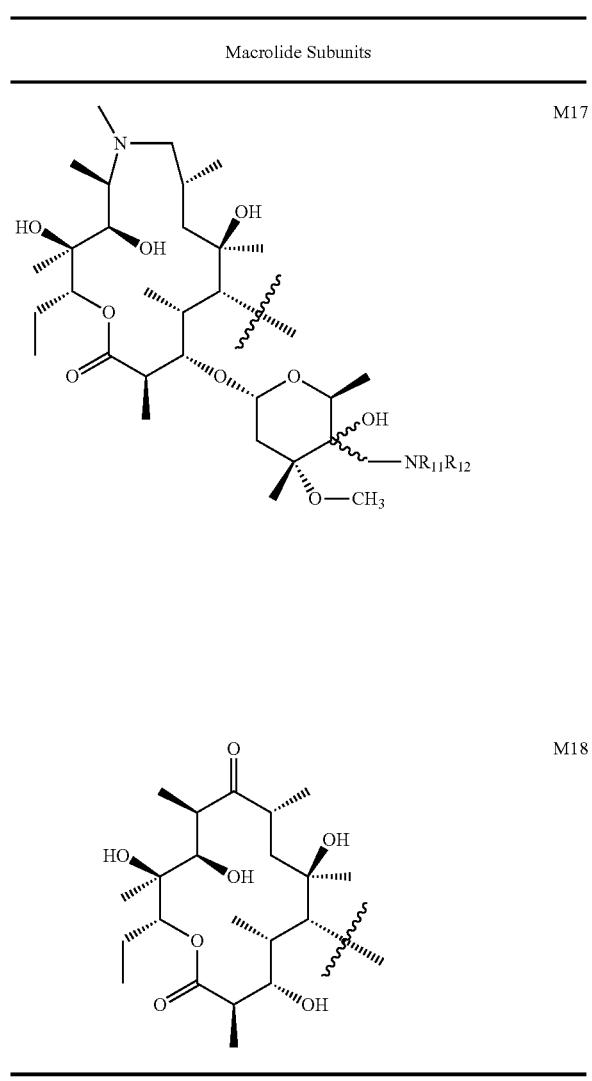
The pyran-ZBG group can be attached to macrolide at various points as shown in Table 2:
TABLE 2
14-Membered Macrolides
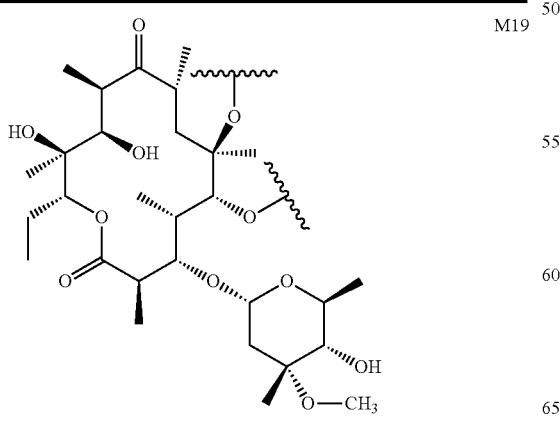
TABLE 2-continued
14-Membered Macrolides
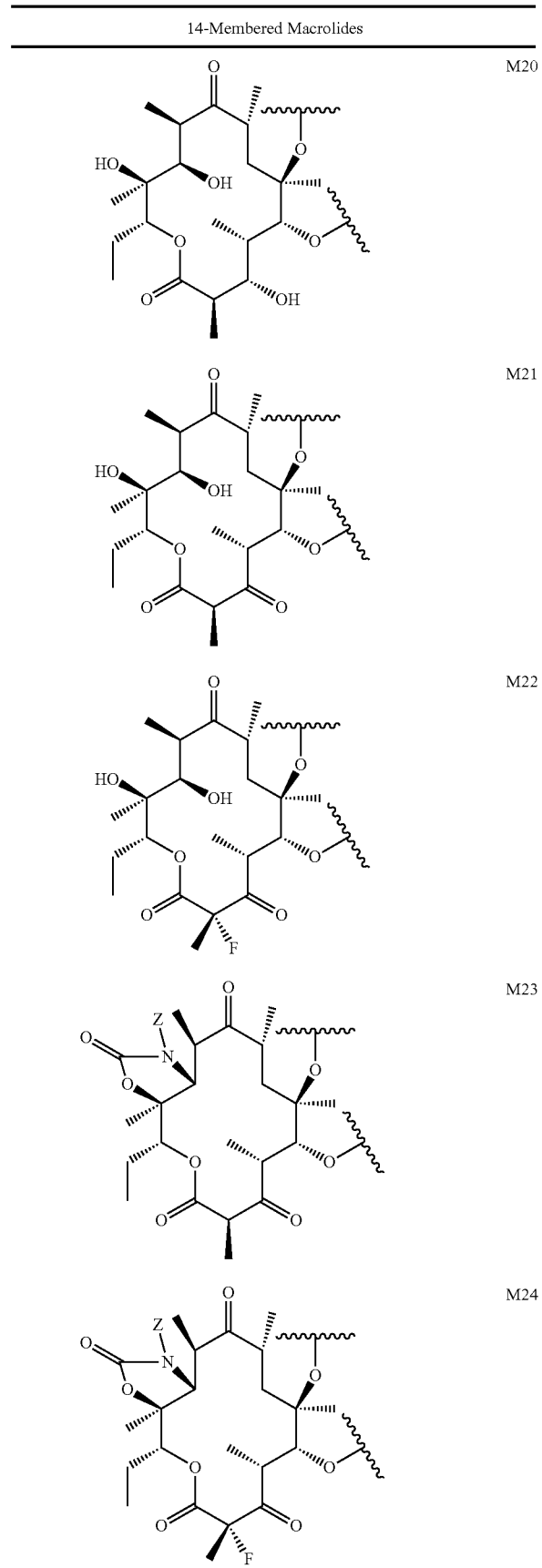

TABLE 2-continued

14-Membered Macrolides

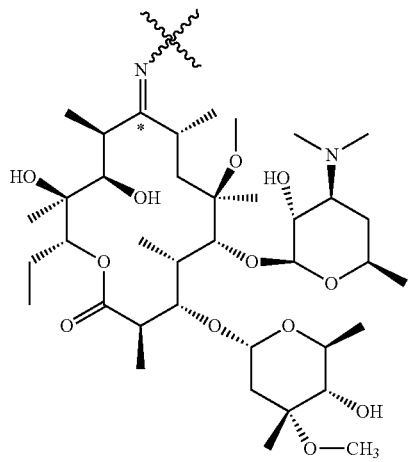

M25

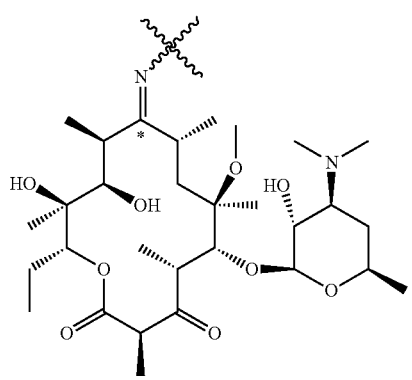

M26

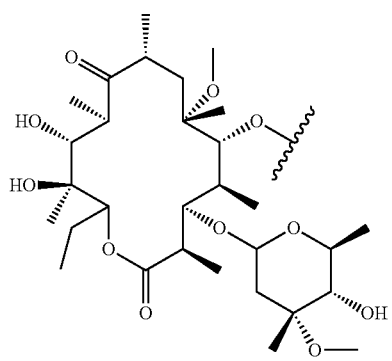 [SMILES: *O[C@@H]1[C@@H](C)[C@@H](OC2C[C@@](C)(OC)[C@@H](O)[C@H](C)O2)[C@@H](C)C(=O)OC(CC)[C@@](C)(O)[C@H](O)[C@@H](C)C(=O)[C@H](C)C[C@]1(C)OC]

M27

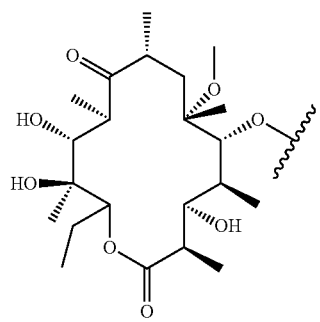 [SMILES: *O[C@@H]1[C@@H](C)[C@@H](O)[C@@H](C)C(=O)OC(CC)[C@@](C)(O)[C@H](O)[C@@H](C)C(=O)[C@H](C)C[C@]1(C)OC]

M28

TABLE 2-continued

14-Membered Macrolides

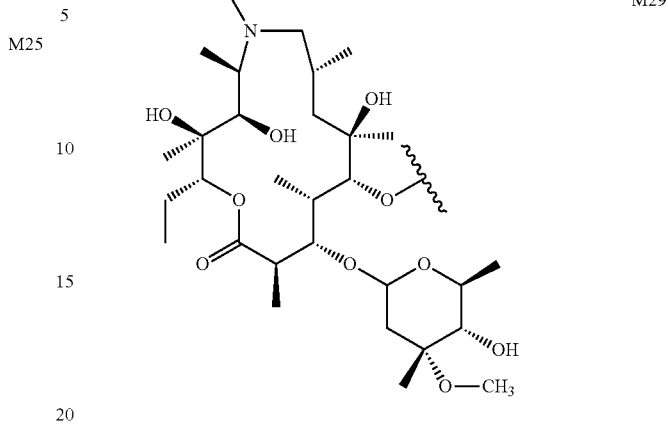

M29

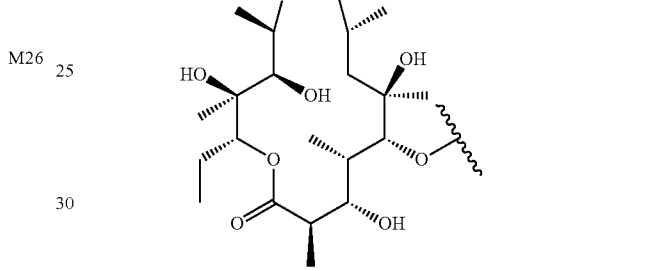

M30

In M25 and M26, the bond between the starred carbon and the nitrogen can be a single bond or a double bond. This is represented by a dashed line in the structures of M25 and M26.

The zinc binding group may be any moiety or moieties that inhibit(s) the activity of zinc metalloenzymes such as HDAC. Exemplary zinc binding groups include hydroxamates, N-formyl hydroxylamine (or retro-hydroxamate), carboxylates, thiols, dithiols, phosphonic acids, thiadiazoles, sulfodiimines, thiadiazines, trithiocarbonates, thioesters, benzamide, keto groups, mercaptoacetamides, 2-ketoamides, epoxides, epoxyketones, trifluoromethyl ketones, hydroxypyridinones, such as 2-hydroxy and 3-hydroxypyridinones, pyrones, hydroxylpyridinethiones, such as 3-hydroxy-2-methylpyridine-4-thione, and thiopyrones.

In some embodiments, the zinc binding group is a heterocyclic moiety. In particular embodiments, the heterocyclic moiety is a heterocyclic group substituted with one or more thiones, hydroxyl groups, thiols, ketones, or combinations thereof. Exemplary zinc binding groups of this type include:

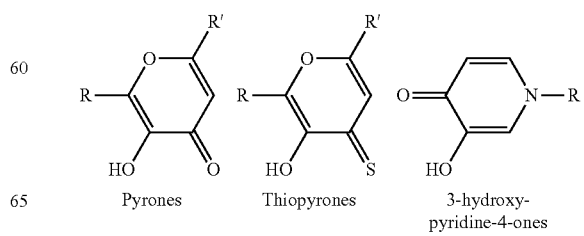

Pyrones     Thiopyrones     3-hydroxy-pyridine-4-ones

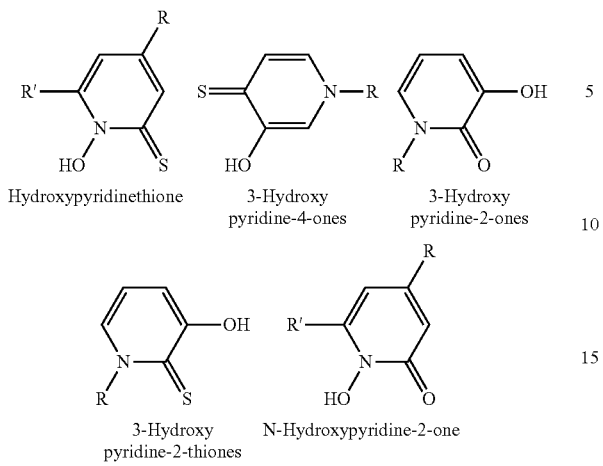

In some embodiments, the zinc binding group can be selected to provide selectivity for a particular HDAC isoform.

In some instances, HDAC inhibitors bearing a zinc binding group containing a heterocyclic group substituted with one or more thiones possesses a higher activity that the same inhibitor bearing a zinc binding group containing a heterocyclic group substituted with one or more ketones. In certain embodiments, the zinc binding group is a 3-hydroxypyridine-2-thione.

The compounds described herein may have one or more chiral centers and thus exist as one or more stereoisomers. Such stereoisomers can exist as a single enantiomer, a mixture of diastereomers or a racemic mixture.

As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

In one embodiment, the HDAC inhibitors have the formula shown below:

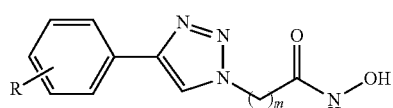

wherein R is:

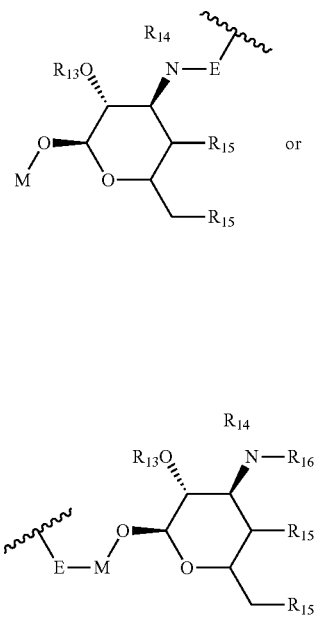

and m is an integer from 1-12, preferably from 1-10, more preferably from 4-10, most preferably from 5-9 inclusive. However, compounds where m is greater than 12 may be prepared and their activity determined as described in the examples.

R can be positioned ortho, meta, or para to the triazolyl group. In one embodiment, R is para to the triazolyl group. In another embodiment, R is meta to the triazolyl group.

The macrolide can be any suitable maroclide. In one embodiment, the macrolide is selected from M9 or M27-M30 in Table 2.

In another embodiment, the HDAC inhibitors have the following formula:

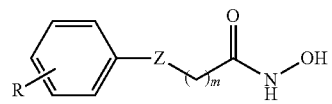

wherein R and M are as defined above and z is oxygen or —NCO—.

In still another embodiment, the HDAC inhibitor has one of the formulas above, wherein the zinc binding group is a pyridine thione, diamino benzene, or hydroxypyridone group.

In another embodiment, the HDAC inhibitors have the formula shown below:

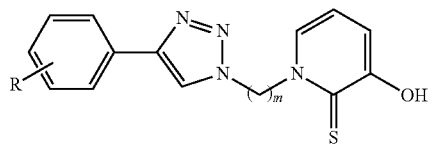

wherein R is:

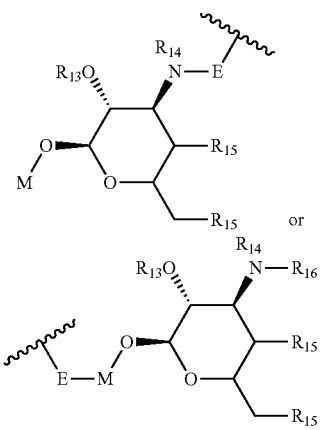

and m is an integer from 1-12, preferably from 1-10, more preferably from 4-10, most preferably from 5-9 inclusive. However, compounds where m is greater than 12 may be prepared and their activity determined as described in the examples.

R can be positioned ortho, meta, or para to the triazolyl group. In one embodiment, R is para to the triazolyl group. In another embodiment, R is meta to the triazolyl group.

The macrolide can be any suitable maroclide. In one embodiment, the macrolide is selected from M9 or M27-M30 in Table 2.

Non-limiting examples of HDAC inhibitors of Formula I and II are shown in Table 3.

TABLE 3

| Non-peptide HDAC Inhibitors |
|---|
| COMPOUND NUMBER — STRUCTURE |
| 7 |
| 8 |

TABLE 3-continued

Non-peptide HDAC Inhibitors

| COMPOUND NUMBER | STRUCTURE |
|---|---|
| 9 | *(structure)* |
| 10 | *(structure)* |
| 11 | *(structure)* |

TABLE 3-continued

Non-peptide HDAC Inhibitors

| COMPOUND NUMBER | STRUCTURE |
|---|---|
| 12 | 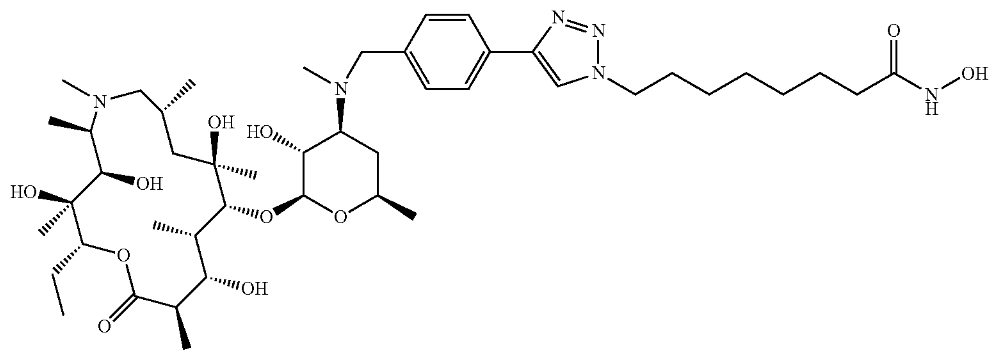 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCC(=O)NO)nn4)cc3)[C@H]2O)[C@](C)(O)C[C@@H](C)CN(C)[C@H](C)[C@@H](O)[C@]1(C)O] |
| 13 | 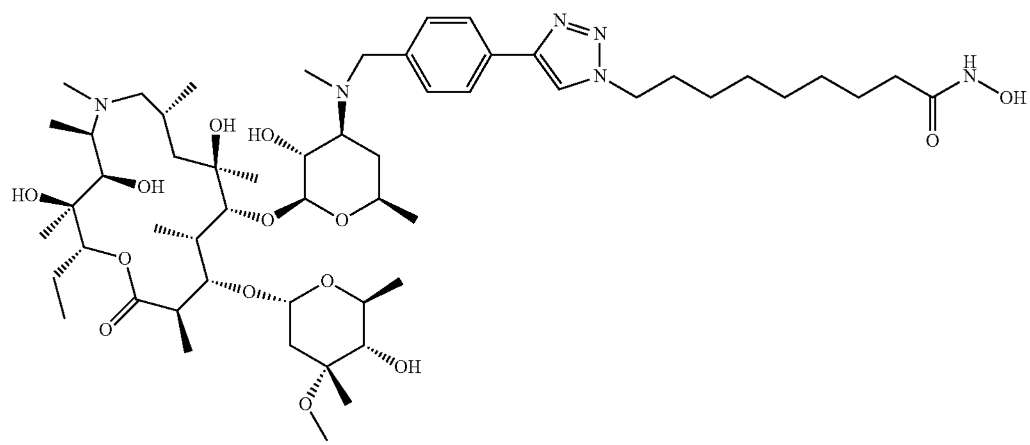 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCCC(=O)NO)nn4)cc3)[C@H]2O)[C@](C)(O)C[C@@H](C)CN(C)[C@H](C)[C@@H](O)[C@]1(C)O] |
| 14 | 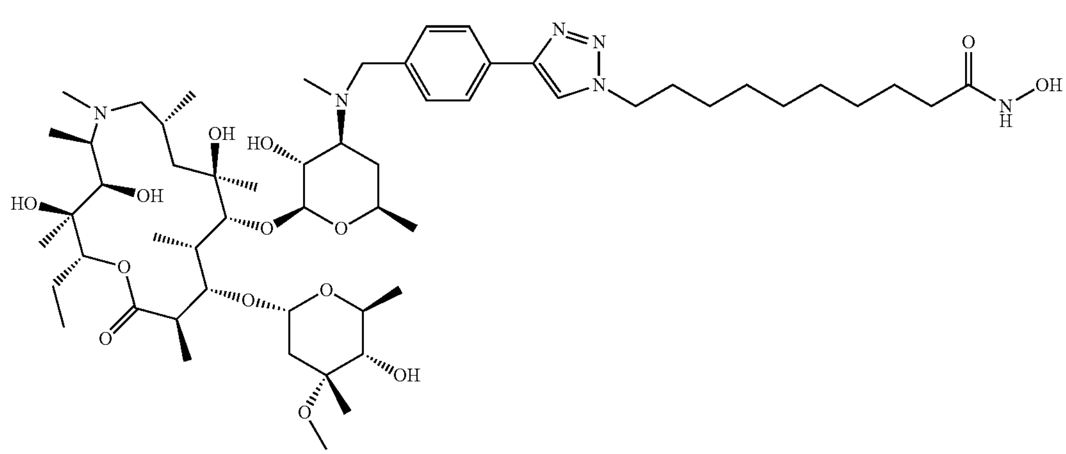 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCCCC(=O)NO)nn4)cc3)[C@H]2O)[C@](C)(O)C[C@@H](C)CN(C)[C@H](C)[C@@H](O)[C@]1(C)O] |

TABLE 3-continued

Non-peptide HDAC Inhibitors

| COMPOUND NUMBER | STRUCTURE |
|---|---|
| 23 | 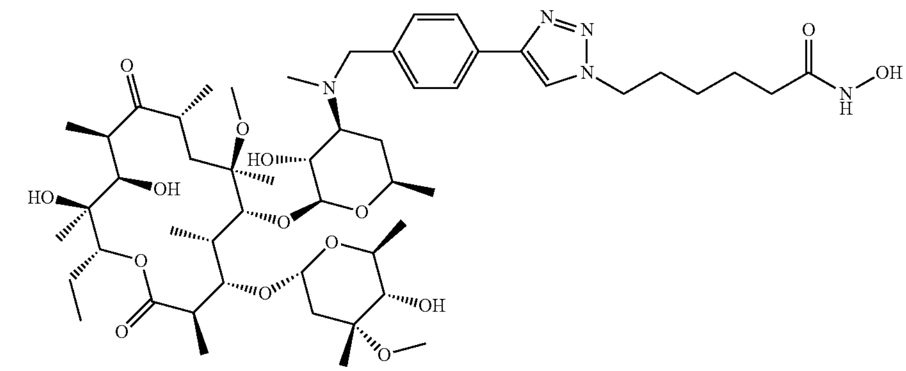 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCC(=O)NO)nn4)cc3)[C@H]2O)[C@](C)(OC)C[C@@H](C)C(=O)[C@H](C)[C@@H](O)[C@]1(C)O] |
| 24 | 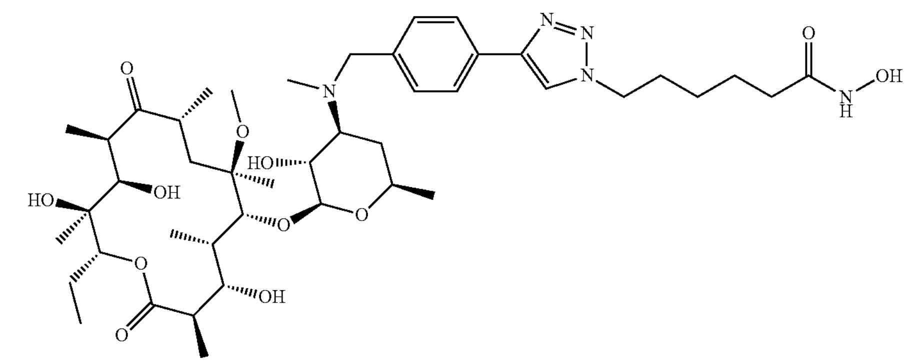 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCC(=O)NO)nn4)cc3)[C@H]2O)[C@](C)(OC)C[C@@H](C)C(=O)[C@H](C)[C@@H](O)[C@]1(C)O] |
| 25 | 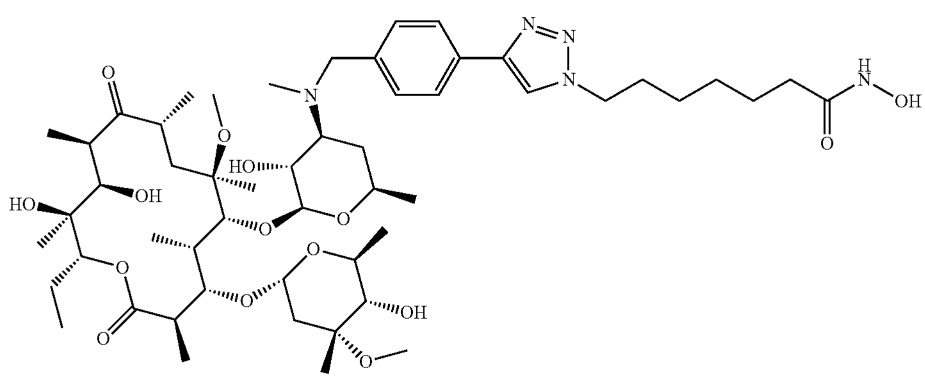 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCC(=O)NO)nn4)cc3)[C@H]2O)[C@](C)(OC)C[C@@H](C)C(=O)[C@H](C)[C@@H](O)[C@]1(C)O] |
| 26 | 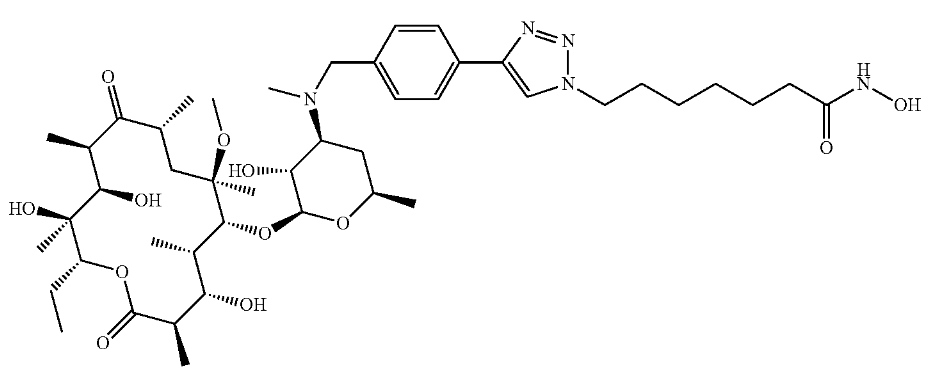 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCC(=O)NO)nn4)cc3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 27 | 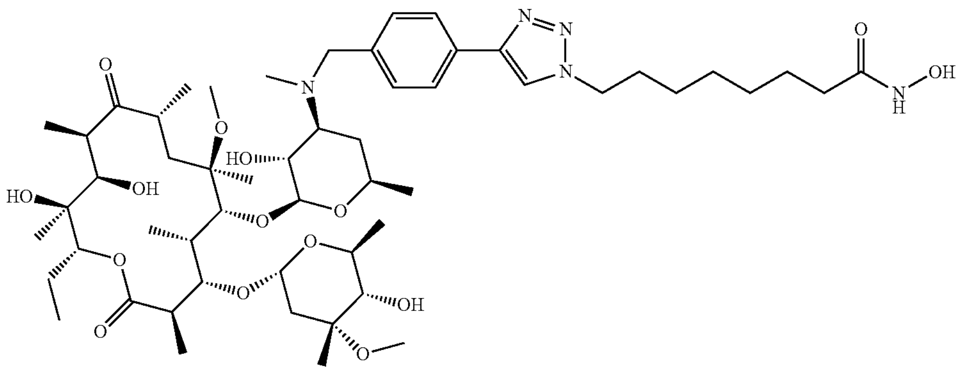 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCC(=O)NO)nn4)cc3)[C@H]2O)[C@](C)(OC)C[C@@H](C)C(=O)[C@H](C)[C@@H](O)[C@]1(C)O] |
| 28 | 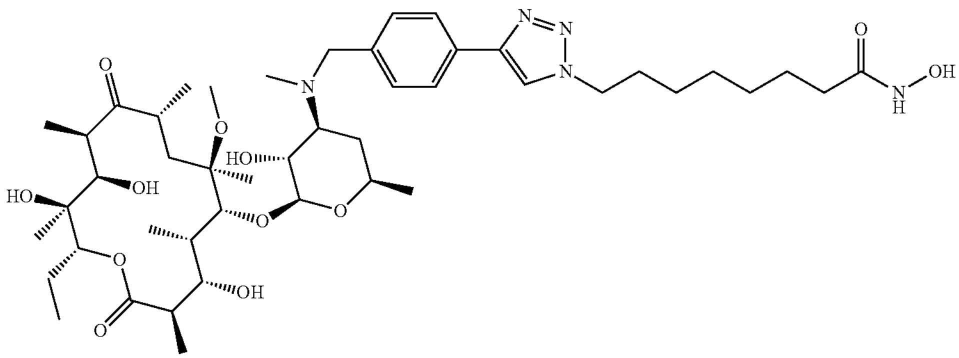 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCC(=O)NO)nn4)cc3)[C@H]2O)[C@](C)(OC)C[C@@H](C)C(=O)[C@H](C)[C@@H](O)[C@]1(C)O] |
| 29 | 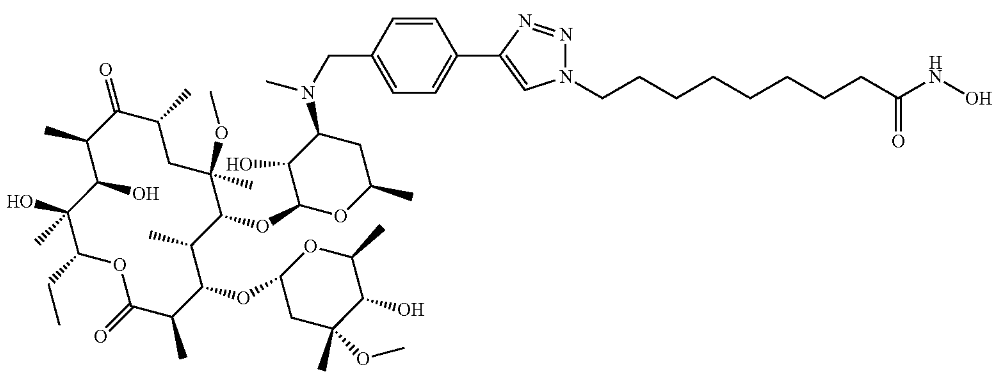 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCCC(=O)NO)nn4)cc3)[C@H]2O)[C@](C)(OC)C[C@@H](C)C(=O)[C@H](C)[C@@H](O)[C@]1(C)O] |
| 30 | 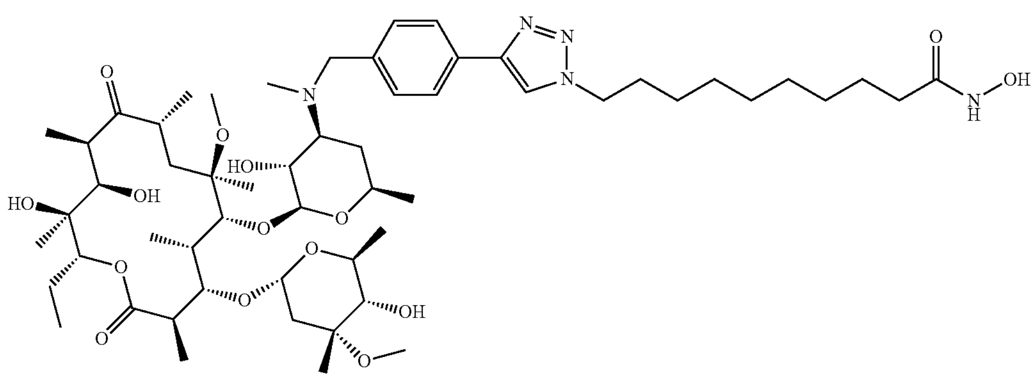 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCCCC(=O)NO)nn4)cc3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 36 | 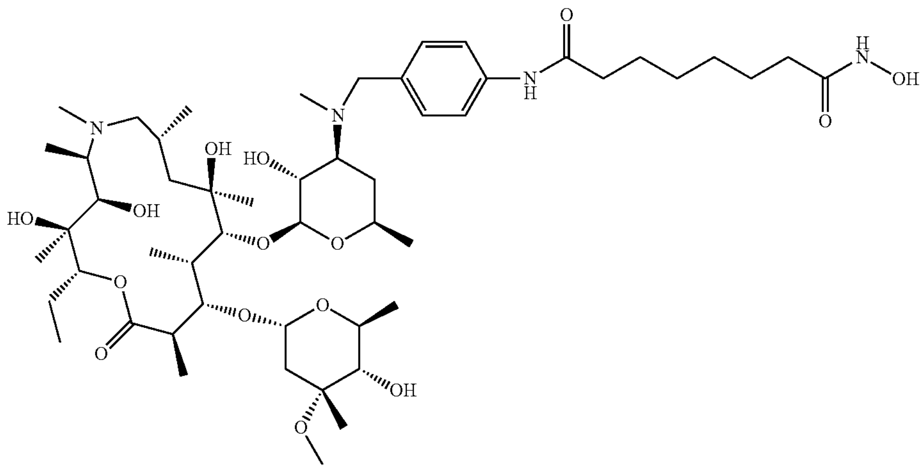 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(NC(=O)CCCCCCC(=O)NO)cc3)[C@H]2O)[C@](C)(O)C[C@@H](C)CN(C)[C@H](C)[C@@H](O)[C@]1(C)O] |
| 38 | 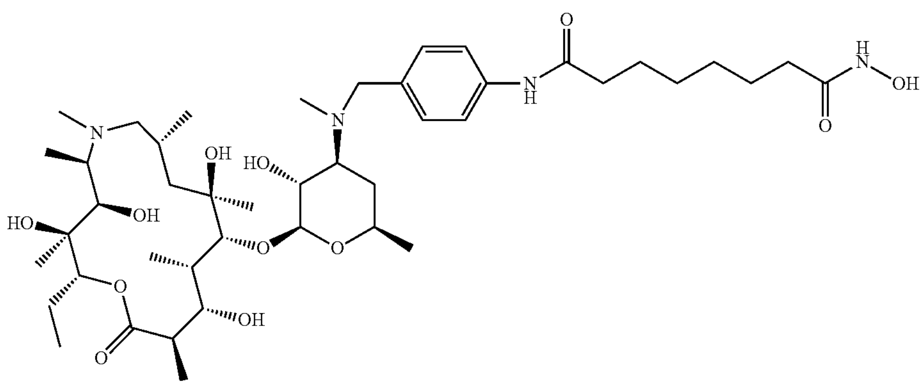 [SMILES: CC[C@H]1OC(=O)[C@H](C)[C@@H](O)[C@H](C)[C@@H](O[C@@H]2O[C@H](C)C[C@H](N(C)Cc3ccc(NC(=O)CCCCCCC(=O)NO)cc3)[C@H]2O)[C@](C)(O)C[C@@H](C)CN(C)[C@H](C)[C@@H](O)[C@]1(C)O] |
| 40 | 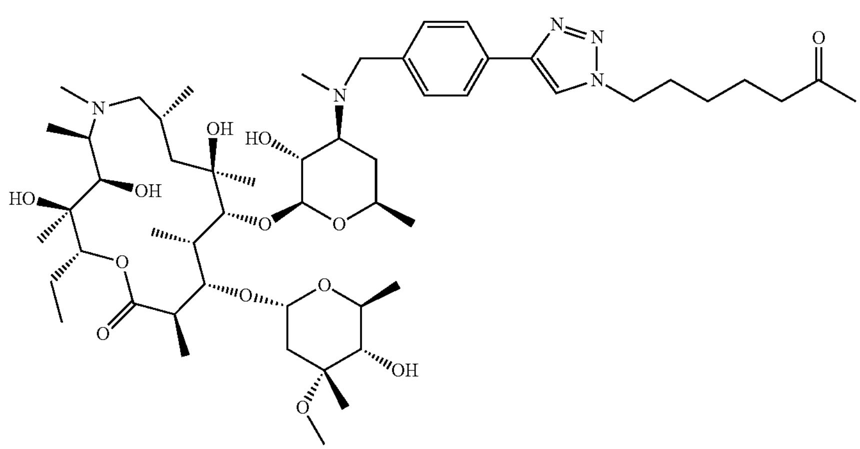 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCC(C)=O)nn4)cc3)[C@H]2O)[C@](C)(O)C[C@@H](C)CN(C)[C@H](C)[C@@H](O)[C@]1(C)O] |

TABLE 3-continued
Non-peptide HDAC Inhibitors
| COMPOUND NUMBER | STRUCTURE |
|---|---|
| 44 | 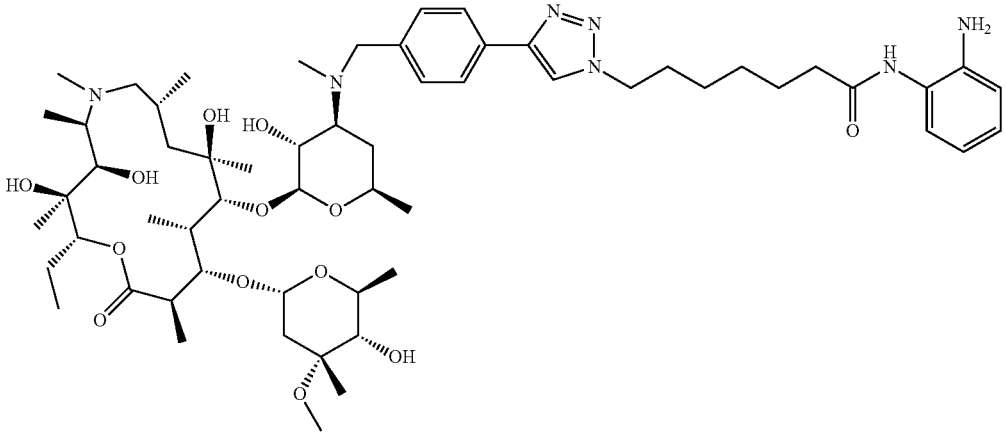 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCC(=O)Nc5ccccc5N)nn4)cc3)[C@H]2O)[C@](C)(O)C[C@@H](C)CN(C)[C@H](C)[C@@H](O)[C@]1(C)O] |
| 47 | 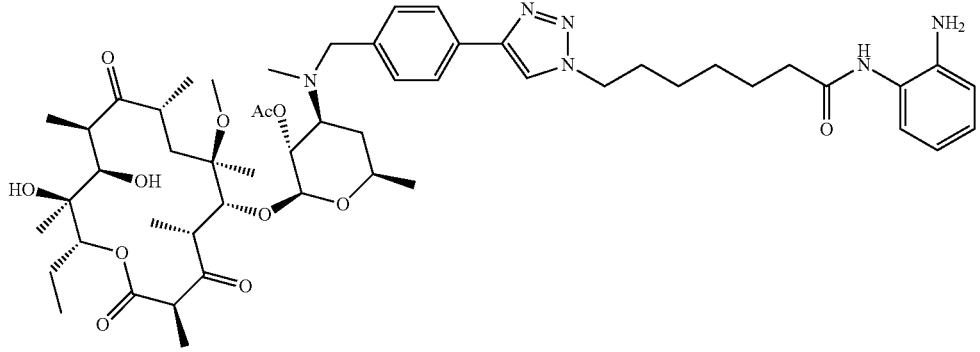 [SMILES: CC[C@H]1OC(=O)[C@H](C)C(=O)[C@H](C)[C@@H](O[C@@H]2O[C@H](C)C[C@H](N(C)Cc3ccc(-c4cn(CCCCCCC(=O)Nc5ccccc5N)nn4)cc3)[C@H]2OC(C)=O)[C@](C)(OC)C[C@@H](C)C(=O)[C@H](C)[C@@H](O)[C@]1(C)O] |
| 48 | 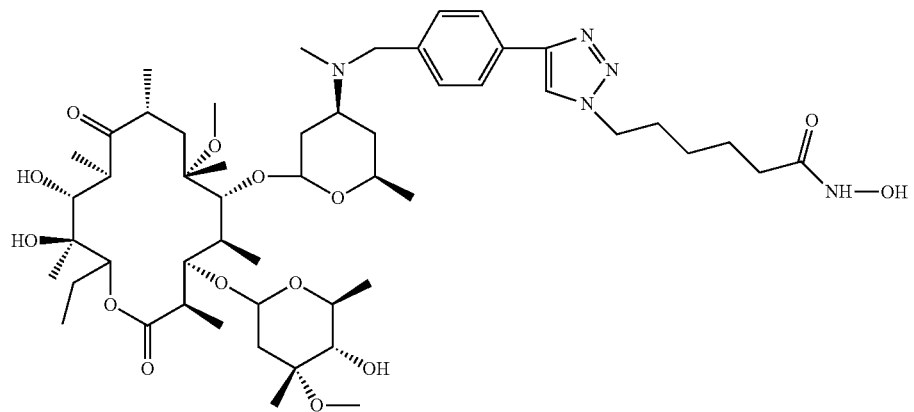 [SMILES: CCC1OC(=O)[C@H](C)[C@H](OC2C[C@@](C)(OC)[C@@H](O)[C@H](C)O2)[C@H](C)[C@@H](OC2C[C@@H](N(C)Cc3ccc(-c4cn(CCCCCC(=O)NO)nn4)cc3)C[C@@H](C)O2)[C@@](C)(OC)C[C@@H](C)C(=O)[C@H](C)[C@@H](O)[C@]1(C)O] |

TABLE 3-continued
Non-peptide HDAC Inhibitors
| COMPOUND NUMBER | STRUCTURE |
| --- | --- |
| 49 | 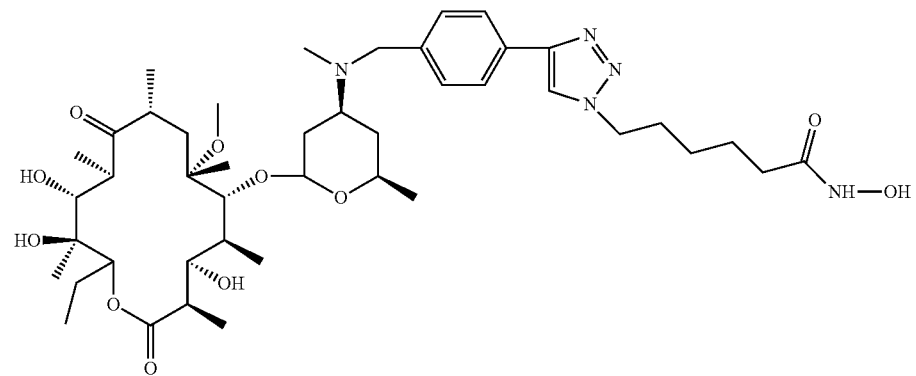 [SMILES: CCC1OC(=O)[C@H](C)[C@H](O)[C@H](C)[C@@H](OC2C[C@@H](N(C)Cc3ccc(-c4cn(CCCCCC(=O)NO)nn4)cc3)C[C@@H](C)O2)[C@@](C)(OC)C[C@@H](C)C(=O)[C@H](C)[C@@H](O)[C@]1(C)O] |
| 50 | 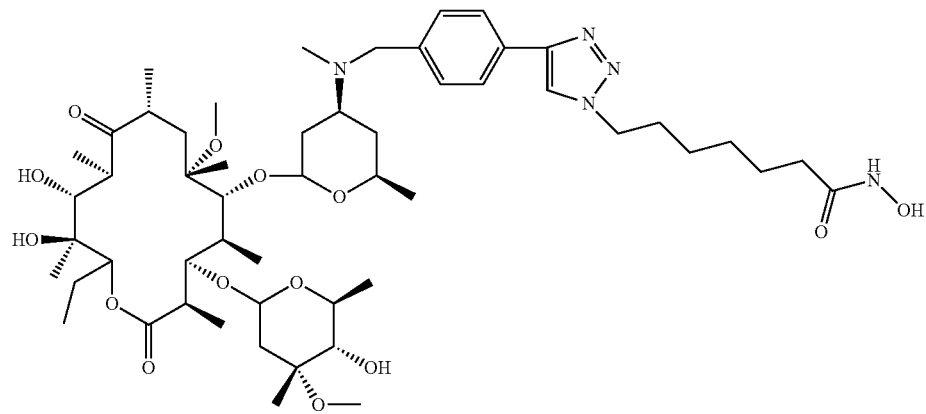 [SMILES: CCC1OC(=O)[C@H](C)[C@H](OC2C[C@@](C)(OC)[C@@H](O)[C@H](C)O2)[C@H](C)[C@@H](OC2C[C@@H](N(C)Cc3ccc(-c4cn(CCCCCCC(=O)NO)nn4)cc3)C[C@@H](C)O2)[C@@](C)(OC)C[C@@H](C)C(=O)[C@H](C)[C@@H](O)[C@]1(C)O] |
| 51 | 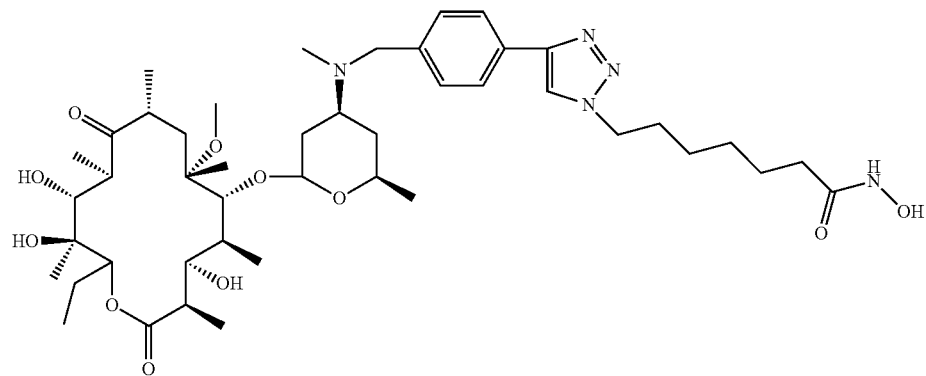 [SMILES: CCC1OC(=O)[C@H](C)[C@H](O)[C@H](C)[C@@H](OC2C[C@@H](N(C)Cc3ccc(-c4cn(CCCCCCC(=O)NO)nn4)cc3)C[C@@H](C)O2)[C@@](C)(OC)C[C@@H](C)C(=O)[C@H](C)[C@@H](O)[C@]1(C)O] |

TABLE 3-continued
Non-peptide HDAC Inhibitors
| COMPOUND NUMBER | STRUCTURE |
|---|---|
| 52 | 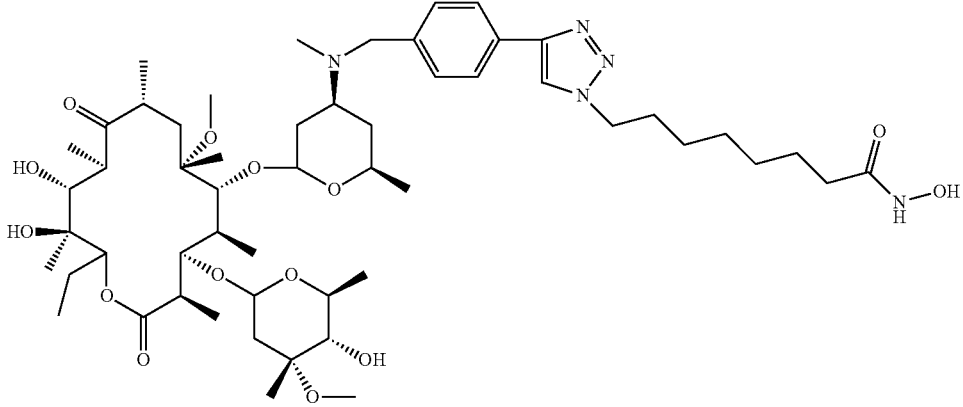 [SMILES: CCC1OC(=O)[C@H](C)[C@H](OC2C[C@@](C)(OC)[C@@H](O)[C@H](C)O2)[C@H](C)[C@@H](OC2C[C@@H](N(C)Cc3ccc(-c4cn(CCCCCCCC(=O)NO)nn4)cc3)C[C@@H](C)O2)[C@@](C)(OC)C[C@@H](C)C(=O)[C@H](C)[C@@H](O)[C@]1(C)O] |
| 53 | 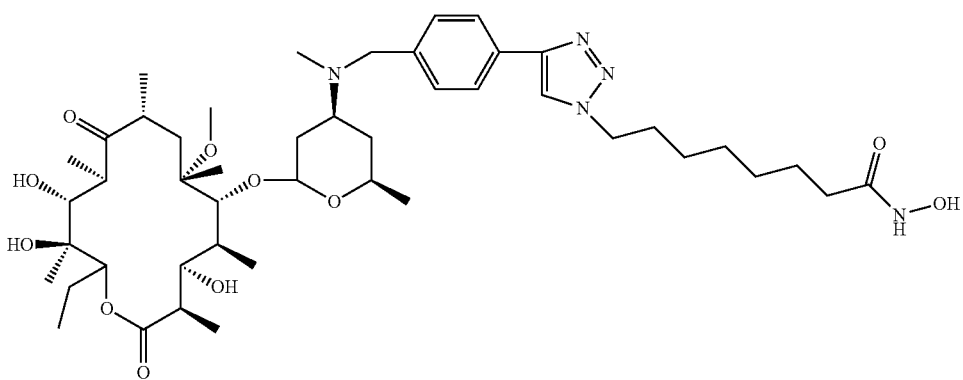 [SMILES: CCC1OC(=O)[C@H](C)[C@H](O)[C@H](C)[C@@H](OC2C[C@@H](N(C)Cc3ccc(-c4cn(CCCCCCCC(=O)NO)nn4)cc3)C[C@@H](C)O2)[C@@](C)(OC)C[C@@H](C)C(=O)[C@H](C)[C@@H](O)[C@]1(C)O] |
| 54 | 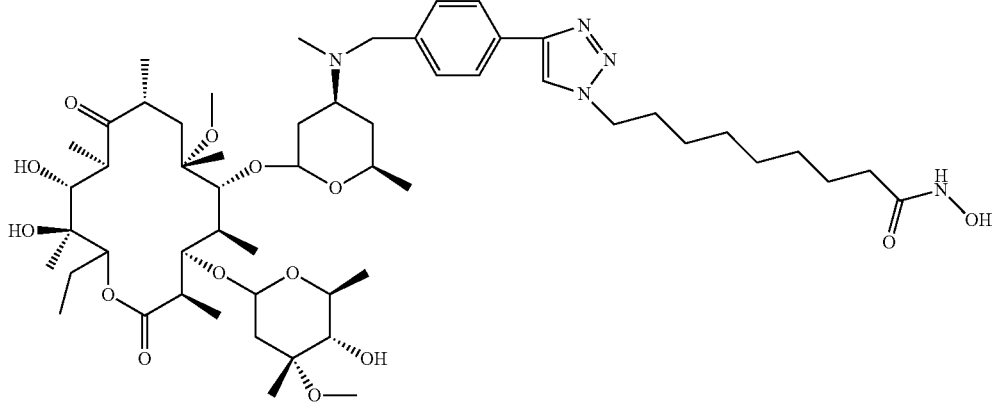 [SMILES: CCC1OC(=O)[C@H](C)[C@H](OC2C[C@@](C)(OC)[C@@H](O)[C@H](C)O2)[C@H](C)[C@@H](OC2C[C@@H](N(C)Cc3ccc(-c4cn(CCCCCCCCC(=O)NO)nn4)cc3)C[C@@H](C)O2)[C@@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 55 | 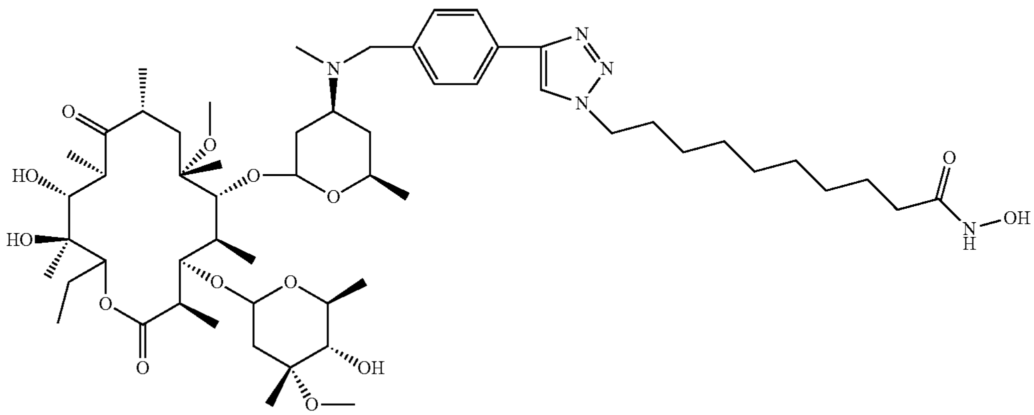 [SMILES: CCC1OC(=O)[C@H](C)[C@H](OC2C[C@@](C)(OC)[C@@H](O)[C@H](C)O2)[C@H](C)[C@@H](OC2C[C@@H](N(C)Cc3ccc(-c4cn(CCCCCCCCCC(=O)NO)nn4)cc3)C[C@@H](C)O2)[C@@](C)(OC)C[C@@H](C)C(=O)[C@H](C)[C@@H](O)[C@]1(C)O] |
| 56 | 56a: n = 1<br>56b: n = 2<br>56c: n = 3<br>56d: n = 4<br>56e: n = 5 |
| 82 | 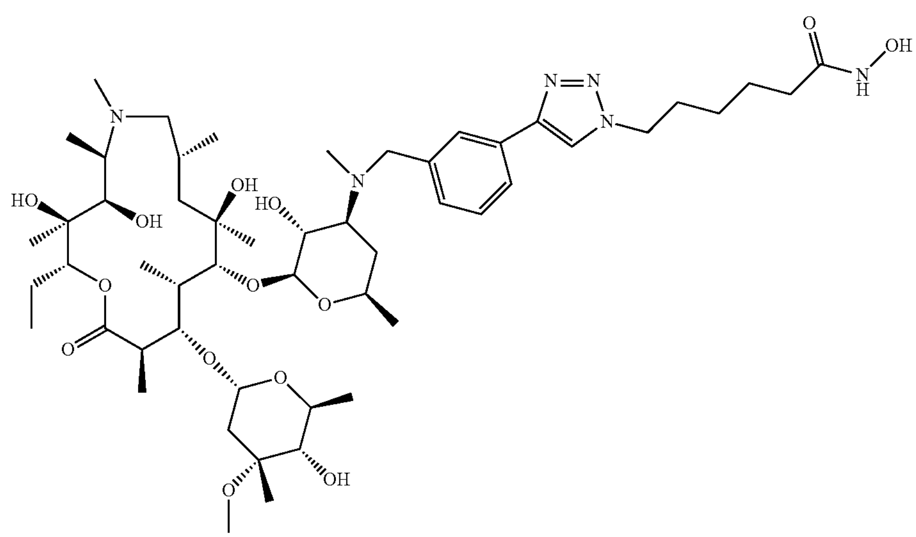 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cccc(-c4cn(CCCCCC(=O)NO)nn4)c3)[C@H]2O)[C@](C)(O)C[C@@H](C)CN(C)[C@H](C)[C@@H](O)[C@]1(C)O] |

TABLE 3-continued

Non-peptide HDAC Inhibitors

| COMPOUND NUMBER | STRUCTURE |
|---|---|
| 83 | 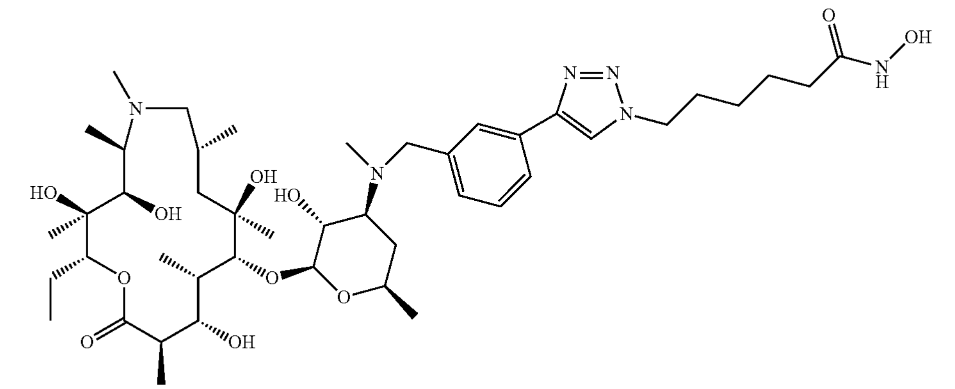 [SMILES: CC[C@H]1OC(=O)[C@H](C)[C@@H](O)[C@H](C)[C@@H](O[C@@H]2O[C@H](C)C[C@H](N(C)Cc3cccc(-c4cn(CCCCCC(=O)NO)nn4)c3)[C@H]2O)[C@](C)(O)C[C@@H](C)CN(C)[C@H](C)[C@@H](O)[C@]1(C)O] |
| 84 | 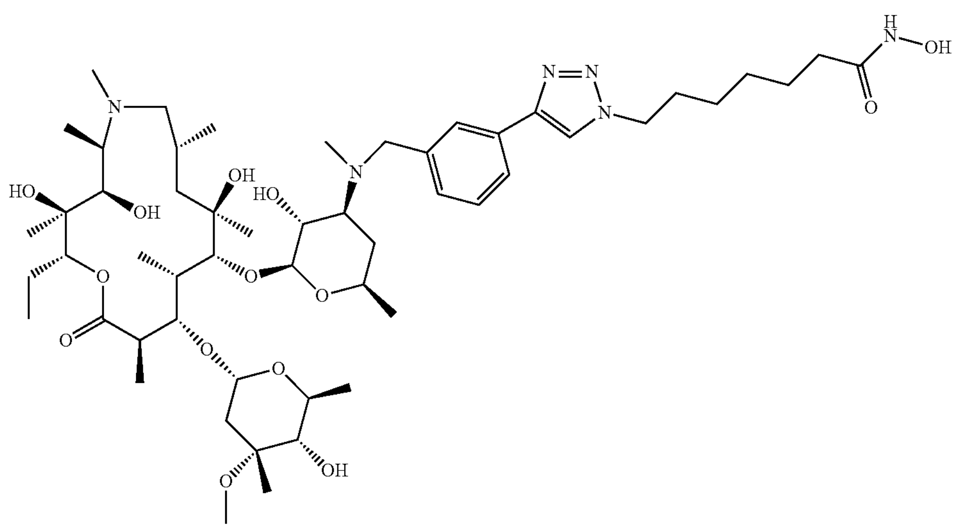 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cccc(-c4cn(CCCCCCC(=O)NO)nn4)c3)[C@H]2O)[C@](C)(O)C[C@@H](C)CN(C)[C@H](C)[C@@H](O)[C@]1(C)O] |
| 85 | 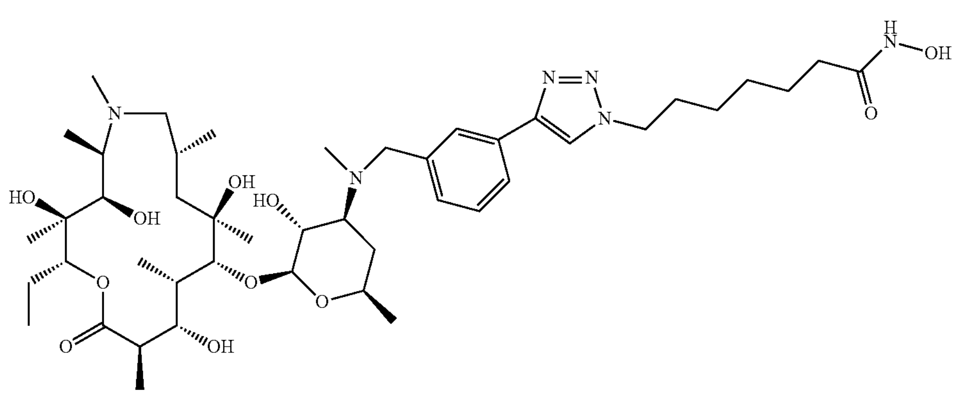 [SMILES: CC[C@H]1OC(=O)[C@H](C)[C@@H](O)[C@H](C)[C@@H](O[C@@H]2O[C@H](C)C[C@H](N(C)Cc3cccc(-c4cn(CCCCCCC(=O)NO)nn4)c3)[C@H]2O)[C@](C)(O)C[C@@H](C)CN(C)[C@H](C)[C@@H](O)[C@]1(C)O] |

TABLE 3-continued

Non-peptide HDAC Inhibitors

| COMPOUND NUMBER | STRUCTURE |
| --- | --- |
| 86 | 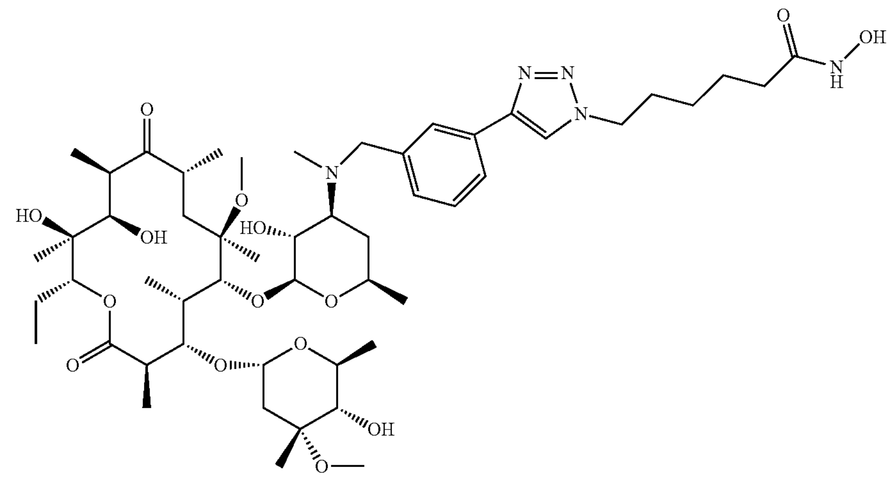 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cccc(-c4cn(CCCCCC(=O)NO)nn4)c3)[C@H]2O)[C@](C)(OC)C[C@@H](C)C(=O)[C@H](C)[C@@H](O)[C@]1(C)O] |
| 87 | 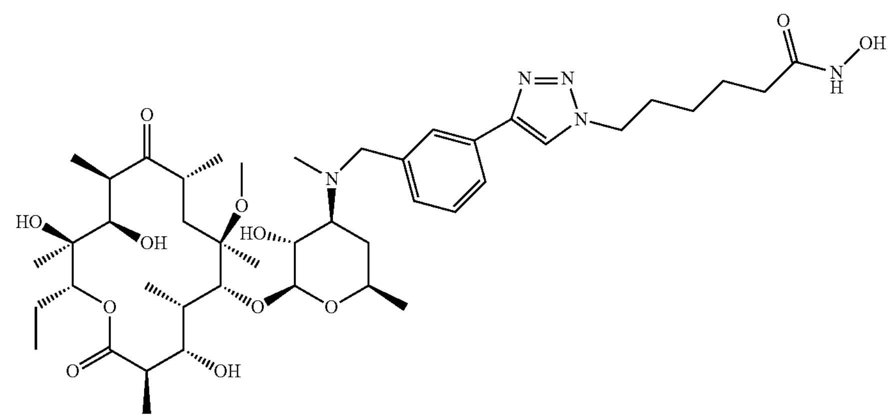 [SMILES: CC[C@H]1OC(=O)[C@H](C)[C@@H](O)[C@H](C)[C@@H](O[C@@H]2O[C@H](C)C[C@H](N(C)Cc3cccc(-c4cn(CCCCCC(=O)NO)nn4)c3)[C@H]2O)[C@](C)(OC)C[C@@H](C)C(=O)[C@H](C)[C@@H](O)[C@]1(C)O] |
| 88 | 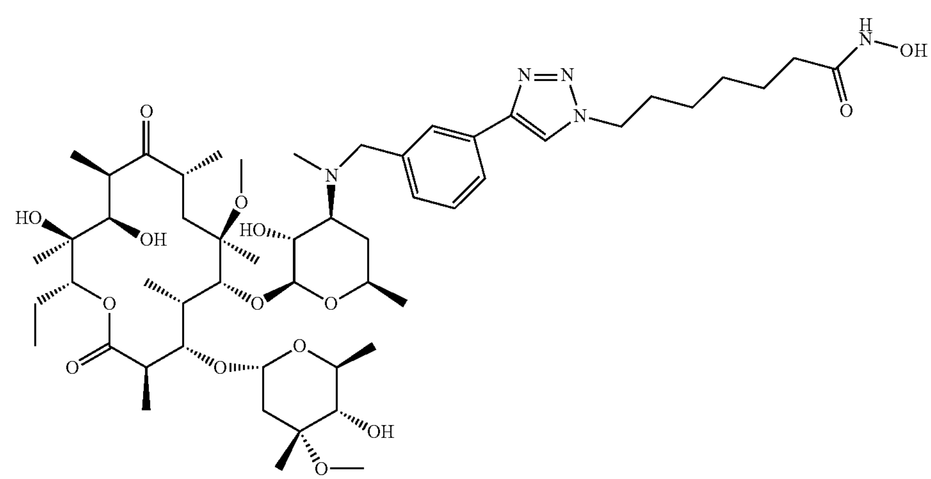 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3cccc(-c4cn(CCCCCCC(=O)NO)nn4)c3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 89 | 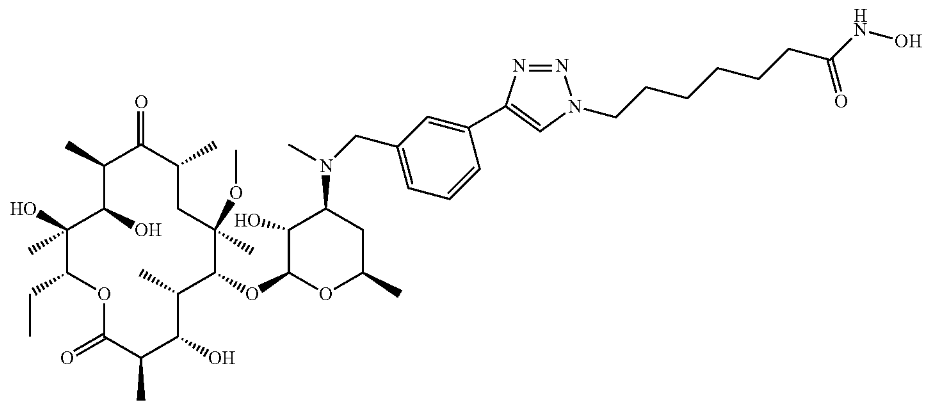 [SMILES: CC[C@H]1OC(=O)[C@H](C)[C@@H](O)[C@H](C)[C@@H](O[C@@H]2O[C@H](C)C[C@H](N(C)Cc3cccc(-c4cn(CCCCCCC(=O)NO)nn4)c3)[C@H]2O)[C@](C)(OC)C[C@@H](C)C(=O)[C@H](C)[C@@H](O)[C@]1(C)O] |
| 90 | 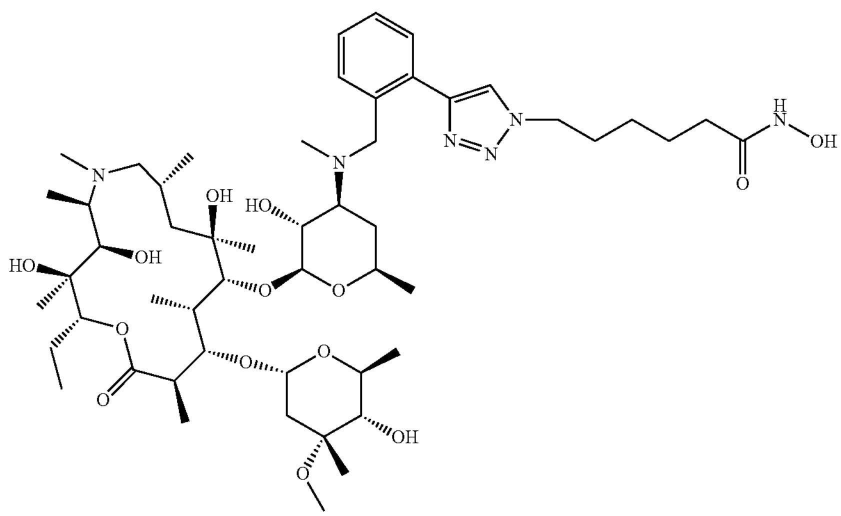 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccccc3-c3cn(CCCCCC(=O)NO)nn3)[C@H]2O)[C@](C)(O)C[C@@H](C)CN(C)[C@H](C)[C@@H](O)[C@]1(C)O] |
| 91 | 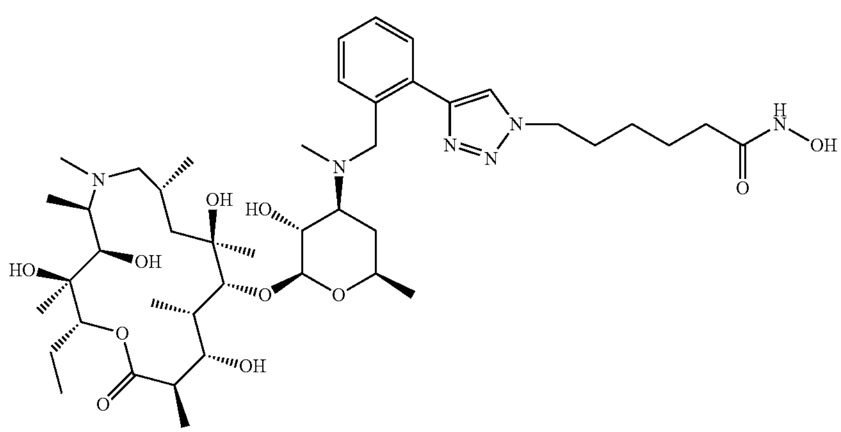 [SMILES: CC[C@H]1OC(=O)[C@H](C)[C@@H](O)[C@H](C)[C@@H](O[C@@H]2O[C@H](C)C[C@H](N(C)Cc3ccccc3-c3cn(CCCCCC(=O)NO)nn3)[C@H]2O)[C@](C)(O)C[C@@H](C)CN(C)[C@H](C)[C@@H](O)[C@]1(C)O] |

TABLE 3-continued
Non-peptide HDAC Inhibitors
| COMPOUND NUMBER | STRUCTURE |
|---|---|
| 92 | 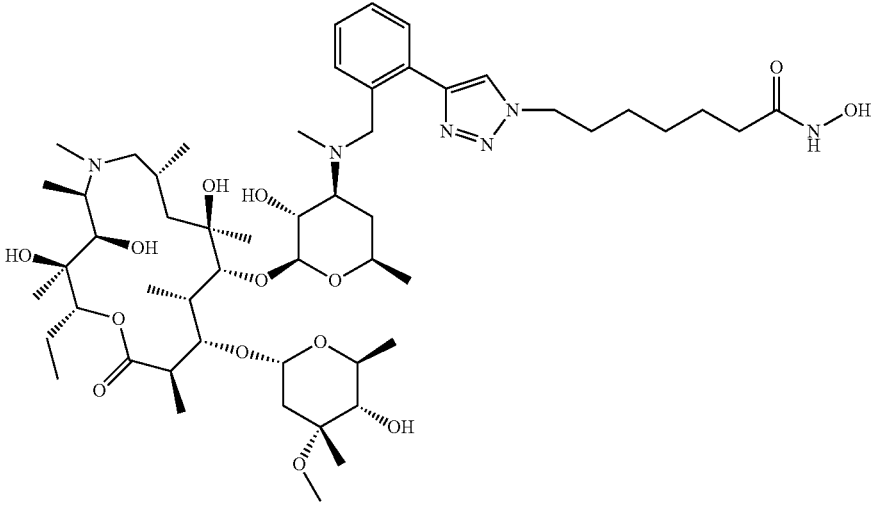 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccccc3-c3cn(CCCCCCC(=O)NO)nn3)[C@H]2O)[C@](C)(O)C[C@@H](C)CN(C)[C@H](C)[C@@H](O)[C@]1(C)O] |
| 93 | 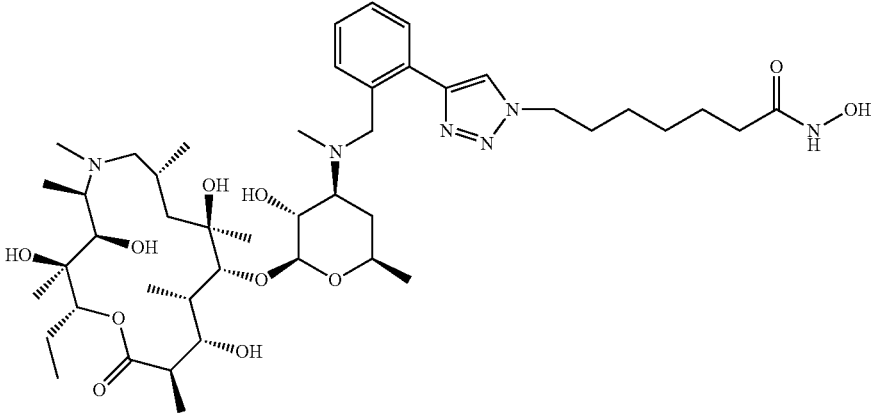 [SMILES: CC[C@H]1OC(=O)[C@H](C)[C@@H](O)[C@H](C)[C@@H](O[C@@H]2O[C@H](C)C[C@H](N(C)Cc3ccccc3-c3cn(CCCCCCC(=O)NO)nn3)[C@H]2O)[C@](C)(O)C[C@@H](C)CN(C)[C@H](C)[C@@H](O)[C@]1(C)O] |
| 94 | 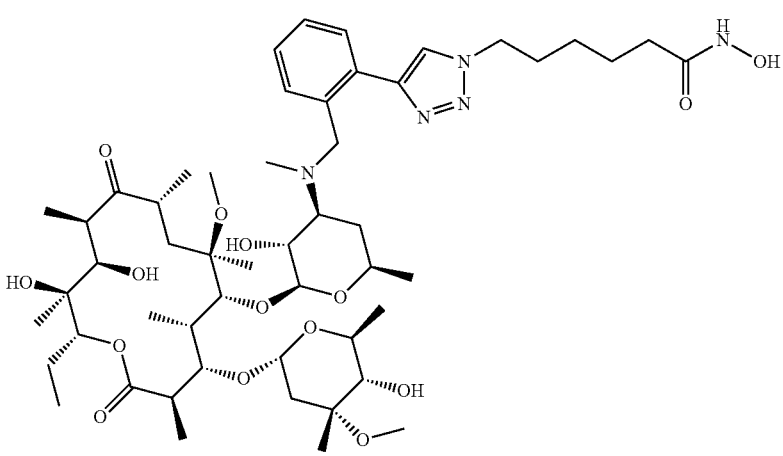 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccccc3-c3cn(CCCCCC(=O)NO)nn3)[C@H]2O)[C@](C)(OC)C[C@@H](C)C(=O)[C@H](C)[C@@H](O)[C@]1(C)O] |

TABLE 3-continued
Non-peptide HDAC Inhibitors
| COMPOUND NUMBER | STRUCTURE |
|---|---|
| 95 | 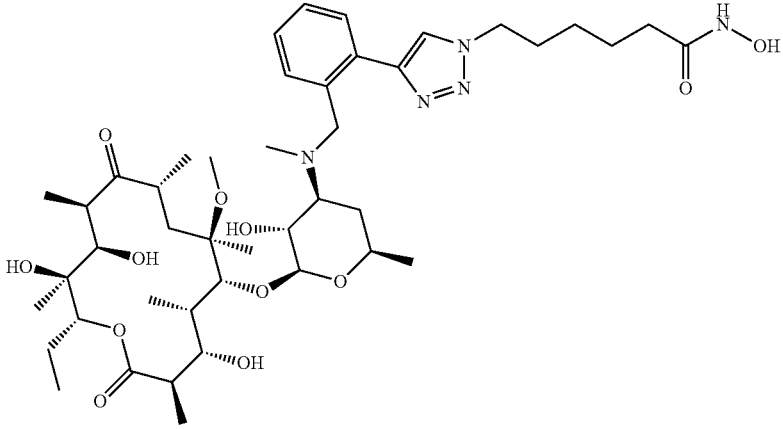 [SMILES: CC[C@H]1OC(=O)[C@H](C)[C@@H](O)[C@H](C)[C@@H](O[C@@H]2O[C@H](C)C[C@H](N(C)Cc3ccccc3-c3cn(CCCCCC(=O)NO)nn3)[C@H]2O)[C@](C)(OC)C[C@@H](C)C(=O)[C@H](C)[C@@H](O)[C@]1(C)O] |
| 96 | 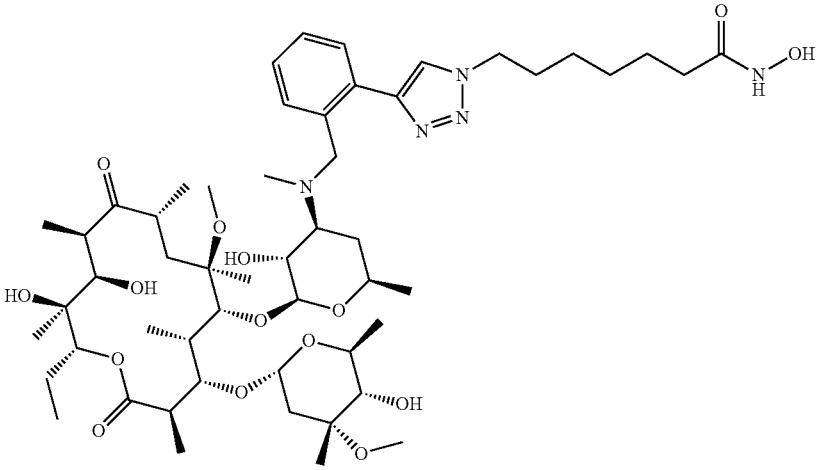 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccccc3-c3cn(CCCCCCC(=O)NO)nn3)[C@H]2O)[C@](C)(OC)C[C@@H](C)C(=O)[C@H](C)[C@@H](O)[C@]1(C)O] |
| 97 | 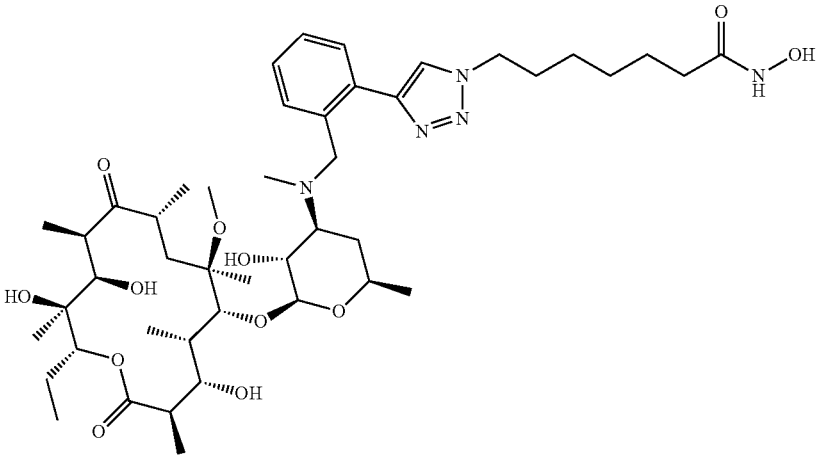 [SMILES: CC[C@H]1OC(=O)[C@H](C)[C@@H](O)[C@H](C)[C@@H](O[C@@H]2O[C@H](C)C[C@H](N(C)Cc3ccccc3-c3cn(CCCCCCC(=O)NO)nn3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 98 | 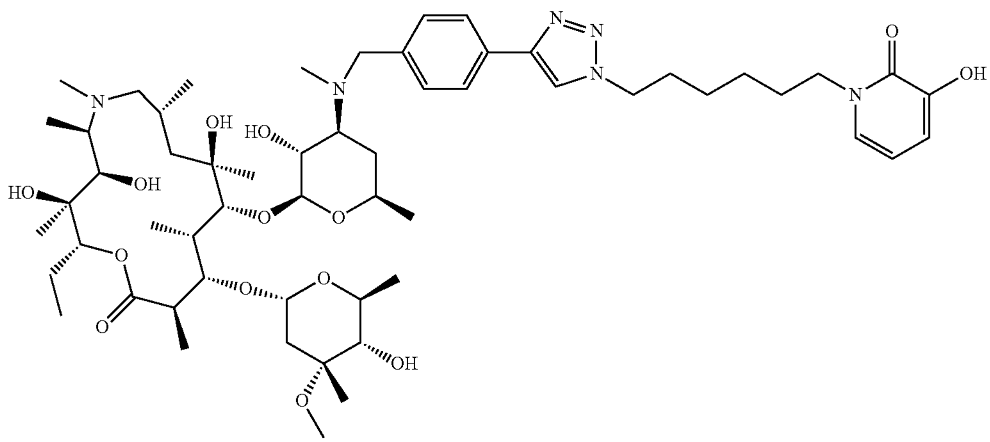 |
| 99 | 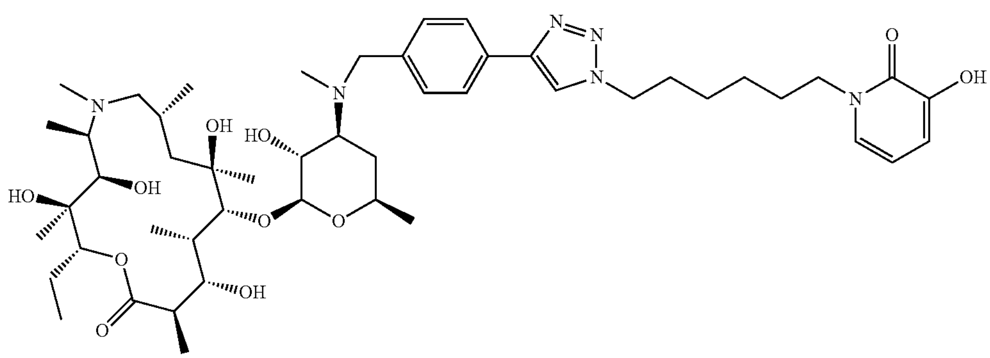 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCn5cccc(O)c5=O)nn4)cc3)[C@H]2O)[C@](C)(O)C[C@@H](C)CN(C)[C@H](C)[C@@H](O)[C@]1(C)O] |
| 100 | 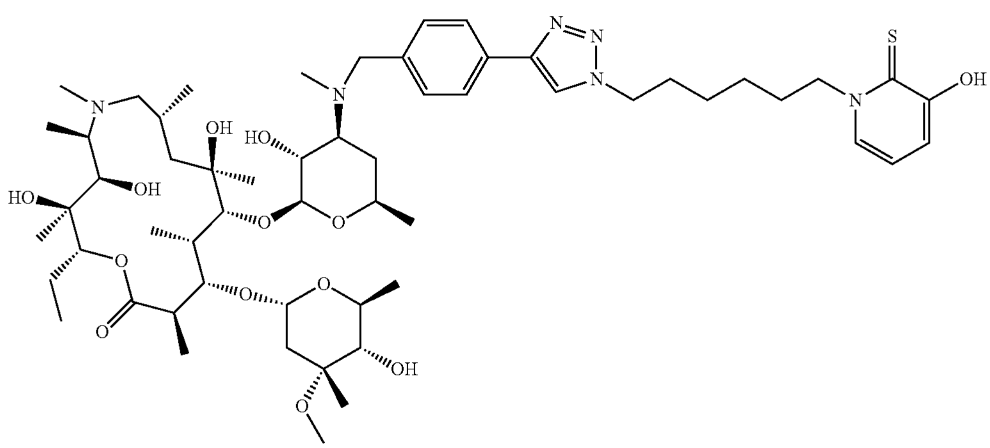 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCn5cccc(O)c5=S)nn4)cc3)[C@H]2O)[C@](C)(O)C[C@@H](C)CN(C)[C@H](C)[C@@H](O)[C@]1(C)O] |

TABLE 3-continued
Non-peptide HDAC Inhibitors
| COMPOUND NUMBER | STRUCTURE |
|---|---|
| 101 | 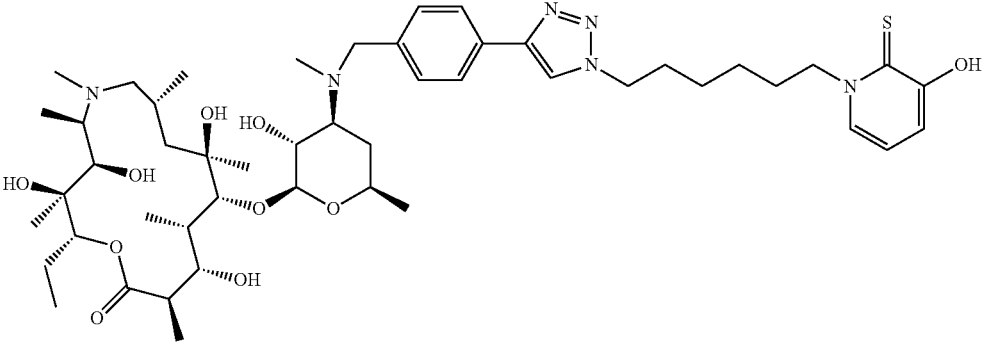 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCn5cccc(O)c5=S)nn4)cc3)[C@H]2O)[C@](C)(O)C[C@@H](C)CN(C)[C@H](C)[C@@H](O)[C@]1(C)O] |
| 102 | 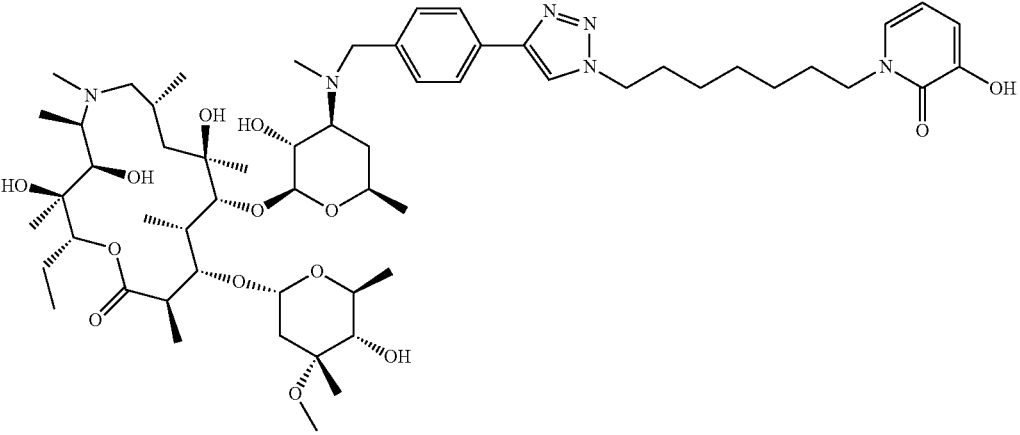 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCn5cccc(O)c5=O)nn4)cc3)[C@H]2O)[C@](C)(O)C[C@@H](C)CN(C)[C@H](C)[C@@H](O)[C@]1(C)O] |
| 103 | 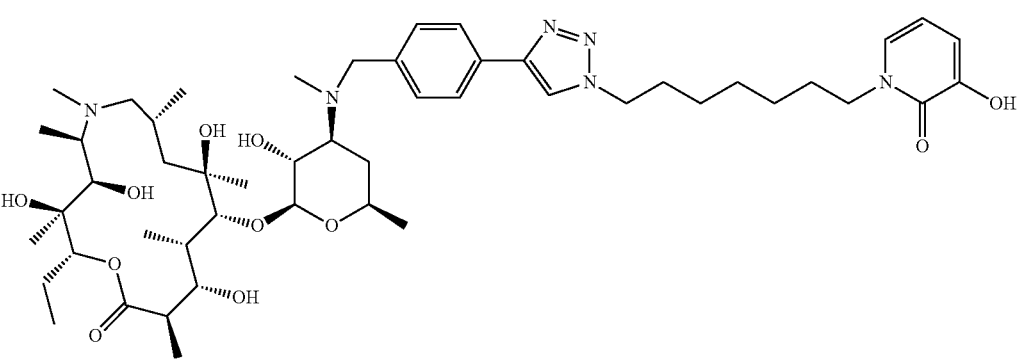 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCn5cccc(O)c5=O)nn4)cc3)[C@H]2O)[C@](C)(O)C[C@@H](C)CN(C)[C@H](C)[C@@H](O)[C@]1(C)O] |

TABLE 3-continued
Non-peptide HDAC Inhibitors
| COMPOUND NUMBER | STRUCTURE |
|---|---|
| 104 | 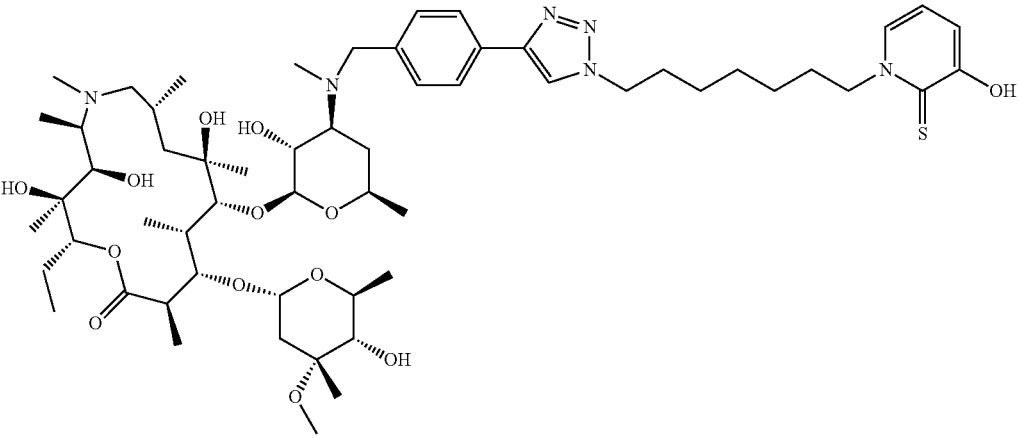 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCn5cccc(O)c5=S)nn4)cc3)[C@H]2O)[C@](C)(O)C[C@@H](C)CN(C)[C@H](C)[C@@H](O)[C@]1(C)O] |
| 105 | 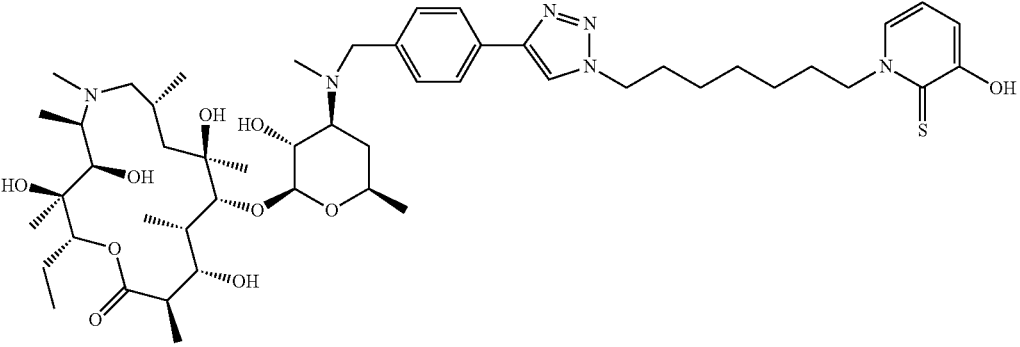 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCn5cccc(O)c5=S)nn4)cc3)[C@H]2O)[C@](C)(O)C[C@@H](C)CN(C)[C@H](C)[C@@H](O)[C@]1(C)O] |
| 106 | 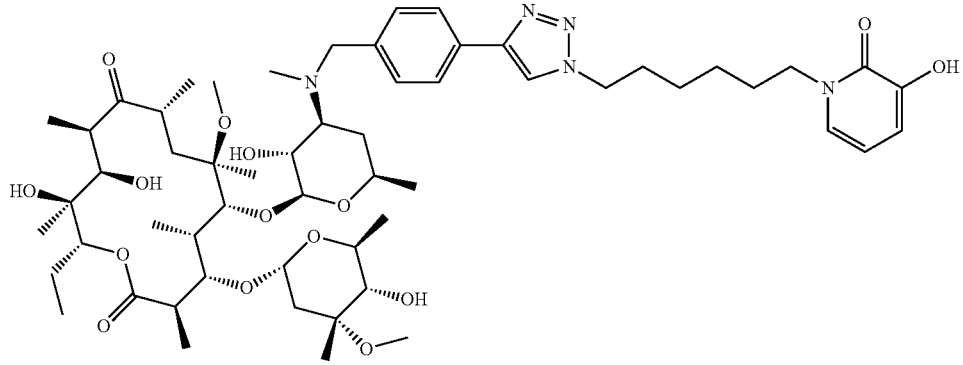 |
| 107 | 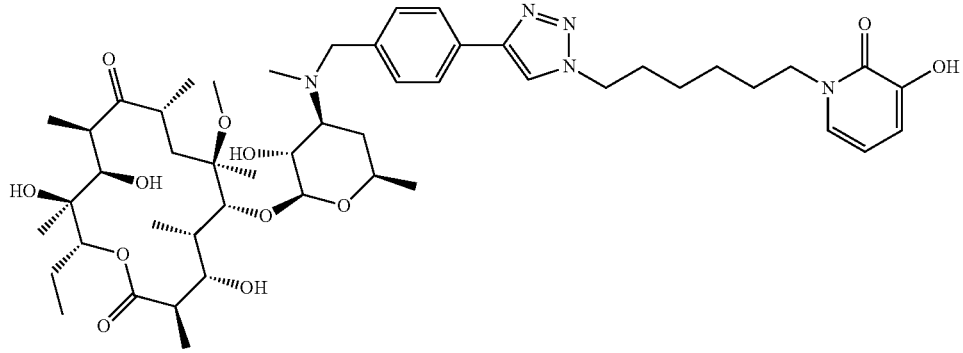 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCn5cccc(O)c5=O)nn4)cc3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 108 | 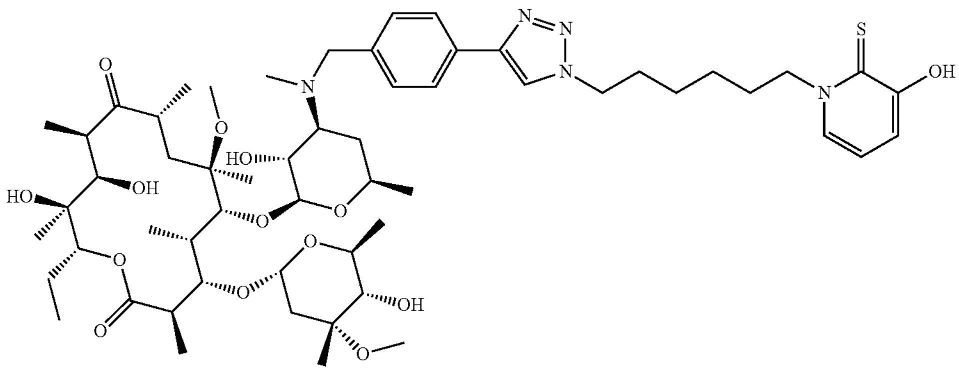 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCn5cccc(O)c5=S)nn4)cc3)[C@H]2O)[C@](C)(OC)C[C@@H](C)C(=O)[C@H](C)[C@@H](O)[C@]1(C)O] |
| 109 | 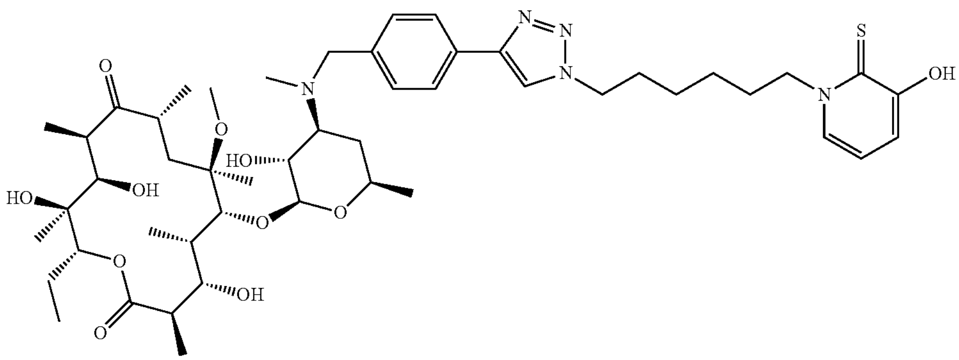 |
| 110 | 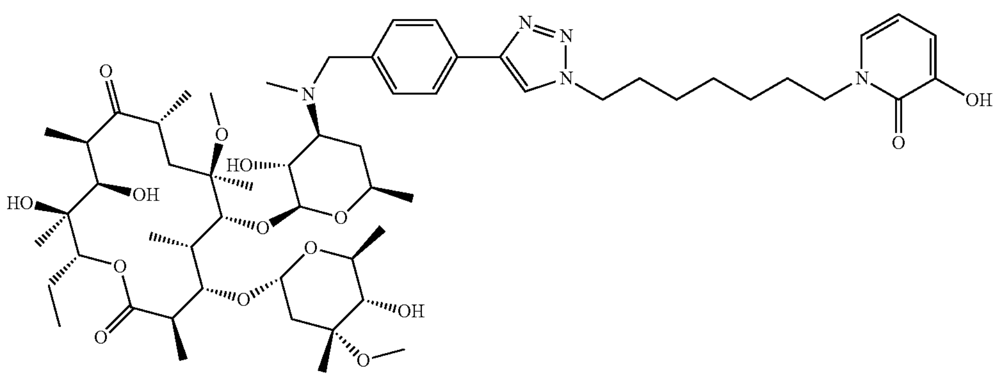 |
| 111 | 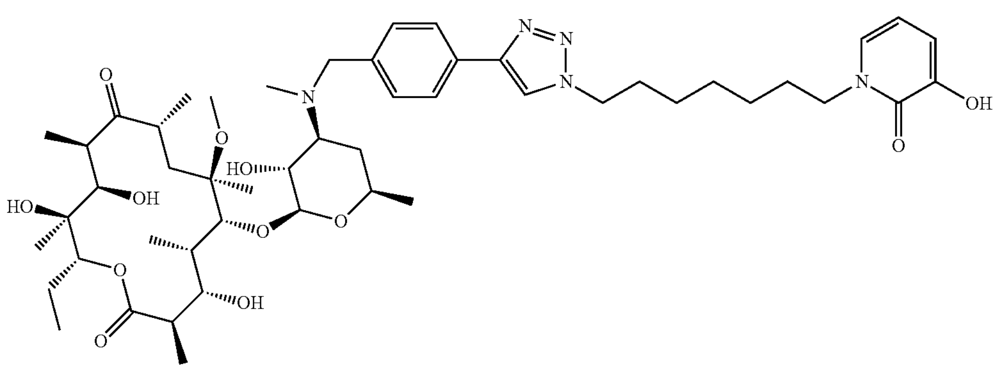 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCn5cccc(O)c5=O)nn4)cc3)[C@H]2O)[C@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 112 | 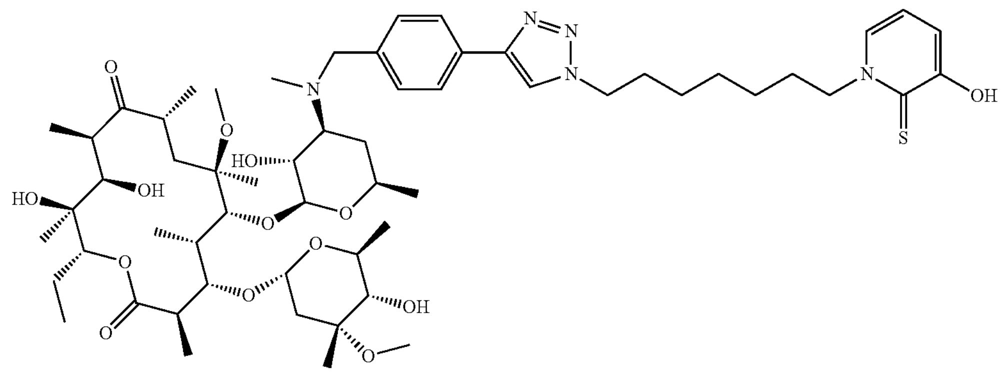 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)Cc3ccc(-c4cn(CCCCCCCn5cccc(O)c5=S)nn4)cc3)[C@H]2O)[C@](C)(OC)C[C@@H](C)C(=O)[C@H](C)[C@@H](O)[C@]1(C)O] |
| 113 | 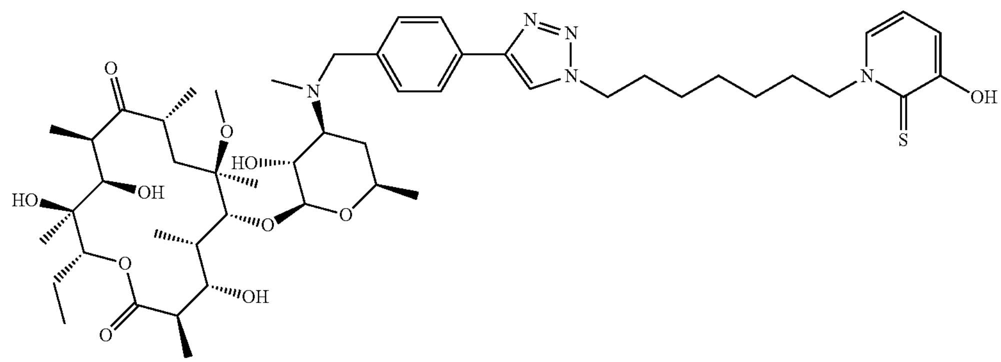 [SMILES: CC[C@H]1OC(=O)[C@H](C)[C@@H](O)[C@H](C)[C@@H](O[C@@H]2O[C@H](C)C[C@H](N(C)Cc3ccc(-c4cn(CCCCCCCn5cccc(O)c5=S)nn4)cc3)[C@H]2O)[C@](C)(OC)C[C@@H](C)C(=O)[C@H](C)[C@@H](O)[C@]1(C)O] |
| 130 | 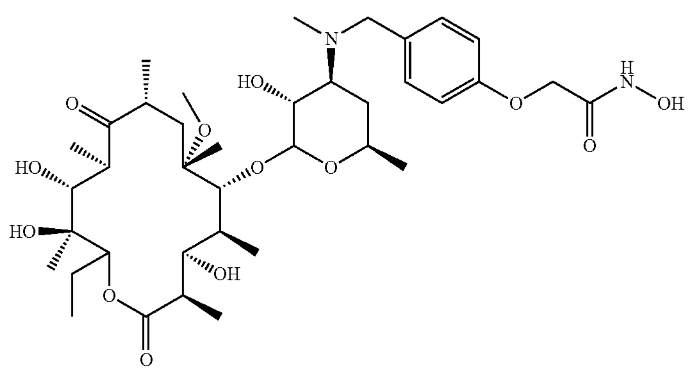 [SMILES: CCC1OC(=O)[C@H](C)[C@H](O)[C@H](C)[C@@H](OC2O[C@H](C)C[C@H](N(C)Cc3ccc(OCC(=O)NO)cc3)[C@H]2O)[C@@](C)(OC)C[C@@H](C)C(=O)[C@H](C)[C@@H](O)[C@]1(C)O] |
| 131 | 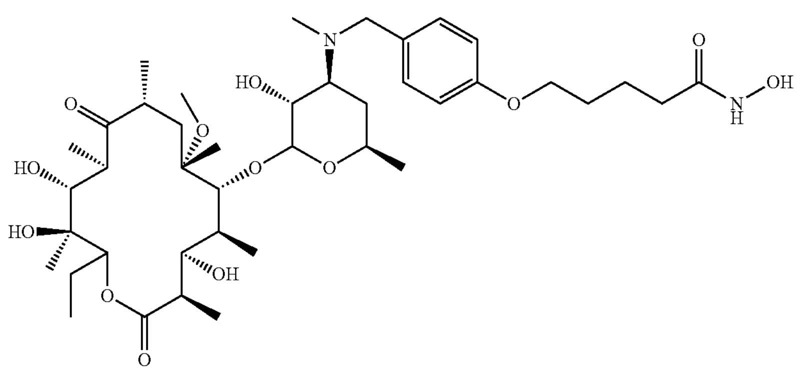 [SMILES: CCC1OC(=O)[C@H](C)[C@H](O)[C@H](C)[C@@H](OC2O[C@H](C)C[C@H](N(C)Cc3ccc(OCCCCC(=O)NO)cc3)[C@H]2O)[C@@](C)(OC)C[C@@H](C)C(=O)[C@H](C)[C@@H](O)[C@]1(C)O] |

TABLE 3-continued

Non-peptide HDAC Inhibitors

| COMPOUND NUMBER | STRUCTURE |
|---|---|
| 132 | 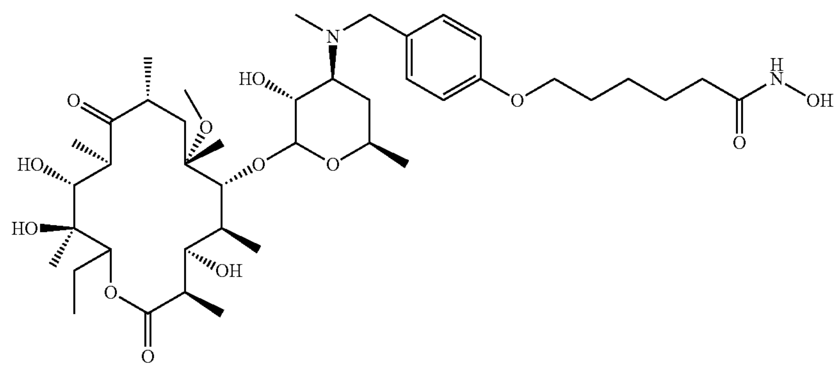 [SMILES: CCC1OC(=O)[C@H](C)[C@H](O)[C@H](C)[C@@H](OC2O[C@H](C)C[C@H](N(C)Cc3ccc(OCCCCCC(=O)NO)cc3)[C@H]2O)[C@@](C)(OC)C[C@@H](C)C(=O)[C@H](C)[C@@H](O)[C@]1(C)O] |
| 133 | 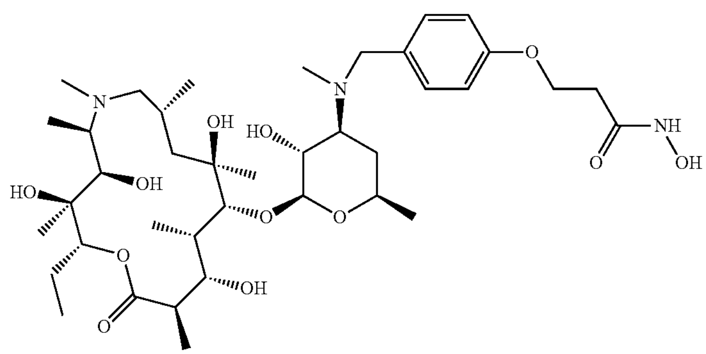 [SMILES: CC[C@H]1OC(=O)[C@H](C)[C@@H](O)[C@H](C)[C@@H](O[C@@H]2O[C@H](C)C[C@H](N(C)Cc3ccc(OCCC(=O)NO)cc3)[C@H]2O)[C@](C)(O)C[C@@H](C)CN(C)[C@H](C)[C@@H](O)[C@]1(C)O] |
| 134 | 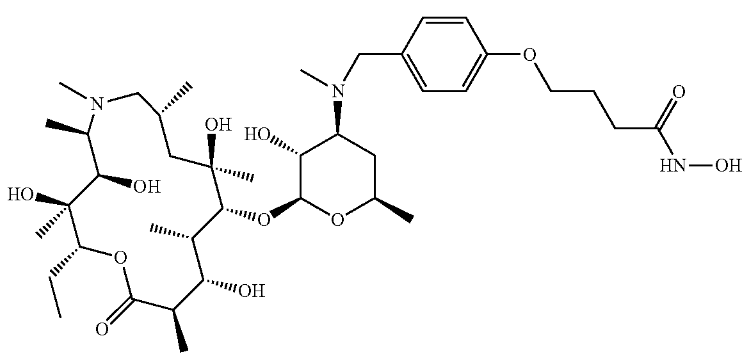 [SMILES: CC[C@H]1OC(=O)[C@H](C)[C@@H](O)[C@H](C)[C@@H](O[C@@H]2O[C@H](C)C[C@H](N(C)Cc3ccc(OCCCC(=O)NO)cc3)[C@H]2O)[C@](C)(O)C[C@@H](C)CN(C)[C@H](C)[C@@H](O)[C@]1(C)O] |
| 136 | 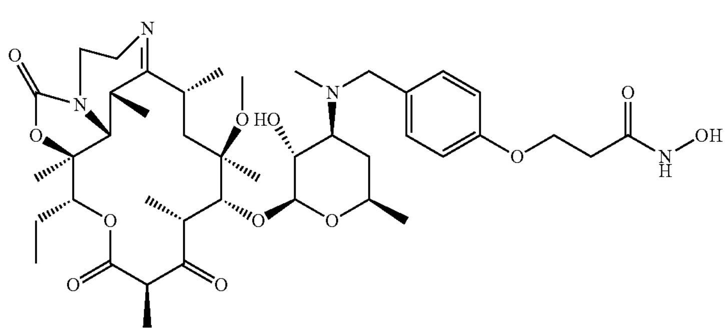 [SMILES: CC[C@H]1OC(=O)[C@H](C)C(=O)[C@H](C)[C@@H](O[C@@H]2O[C@H](C)C[C@H](N(C)Cc3ccc(OCCC(=O)NO)cc3)[C@H]2O)[C@](C)(OC)C[C@@H](C)C2=NCCN3C(=O)O[C@@]1(C)[C@H]3[C@H]2C] |

TABLE 3-continued

Non-peptide HDAC Inhibitors

| COMPOUND NUMBER | STRUCTURE |
|---|---|
| 137 | (structure) |

It is believed that substitution of the cyclic peptide moiety of a prototypical cyclic-peptide HDAC inhibitor with macrolide skeletons will generate a new class of potent HDAC inhibitors. Furthermore, this class of HDAC inhibitors may possess targeted activity, such as targeted anti-cancer activity due to selective tissue distribution conferred by the macrolide moiety. The biological effects of macrolides are aided by their high distribution into target tissues. Macrolides accumulate in higher concentration within leukocytes as compared to levels found in serum.

III. Formulations

The compounds described herein can be formulated for enteral, parenteral, and/or topical (e.g., transdermal, mucosal, etc.) administration. The compounds and their pharmaceutically-acceptable addition salts, prodrugs, and/or solvates can also be used in the form of pharmaceutical preparations which facilitate bioavailability. One or more compounds described herein may be administered in a single dosage form or in multiple dosage forms Formulations containing one or more of the compounds described herein may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of coating compositions which may include plasticizers, pigments, colorants, stabilizing agents, and glidants. Delayed release, extended release, and/or pulsatile release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine, If desired, the tablets, beads, granules, or particles may also contain minor amount of nontoxic auxiliary substances such as wetting or emulsifying agents, dyes, pH buffering agents, or preservatives.

Enteral Formulations

Pharmaceutical compositions for oral administration can be liquid or solid. Liquid dosage forms suitable for oral administration include, but are not limited to, pharmaceutically acceptable emulsions, microemulsions, solutions, suspensions, syrups and elixirs. In addition to an encapsulated or unencapsulated HDAC inhibitor, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan and mixtures thereof. Besides inert diluents, the oral compositions can also include adjuvants, wetting agents, emulsifying and suspending agents, sweetening, flavoring and perfuming agents.

Solid dosage forms for oral administration include, but are not limited to, capsules, tablets, caplets, dragees, powders and granules. In such solid dosage forms, the encapsulated or unencapsulated compound is typically mixed with at least one inert, pharmaceutically acceptable excipient or carrier such as sodium citrate or dicalcium phosphate and/or (a) fillers or extenders such as starches, lactose, sucrose, glucose, mannitol and silicic acid, (b) binders such as, for example, carboxymethylcellulose, alginates, gelatin, polyvinylpyrrolidinone, sucrose and acacia, (c) humectants such as glycerol, (d) disintegrating agents such as agar-agar, calcium carbonate, potato or tapioca starch, alginic acid, certain silicates and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay and (i) lubricants such as talc, calcium stearate, magnesium stearate, solid polyethylene glycols, sodium lauryl sulfate and mixtures thereof. In the case of capsules, tablets and pills, the dosage form may also contain buffering agents.

Solid compositions of a similar type may also be employed as fill materials in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well known in the pharmaceutical formulating art.

Parenteral Formulations

Pharmaceutical preparations in the form suitable for injection are subjected to conventional pharmaceutical operations such as sterilization and/or may contain adjuvants including, but not limited to, preservatives, stabilizers, wetting or emulsifying agents, and buffers.

Injectable preparations, for example, sterile injectable aqueous or oleaginous suspensions may be formulated as known in the art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid can be used in the preparation of injectable formulations. In a particularly preferred embodiment, the compound is suspended in a carrier fluid containing 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Topical Formulations.

The compounds described here can also be formulated for topical, transdermal, or mucosal delivery. Dosage forms for topical or transdermal administration include, but are not limited to, ointments, pastes, creams, lotions, gels, powders, solutions, sprays, inhalants, or patches. The compounds are typically admixed under sterile conditions with a pharmaceutically acceptable carrier and any excipients (e.g., preservatives, buffers, etc.) that may be required. Ophthalmic formulations, ear drops and eye drops can also be prepared. The ointments, pastes, creams and gels may contain, in addition to the active agent, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound to the body. Such dosage forms can be made by dissolving or dispensing the compounds described herein in a proper medium. Absorption enhancers can also be used to increase the flux of the compound across the skin. The rate can be controlled by either providing a rate controlling membrane or by dispersing the compound(s) in a polymer matrix or gel.

Powders and sprays can contain, in addition to the active agent, excipients such as lactose, talc, silicic acid, aluminum hydroxide, calcium silicates and polyamide powder, or mixtures of these drugs. Sprays can additionally contain customary propellants such as chlorofluorohydrocarbons.

Compositions for rectal or vaginal administration are preferably suppositories which can be prepared by mixing the compounds described herein with suitable non-irritating excipients or carriers such as cocoa butter, polyethylene glycol, or a suppository wax which are solid at ambient temperature but liquid at body temperature and therefore melt in the rectum or vaginal cavity and release the compound(s).

A. Other Active Agents

The HDAC inhibitors described herein can be administered adjunctively with other active compounds. These compounds include but are not limited to analgesics, anti-inflammatory drugs, antipyretics, antidepressants, antiepileptics, antihistamines, antimigraine drugs, antimuscarinics, anxiolytics, sedatives, hypnotics, antipsychotics, bronchodilators, anti-asthma drugs, cardiovascular drugs, corticosteroids, dopaminergics, electrolytes, gastro-intestinal drugs, muscle relaxants, nutritional agents, vitamins, parasympathomimetics, stimulants, anorectics and anti-narcoleptics. "Adjunctive administration", as used herein, means the HDAC inhibitors can be administered in the same dosage form or in separate dosage forms with one or more other active agents.

Specific examples of compounds that can be adjunctively administered with the GDAC inhibitors include, but are not limited to, aceclofenac, acetaminophen, adomexetine, almotriptan, alprazolam, amantadine, amcinonide, aminocyclopropane, amitriptyline, amolodipine, amoxapine, amphetamine, aripiprazole, aspirin, atomoxetine, azasetron, azatadine, beclomethasone, benactyzine, benoxaprofen, bermoprofen, betamethasone, bicifadine, bromocriptine, budesonide, buprenorphine, bupropion, buspirone, butorphanol, butriptyline, caffeine, carbamazepine, carbidopa, carisoprodol, celecoxib, chlordiazepoxide, chlorpromazine, choline salicylate, citalopram, clomipramine, clonazepam, clonidine, clonitazene, clorazepate, clotiazepam, cloxazolam, clozapine, codeine, corticosterone, cortisone, cyclobenzaprine, cyproheptadine, demexiptiline, desipramine, desomorphine, dexamethasone, dexanabinol, dextroamphetamine sulfate, dextromoramide, dextropropoxyphene, dezocine, diazepam, dibenzepin, diclofenac sodium, diflunisal, dihydrocodeine, dihydroergotamine, dihydromorphine, dimetacrine, divalproxex, dizatriptan, dolasetron, donepezil, dothiepin, doxepin, duloxetine, ergotamine, escitalopram, estazolam, ethosuximide, etodolac, femoxetine, fenamates, fenoprofen, fentanyl, fludiazepam, fluoxetine, fluphenazine, flurazepam, flurbiprofen, flutazolam, fluvoxamine, frovatriptan, gabapentin, galantamine, gepirone, ginko bilboa, granisetron, haloperidol, huperzine A, hydrocodone, hydrocortisone, hydromorphone, hydroxyzine, ibuprofen, imipramine, indiplon, indomethacin, indoprofen, iprindole, ipsapirone, ketaserin, ketoprofen, ketorolac, lesopitron, levodopa, lipase, lofepramine, lorazepam, loxapine, maprotiline, mazindol, mefenamic acid, melatonin, melitracen, memantine, meperidine, meprobamate, mesalamine, metapramine, metaxalone, methadone, methadone, methamphetamine, methocarbamol, methyldopa, methylphenidate, methylsalicylate, methysergid(e), metoclopramide, mianserin, mifepristone, milnacipran, minaprine, mirtazapine, moclobemide, modafinil (an anti-narcoleptic), molindone, morphine, morphine hydrochloride, nabumetone, nadolol, naproxen, naratriptan, nefazodone, neurontin, nomifensine, nortriptyline, olanzapine, olsalazine, ondansetron, opipramol, orphenadrine, oxaflozane, oxaprazin, oxazepam, oxitriptan, oxycodone, oxymorphone, pancrelipase, parecoxib, paroxetine, pemoline, pentazocine, pepsin, perphenazine, phenacetin, phendimetrazine, phemnetrazine, phenylbutazone, phenytoin, phosphatidylserine, pimozide, pirlindole, piroxicam, pizotifen, pizotyline, pramipexole, prednisolone, prednisone, pregabalin, propanolol, propizepine, propoxyphene, protriptyline, quazepam, quinupramine, reboxitine, reserpine, risperidone, ritanserin, rivastigmine, rizatriptan, rofecoxib, ropinirole, rotigotine, salsalate, sertraline, sibutramine, sildenafil, sulfasalazine, sulindac, sumatriptan, tacrine, temazepam, tetrabenozine, thiazides, thioridazine, thiothixene, tiapride, tiasipirone, tizanidine, tofenacin, tolmetin, toloxatone, topiramate, tramadol, trazodone, triazolam, trifluoperazine, trimethobenzamide, trimipramine, tropisetron, valdecoxib, valproic acid, venlafaxine, viloxazine, vitamin E, zimeldine, ziprasidone, zolmitriptan, zolpidem, zopiclone and isomers, salts, and combinations thereof.

IV. Methods of Preparation

Compound numberings, e.g., 1, 2, 3, etc. as used below are for reference within this section only are not to be confused with any similar numberings in the synthetic schemes described below or in the examples.

The schemes below describe exemplary chemistries that can be used to synthesize the compounds described herein. It is to be appreciated the compounds described herein may be synthesized by other methods known in the art.

General Synthetic Schemes

Scheme 1a-c illustrates representative general syntheses of compounds of types 5 and 6, 9 and 10, and 12 and 13. The starting des-N-methyl macrolide 1 could be sourced from a variety of N-demethylation reactions of the tertiary amities of basic sugars on macrolides known in the art (see Flynn et al. (1954) *J. Am. Chem. Soc.*, 76: 3121; U.S. Pat. No. 3,725,385; Ku et al. (1997) *Bioorg. Med. Chem. Lett.*, 7: 1203; Stenmark et al. (2000) *J. Org. Chem.*, 65: 3875; Randolph et al. (2004) *J. Med. Chem.*, 47, 1085; and U.S. Pat. No. 7,335,753).

Reaction of 1 with electrophiles 2 and 7 yields alkynes and nitriles 3 and 8 respectively. Reactions of azide 4 and nitrile oxide 11 with alkynes 3 generate two regioisomeric triazole and isoxazole products 5 and 6 and 12 and 13 respectively. The triazole products' regioisomeric ratios and reaction rates could be altered by heating the reaction and/or by the use of catalysts (such as, but not limited to, copper (I) and Ru (H) salts and complexes: see Rostovtsev et al. (2002) *Angew. Chem. Int. Ed.*, 41: 2596; Tornoe et al. (2002) *J. Org. Chem.*, 67: 3057; Zhang et al. (2005) *J. Am. Chem. Soc.*, 127: 15998). Similarly, reaction of nitrile 8 and azide 4 generates two regioisomeric tetrazole products, 9 and 10. The ZBG in azide 4 can be protected if necessary. Suitable ZBG protecting groups include are described herein.

Scheme 1

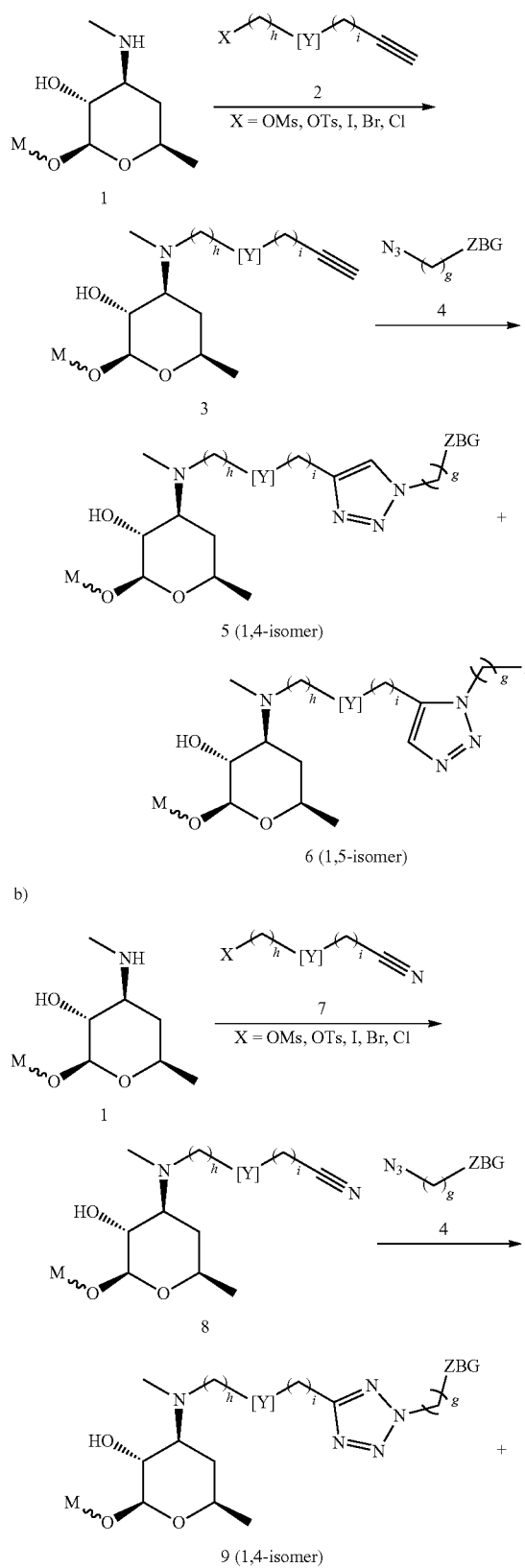

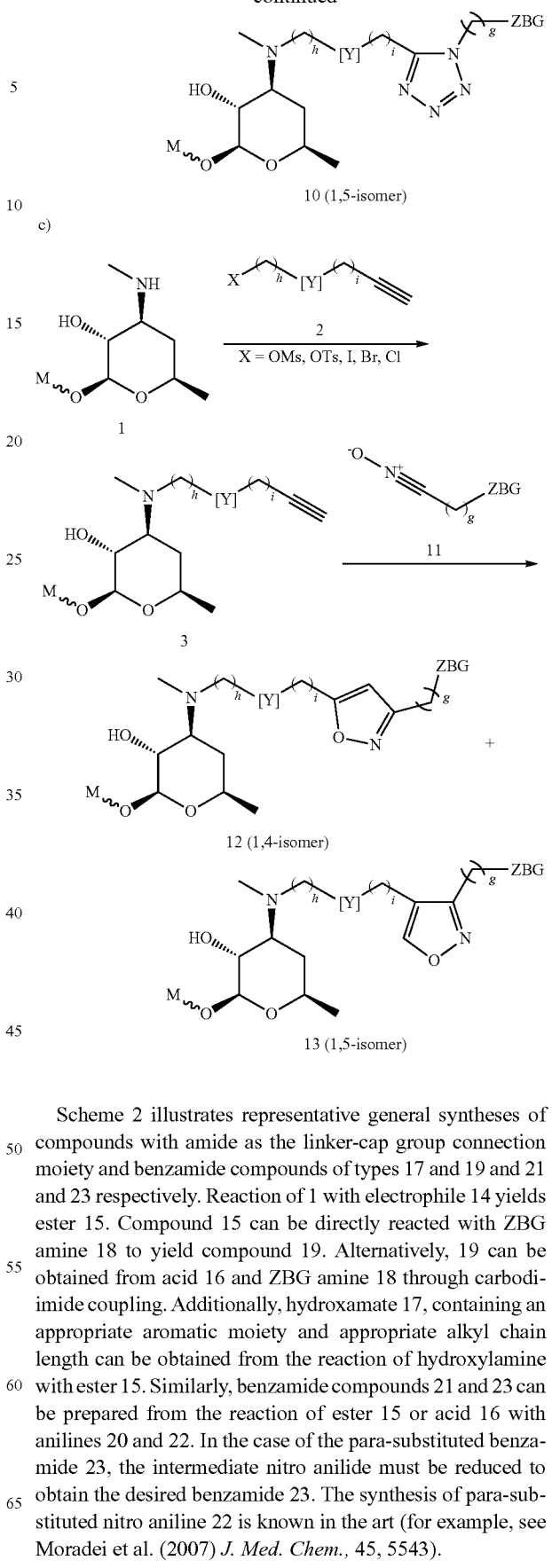

Scheme 2 illustrates representative general syntheses of compounds with amide as the linker-cap group connection moiety and benzamide compounds of types 17 and 19 and 21 and 23 respectively. Reaction of 1 with electrophile 14 yields ester 15. Compound 15 can be directly reacted with ZBG amine 18 to yield compound 19. Alternatively, 19 can be obtained from acid 16 and ZBG amine 18 through carbodiimide coupling. Additionally, hydroxamate 17, containing an appropriate aromatic moiety and appropriate alkyl chain length can be obtained from the reaction of hydroxylamine with ester 15. Similarly, benzamide compounds 21 and 23 can be prepared from the reaction of ester 15 or acid 16 with anilines 20 and 22. In the case of the para-substituted benzamide 23, the intermediate nitro anilide must be reduced to obtain the desired benzamide 23. The synthesis of para-substituted nitro aniline 22 is known in the art (for example, see Moradei et al. (2007) *J. Med. Chem.*, 45, 5543).

Scheme 2

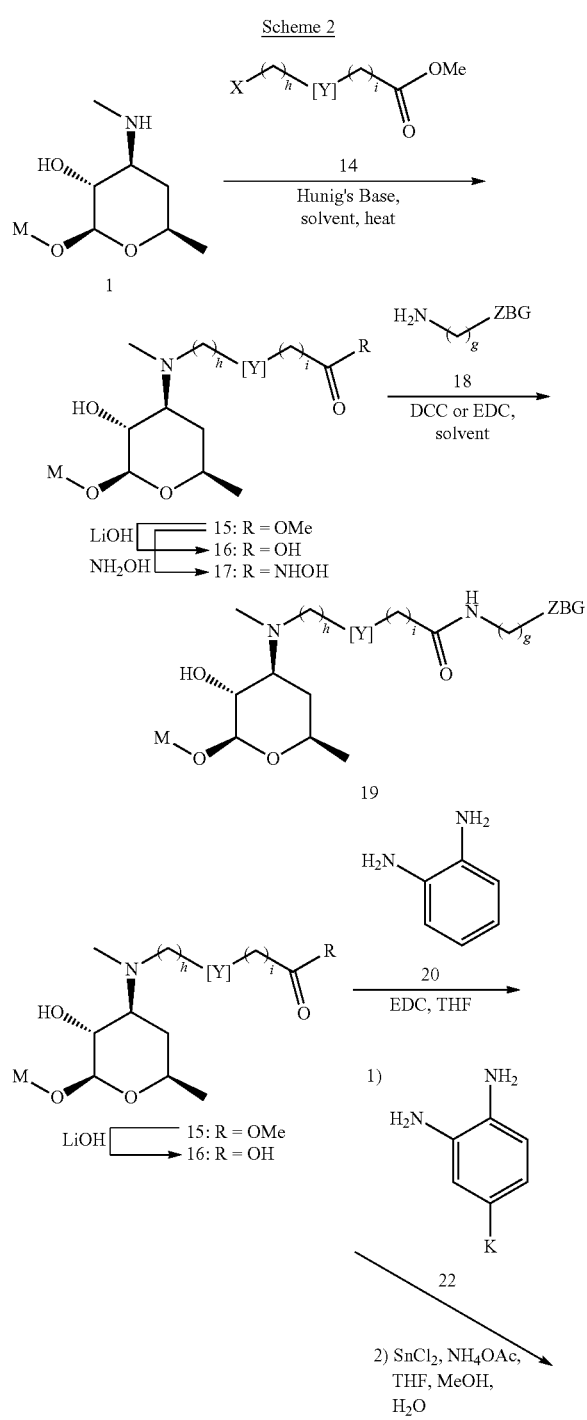

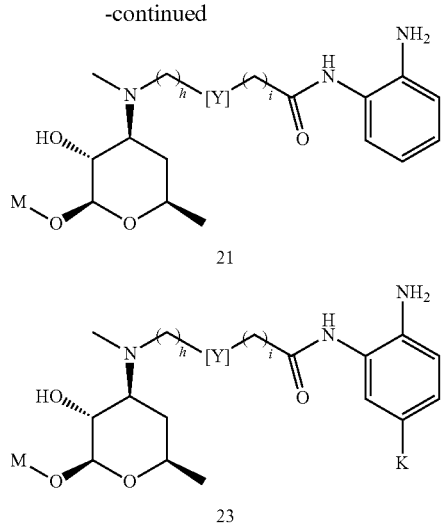

Scheme 3 illustrates representative general syntheses of ketolide and bridged-ketolide based triazole derivatives. Clarithromycin 24 can be N-demethylated to give des-N-methyl clarithromycin 25. Reaction of 25 with electrophile 2 yields alkyne 26. Alternatively, alkyne 26 can be obtained by reductive amination of appropriate aldehydes and ketones. Descladinose 27 can be prepared from the treatment of alkyne 26 with dilute mineral acid, such as HCl. Compound 27, where $R_{13}$ is $CH_3$, can be similarly obtained from reaction of 24 with dilute mineral acid. Selective acylation of the hydroxyl group of the amine sugar can be achieved by treatment of compound 27 with acetic anhydride in appropriate non-protic solvents such as, but not limited to, acetone, in the absence of base to yield compound 28. Oxidation of 28 under Corey-Kim or similar conditions (see Corey & Kim (1972) *J. Am. Chem. Soc.*, 94: 7586; Pfitzner & Moffatt (1965) *J. Am. Chem. Soc.*, 87: 5661; Ley et al. (1994) *Synthesis*, 639) leads to ketolide 29. Treatment of 29 with carbonyldiimidazole and NaHMDS will give carbamate 30. Reaction of 30 with amines 31, 32 and ethane-1,2-diamine will afford intermediate 33, 34, and 35, respectively (see U.S. Pat. No. 5,631,355; Kashimura et al. (2003), *J. Antibiot.*, 56: 1062; Randolph et al. (2004) *J. Med. Chem.*, 47, 1085; Plata et al. (2004) *Tetr.*, 60: 10171). Subsequent reactions of intermediates 33, 34, and 35 with azide 4 will lead to bridged-ketolides 36 and 37, 38 and 39, and 40 and 41, respectively. When $R_{13}$ contains an appropriate aromatic moiety and alkyl chain length, ketolide 29 can be modified to form compound 30 by methanolysis at elevated temperatures. Subsequent reaction of 30 with azide 4 will furnish ketolide 43. Again, it should be appreciated that the ZBG in azides of type 4 can be appropriately protected. Moreover, similar chemistries can be applied for the synthesis of the tetrazoles and oxazoles analogs of the ketolide and bridged-ketolide exemplified in scheme 3.

Scheme 3

R₁₃ is
1) C1-C6 alkyl, optionally attached to nitrogen through primary or secondary carbon 2) [structure with [Y], h, i showing alkyne terminus]

[Y] is —CH₂—, heteroatom, aryl, Ar
h = 1-6
h = 2-6, when [Y] is heteroatom
i = 0-6
g = 1-10

Z is
1) H
2) C1-C5 alkyl, alkenyl, or alkynyl, optionally substituted with aryl, biphenyl or fused aryl groups
3) NHR, where R is H, C1-C6 alkyl, alkenyl, or alkynyl, optionally substituted with aryl, biphenyl or fused aryl groups -continued
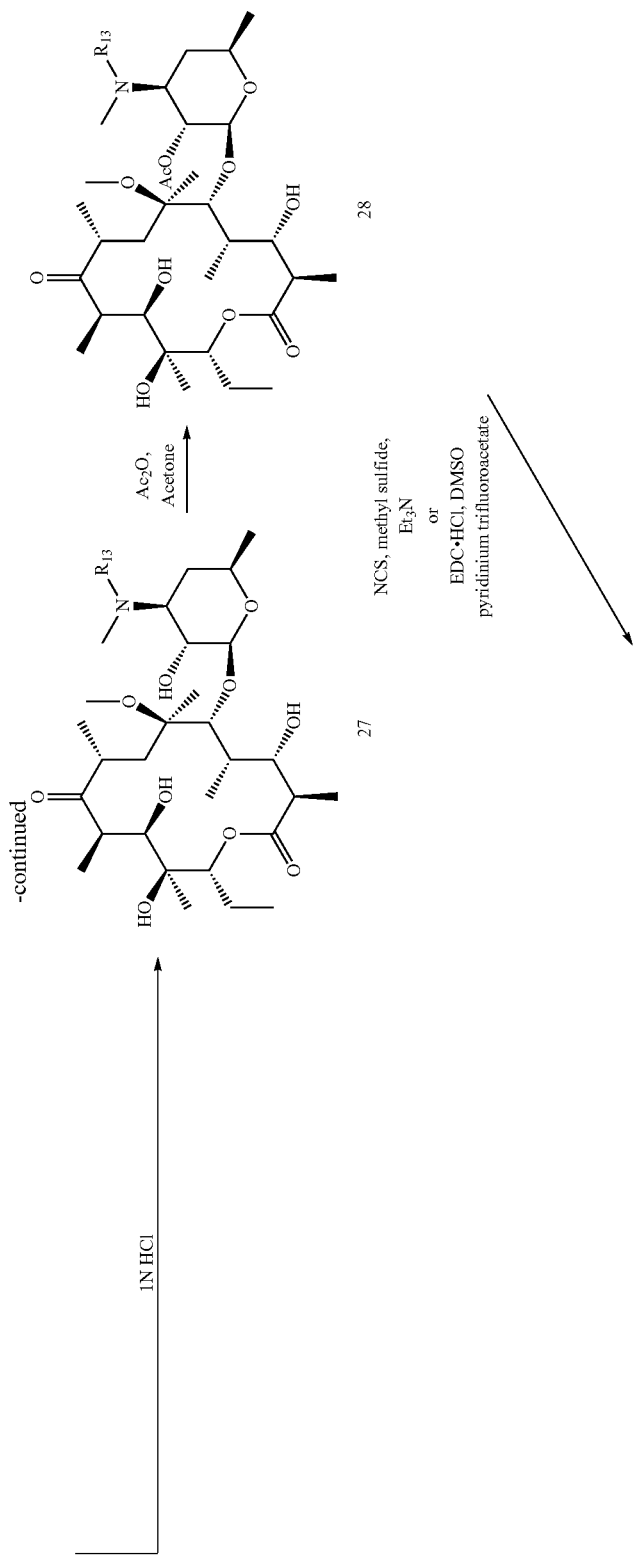

-continued
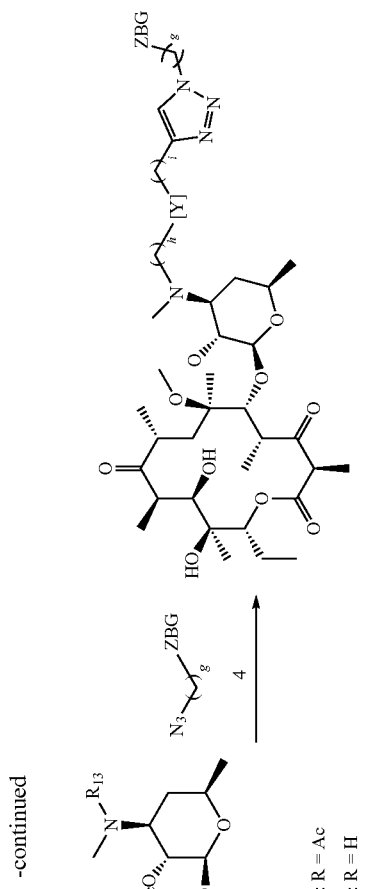
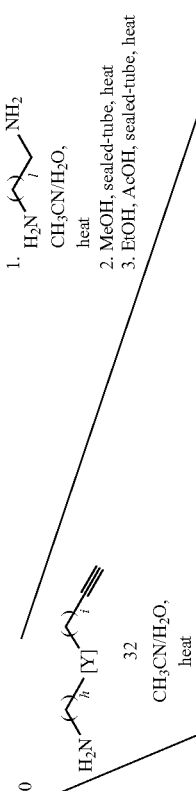
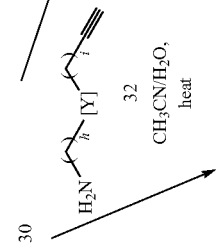
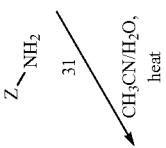

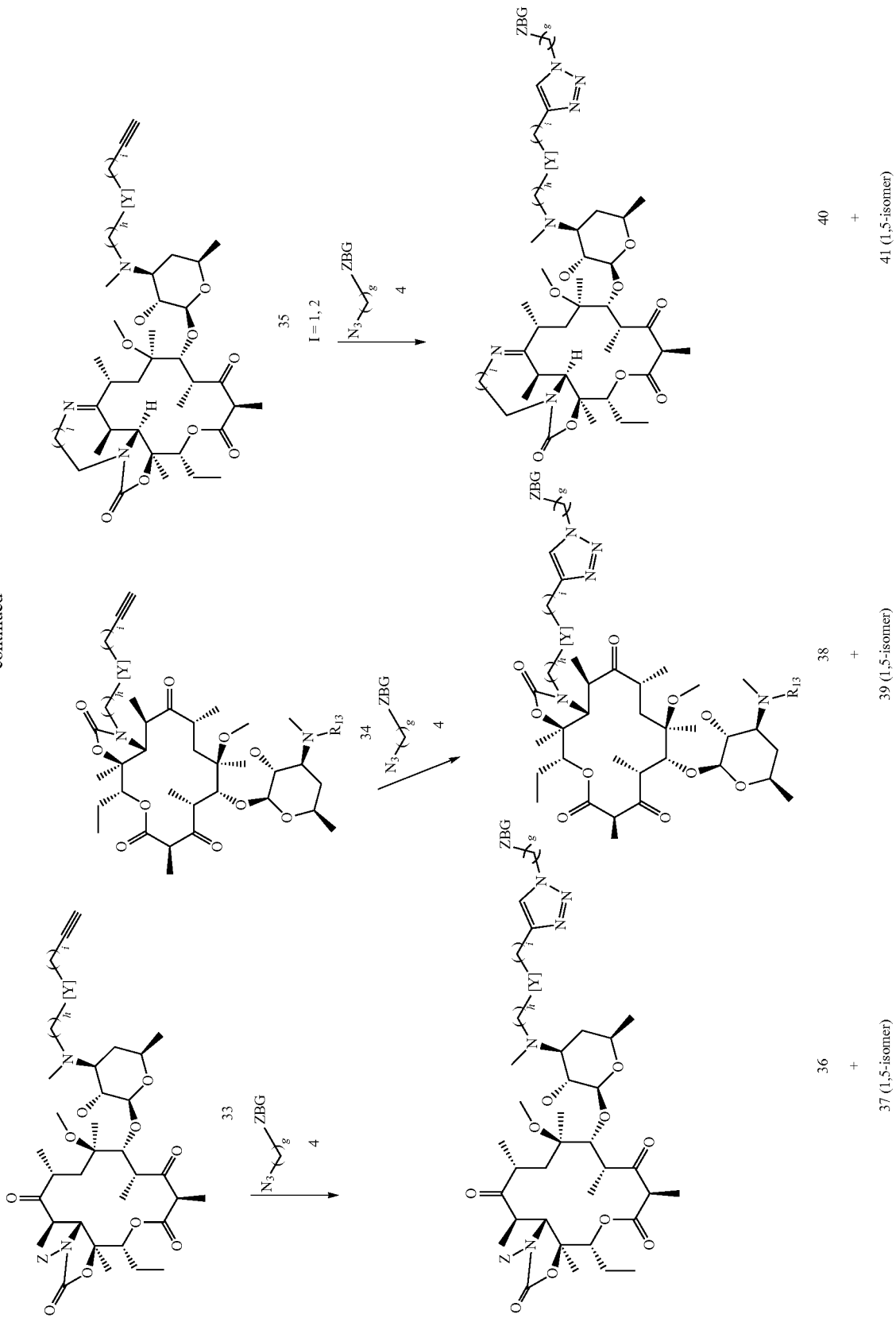

Scheme 4 illustrates representative general synthesis of triazole compounds with HDAC recognition cap-group connected to the macrocyclic ring at O6 position of 14-membered macrolide such as, but not limiting to, erythromycin. Adapting known protocols (see, Plata et al. (2004) *Tetra.*, 60: 10171), the aryl alkyne 47 can be obtained from readily available erythromycin A-9-oxime (see, Morimoto et al. (1990) *J. Antibiot.*, 43:286) through the intermediacy of 45.

Sequential base treatment with aqueous alkali and potassium carbonate in methanol will lead to alkyne 48 which can be reacted with azide 4 to give triazole 49. Methanolysis of 49 will afford triazole 50. Triazole 50 can be modified to form compound 51 by treatment with dilute mineral acid. Alternatively, methanolysis of alkyne 48 yields alkyne 51. Reaction of 51 with azide 4 will yield triazole 50.

Scheme 4

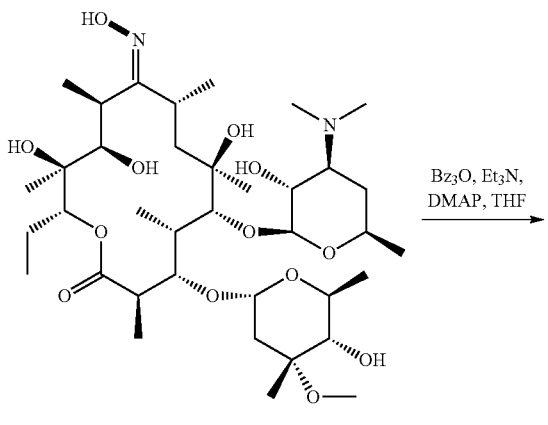

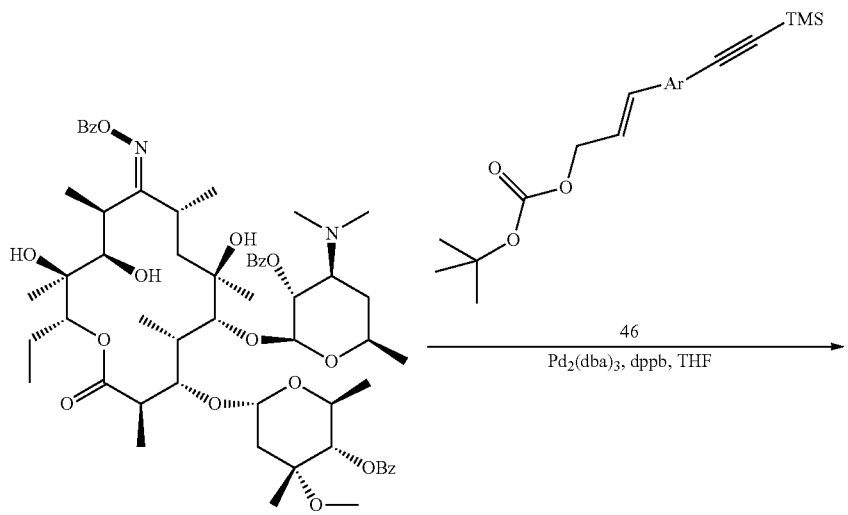

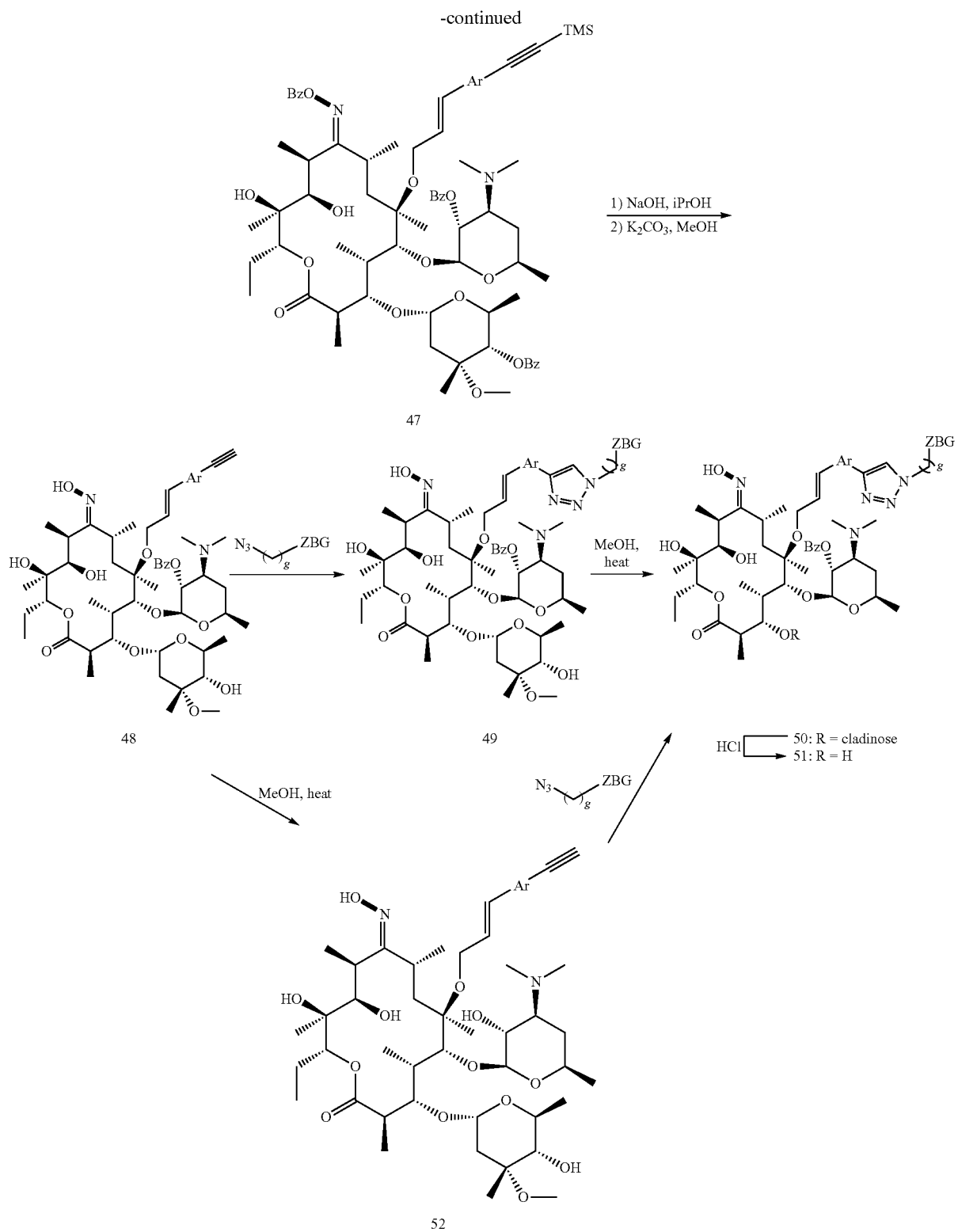

Scheme 5 illustrates representative general syntheses of triazole compounds with HDAC recognition cap-groups connected to the macrocyclic ring at the O6 position of 14-membered ketolides and carbamate modified macrolides. Selective benzoyl deprotection and silyl group removal will afford aryl alkyne 53. The oxime group in 53 can be removed by heating 53 in a THF/$H_2O$ containing $NaHSO_3$ and L-tartaric acid to afford aryl alkyne 54 (adapting protocols described by Plata et al. (2004) *Tetra.*, 60: 10171). Reaction of 54 with azide 4 followed by debenzoylation by sequential treatment with potassium carbonate in methanol and methanolysis at elevated temperatures will yield triazole 55. Triazole 55 can be modified to form compound 56 by treatment with dilute mineral acid. Aryl alkyne 54 can be modified to form aryl alkyne 57 by adapting procedures exemplified for similar transformations in scheme 3 or alternative protocols described in the art (see U.S. Pat. No. 5,631,355; Kashimura et al. (2003), *J. Antibiot.*, 56: 1062; Randolph et al. (2004) *J. Med. Chem.*, 47, 1085; Plata et al. (2004) *Tetra.*, 60: 10171). Reaction of 57 with azide 4 followed by debenzoylation by sequential treatment with potassium carbonate in methanol and methanolysis at elevated temperatures will yield triazole 58. Triazole 58 can be converted to compound 59 by treatment with dilute mineral acid. A direct treatment of 57 with dilute mineral acid will afford alcohol 60. Oxidation of 60 under Corey-Kim or similar conditions followed by methanolysis at elevated temperatures will yield alkyne ketolide 61. Reaction of 61 with azide 4 will yield triazole 62.

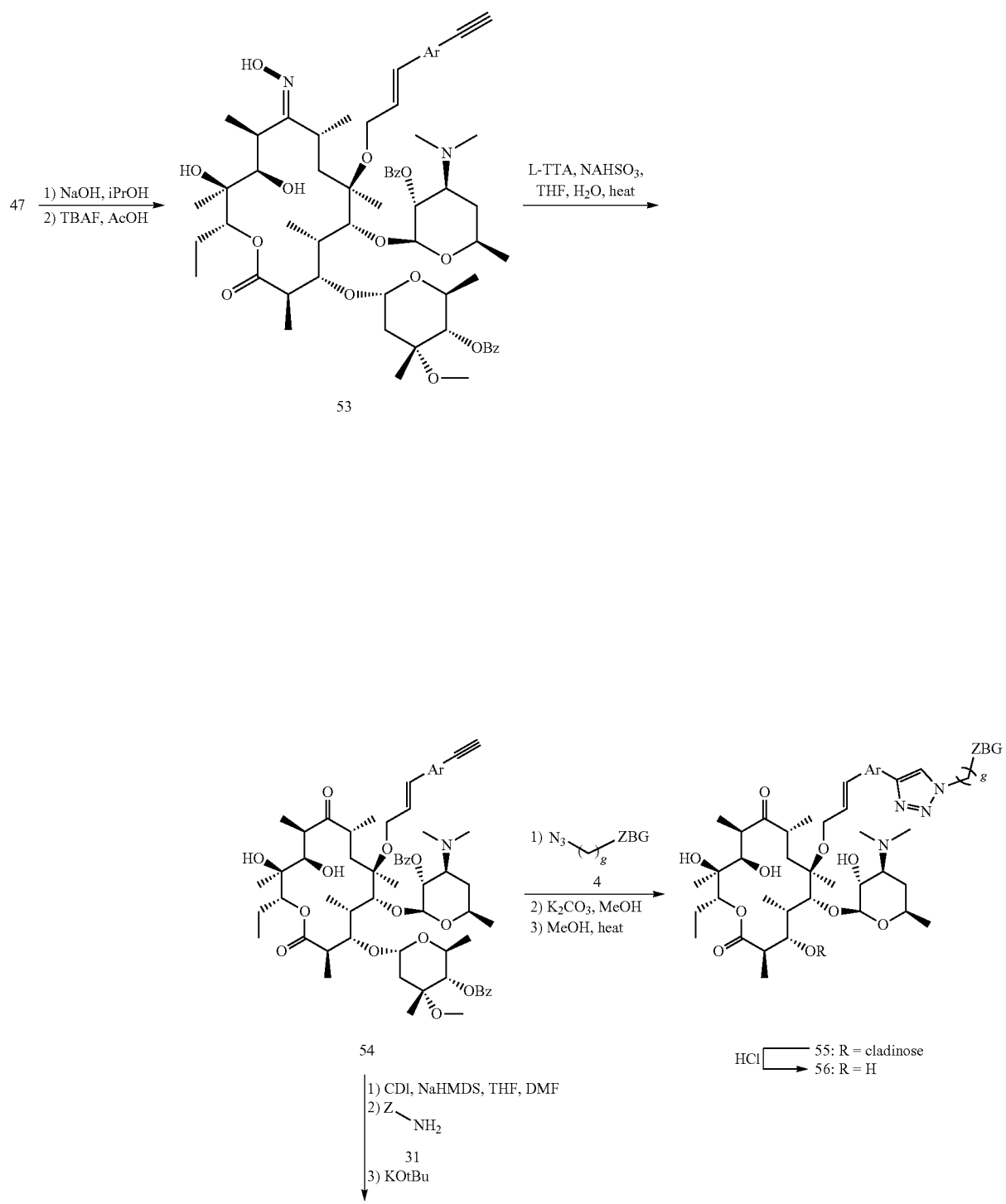

-continued

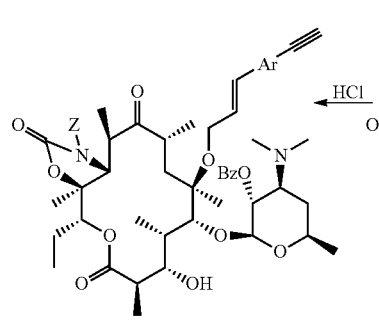

60

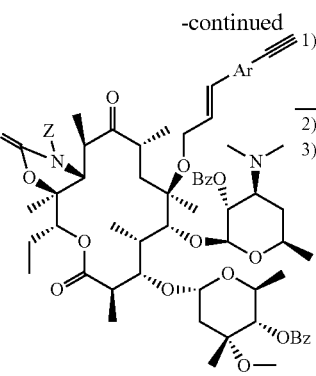

57

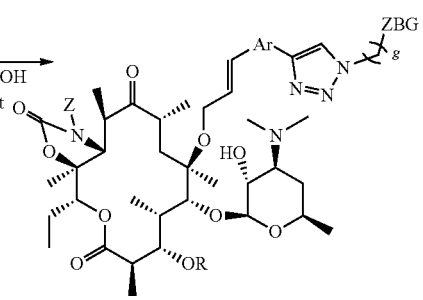

58: R = cladinose
59: R = H

1) NCS, methyl sulfide,
   Et₃N or EDC•HCl, DMSO,
   pryridinium trifluoroacetate
2) MeOH, heat

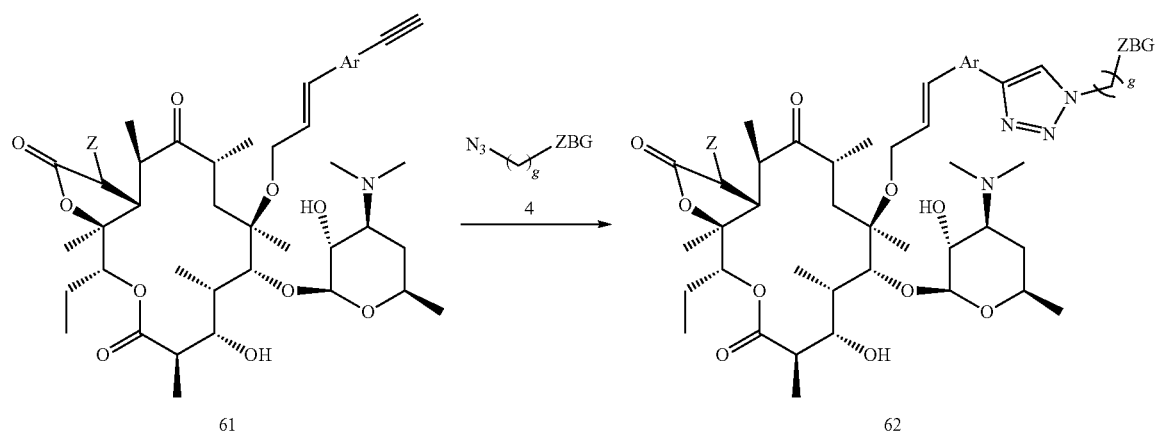

Intermediates such as electrophiles 2, 7 and 14, azide 4, nitrile oxide 11, amine 30 and carbonate alkyne 46 are all easily accessible by synthetic protocols known in the art. Exemplary examples for the synthesis of compounds whose general structures fit the forgoing are illustrated in schemes 6, 7, 8, and 9. Halogenated aryl alkyne 63 can undergo Heck coupling with ethyl acrylate to furnish α,β-unsaturated ester 64. Reduction of 64 with DIBAL should generate alkenol 65, which can be transformed to carbonate 66 using methods known in the art (see U.S. Pat. No. 6,579,986; Plata et al. (2004), *Tetra.*, 60: 10171). Alternatively, alkenol 65 can be prepared from alkenol 67 through Hagihara-Sonogashira coupling (Belema et al. *Tet. Lett.*, (2004), 45: 1693). Reactions of carboxylic acid 68 with thionyl chloride in methanol follow by treatment with sodium azide should furnish azido methyl ester 69. Treatment of 69 with hydroxylamine should provide azido hydroxamate 70 (Ho et al., (2005), *J. Org. Chem.*, 70, 4873). The hydroxamate group of 70 can be appropriately protected with a silyl group to provide silyl azide 71 (Muri et al. *Org. Lett.*, (2000) 2: 539). Hagihara-Sonogashira coupling between alcohol 72 and TMS-acetylene should yield alkyne 73. TMS deprotection should furnish alkyne 74, which can be reacted with MsCl to provide mesylate 75. Reaction of phthalimide salt with 75 should provide phthalimide 76, which can be converted to amine 77 by hydrazinolysis or other suitable protocol known in the art. Treatment of alcohol 78, incorporating ZBG (appropriately protected when necessary), with oxidants such as PDC, should provide aldehyde 79. Reaction of 79 with hydroxylamine should furnish oxime 80, which can be converted to nitrile oxide 81 by treatment with NBS or other reagents such NCS, chloramine T, etc. Because of the likely instability of nitrile oxides, the generation of nitrile oxide can be performed in the presence of the appropriate alkyne 3 (scheme 1) to furnish the regioisomeric mixture of the isoxazoles.

Scheme 6
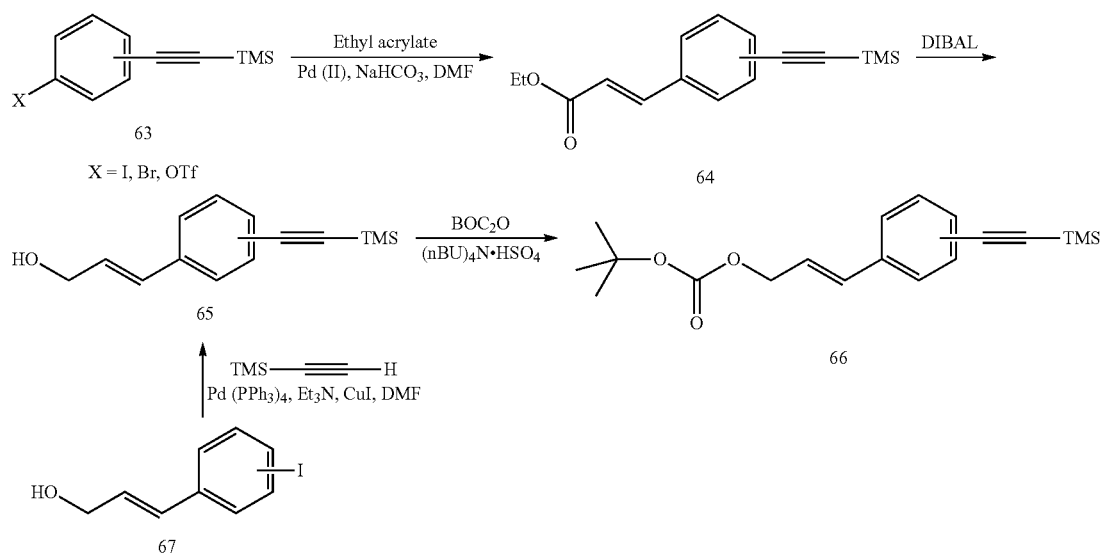
Scheme 7
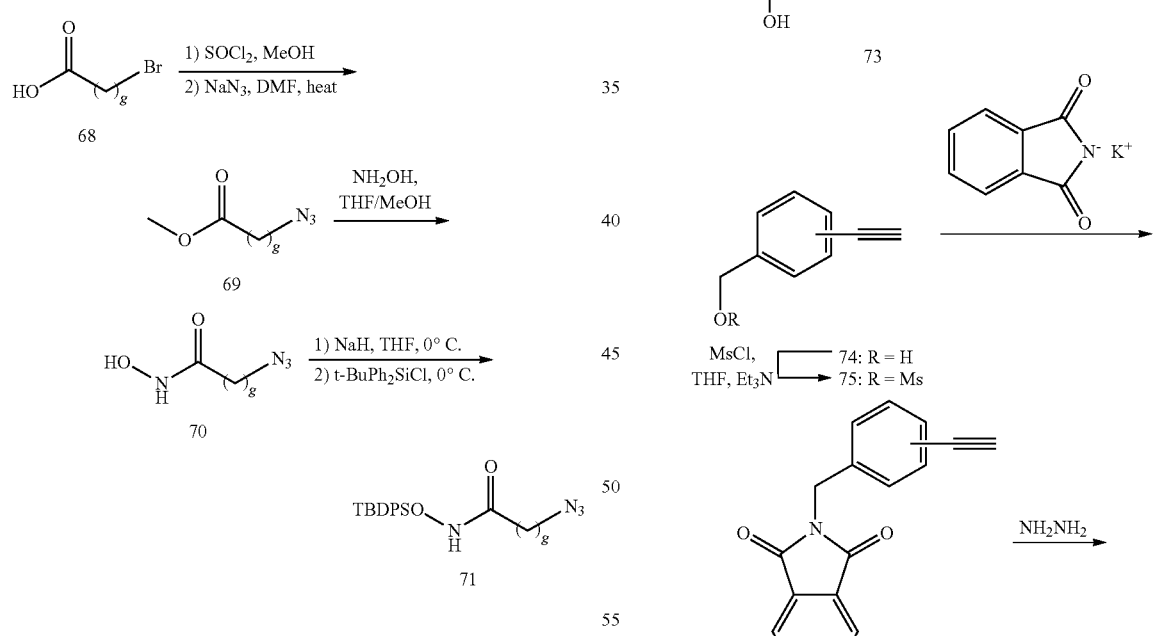
Scheme 8
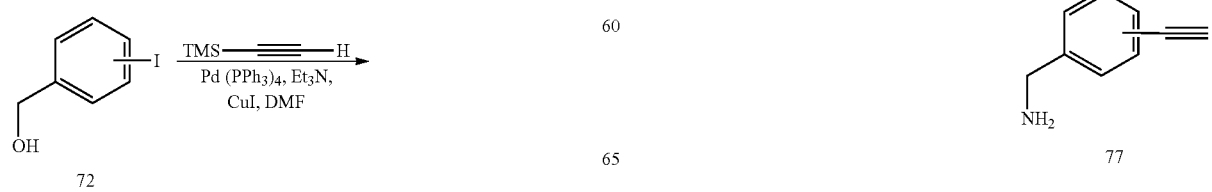

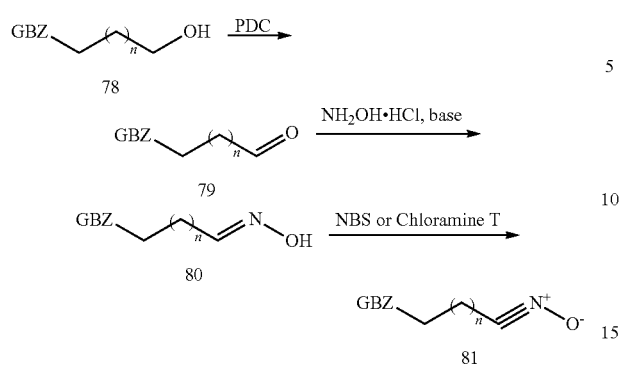
Scheme 9
Schemes 10 and 11 illustrate the synthesis of compounds 7-14 and 23-30 in Table 3.

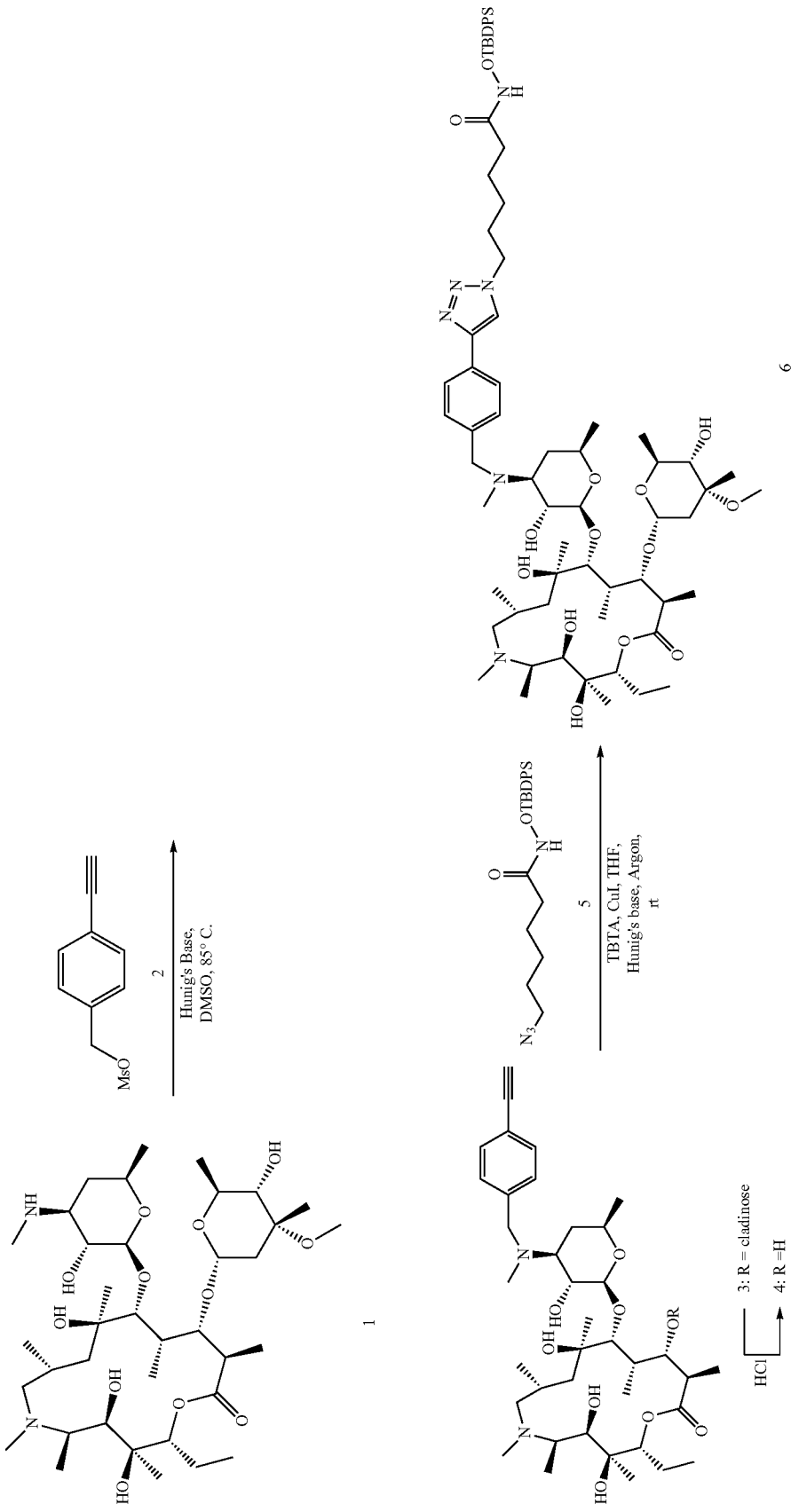
Scheme 10: Synthesis of compounds 7-14

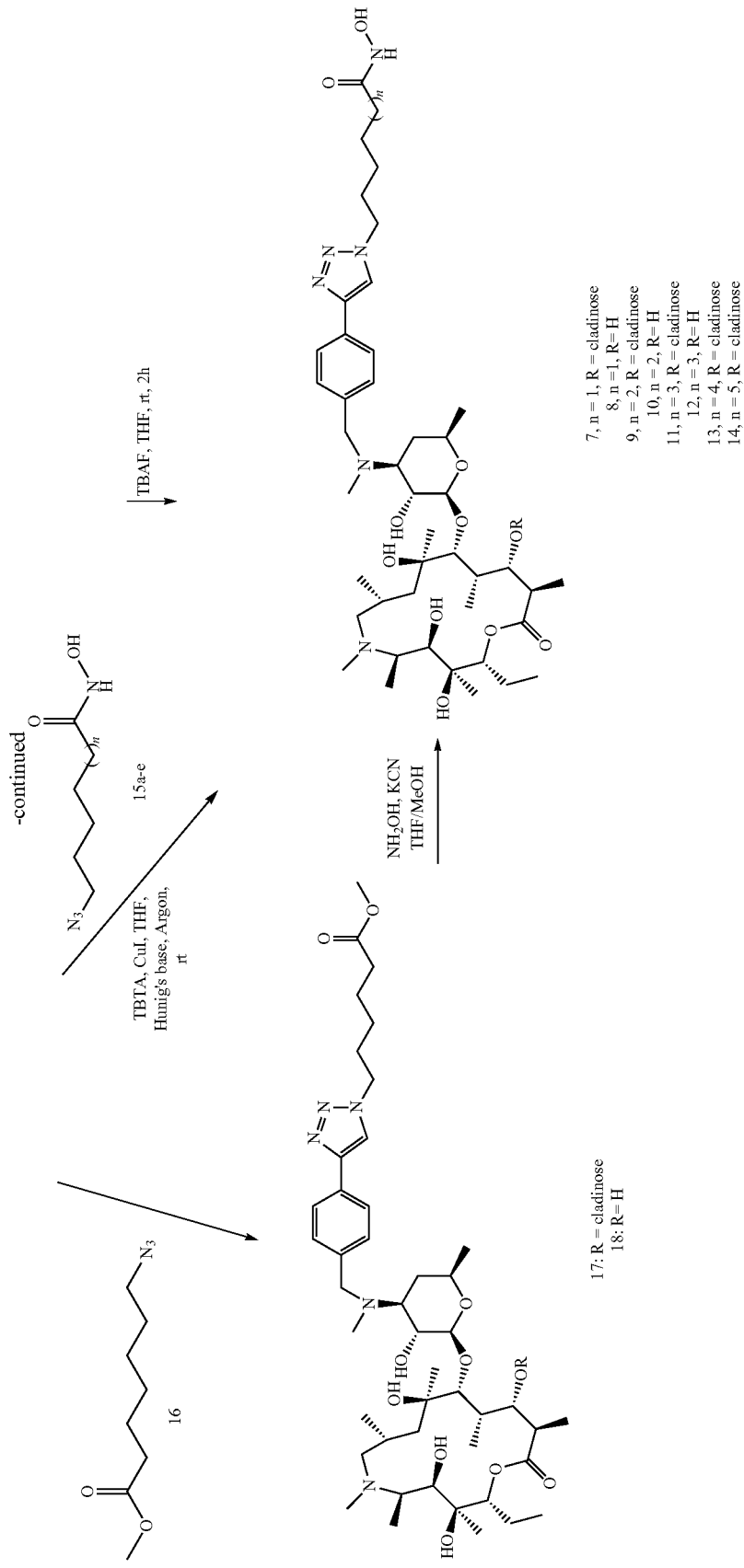

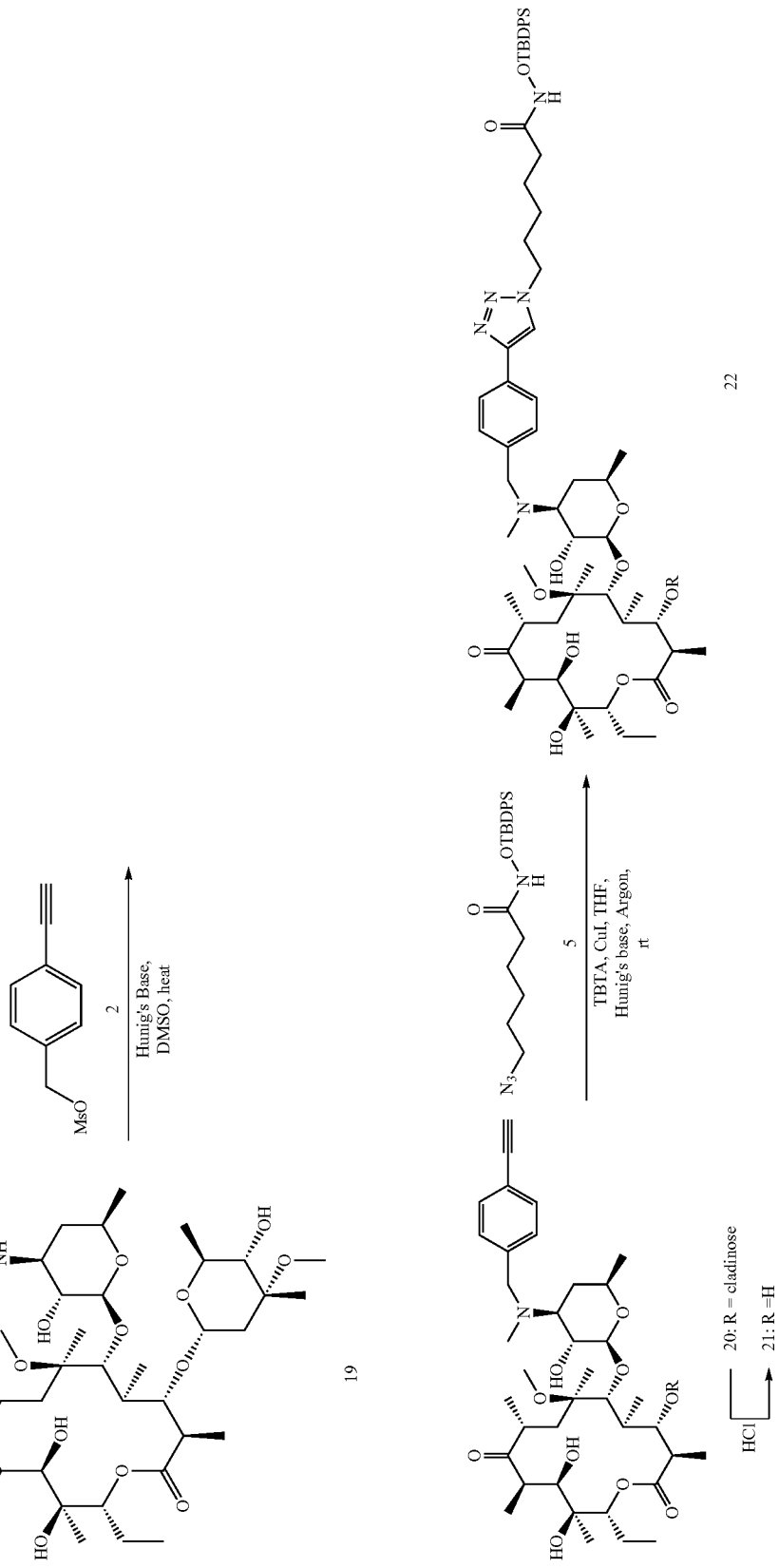
Scheme 11: Synthesis of compounds 23-30

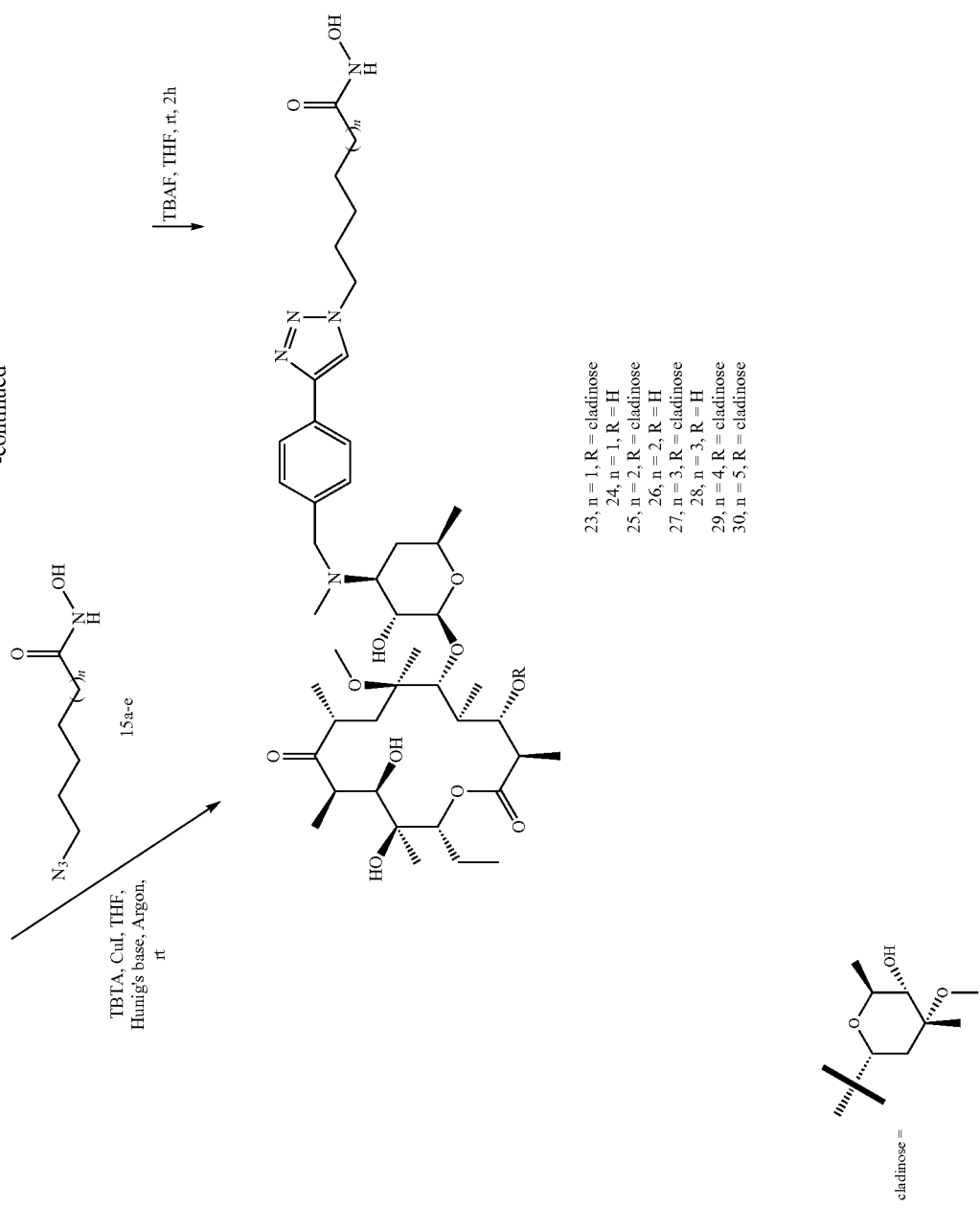

Scheme 12 illustrates the synthesis of compounds 36 and 38 in Table 3.

Scheme 12: Synthesis of compounds 36 and 38
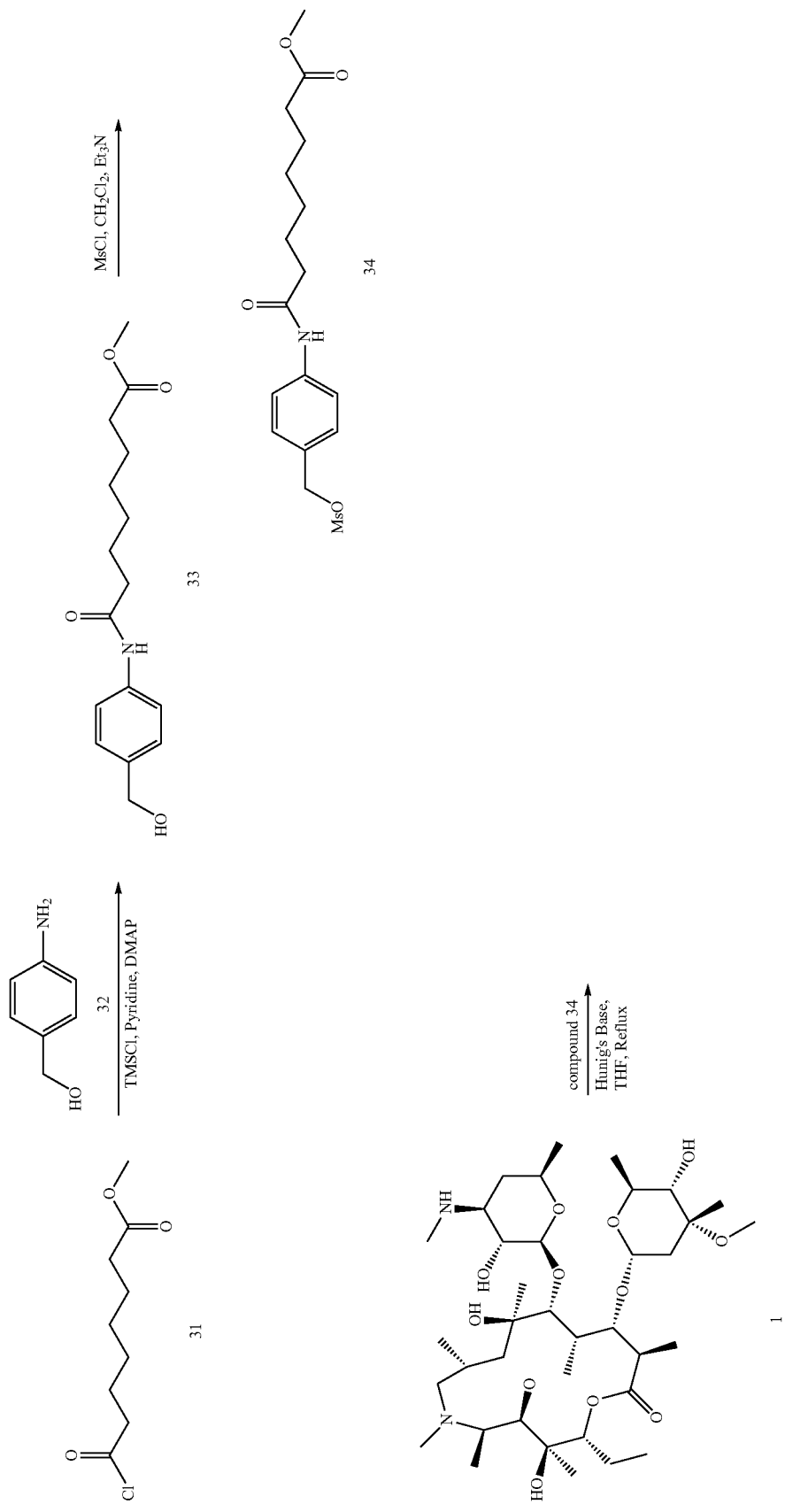

-continued
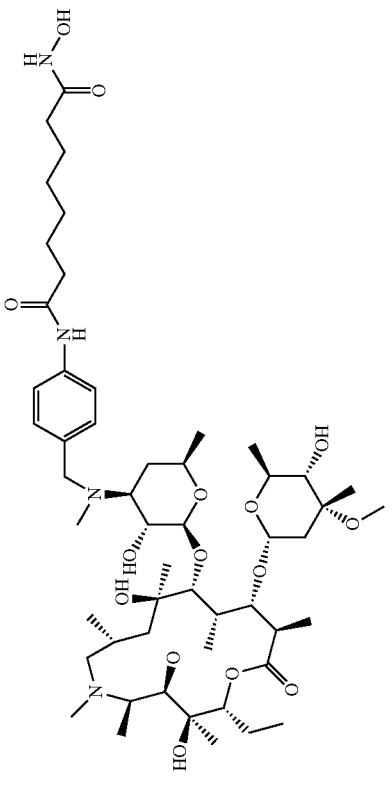
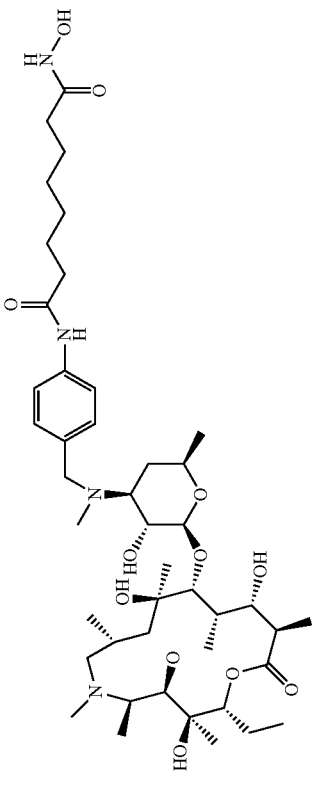
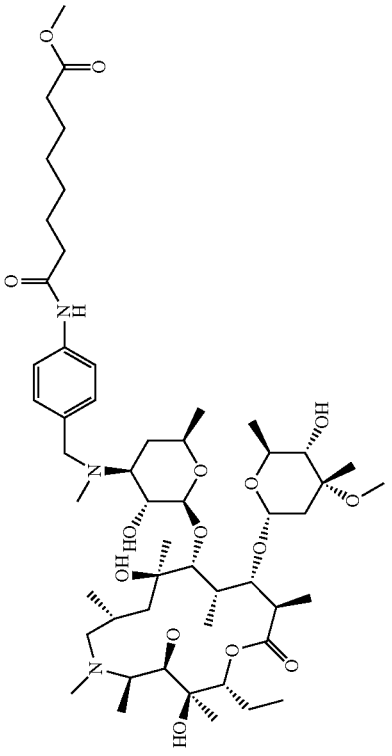
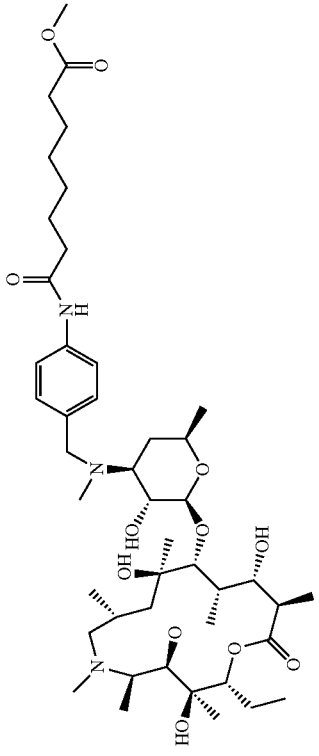

Schemes 13, 14 and 15 below illustrate the synthesis of compounds 40, 44 and 47 in Table 3.
Scheme 13: Synthesis of compound 40
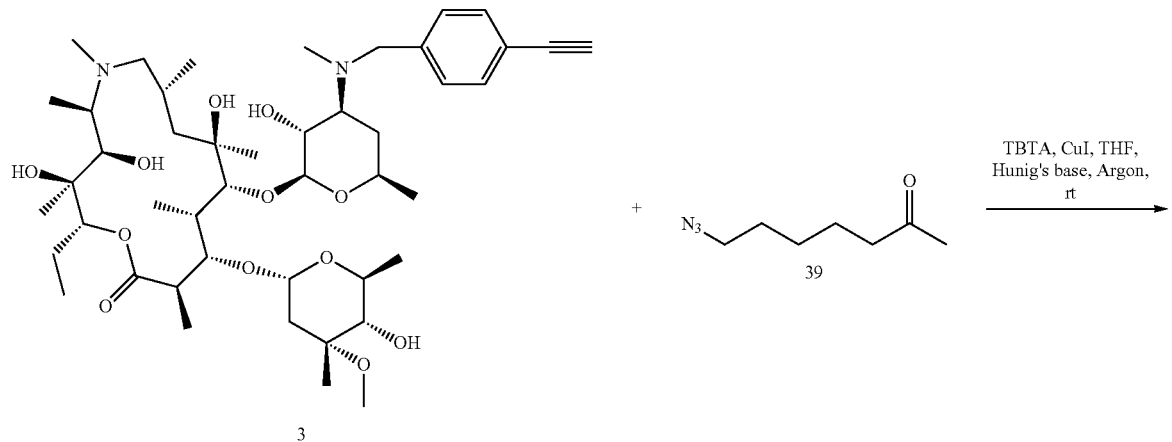
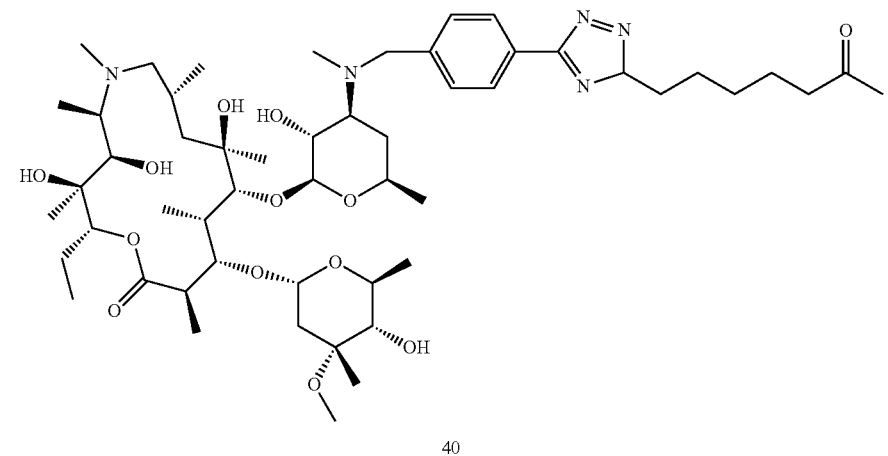
Scheme 14: Synthesis of compound 44
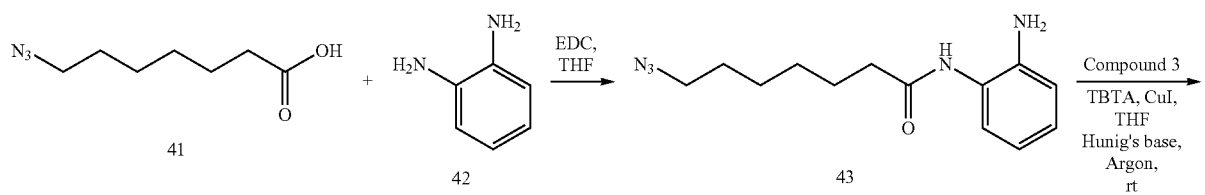

111
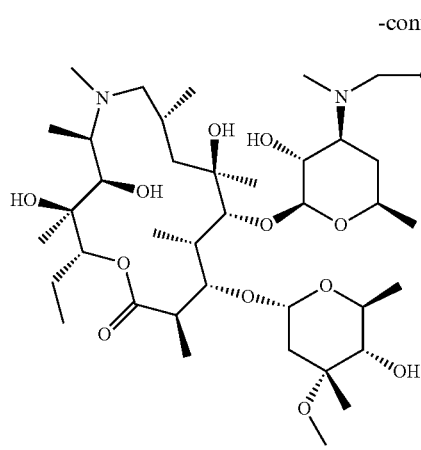
-continued
112
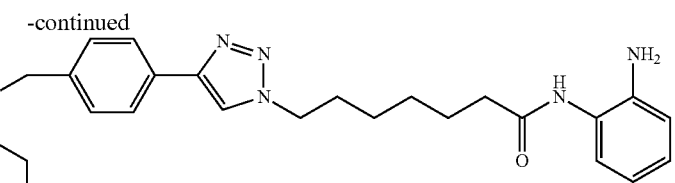
44
Scheme 15: Synthesis of compound 47
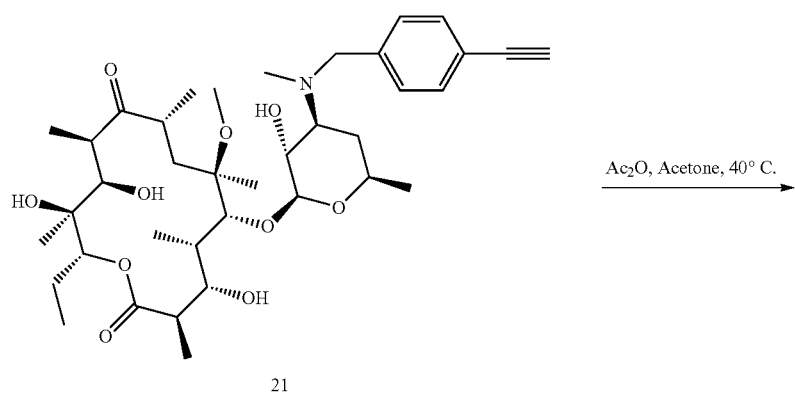
21
Ac₂O, Acetone, 40° C. →
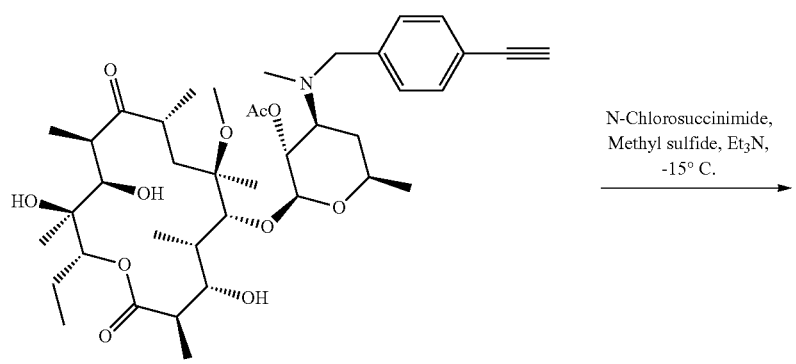
45
N-Chlorosuccinimide,
Methyl sulfide, Et₃N,
-15° C. →

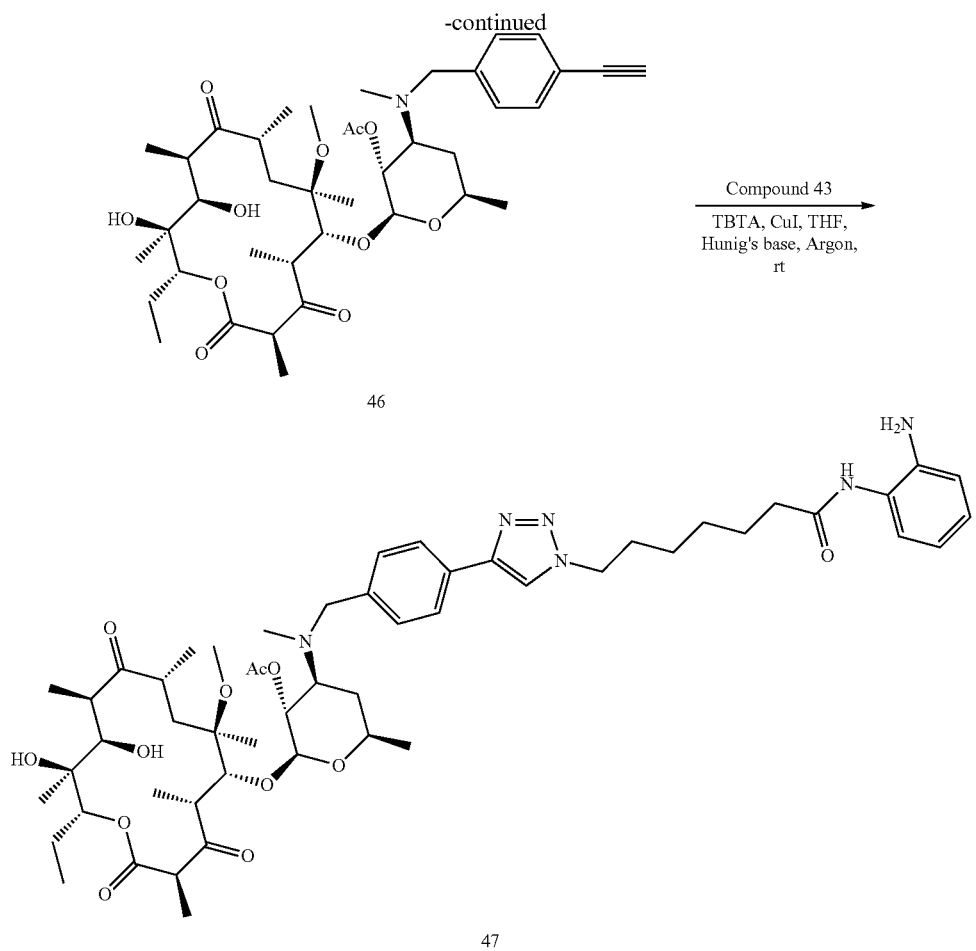

Schemes 16A and 16B. Synthesis of Compound 56 Compound 56 can be synthesized via the 4'-ethynylbenzylketolide intermediate 9. Demethylation of clarithromycin 1 under standard conditions forms 4-desmethyl-clarithromycin 2 in 70% yield. Subsequent alkylation of 2 with 4-ethynylbenzyl methanesulfonate afforded the modified 4'-ethynylbenzyl-clarithromycin 4 which was treated with 1N HCl to selectively cleave the cladinose sugar to form compound 5. Reaction time for this step should be carefully controlled as longer reaction times led to the formation of significant amounts of byproduct. Selective acetylation of the 2'-OH group was accomplished by treating an acetone solution of 5 with acetic anhydride at 40° C. for 24 h to give compound 6 in 70% yield. Subsequent oxidation of the 3-hydroxyl group of compound 6 to a 3-keto functional group, under anhydrous condition with NCS, afforded the ketolide 7 almost quantitatively. Treatment of 7 with excess carbonyldiimidazole (CDI) and NaHMDS in a mixture of THF/DMF afforded the 12-acyl imidazolide 8 in 52% yield. Transformation into the desired tricyclic ketolide was achieved in two successive cyclization steps adapting literature procedures. Reaction of imidazolide 8 with ethylenediamine followed by intramolecular Michael addition led to the formation of 11,12-cyclic carbamate. Subsequent intramolecular dehydration completed the cyclization process, affording the desired product 9 in 42% yield (Scheme 16A).

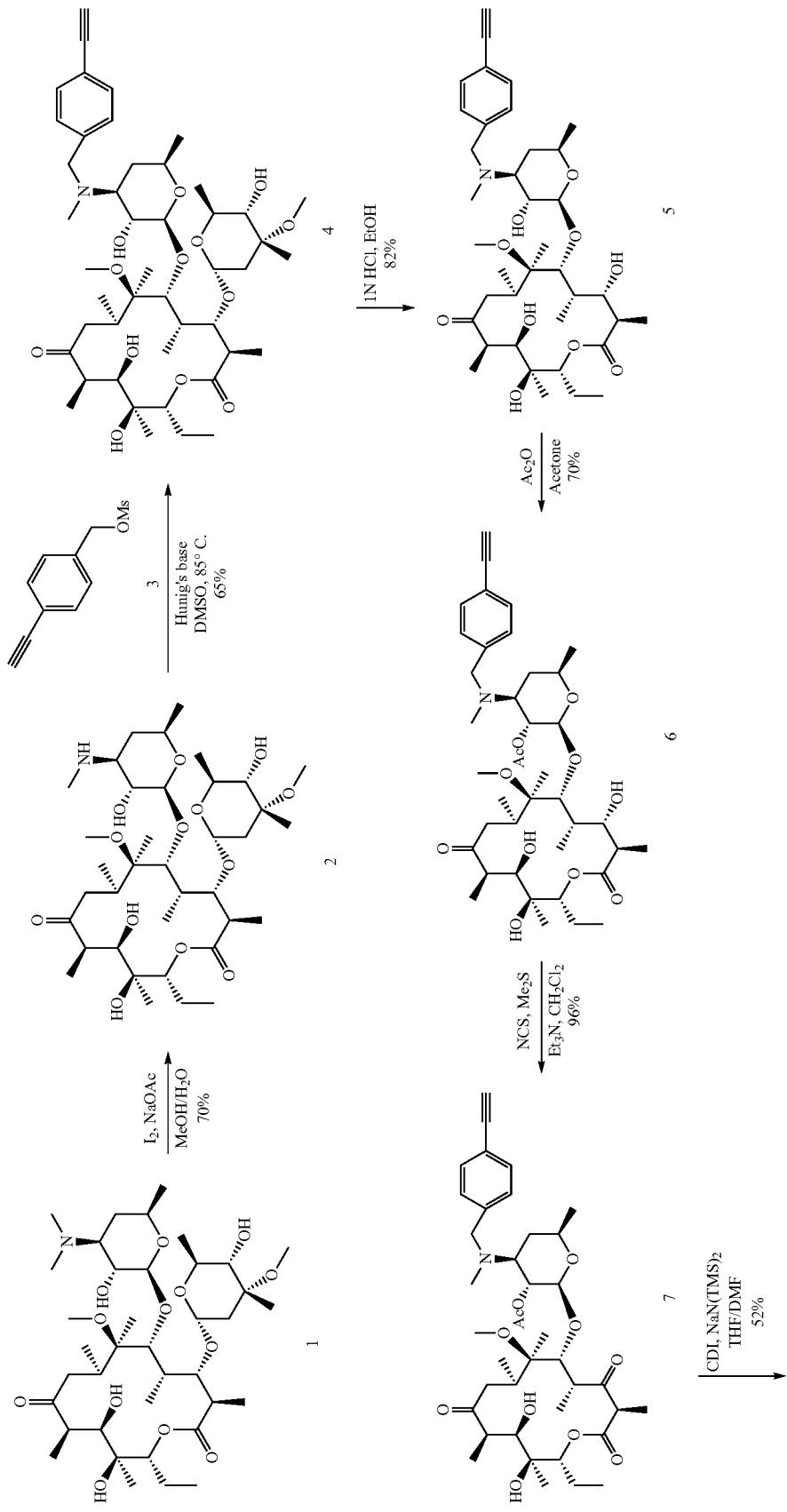

-continued
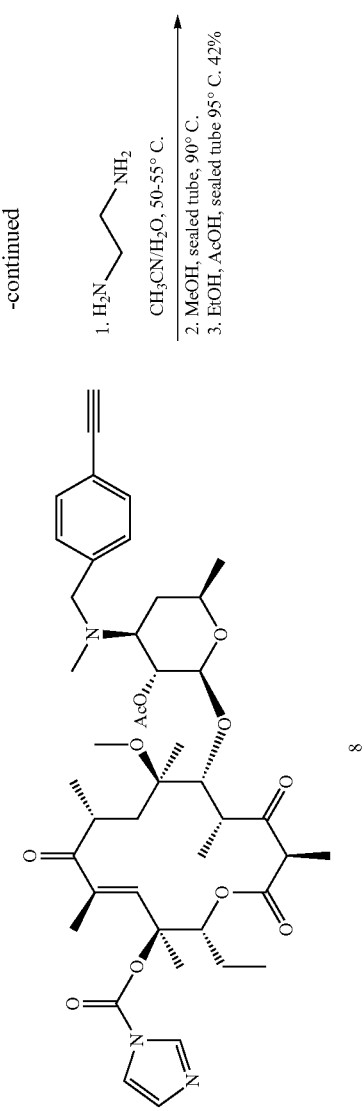
1. $H_2N\diagup\diagdown NH_2$
  $CH_3CN/H_2O$, 50-55° C.
2. MeOH, sealed tube, 90° C.
3. EtOH, AcOH, sealed tube 95° C. 42%
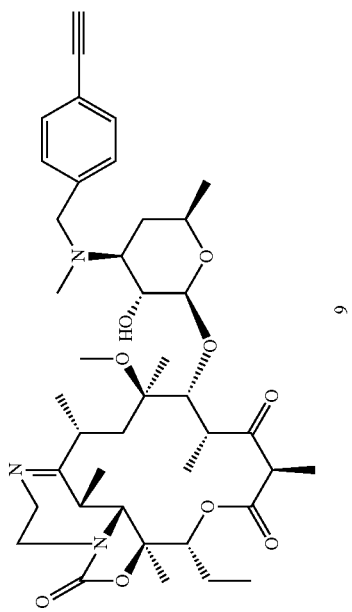

Copper (I) catalyzed cycloaddition of 9 with O-trityl protected azidohydoxamate analogs 10a-e (route A), afforded the 1,2,3-triazole linked derivatives 11a-e. Deprotection of the trityl group in 11a-e with TFA (route 13) gave the desired products (56a-e) in good yields. A similar outcome was obtained when trityl group deprotection was effected with $BF_3.OEt_2$ (route C). Additionally, the desired hydroxamates could be obtained through direct copper (I) catalyzed cycloaddition between unprotected azidohydroxamate 13 and alkyne 9 (route D).

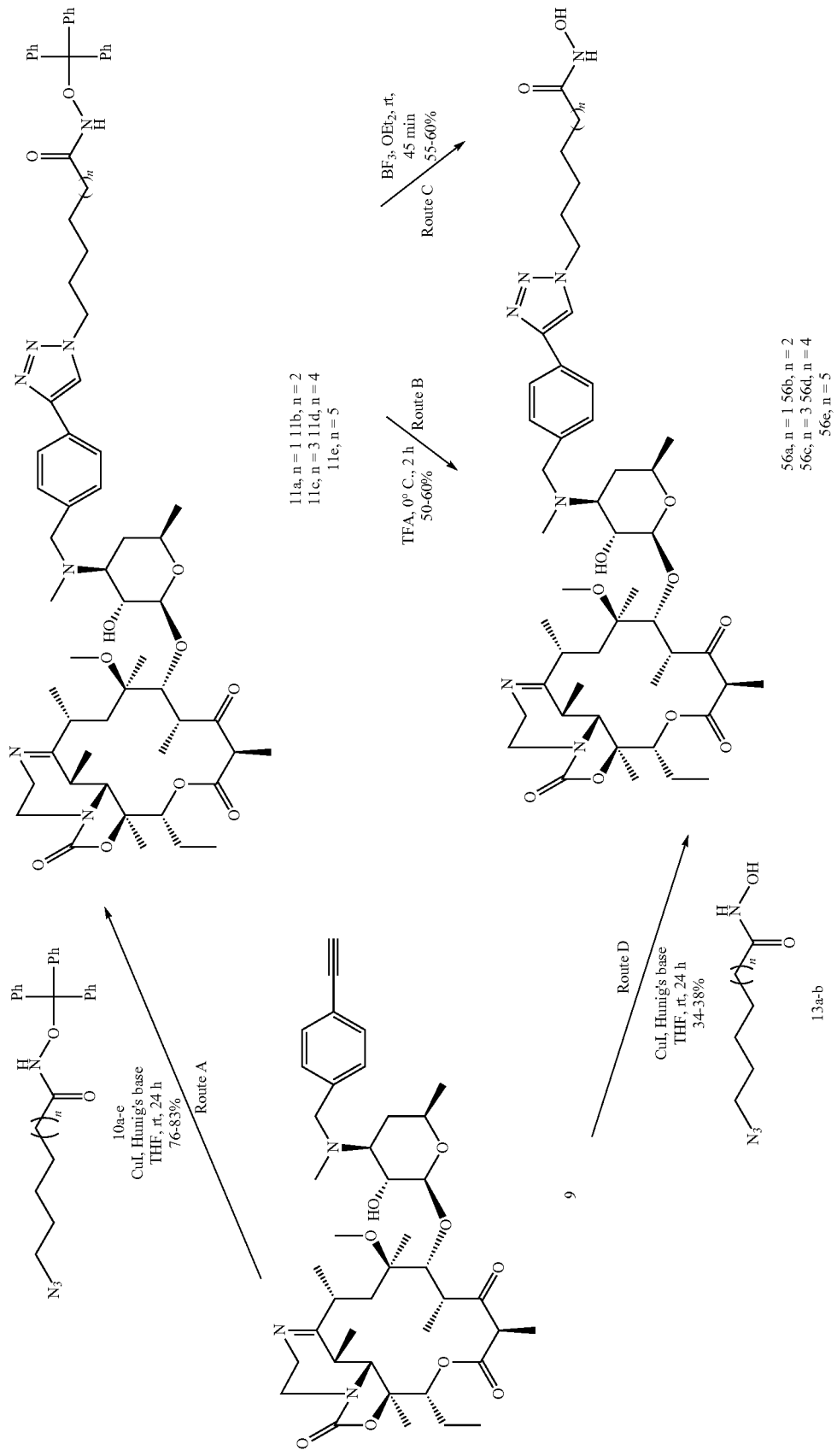

Methods of Purifying HDAC Intermediates on Multi-Gram Scales

To improve the efficiency of the multi-gram synthesis, methods of purifying intermediates, such as compound B below (where R is a macrolide such as azithromycin or clarithromycin) by extraction were developed.

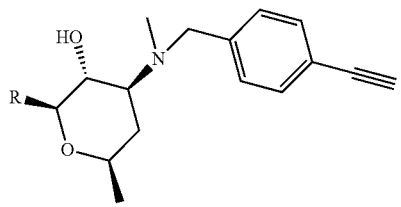

Compound B containing an azithromycin macrolide can be purified by dissolving B in a suitable alcohol, such as methanol, and adding an aqueous buffer solution, such as an acetate buffer, to form a weakly acidic solution. The solution can then be extracted with one or more mixtures of a polar and non-polar organic solvent, such as mixtures of hexanes and ethyl acetate. The aqueous phase is then basified, for example by addition of aqueous ammonium hydroxide, and extracted with one or more organic solvents, such as hexanes and/or mixtures of hexanes and ethyl acetate. The organic phases can then be collected and dried in vacu to obtain B.

Compound B containing a clarithromycin macrolide can be purified by dissolving B in a suitable alcohol, such as methanol, and adding an aqueous buffer solution, such as an acetate buffer, to four a weakly acidic solution. The solution can then be extracted with one or more mixtures of a polar and non-polar organic solvent, such as mixtures of hexanes and ethyl acetate. The organic phases can then be collected and dried in vacu. Compound B containing a clarithromycin macrolide can be purified by recrystallization, for example, from a mixture of hexanes and dichloromethane.

V. Methods of Use

The compounds described herein may be used as anti-cancer agents, anti-inflammatory agents, anti-infective agents, anti-malarial agents, cytoprotective agents, neuroprotective agents, chemopreventive agents, prokinetic agents, and/or cognitive enhancing agents. Examples of cancer which may be treated include, but are not limited to, epithelial cancers, such as melanoma, lung cancer, breast cancer, pancreatic cancer, ovarian cancer, prostate cancer, colon cancer, and bladder cancer; hematological cancers, such as multiple myeloma, leukemia, and lymphoma; cervical cancer; and liver cancer.

The potency of the compounds described herein were investigated by determining the drug concentrations necessary for 50% inhibition of cell viability ($IC_{50}$) in SKMES 1, NCI-H69, DU 145 cells, lung fibroblasts, and HMEC. Drug concentrations necessary for 50% inhibition of cell viability ($EC_{50}$) were quantitatively measured using trypan blue exclusion according to literature protocol. Table 5 in the examples shows the $EC_{50}$ values for each compound. All compounds inhibited the proliferation of the transformed cells studied with $EC_{50}$ in the low micromolar range. Most importantly, the compounds we less toxic to untransformed cell-lines (lung fibroblast and HMEC).

The compounds described herein were also evaluated for parasitic activity against Plasmodium falciparum and Leishmania donovani. P. falciparum and L. donovani are the causative parasites of malaria and leishmaniasis, two human diseases which constitute a serious threat to public health in tropical and sub-tropical countries. Antimalarial activity was evaluated in vitro using chloroquine-sensitive (D6, Sierra Leone) and chloroquine-resistant (W2, Indochina) strains of P. falciparum. Antileishmanial activity was evaluated in vitro against the promastigote stage of L. donovani.

Plasmodium growth inhibition was determined by a parasite lactate dehydrogenase assay using Malstat reagent. Inhibition of viability of the promastigote stage of L. donovani was determined using standard Alamar blue assay, modified to a fluorometric assay. Amphotericin B and pentamidine, standard antileishmanial agents; chloroquine and artemisinin, standard antimalarials; and suberoylanilide hydroxamic acid (SAHA), a standard HDAC inhibitor (HDACi) were all used as positive controls. To determine selective toxicity index, all compounds were tested against nontransformed mammalian cell lines namely, monkey kidney fibroblasts (Vero) and murine macrophages (J774.1) using Neutral Red assay.

The non-peptide macrocyclic HDAC inhibitors potently inhibited the proliferation of both the sensitive and resistant strains of P. falciparum with an $IC_{50}$ ranging from 0.1 µg/mL to 3.5 µg/mL. In particular, compounds 5-8 in Table 16, derived from either the 14- or 15-membered macrolide analogs and having 6 methylene spacers separating the triazole ring from the zinc-binding hydroxamic acid group (n=6), had the most potent antimalarial activities in this series. These compounds are equipotent or >4-fold more potent than the control compound SAHA. Moreover, they are several folds more selectively toxic to either strains of P. falciparum compared to SAHA.

The antimalarial activities of these macrocyclic HDACi followed a similar trend as their anti-HDAC activity against HDAC1/2 from HeLa nuclear extract, suggesting that parasite HDACs could be an intracellular target of the these compounds.

Compounds 5 and 9 exhibited modest activity against the promastigote stage of L. donovani. A comparison of the antileishmanial activities of compounds 13 and 14, analogs with n=8, revealed a disparity between the activity of 14- and 15-membered macrocyclic rings. 14-Membered compound 13 is 5- to 6-fold more potent than its 15-membered congener 14. However, this disparity dissipates after a single methylene group extension (n=9), as compounds 15 and 16 have virtually indistinguishable antileishmanial activities. Comparatively, compounds 13, 15 and 16, analogs with the most potent antileishmanial activities, are about 7- to 10-fold more potent than SAHA and approximately 3-fold less potent than pentamidine.

Since these non-peptide macrocyclic HDACi have nanomolar anti-HDAC activities, the observed disparity in the trend of their antimalarial and antileishmanial activities may have implication in the organization of the active sites of the relevant P. falciparum and L. donovani HDAC isozymes. These observations provide additional evidence of the suitability of HDAC inhibition as a viable therapeutic option to curb infections caused by apicomplexan protozoans and trypanosomatids (1, 5, 6, 14) and could facilitate the identification of other HDACi that are more selective for either parasite.

The formulations contain an effective amount of one or more HDAC inhibitors. The doses in which the HDAC inhibitors and their salts, prodrugs, or solvates can be administered may vary widely depending on the condition of the patient and the symptoms to be treated. One of ordinary skill in the art can readily determine the necessary dosage based on the condition of the patient and the disease to be treated.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Materials

"Preparative TLC" or "prep TLC" refers to preparative thin layer chromatography and was performed on Analtech preparative TLC plates (UV 254, 2000 μm), unless otherwise stated. "Column chromatography" or "flash column chromatography" was performed with 200-400 Mesh silica gel, unless otherwise noted.

Nuclear magnetic resonance (NMR) spectra were recorded on a Varian-Gemini 400 magnetic resonance spectrometer. $^1$H NMR spectra were recorded in parts per million (ppm) relative to the peak of $CDCl_3$, (7.24 ppm), $CD_3OD$ (3.31 ppm), or DMSO-$d_6$ (2.49 ppm). $^{13}$C spectra were recorded relative to the central peak of the $CDCl_3$ triplet (77.0 ppm), $CD_3OD$ (49.0 ppm), or the DMSO-$d_6$ septet (39.7 ppm), and were recorded with complete hetero-decoupling.

Common reaction solvents were either high performance liquid chromatography (HPLC) grade or American Chemical Society (ACS) grade, and used without further purification. Anhydrous solvents and other reagents were purchased and used without further purification.

Fluor de Lys™ is a fluorescence based HDAC activity assay comprising a combination of fluorogenic Histone deAcetylase Lysyl substrate and a developer. The kit is a highly sensitive and convenient alternative to radiolabeled, acetylated histones or peptide/HPLC methods for the assay of histone deacetylases. This assay is based on the ability of HeLa nuclear extract, which is enriched in HDAC activity, to mediate the deacetylation of the acetylated lysine side chain of the Fluor de Lys substrate. The assay procedure requires two steps. First, incubation of the HeLa nuclear extract with the Fluor de Lys substrate results in substrate deacetylation and thus sensitizes it to the second step. In the second step, treatment of the deacetylated substrate with the Fluor de Lys developer produces a fluorophore. The substrate-developer reaction, under normal circumstances goes to completion in less than 1 min at 25° C. The kit used was the Fluorimetric Assay/Drug Discovery Kit—AK-500 Manual Fluorescent Assay System available from BIOMOL® International, Plymouth Meeting, Pa.

The numbers used to identify the compounds described in the examples correspond to the references numbers in Table 3 and/or reaction schemes 10-15.

Example 1

Synthesis of Compounds 7-14 and 23-30 in Table 3

Synthesis of Azithromycin-N-phenylacetylene (3)

To a solution of N-demethylated azithromycin 1 (2.0 g, 2.56 mmol) in anhydrous DMSO (30 ml) was added Hunig's base (4 ml) and 4-ethynylbenzyl methanesulfonate 2 (0.760 g, 3.60 mmol). The reaction mixture was heated with stirring under argon at 85° C. for 2.5 h. The reaction was cooled and diluted with ethyl acetate (EtOAc, 100 mL) and washed with saturated $NaHCO_3$ (3×60 mL) and saturated brine (60 mL). The organic layer was dried over $Na_2SO_4$ and concentrated in vacuo. The crude product was purified by flash chromatography (silica, 12:1:0.05 $CH_2Cl_2$/MeOH/conc. $NH_4OH$) to give 1.2 g (52%) of 3 as a brownish white solid. $^1$H-NMR ($CDCl_3$, 400 MHz) δ 0.84 (m), 0.97 (d, J=7.6 Hz), 1.04 (m), 1.12-1.32 (m), 1.36-1.53 (m), 1.66-1.75 (m), 1.81-2.07 (m), 2.19 (s), 2.25-2.29 (m), 2.48 (m), 2.63-2.73 (m), 2.89 (bs), 2.96 (1, J=9.8 Hz), 3.02 (s), 3.08 (s), 3.27-3.32 (m), 3.38-3.45 (m), 3.56 (d, J=6.8 Hz), 3.63 (s), 3.72 (d, J=13.2 Hz), 3.97 (m), 4.19 (m), 4.36 (d, J=7.2 Hz), 4.63 (d, J=10 Hz), 5.04 (d, J=4.4 Hz), 7.21 (d, J=8 Hz), 7.39 (d, J=8 Hz); $^{13}$C-NMR ($CDCl_3$, 100 MHz) δ 7.5, 9.2, 11.3, 14.9, 16.3, 18.3, 21.3, 21.4, 21.6, 22.0, 26.8, 27.6, 29.6, 34.7, 36.3, 36.9, 42.0, 42.3, 45.2, 49.2, 57.7, 62.3, 63.7, 65.4, 68.5, 70.0, 70.6, 72.7, 73.5, 73.8, 74.2, 77.1, 77.9, 78.0, 83.4, 83.7, 94.5, 102.6, 120.8, 128.5, 132.0, 139.6, 178.3; HRMS (FAB, mnba) calc for $[C_{46}H_{76}N_2O_{12}+H]^+$ 849.5476. found 849.5411.

Synthesis of Azithromycin-arylalkyltriazolyl methyl ester (17)

Azithromycin-N-phenylacetylene 3 (0.045 g, 0.053 mmol) and azido-ester 16 (0.014 g, 0.080 mmol) were dissolved in anhydrous THF (5 mL) and stirred under argon at room temperature. Copper (I) iodide (0.010 g, 0.053 mmol), and Hunig's base (0.05 mL) were then added to the reaction mixture, and stirring continued for 12 h. The reaction mixture was diluted with $CH_2Cl_2$ (30 mL) and washed with 1:4 $NH_4OH$/saturated $NH_4Cl$ (3×25 mL) and again with saturated $NH_4Cl$ (25 mL). The organic layer was dried over $Na_2SO_4$ and concentrated under vacuum. The crude product was purified by preparative TLC, eluting with Hexane/EtOAc/$Et_3N$ 3:2:0.1 to give 50 mg (92%) of 17 as a white-brown solid. $^1$H-NMR ($CDCl_3$, 400 MHz) δ 0.82-0.90 (m), 0.98 (d, J=7.6 Hz), 1.05-1.13 (m), 1.19-1.23 (m), 1.25-1.30 (m), 1.40-1.52 (m), 1.60-1.74 (m), 1.80-1.96 (m), 2.00-2.06 (m), 2.22-2.37 (m), 2.56 (m), 2.67 (m), 2.95 (t, J=9.8 Hz), 3.07 (s), 3.29-3.34 (m), 3.46 (bs), 3.54 (d, J=6.8 Hz), 3.61 (s), 3.68 (bs), 3.77 (m), 3.97 (m), 4.18 (m), 4.34-4.38 (m), 4.69 (m), 5.06 (d, J=4 Hz), 7.32 (d, J=6.4 Hz), 7.73-7.75 (m); $^{13}$C-NMR ($CDCl_3$, 100 MHz) δ 8.7, 9.2, 11.3, 14.2, 14.7, 16.5, 18.2, 21.4, 21.5, 22.2, 24.2, 25.9, 26.6, 27.3, 29.7, 30.0, 33.6, 34.6, 36.4, 36.9, 42.4, 45.3, 45.8, 49.3, 50.0, 51.5, 57.7, 63.9, 65.5, 68.6, 69.4, 70.5, 72.7, 73.8, 74.2, 77.2, 77.6, 78.0, 83.4, 94.4, 102.7, 119.3, 125.5, 129.1, 129.4, 147.2, 173.4, 178.1. MS (FAB, mnba) 1020.3 $(M+H)^+$.

Synthesis of Descladinoseazithromycin-arylalkyltriazolyl methyl ester (18)

A mixture of compound 3 (0.12 g, 0.14 mmol) in 0.25 N HCl (15 mL) was stirred at room temperature for 20 h and poured into EtOAc (20 mL). The two layers were separated and the aqueous layer was washed with EtOAc (2×20 mL), basified with concentrated $NH_4OH$ and then extracted with 5% MeOH in $CH_2Cl_2$ (2×30 mL). The combined organic layer was washed with saturated brine (30 mL) and dried over $Na_2SO_4$. Solvent was evaporated off to give 89 mg (91%) of descladinose compound 4 as a white solid. $^1$H-NMR ($CDCl_3$, 400 MHz) δ 0.81-0.87 (m), 0.90-1.07 (m), 1.17-1.27 (m), 1.31-1.59 (m), 1.68-1.71 (m), 1.80-1.87 (m), 1.99-2.03 (m), 2.08 (s), 2.23-2.27 (m), 2.31 (s), 2.44-2.48 (m), 2.59-2.73 (m), 3.32-3.39 (m), 3.48-3.53 (m), 3.60-3.65 (m), 3.73 (d, J=9.6 Hz), 3.84-3.91 (m), 4.43 (d, J=7.2 Hz), 4.69-4.72 (m), 7.16 (d, J=8.0 Hz), 7.39 (d, J=8.4 Hz); $^{13}$C NMR (CDCl$_3$, 100 MHz) δ 7.7, 7.9, 10.9, 14.2, 16.1, 20.9, 21.1, 21.2, 25.9, 26.6, 29.3, 36.0, 36.4, 37.1, 42.1, 44.5, 57.6, 60.3, 62.5, 65.3, 69.9, 70.5, 70.9, 73.0, 74.1, 75.4, 77.2, 79.5, 83.3, 94.9, 106.5, 120.8, 128.3, 132.0, 139.3, 177.2. MS (FAB, mnba) 691.2 (M+H)$^+$.

The descladinose compound 4 (0.080 g, 0.115 mmol) and azido-ester 16 (0.030 g, 0.173 mmol) were dissolved in anhydrous THF (5 mL) and stirred under argon at room temperature. Copper (I) iodide (0.010 g, 0.053 mmol), and Hunig's base (0.05 mL) were then added to the reaction mixture, and stirring continued for 12 h. The reaction mixture was diluted with CH$_2$Cl$_2$ (30 mL) and washed with 1:4 NH$_4$OH/saturated NH$_4$Cl (3×25 mL) and again with saturated NH$_4$Cl (25 mL). The organic layer was dried over Na$_2$SO$_4$ and concentrated in vacuo. The crude product was purified by preparative TLC, eluting with Hexane/EtOAc/Et$_3$N 3:2:0.1 to give 65 mg (65%) of 18 as a white-brown solid. $^1$H-NMR (CDCl$_3$, 400 MHz) δ 0.79-0.86 (m), 1.00-1.07 (m), 1.17-1.35 (m), 1.42-1.51 (m), 1.55-1.72 (m), 1.80-1.94 (m), 2.00-2.05 (m), 2.1 (s), 2.23-2.27 (m), 2.33 (s), 2.47 (d, J=10.4 Hz), 2.58-2.72 (m), 3.32-3.41 (m), 3.52-3.73 (m), 3.92-4.00 (m), 4.34 (t, J=7.0 Hz), 4.41 (d, J=7.6 Hz), 4.69 (d, J=10.8 Hz), 7.24 (d, J=8.4 Hz), 7.71 (d, J=8 Hz), 7.73 (s); $^{13}$C NMR (CDCl$_3$, 100 MHz) δ 7.7, 7.9, 8.7, 10.9, 16.1, 16.1, 20.9, 21.2, 24.2, 25.8, 25.9, 26.6, 29.2, 29.6, 30.0, 33.6, 36.0, 36.3, 37.1, 42.0, 44.5, 45.8, 50.0, 51.5, 57.7, 62.6, 65.1, 69.9, 70.4, 73.1, 74.1, 75.3, 79.4, 94.8, 106.4, 119.3, 125.5, 128.9, 129.6, 138.2, 147.1, 173.4, 177.2. MS (FAB, mnba) 862.2 (M+H)$^+$.

Synthesis of Azithromycin-N-phenyltriazolylhexahydroxamic acid (7)

Method A

To a solution of compound 17 (0.04 g, 0.04 mmol) in 1:1 THF/MeOH (3 mL) was added hydroxylamine (50% in H$_2$O) (0.03 mL, 0.54 mmol) and a catalytic amount of KCN. The mixture was stirred at room temperature for 24 h. The reaction was partitioned between 5% MeOH in CH$_2$Cl$_2$ (30 mL) and saturated sodium bicarbonate (25 mL), the two layers were separated and the aqueous layer was extracted with 5% MeOH in CH$_2$Cl$_2$ (2×20 mL). The combined organic layer was washed with saturated brine (40 mL) and dried over Na$_2$SO$_4$. Solvent was evaporated off and the crude was purified by preparative TLC, eluting with CH$_2$Cl$_2$/MeOH/NH4OH 10:1:0.1 to give compound 7 (6.5 mg, 16%) as brown-white solid.

Method B

Azithromycin-N-phenylacetylene 3 (0.100 g, 0.109 mmol) and 6-azidohexahydroxamic acid 15a (0.081 g, 0.117 mmol) were dissolved in anhydrous THF (5 mL) and stirred under argon at room temperature. Copper (I) iodide (0.011 g, 0.07 mmol) and Hunig's base (0.5 mL) were then added to the reaction mixture, and stirring continued for 4 h. The reaction mixture was diluted with CH$_2$Cl$_2$ (40 mL) and washed with 1:4 NH$_4$OH/saturated NH$_4$Cl (3×30 mL) and saturated NH$_4$Cl (30 mL). The organic layer was dried over Na$_2$SO$_4$ and concentrated in vacuo. The crude product was purified by prep TLC (silica, 12:1:0.1 CH$_2$Cl$_2$/conc. NH$_4$OH) to give 71 mg (59%) of 7 as a brownish white solid.

Method C

Azithromycin-N-phenylacetylene 3 (0.045 g, 0.050 mmol) and 6-azido-O-silyl hexahydroxamate 6 (0.060 g, 0.146 mmol) were dissolved in anhydrous THF (5 mL) and stirred under argon at room temperature (Note: compound 6 was prepared from the corresponding azido carboxylic acid, t-BuPh$_2$SiCl and NaH, according to the procedure described by Muri et al. ORG. LETT (2000) 2: 539). Copper (I) iodide (0.010 g, 0.05 mmol), Hunig's base (0.5 mL) and tris[(1-benzyl-1H-1,2,3-triazol-4-yl)methyl]amine, (TBTA) (0.016 g, 0.030 mmol) were then added to the reaction mixture, and stirring continued for 2 h (Note: TBTA was synthesized according to Chen et al. *Org. Lett.*, (2004) 6: 2853). The reaction mixture was diluted with CH$_2$Cl$_2$ (40 mL) and washed with 1:4 NH$_4$OH/saturated NH$_4$Cl (2×30 mL) and saturated NH$_4$Cl (30 mL). The organic layer was dried over Na$_2$SO$_4$ and concentrated in vacuo. The crude product was purified by prep TLC (silica, 12:1:0.1 CH$_2$Cl$_2$/MeOH/conc. NH$_4$OH) to give 38 mg (60%) of silyl protected compound 6 as a brownish white solid. $^1$H-NMR (CDCl$_3$, 400 MHz) δ 0.82-0.92 (m), 1.00-1.14 (m), 1.17-1.27 (m), 1.30-1.32 (m), 1.35-1.59 (m), 1.73-1.92 (m), 2.01-2.15 (m), 2.24-2.32 (m), 2.36 (br s), 2.56 (d, J=10.4 Hz), 2.69 (m), 2.98 (d, J=10 Hz), 3.07-3.09 (m), 3.32-3.36 (In), 3.42-3.46 (m), 3.55-3.63 (m), 3.66 (s), 3.78 (d, J=13.2 Hz), 4.01 (m), 4.15-4.25 (m), 4.40 (d, J=6.8 Hz), 4.63 (d, J=7.2 Hz), 4.69 (s), 5.10 (d, J=4.4 Hz), 7.31-7.43 (m), 7.65-7.75 (m).

To a solution of silyl protected compound 6 (0.025 g, 0.02 mmol) in THF (1 mL) was added 1 M TBAF in THF (0.030 mL, 0.030 mmol) and the mixture was stirred at room temperature for 2 h during which TLC revealed a near quantitative conversion to a lower Rf product. The reaction was partitioned between CH$_2$Cl$_2$ (30 mL) and saturated NH$_4$Cl (25 mL), the two layers were separated and the organic layer dried over Na$_2$SO$_4$ and concentrated in vacuo. The crude product was purified by prep TLC (silica, 12:1:0.1 CH$_2$Cl$_2$/MeOH/Et$_3$N) to give 15 mg (73%) of 7 as a brownish white solid.

$^1$H-NMR (Acetone-d6, 400 MHz) δ 0.83-0.92 (m), 1.02 (d, J=7.6 Hz), 1.08-1.11 (m), 1.14 (d, J=7.6 Hz), 1.18 (d, J=6 Hz), 1.24-1.29 (m), 1.33-1.47 (m), 1.54 (dd, J=4.8 Hz, 15.2 Hz), 1.66 (m), 1.80-2.01 (m), 2.06-2.12 (m), 2.18-2.24 (m), 2.26 (s), 2.28-2.31 (m), 2.35-2.41 (m), 2.51 (d, J=10 Hz), 2.65-2.96 (m), 3.12 (s), 3.22-3.29 (m), 3.41-3.47 (m), 3.54-3.69 (m), 3.81 (d, J=13.2 Hz), 4.11 (m), 4.24 (m), 4.45 (t, J=7.0 Hz), 4.50 (d, J=6.8 Hz), 4.75 (d, J=7.2 Hz), 4.97 (d, J=5.2 Hz), 7.42 (d, J=8.0 Hz), 7.84 (d, J=8.0 Hz), 8.35 (s). MS (FAB, mnba) 1021.2 (M+H)$^+$.

Synthesis of Descladinose-Azithromycin-N-phenyltriazolylhexahydroxamic acid (8)

Method A

To a solution of compound 18 (0.04 g, 0.05 mmol) in 1:1 THF/MeOH (3 mL) was added hydroxylamine (50% in H$_2$O) (0.04 mL, 0.54 mmol) and a catalytic amount of KCN. The mixture was stirred at room temperature for 24 h. The reaction was partitioned between 5% MeOH in CH$_2$Cl$_2$ (30 mL) and saturated sodium bicarbonate (25 mL), the two layers were separated and the aqueous layer was extracted with 5% MeOH in CH$_2$Cl$_2$ (2×20 mL). The combined organic layer was washed with saturated brine (40 mL) and dried over Na$_2$SO$_4$. Solvent was evaporated off and the crude was purified by preparative TLC, eluting with CH$_2$Cl$_2$/MeOH/NH4OH 10:1:0.1 to give compound 8 (9.0 mg, 23%) as brown-white solid.

Method B

Reaction of descladinose-azithromycin-N-phenylacetylene 4 (0.134 g, 0.188 mmol) and 6-azidohexahydroxamic acid 15a (0.130 g, 0.755 mmol) within 8 h (according to the protocols of Method B described for the synthesis of compound 7 above), followed by prep TLC (silica, 10:1:0.1 CH$_2$Cl$_2$/MeOH/conc. NH$_4$OH) gave 73 mg (43%) of 8 as a brownish white solid.

$^1$H-NMR (Acetone-d6, 400 MHz) δ 0.82-0.90 (m), 1.02 (d, J=7.2 Hz), 1.07 (s), 1.09 (d, J=6.8 Hz), 1.18-1.23 (m), 1.28 (bs), 1.31-1.39 (m), 1.46-1.56 (m), 1.65 (m), 1.81-1.83 (m), 1.87-1.99 (m), 2.05-2.11 (m), 2.18-2.21 (m), 2.18-2.21 (m), 2.24 (s), 2.25-2.29 (m), 2.35 (s), 4.47 (d, J=9.2 Hz), 2.61-2.67 (m), 2.70-2.77 (m), 3.30-3.34 (m), 3.41 (m), 3.52-3.65 (m), 2.81 (d, J=13.2 Hz), 4.44 (t, J=7.0 Hz), 4.59 (d, J=7.6 Hz), 4.87 (dd, J=1.8 Hz, 11.0 Hz), 7.43 (d, J=8.4 Hz), 7.83 (d, J=8.4 Hz), 8.34 (m); HMRS (ESI) calcd for [C$_{44}$H$_{74}$N$_6$O$_{11}$+H]$^+$ 863.5488. found 863.5528.

Accordingly, compounds 9-14 and 23-30 (in this section) were synthesized according to the protocols of Method B described for the synthesis of compound 7 above.

Synthesis of Azithromycin-N-phenyltriazolylheptahydroxamic acid (9)

Reaction of azithromycin-N-phenylacetylene 3 (0.134 g, 0.158 mmol) and 7-azidoheptahydroxamic acid 15b (0.125 g, 0.672 mmol) within 4 h, followed by prep TLC (silica, 12:1: 0.1 CH$_2$Cl$_2$/MeOH/conc. NH$_4$OH) gave 93 mg (56%) of 9 as a brownish white solid. $^1$H-NMR (CDCl$_3$, 400 MHz) δ 0.81-1.51 (m), 1.54-1.65 (m), 1.70-2.14 (m), 2.20-2.38 (m), 2.46-2.56 (m), 2.60-2.70 (m), 3.00 (s), 3.31 (t, J=8.8 Hz), 3.38-3.54 (m), 3.60 (s), 3.78 (d, J=12.8 Hz), 3.98-4.20 (m), 4.36 (d, J=7.2 Hz), 4.49 (d, J=7.2 Hz), 5.11 (d, J=4.0 Hz), 7.32 (d, J=7.6 Hz), 7.73 (s), 7.75 (d, J=7.6 Hz); $^{13}$C NMR (CDCl$_3$, 100 MHz) δ 6.6, 8.8, 11.5, 14.4, 16.6, 17.7, 21.3, 21.6, 21.8, 25.1, 26.0, 26.7, 27.1, 28.2, 29.2, 29.6, 30.0, 33.1, 34.5, 35.7, 36.7, 41.8, 42.7, 45.3, 49.3, 50.3, 50.7, 57.9, 62.7, 63.0, 65.8, 68.6, 69.4, 70.4, 72.6, 73.2, 73.8, 77.8, 78.1, 78.2, 83.5, 94.4, 102.8, 119.3, 125.7, 129.4, 129.7, 138.4, 147.4, 171.3, 178.4; HMRS (ESI) calcd for [C$_{53}$H$_{90}$N$_6$O$_{14}$+H]$^+$ 1035.6587. found 1035.6628.

Synthesis of Descladinose-Azithromycin-N-phenyl-triazolylheptahydroxamic acid (10)

Reaction of descladinose-azithromycin-N-phenylacetylene 4 (0.130 g, 0.188 mmol) and 7-azidoheptahydroxamic acid 15b (0.130 g, 0.755 mmol) within 8 h, followed by prep TLC (silica, 10:1:0.1 CH$_2$Cl$_2$/MeOH/conc. NH$_4$OH) gave 78 mg (47%) of 10 as a brownish white solid. $^1$H-NMR (CDCl$_3$, 400 MHz) δ 0.66-2.32 (m), 2.47 (d, J=10.8 Hz), 2.63-2.70 (m), 3.34-3.51 (m), 3.62-3.69 (m), 4.20-4.40 (m), 4.74 (br s), 7.26 (br s), 7.73 (br s); $^{13}$C NMR (CDCl$_3$, 100 MHz) δ 7.4, 7.9, 10.7, 16.0, 16.1, 20.9, 21.1, 25.0, 25.7, 26.5, 28.0, 28.9, 29.8, 35.8, 36.3, 36.9, 42.0, 44.4, 50.1, 57.9, 62.7, 63.9, 69.9, 70.4, 70.8, 73.3, 74.1, 75.2, 79.5, 94.9, 106.6, 119.7, 125.7, 129.2, 129.6, 138.4, 147.3, 177.5; HMRS (ESI) calcd for [C$_{45}$H$_{76}$N$_6$O$_{11}$+H]$^+$ 877.5645. found 877.5665.

Synthesis of Azithromycin-N-phenyltriazolyloctahydroxamic acid (11)

Reaction of azithromycin-N-phenylacetylene 3 (0.10 g, 0.120 mmol) and 8-azidooctahydroxamic acid 15c (0.047 g, 0.24 mmol) within 2.5 h, followed by prep TLC (silica, 12:1: 0.1 CH$_2$Cl$_2$/MeOH/conc. NH$_4$OH) gave 72 mg (58%) of 11 as a brownish white solid. $^1$H NMR (CDCl$_3$, 400 MHz) δ 0.85 (t, J=4.0 Hz), 0.87-1.22 (m), 1.29 (s), 1.30-2.28 (m), 2.29 (s), 2.30-3.00 (m), 3.10 (s), 3.20-3.79 (m), 3.99-4.03 (m), 4.35-4.40 (m), 4.65 (d, J=8.0 Hz), 5.11 (d, J=4.8 Hz), 7.34 (d, J=8.0 Hz), 7.72 (s), 7.77 (d, J=8.0 Hz); $^{13}$C NMR (DMSO-d$_6$, 400 MHz) δ 7.5, 9.8, 11.6, 15.4, 18.2, 19.1, 21.5, 22.1, 22.7, 25.6, 26.3, 26.6, 28.7, 29.0, 29.6, 30.2, 32.0, 32.8, 35.2, 36.4, 37.2, 42.2, 45.3, 49.2, 50.1, 58.3, 63.2, 65.4, 67.7, 70.8, 73.3, 74.2, 77.0, 78.4, 83.4, 102.8, 121.6, 125.6, 129.7, 130.0, 135.0, 147.0, 177.8; HRMS (FAB, thioglycerol) calc for [C$_{54}$H$_{92}$N$_6$O$_{14}$+H]$^+$ 1049.6749. found 1049.6648.

Synthesis of Descladinose-Azithromycin-N-phenyl-triazolyloctahydroxamic acid (12)

Reaction of azithromycin-N-phenylacetylene 4 (0.10 g, 0.144 mmol) and 8-azidooctahydroxamic acid 15c (0.049 g, 0.246 mmol) within 2.5 h, followed by prep TLC (silica, 10:1:0.1 CH$_2$Cl$_2$/MeOH/conc. NH$_4$OH) gave 94 mg (73%) of 12 as a brownish white solid. HRMS (FAB, thioglycerol) calc for [C$_{46}$H$_{79}$N$_6$O$_{11}$+H]$^+$ 891.5806. found 891.5910.

Synthesis of Azithromycin-N-phenyltriazolylnonahydroxamic acid (13)

Reaction of azithromycin-N-phenylacetylene 3 (0.10 g, 0.120 mmol) and 9-azidononahydroxamic acid 15d (0.043 g, 0.20 mmol) within 2.5 h, followed by prep TLC (silica, 12:1: 0.1 CH$_2$Cl$_2$/MeOH/conc. NH$_4$OH) gave 64 mg (51%) of 13 as a brownish white solid. $^1$H NMR (CDCl$_3$, 400 MHz) δ 0.84-1.30 (m), 1.33-2.26 (m), 2.30 (s), 2.38-2.68 (m), 2.99 (s), 3.32-3.84 (m), 4.03-4.08 (m), 4.35-4.41 (m), 4.53 (d, J=8.0 Hz), 5.13 (d, J=4.0 Hz), 7.35 (d, J=8.0 Hz), 7.75 (s), 7.78 (d, J=8.0 Hz); $^{13}$C NMR (DMSO-d$_6$, 400 MHz) δ 6.9, 9.0, 11.6, 14.7, 16.9, 18.0, 21.6, 21.8, 22.1, 25.6, 26.4, 26.9, 27.3, 28.8, 29.0, 29.1, 29.5, 29.9, 30.4, 34.8, 36.0, 37.0, 42.1, 43.0, 45.6, 49.5, 50.5, 58.1, 63.5, 66.1, 68.8, 70.7, 72.9, 74.1, 78.1, 78.3, 78.5, 83.7, 94.4, 94.7, 103.1, 119.6, 126.0, 129.7, 130.0, 147.6, 178.7; LRMS (MALDI) calc for [C$_{55}$H$_{94}$N$_6$O$_{14}$+H]$^+$ 1063.6. found 1063.7.

Synthesis of Azithromycin-N-phenyltriazolyldecahydroxamic acid (14)

Reaction of azithromycin-N-phenylacetylene 3 (0.10 g, 0.120 mmol) and 10-azido-decahydroxamic acid 15e (0.045 g, 0.20 mmol) within 4.5 h, followed by prep TLC (silica, 12:1:0.1 CH$_2$Cl$_2$/MeOH/conc. NH$_4$OH) gave 70 mg (56%) of 14 as a brownish white solid. $^1$H NMR (CDCl$_3$, 400 MHz) δ 0.85-1.36 (m), 1.41-2.24 (m), 2.28, 2.36 (s), 2.33-3.10 (m), 3.05 (s), 3.23-3.82 (m), 4.06-4.10 (m), 4.36-4.41 (m), 4.49 (d, J=8.0 Hz), 5.15 (d, J=4.0 Hz), 7.34 (d, J=8 Hz), 7.75 (s), 7.78 (d, J=8.0 Hz); $^{13}$C NMR (DMSO-d$_6$, 400 MHz) δ 6.7, 9.0, 11.7, 14.6, 16.9, 17.9, 21.6, 21.9, 22.0, 25.6, 26.4, 26.8, 27.0, 27.3, 28.8, 29.0, 21.9, 29.3, 29.5, 29.9, 30.3, 33.6, 34.9, 35.8, 37.0, 42.1, 43.0, 45.6, 49.6, 50.6, 51.6, 58.0, 62.8, 63.9, 66.2, 68.9, 69.6, 70.7, 72.9, 73.5, 74.0, 74.1, 78.2, 78.6, 83.6, 94.6, 103.0, 119.6, 126.0, 129.6, 129.9, 138.9, 147.6, 178.6; HRMS (MALDI) calc for [C$_{56}$H$_{96}$N$_6$O$_{14}$+H]$^+$ 1077.7057. found 1077.6971.

Synthesis of Clarithromycin-N-phenylacetylene (20)

To a solution of N-demethylated clarithromycin 19 (2.40 g, 3.34 mmol) in anhydrous DMSO (30 ml) was added Hunig's base (3 ml) and 4-ethynylbenzyl methanesulfonate 2 (0.920 g, 4.34 mmol). The reaction mixture was then heated with stirring under argon at 85° C. for 2.5 h. The reaction was cooled and diluted with EtOAc (100 mL) and washed with saturated NaHCO$_3$ (3×60 mL) and saturated brine (60 mL). The organic layer was dried over Na$_2$SO$_4$ and concentrated in vacuo. The crude product was purified by flash chromatography (silica, gradient 12:1; 10:1; 8:1; CH$_2$Cl$_2$/acetone) to give 1.8 g (63%) of 20 as a brownish white solid. $^1$H-NMR (CDCl$_3$, 400 MHz) δ 0.82 (t, J=7.2 Hz), 1.03-1.28 (m), 1.37 (s), 1.40-1.55 (m), 1.65-1.90 (m), 2.03 (d, J=10.0 Hz), 2.22 (s), 2.30 (d, J=15.2 Hz), 2.40-2.60 (m), 2.80-2.90 (m), 2.94-3.00 (m), 3.04 (s), 3.09 (s), 3.16 (s), 3.24-3.29 (m), 3.38-3.46 (m), 3.59 (d, J=6.8 Hz), 3.70-3.75 (m), 3.88-3.95 (m), 4.37 (d, J=7.2 Hz), 4.88 (d, J=4.4 Hz), 5.02 (dd, J=11.6, 2.4 Hz), 7.23 (d, J=12.0 Hz), 7.42 (d, J=8.0 Hz); $^{13}$C NMR (CDCl$_3$, 100 MHz) δ 9.2, 10.7, 12.4, 16.1, 18.1, 18.7, 19.9, 21.1, 21.5, 29.3, 32.4, 34.8, 36.9, 37.2, 39.2, 45.0, 45.2, 49.3, 50.6, 53.4, 57.6, 63.3, 65.6, 68.5, 69.0, 70.6, 72.5, 74.2, 76.5, 77.8, 78.1, 78.2, 80.8, 95.8, 102.5, 120.9, 128.6, 132.0, 133.5, 139.4, 175.4; HRMS (ESI) calc for [C$_{46}$H$_{73}$NO$_{13}$+H]$^+$ 848.5155. found 848.5181.

Synthesis of Descladinose-Clarithromycin-N-phenylacetylene (21)

To a solution of clarithromycin-N-phenylacetylene 20 (0.500 g, mmol) in ethanol (20 mL) was added 1N HCl (20 mL), and stirring continued for 22 h at room temperature. The reaction mixture was basified with concentrated NH$_4$OH to about pH=9. The reaction mixture was diluted with distilled water (40 mL) and extracted with EtOAc (3×60 mL). The combined organic layers were washed with saturated brine (40 mL), dried over Na$_2$SO$_4$, and concentrated in wino. The crude product was purified by flash chromatography (silica, 8:1 CH$_2$Cl$_2$/acetone) to give 320 mg (79%) of 21 as a brownish white solid. $^1$H-NMR (CDCl$_3$, 400 MHz) δ 0.82 (t, J=7.6 Hz), 1.09-1.28 (m), 1.34 (s), 1.40-1.55 (m), 1.70-1.74 (m), 1.87-1.94 (m), 2.08-2.15 (m), 2.54-2.66 (m), 2.94-2.98 (m), 3.05 (s), 3.25 (s), 3.31-3.42 (m), 3.48-3.56 (m), 3.66 (d, J=10.0 Hz), 3.82 (s), 3.90 (s), 4.35 (d, J=7.6 Hz), 5.14 (dd, J=10.8, 2.0 Hz), 7.18 (d, J=8.0 Hz), 7.42 (d, J=8.4 Hz); $^{13}$C NMR (CDCl$_3$, 100 MHz) δ 8.4, 10.5, 12.7, 15.3, 16.3, 17.8, 18.8, 21.4, 29.2, 35.9, 36.6, 37.5, 38.7, 44.5, 45.5, 49.6, 57.8, 65.0, 69.7, 70.1, 70.6, 74.1, 77.9, 78.9, 83.3, 88.5, 106.5, 121.0, 128.4, 132.1, 139.1, 174.7; HRMS (ESI) calc for [C$_{38}$H$_{59}$NO$_{10}$+H]$^+$ 690.4212. found 690.4259.

Synthesis of Clarithromycin-N-phenyltriazolylhexahydroxamic acid (23)

Reaction of clarithromycin-N-phenylacetylene 20 (0.100 g, 0.120 mmol) and 6-azidohexahydroxamic acid 15a (0.080 g, 0.470 mmol) within 2.5 h, followed by prep TLC (silica, 12:1:0.1 CH$_2$Cl$_2$/MeOH/conc. NH$_4$OH) gave 70 mg (58%) of 23 as a brownish white solid. $^1$H-NMR (CDCl$_3$, 400 MHz) δ 0.81 (t, J=7.6 Hz), 1.03-1.52 (m), 1.62-1.92 (m) 2.04-2.29 (m), 2.48-2.60 (m), 2.82-2.90 (m), 2.93-2.99 (m), 3.09 (s), 3.19 (s), 3.28-3.33 (m), 3.42-3.46 (m), 3.60 (d, J=7.6 Hz), 3.70-3.80 (m), 3.90-3.98 (m), 4.37-4.40 (m), 4.87 (d, J=4.8 Hz), 5.03 (dd, J=11.6, 2.4 Hz), 7.34 (d, J=7.6 Hz), 7.77 (d, J=7.6 Hz), 7.82 (s); $^{13}$C NMR (CDCl$_3$, 100 MHz) δ 9.1, 10.5, 12.2, 15.9, 17.9, 18.5, 19.7, 20.9, 21.2, 21.4, 24.3, 25.5, 29.4, 29.6, 34.7, 36.8, 37.1, 39.0, 39.1, 45.0, 45.1, 49.3, 49.9, 50.5, 53.3, 57.5, 63.6, 65.5, 68.5, 69.0, 70.7, 72.4, 74.2, 77.8, 78.2, 80.9, 95.9, 102.6, 119.8, 125.6, 129.4, 147.4, 175.8; HMRS (ESI) calcd for [C$_{52}$H$_{85}$N$_5$O$_{15}$+H]$^+$ 1020.6114. found 1020.6121.

Synthesis of Descladinose-Clarithromycin-N-phenyltriazolylhexahydroxamic acid (24)

Reaction of descladinose-clarithromycin-N-phenylacetylene 21 (0.075 g, 0.109 mmol) and 6-azidohexahydroxamic acid 15a (0.040 g, 0.233 mmol) within 4 h, followed by prep TLC (silica, 10:1:0.1 CH$_2$Cl$_2$/MeOH/conc. NH$_4$OH) gave 47 mg (51%) of 24 as a brownish white solid. $^1$H-NMR (CDCl$_3$, 400 MHz) δ 0.79 (t, J=7.2 Hz), 1.08-1.32 (m), 1.39-1.64 (m), 1.71-1.81 (m), 1.82-1.96 (m), 2.04-2.18 (m), 2.51-2.70 (m), 2.92-2.98 (m), 3.18-3.38 (m), 3.45-3.55 (m), 3.60-3.74 (m), 3.81 (s), 3.90 (s), 4.33 (br s), 5.13 (d, J=10.4 Hz), 7.29 (br s), 7.74 (br s); $^{13}$C NMR (CDCl$_3$, 100 MHz) δ 8.6, 10.7, 12.9, 15.5, 16.4, 18.0, 19.0, 21.5, 21.6, 29.5, 29.9, 36.1, 36.7, 37.7, 39.0, 44.7, 45.7, 49.8, 50.3, 58.2, 64.6, 70.0, 70.3, 70.9, 74.4, 78.3, 79.1, 88.5, 106.7, 120.3, 126.1, 129.6, 129.9, 147.7, 175.4; HMRS (ESI) calcd for [C$_{44}$H$_{71}$N$_5$O$_{12}$+H]$^+$ 862.5172. found 862.5155.

Synthesis of Clarithromycin-N-phenyltriazolylheptahydroxamic acid (25)

Reaction of clarithromycin-N-phenylacetylene 20 (0.130 g, 0.153 mmol) and 7-azidoheptahydroxamic acid 15b (0.105 g, 0.565 mmol) within 2.5 h, followed by prep TLC (silica, 12:1:0.1 CH$_2$Cl$_2$/MeOH/conc. NH$_4$OH) gave 105 mg (67%) of 25 as yellowish solid. $^1$H-NMR (CDCl$_3$, 400 MHz) δ 0.82 (t, J=8.0 Hz), 1.04-1.52 (m), 1.67-1.92 (m), 2.14-2.29 (m), 2.52-2.60 (m), 2.82-2.90 (m), 2.95-3.00 (m), 3.10 (s), 3.16 (s), 3.27-3.32 (m), 3.41-3.46 (m), 3.59 (d, J=6.8 Hz), 3.69-3.79 (m), 3.90-3.95 (m), 4.34-4.39 (m), 4.87 (d, J=4.4 Hz), 5.02 (d, J=9.2 Hz), 7.33 (d, J=6.4 Hz), 7.77 (d, J=8.4 Hz); $^{13}$C NMR (CDCl$_3$, 100 MHz) δ 9.1, 10.5, 12.2, 15.9, 17.9, 18.5, 19.8, 20.9, 21.2, 21.4, 24.7, 25.5, 27.7, 29.8, 34.7, 36.8, 37.1, 39.1, 45.0, 45.2, 49.3, 50.0, 50.5, 57.6, 63.6, 65.6, 68.6, 69.0, 70.7, 72.4, 74.2, 77.8, 78.3, 80.9, 95.9, 102.7, 119.5, 125.7, 129.4, 147.5, 175.8; HMRS (ESI) calcd for [C$_{53}$H$_{87}$N$_5$O$_{15}$+H]$^+$ 1034.6271. found 1034.6246.

Synthesis of Descladinose-Clarithromycin-N-phenyltriazolylheptahydroxamic acid (26)

Reaction of descladinose-clarithromycin-N-phenylacetylene 21 (0.075 g, 0.109 mmol) and 7-azidoheptahydroxamic acid 15b (0.040 g, 0.233 mmol) within 4 h, followed by prep TLC (silica, 10:1:0.1 CH$_2$Cl$_2$/MeOH/conc. NH$_4$OH) gave 80 mg (84%) of 26 as a brownish white solid. $^1$H-NMR (CDCl$_3$, 400 MHz) δ 0.78 (t, J=7.2 Hz), 1.06-1.31 (m), 1.40-1.53 (m), 1.71 (d, J=11.6 Hz), 1.80-1.91 (m), 2.01-2.20 (m), 2.50-2.65 (m), 2.91-2.97 (m), 3.16 (t, J=6.4 Hz), 3.26-3.35 (m), 3.42-3.54 (m), 3.64-3.71 (m), 3.80 (br s), 3.90 (br s), 4.30-4.34 (m), 5.12 (dd, J=11.6, 2.4 Hz), 7.27 (d, J=8.0 Hz), 7.72 (d, J=7.2 Hz), 7.80 (s); $^{13}$C NMR (CDCl$_3$, 100 MHz) δ 8.3, 10.3, 12.5, 15.2, 16.1, 17.6, 18.6, 21.1, 21.3, 24.8, 25.1, 25.5, 26.2, 27.8, 28.5, 29.1, 29.6, 29.7, 32.3, 35.8, 36.3, 37.4, 38.6, 44.3, 45.4, 49.5, 50.0, 51.2, 57.8, 64.2, 69.7, 69.9, 70.6, 74.1, 77.9, 78.7, 88.0, 106.3, 119.9, 125.7, 129.3, 129.5, 138.3, 147.3, 175.1; HMRS (ESI) calcd for [C$_{45}$H$_{73}$N$_5$O$_{12}$+H]$^+$ 876.5329. found 876.5301.

Synthesis of Clarithromycin-N-Phenyltriazolyloctahydroxamic acid (27)

Reaction of clarithromycin-N-phenylacetylene 20 (0.101 g, 0.120 mmol) and 8-azidooctahydroxamic acid 15e (0.047 g, 0.24 mmol) within 2.5 h, followed by prep TLC (silica, 12:1:0.1 CH$_2$Cl$_2$/MeOH/conc. NH$_4$OH) gave 92 mg (74%) of 27 as a brownish white solid. $^1$H NMR (CDCl$_3$, 400 MHz) δ 0.81 (t, J=7.2 Hz), 1.04-2.05 (m), 2.22 (s), 2.19-2.82 (m), 3.00 (s), 3.08 (s), 2.91-3.80 (m), 3.95 (m), 4.38 (m), 4.88 (d, J=4.4 Hz), 5.04 (dd, J=10.8, 2.0 Hz), 7.33 (d, J=7.6 Hz), 7.71 (s), 7.77 (d, J=8.0 Hz); $^{13}$C NMR (CDCl$_3$, 400 MHz) δ 8.8, 9.4, 10.8, 12.5, 16.2, 18.2, 18.8, 20.0, 21.2, 21.5, 21.6, 25.1, 26.0, 26.7, 28.2, 28.6, 28.9, 29.9, 30.1, 35.0, 36.9, 37.4, 39.2, 39.4, 45.2, 45.4, 46.1, 49.6, 50.4, 50.8, 51.6, 58.1, 63.6, 65.9, 68.4, 69.3, 70.9, 72.8, 74.4, 78.0, 78.5, 81.2, 96.1, 120.1, 102.6, 126.1, 130.2, 147.4, 176.0; HRMS (ESI) calc for [C$_{54}$H$_{90}$N$_5$O$_{15}$+H]$^+$ 1048.6427. found 1048.6486.

Synthesis of Descladinose-Clarithromycin-N-Phenyltriazolyloctahydroxamic acid (28)

Reaction of clarithromycin-N-phenylacetylene 21 (0.10 g, 0.144 mmol) and 8-azidooctahydroxamic acid 15c (0.049 g, 0.246 mmol) within 2.5 h, followed by prep TLC (silica, 10:1:0.1 CH$_2$Cl$_2$/MeOH/conc. NH$_4$OH) gave 117 mg (90%) of 28 as a brownish white solid. $^1$H NMR (CDCl$_3$, 400 MHz) δ 0.81 (t, J=7.2 Hz), 1.10-2.09 (m), 2.18 (s), 2.19-2.68 (m), 2.98-3.73 (m), 3.83 (s), 3.93 (m), 4.36 (m), 5.16 (d, J=8.0 Hz), 7.31 (d, J=8.0 Hz), 7.77 (2H, d, J=8.0 Hz), 7.79 (1H, s); $^{13}$C NMR (CDCl$_3$, 400 MHz) δ 8.5, 10.6, 12.8, 15.4, 16.4, 17.9, 18.9, 21.4, 21.6, 29.4, 36.1, 36.7, 37.7, 38.9, 44.7, 45.7, 49.8, 58.0, 65.2, 70.0, 70.4, 70.8, 74.4, 76.8, 78.2, 79.2, 83.6, 88.8, 106.9, 121.3, 128.7, 132.5, 139.6, 175.2; HRMS (FAB, thioglycerol) calc for [C$_{46}$H$_{76}$N$_5$O$_{12}$+H]$^+$ 890.5490. found 890.5562.

Synthesis of Clarithromycin-N-Phenyltriazolylnonahydroxamic acid (29)

Reaction of clarithromycin-N-phenylacetylene 20 (0.100 g, 0.120 mmol) and 9-azidononahydroxamic acid 15d (0.043 g, 0.20 mmol) within 2.5 h, followed by prep TLC (silica, 12:1:0.1 CH$_2$Cl$_2$/MeOH/conc. NH$_4$OH) gave 54 mg (42%) of 29 as a brownish white solid. $^1$H NMR (CDCl$_3$, 400 MHz) δ 0.81 (t, J=7.2 Hz), 1.04-2.02 (m), 2.24 (s), 2.10-2.97 (m), 3.00 (s), 3.09 (s), 3.20-3.82 (m), 3.88 (m), 4.39 (m), 4.88 (d, J=4.0 Hz), 5.05 (d, J=10.0 Hz), 7.35 (d, J=8.0 Hz), 7.77 (d, J=4.0 Hz); $^{13}$C NMR (CDCl$_3$, 400 MHz) δ 9.0, 9.3, 10.8, 12.5, 16.1, 18.2, 18.8, 21.2, 21.5, 21.6, 21.7, 21.8, 26.3, 26.8, 28.7, 28.9, 29.1, 29.9, 30.3, 35.0, 37.0, 37.4, 39.3, 39.4, 45.2, 45.4, 49.6, 50.5, 50.8, 51.6, 57.8, 63.8, 65.8, 68.8, 69.2, 70.9, 72.7, 74.5, 76.8, 78.1, 78.4, 78.5, 81.1, 96.1, 102.9, 119.7, 125.9, 129.6, 129.9, 138.7, 147.6, 176.1; HRMS (ESI) calc for [C$_{55}$H$_{91}$N$_5$O$_{15}$+H]$^+$ 1062.6584. found 1062.6586.

Synthesis of Clarithromycin-N-Phenyltriazolyldecahydroxamic acid (30)

Reaction of clarithromycin-N-phenylacetylene 20 (0.10 g, 0.120 mmol) and 10-azidodecahydroxamic acid 15e (0.045 g, 0.197 mmol) within 2.5 h, followed by prep TLC (silica, 12:1:0.1 CH$_2$Cl$_2$/MeOH/conc. NH$_4$OH) gave 68 mg (53%) of 30 as a brownish white solid. $^1$H NMR (CDCl$_3$, 400 MHz) δ 0.82 (t, J=7.2 Hz), 1.05-2.12 (m), 2.24 (s), 2.26-2.97 (m), 3.01, 3.10 (s), 3.19-3.80 (m), 3.95 (m), 4.39 (m), 4.89 (d, J=4.0 Hz), 5.04 (d, J=8.0 Hz), 7.35 (d, J=8.0 Hz), 7.76 (s), 7.79 (d, J=8.0 Hz); $^{13}$C NMR (CDCl$_3$, 400 MHz) δ 9.3, 10.8, 12.5, 16.1, 18.2, 18.8, 20.0, 21.2, 21.5, 21.7, 25.4, 26.2, 28.9, 29.0, 29.3, 29.6, 29.9, 30.2, 35.0, 37.0, 37.4, 39.3, 39.4, 45.2, 45.4, 49.6, 50.5, 50.8, 51.6, 57.8, 63.8, 65.8, 68.8, 69.2, 70.9, 72.7, 74.5, 76.8, 78.1, 78.5, 81.1, 96.1, 102.9, 119.7, 125.9, 129.6, 129.8, 138.9, 147.6, 176.1; HRMS (ESI) calc for [C$_{56}$H$_{93}$N$_5$O$_{15}$+H]$^+$ 1076.6740. found 1076.6667.

Example 2

Synthesis of Compounds 36 and 38 in Table 3

Synthesis of Methyl 8-(4-(hydroxymethyl)phenylamino)-8-oxooctanoate (33)

To a mixture of 8-methoxy-8-oxooctanoic acid (0.40 g, 2.10 mmol), benzotriazole (0.28 g, 2.23 mmol) in anhydrous CH$_2$Cl$_2$ (15 mL) was added SOCl$_2$ (0.17 mL, 2.23 mmol) at 0° C., the mixture was kept stirring at 0° C. for 2.5 h and then filtered. The solvent was evaporated off to give crude acid chloride 31 which was used without further purification.

To a solution of (4-aminophenyl)methanol 32 (0.31 g, 2.50 mmol) in anhydrous pyridine (8 mL) was added chlorotrimethylsilane (0.32 mL, 2.50 mmol) at room temperature and stirring continued for 2 h. The mixture, together with a catalytic amount of DMAP, was added to a mixture of crude chloride 31 (obtained as described above) in pyridine at 0° C. The reaction was allowed to warm to room temperature and stirring continued overnight. Water (5 mL) and 1 M TBAF in tetrahydrofuran (THF) (0.25 mL, 0.25 mmol) were added and stirring continued for additional 30 min. EtOAc (50 mL) and 1N HCl (30 mL) were added, the two layers were separated, the organic layer was washed with 1N HCl (30 mL) and saturated brine (30 mL) and dried over Na$_2$SO$_4$. Solvent was evaporated off and the crude was purified by preparative TLC, eluting with acetone/hexanes 1:1 to give compound 33 (195 mg, 30%) as yellow-white solid. $^1$H-NMR (CDCl$_3$, 400 MHz) δ 1.24 (4H, m), 1.49-1.59 (4H, m), 2.17-2.25 (4H, m), 3.58 (3H, s), 4.50 (2H, s), 7.13 (2H, d, J=8.4 Hz), 7.37 (2H, d, J=8.4 Hz).

Synthesis of Azithromycin-arylalkyl methyl ester (35)

To a solution of crude preparation of compound 33 (0.64 g, 2.20 mmol) in CH$_2$Cl$_2$ (15 mL) and triethylamine (Et$_3$N) (0.90 mL, 6.60 mmol) was added mesyl chloride (0.70 mL, 8.85 mmol) at 0° C. and the reaction was allowed to warm to room temperature. Stirring continued for 2 h, CH$_2$Cl$_2$ (40 mL) and saturated sodium bicarbonate (30 mL) were added. The two layers were separated; the organic layer was washed with sodium bicarbonate (1×30 mL), saturated brine (30 mL) and dried over Na$_2$SO$_4$. Solvent was evaporated off and the crude was purified by flash chromatography (silica gel, eluting with Hexane/EtOAc, gradient 3:1, 2:1, 1:1) to give compound 34 (320 mg, 40%) as white solid.

A mixture of 4'-Desmethylazithromycin 1 (0.45 g, 0.62 mmol), compound 34 (0.32 g, 0.86 mmol), catalytic amount of potassium iodide in THF (15 mL) and Hunig's base (3 mL) was heated under refluxing condition for 48 h. CH$_2$Cl$_2$ (80 mL) and saturated sodium bicarbonate (40 mL) were added and the two layers were separated. The organic layer was washed with sodium bicarbonate (40 mL), saturated brine (40 mL) and dried over Na$_2$SO$_4$. Solvent was evaporated off and the crude was purified by preparative TLC, eluting with EtOAc/hexanes/Et$_3$N 3:2:0.1 to give compound 35 (176 mg, 28%) as brown-white solid. $^1$H-NMR (CDCl$_3$, 400 MHz) δ 0.79-0.83 (m), 0.94-1.01 (m), 1.09-1.20 (m), 1.22-1.32 (m), 1.37-1.59 (m), 1.62-1.73 (m), 1.77-2.01 (m), 2.08-2.28 (m), 2.38-2.52 (m), 2.61-2.71 (m), 2.91-3.01 (m), 3.11 (s), 3.25-3.33 (m), 3.42 (m), 3.54-3.65 (m), 3.97 (m), 4.18 (m), 4.36 (d, J=6.8 Hz), 4.61 (m), 5.03 (d, J=4.4 Hz), 7.14 (d, J=8.4 Hz), 7.42 (d, J=8.4 Hz), 7.73 (s), 8.97 (bs); $^{13}$C-NMR (CDCl$_3$, 100 MHz) δ 7.5, 9.1, 11.3, 14.8, 16.2, 16.9, 18.2, 20.5, 21.2, 21.4, 21.5, 21.9, 24.6, 25.3, 26.7, 27.5, 28.7, 29.6, 33.9, 34.7, 36.2, 36.7, 37.3, 39.1, 41.9, 42.2, 45.1, 48.5, 49.3, 51.4, 57.3, 62.2, 64.3, 65.4, 68.5, 69.9, 70.5, 72.7, 73.5, 73.8, 74.1, 77.7, 77.9, 83.4, 94.4, 102.6, 119.5, 129.0, 134.2, 137.0, 171.0, 173.8, 178.4. MS (FAB, mnba) 1010.3 (M+H)$^+$.

Synthesis of Azithromycin-arylalkyl hydroxamic acid (36)

To a solution of compound 35 (0.09 g, 0.09 mmol) in 1:1 THF/MeOH (3 mL) was added hydroxylamine (50% in H$_2$O) (0.03 mL, 0.54 mmol) and a catalytic amount of KCN. The mixture was stirred at room temperature for 24 h. The reaction was partitioned between 5% MeOH in CH$_2$Cl$_2$ (30 mL) and saturated sodium bicarbonate (25 mL), the two layers were separated and the aqueous layer was extracted with 5% MeOH in CH$_2$Cl$_2$ (2×20 mL). The combined organic layer was washed with saturated brine (40 mL) and dried over Na$_2$SO$_4$. Solvent was evaporated off and the crude was purified by preparative TLC, eluting with CH$_2$Cl$_2$/MeOH/NH$_4$OH 10:1:0.1 to give compound 36 (22 mg, 25%) as brown-white solid. $^1$H-NMR (CD$_3$OD, 400 MHz) δ 0.87-0.92 (m), 1.02-1.12 (m), 1.17-1.37 (m), 1.43-1.69 (m), 1.75-1.88 (m), 1.99 (m). 2.08 (m), 2.13-2.19 (m), 2.24 (s), 2.30 (s), 2.33-2.41 (m), 2.54 (d, J=11.2 Hz), 2.75-2.80 (m), 3.00 (d, J=9.6 Hz), 3.19 (bs), 3.47-3.51 (m), 3.60 (bs), 3.63-3.78 (m), 4.14-4.22 (m), 4.50 (d, J=7.2 Hz), 5.02 (d, J=4.8 Hz), 7.29 (d, J=8.0 Hz), 7.49 (d, J=8.4 Hz). MS (FAB, mnba) 1011.3 (M+H)$^+$.

Synthesis of Desclasinose-azithromycin-arylalkyl hydroxamic acid (38)

A mixture of compound 35 (0.05 g, 0.05 mmol) in 0.25 N HCl (15 mL) was stirred at room temperature for 20 h and poured into EtOAc (20 mL). The two layers were separated and the aqueous layer was washed with EtOAc (2×20 mL), basified with concentrated NH$_4$OH and then extracted with 5% MeOH in CH$_2$Cl$_2$ (2×30 mL). The combined organic layer was washed with saturated brine (30 mL) and dried over Na$_2$SO$_4$. Solvent was evaporated off to give compound 37 which was used for the next reaction without further purification.

To a solution of compound 37 (obtained as described above) in 1:1 THF/MeOH (2 mL) was added hydroxylamine (50% in H$_2$O) (0.05 mL, 0.79 mmol) and a catalytic amount of KCN. The mixture was stirred at room temperature for 24 h. The reaction was partitioned between 5% MeOH in CH$_2$Cl$_2$ (30 mL) and saturated brine (20 mL), the two layers were separated and the organic layer was dried over Na$_2$SO$_4$. Solvent was evaporated off and the crude was purified by preparative TLC, eluting with CH$_2$Cl$_2$/MeOH/NH$_4$OH 9:1:0.1 to give compound 38 (7 mg, 16%) as brown-white solid. $^1$H-NMR (CD$_3$OD, 400 MHz) δ 0.78 (m), 0.85 (d, J=7.2 Hz), 0.91 (d, J=8.0 Hz), 0.99 (s), 1.11 (m), 1.26-1.76 (m), 1.98 (t, J=7.4 Hz), 2.08 (m), 2.17 (s), 2.25 (t, J=7.4 Hz), 2.40 (bs), 2.58 (m), 2.95 (bs), 3.24 (m), 3.37-3.56 (m), 3.67 (d, J=13.2 Hz), 4.53 (d, J=7.6 Hz), 7.19 (d, J=8.4 Hz), 7.39 (d, J=8.4 Hz). MS (FAB, mnba) 853.3 (M+H)$^+$.

Example 3

Synthesis of Compounds 40, 44 and 47 in Table 3

Synthesis of Azithromycin-N-phenyltriazolylhepta-2-methyl ketone (40)

Compound 3 (0.040 g, 0.047 mmol) and azido-2-methyl ketone 39 (0.011 g, 0.071 mmol) were dissolved in anhydrous THF (7 mL) and stirred under argon at room temperature. Copper (I) iodide (0.010 g, 0.053 mmol) and Hunigs' base (0.1 mL) were then added to reaction mixture and stirring continued for 2 h. The reaction mixture was diluted with CH$_2$Cl$_2$ (40 mL) and washed with 1:4 NH$_4$OH/saturated NH$_4$Cl (3×30 mL) and saturated NH$_4$Cl (30 mL). The organic layer was dried over Na$_2$SO$_4$ and concentrated in vacua. The crude product was purified by preparative TLC (12:1 CH$_2$Cl$_2$:MeOH) to give 38 mg (81%) of 40 as a white solid. $^1$H NMR (CDCl$_3$, 400 MHz) δ 0.86-0.89 (t, J=7.2 Hz), 0.92-0.98 (m), 1.01-1.02 (d, J=7.2 Hz), 1.086 (s), 1.12-1.24 (m), 1.29-1.34 (m), 1.42-1.66 (m), 1.74-1.78 (d, J=16 Hz), 1.84-2.08 (m), 2.11 (s), 2.15 (m), 2.26-2.48 (m), 2.56-2.74 (m), 2.84 (s), 2.74-3.08 (m), 3.11 (s), 3.32-3.40 (m), 3.46-3.84 (m), 3.98-4.46 (m), 4.23 (broad singlet), 4.38-4.51 (m), 4.72 (broad singlet), 5.06-5.12 (m), 7.31-7.38 (m), 7.75 (s), 7.77-7.79 (d, J=8 Hz); HRMS (ESI) calc for [C$_{53}$H$_{89}$N$_5$O$_{13}$+H]$^+$ 1004.6529. found 1004.6482.

Synthesis of Azidobenzamide (43)

A solution of azido acid 41 (0.150 g, 0.877 mmol) in dry THF (10 mL) was treated with 1,2-diaminobenzene 42 (0.568 g, 5.26 mmol) and EDC (0.219 g, 1.14 mmol). The resulting mixture was stirred at room temperature for about 24 h and then concentrated in vacua. The crude was diluted with EtOAc (40 mL), washed in succession with water (30 mL) and brine (30 mL) and the organic layer was dried over Na$_2$SO$_4$. Solvent was evaporated off and the crude was purified by flash chromatography (silica, Hexanes/EtOAc 1:2) to give 79 mg (35%) of 43 as a yellow solid. $^1$H NMR (CDCl$_3$, 400 MHz) δ 1.34-1.68 (m), 2.27-2.31 (m), 3.84 (s), 6.72-6.75 (m), 7.00-7.05 (m), 7.09-7.11 (d, J=8 Hz); HRMS (ESI) calcd for [C$_{13}$H$_{19}$N$_5$O+H]$^+$ 262.1662. found 262.1635.

Synthesis of Azithromycin-N-phenyltriazolylheptabenzamide (44)

Compound 3 (0.050 g, 0.059 mmol) and azido benzamide 43 (0.023 g, 0.088 mmol) were dissolved in anhydrous THF (10 mL) and stirred under argon at room temperature. Copper (I) iodide (0.010 g, 0.0526 mmol) and Hunigs' base (0.1 mL) were then added to reaction mixture and stirring continued for 2 h. The reaction mixture was diluted with CH$_2$Cl$_2$ (40 mL), washed with 1:4 NH$_4$OH/saturated NH$_4$Cl (3×30 mL) and saturated NH$_4$Cl (30 mL). The organic layer was dried over Na$_2$SO$_4$ and concentrated in vacuo. The crude product is purified by prep TLC (12:1 CH$_2$Cl$_2$/MeOH) to give 38 mg (59%) of 44 as a white solid. $^1$H NMR (CDCl$_3$, 400 MHz) δ 0.80-1.57 (m), 1.70-1.75 (m), 1.85-1.91 (m), 2.01-2.07 (m), 2.13 (s), 2.22-2.26 (m), 2.36-2.41 (m), 2.58 (br s), 2.68 (br s), 2.75-3.07 (m), 3.25-3.62 (m), 3.69 (s), 3.81 (br s), 3.98 (br s), 4.17 (s), 4.32-4.48 (m), 4.72 (br s) 5.05 (s), 6.70-6.76 (m), 6.92-7.02 (m), 7.18-7.21 (d, J=12 Hz), 7.32 (br s), 7.71-7.73

(d, J=8 Hz), 7.78 (s). 7.87 (br s); HRMS (ESI) calcd for [C$_{59}$H$_{95}$N$_7$O$_{13}$+H]$^+$ 1110.7060. found 1110.7012.

Synthesis of Descladinose-clarithromycin-N-phenylacetylene-O-Acetate (45)

Descladinose-clarithromycin-N-phenylacetylene 21 (3.80 g, 5.5 mmol) was dissolved in acetone (20 ml) followed by addition of acetic anhydride (0.62 g, 6.0 mmol) and stirred at 40° C. for 36 h. The reaction mixture was diluted with EtOAc (100 mL), washed with aqueous NaHCO$_3$ and brine, and then purified on silica column eluting with 6:1 CH$_2$Cl$_2$/Acetone to obtain 2.8 g (70%) of 45 as a brownish white solid. $^1$H NMR (CDCl$_3$, 400 MHz) δ 0.80 (t, J=7.2 Hz), 0.90 (d, J=7.2 Hz), 1.08-1.47 (m), 1.58 (s), 1.63-2.05 (m), 2.08 (s), 2.16 (s), 2.42-2.80 (m), 2.92 (s), 2.94-3.00 (m), 3.03-3.68 (m), 3.79 (s), 3.94 (s), 4.08 (m), 4.54 (d, J=8.0 Hz), 4.80 (m), 5.15 (dd, J=11.6, 2.4 Hz), 7.17 (d, J=8.4 Hz), 7.38 (d, J=8.0 Hz).

Synthesis of clarithromycin-N-phenylacetylene ketolide (46)

Methyl sulfide (0.35 g, 5.7 mmol), was added to a mixture of N-chlorosuccinimide (0.65 g, 4.8 mmol) and CH$_2$Cl$_2$ (3 mL) while maintaining the temperature at −15° C. Compound 45 (2.5 g, 3.4 mmol) dissolved in CH$_2$Cl$_2$ (20 mL) was added to the reaction mixture, followed by triethylamine (0.39 g, 3.8 mmol). The mixture was stirred at −15° C. for 3.5 h and partitioned between EtOAc (100 mL) and 0.5 N aqueous NaOH (150 mL). The organic layer was separated, washed with brine (70 mL), and dried over Na$_2$SO$_4$. Solvent was evaporated off and the crude was purified on silica column eluting with 1:4:0.1 EtOAc/Hexane/Et$_3$N, increasing solvent polarity to 2:3:0.1, to afford 2.0 g (80%) of 46 as off-white solid. $^1$H NMR (CDCl$_3$, 400 MHz) δ 0.80-0.86 (m), 1.09-1.57 (m), 1.58 (s), 1.62-2.02 (m), 2.05 (s), 2.15 (s), 2.44-2.80 (m), 2.92 (s), 2.95-3.00 (m), 3.05-3.82 (m), 4.12 (m), 4.38 (d, J=8.0 Hz), 4.79-4.83 (m), 5.14 (dd, J=11.2, 2.0 Hz), 7.16 (d, J=7.6 Hz), 7.38 (d, J=7.6 Hz).

Synthesis of Ketolide-N-phenyltriazolylheptabenzamide (47)

Ketolide 46 (0.050 g, 0.069 mmol) and azido benzamide 43 (0.027 g, 0.103 mmol) were dissolved in anhydrous THF (10 mL) and stirred under argon at room temperature. Copper (I) iodide (0.010 g, 0.0526 mmol) and Hunigs' base (0.1 mL) were then added to reaction mixture and stirring continued for 2 h. The reaction mixture was diluted with CH$_2$Cl$_2$ (40 mL) and washed with 1:4 NH$_4$OH/saturated NH$_4$Cl (3×30 mL) and saturated NH$_4$Cl (30 mL). The organic layer was dried over Na$_2$SO$_4$ and concentrated in vacuo. The crude was purified by prep TLC (3:2 CH$_2$Cl$_2$/Acetone) to give 51 mg (75%) of 47 as a white solid. $^1$H NMR (CDCl$_3$, 400 MHz) δ 0.78-0.88 (m), 1.18-1.25 (m), 1.31-1.70 (m), 1.87-2.00 (m), 2.14 (s), 2.28-2.35 (m), 2.42-2.51 (m), 2.62-2.75 (m), 3.12 (s), 3.31-3.35 (t, J=8 Hz), 3.42 (s), 3.47 (br s), 3.62-3.82 (m), 4.32-4.40 (m), 5.05-5.09 (d, J=16 Hz), 5.44 (s), 5.77 (s), 6.64-6.74 (m), 6.95-7.00 (m), 7.10-7.15 (m), 7.18-7.21 (m), 7.27-7.31 (m), 7.60 (s) 7.72-7.74 (d, J=8 Hz), 7.77 (s).

Example 4

Synthesis of Compounds 56a-e

The procedure for the synthesis of compounds 56a-e as shown in Scheme 16 is described below.

4'-Desmethylclarithromycin (2)

To a solution of clarithromycin 1 (50.0 g, 68.1 mmol) and sodium acetate (50.3 g, 61.3 mmol) in 80% aqueous methanol (350 mL) at 75-80° C. was added iodine (19.0 g, 74.8 mmol) in three batches within 5 min. The reaction was maintained at pH 8-9 by additions of 1M NaOH (2×50 ml, once at 10 min and 45 min of reaction time). Stirring was continued at 80° C. for 4.5 h. A solution of 5% sodium thiosulfate (300 mL) and dichloromethane (250 mL) were added and the two layers were separated. The aqueous layer was extracted with CH$_2$Cl$_2$ (150 mL), the combined organic layers were washed with saturated brine, dried over Na$_2$SO$_4$, and concentrated in vacuo to give 44.0 g of 2, which was used without further purification.

4-Ethynylbenzyl methanesulfonate (3)

To a solution of 4-ethynylbenzyl alcohol (5.0 g, 37.8 mmol) in CH$_2$Cl$_2$ (50 mL) and triethylamine (Et$_3$N) (14.4 mL, 104.0 mmol) was added mesyl chloride (8.04 mL, 104.0 mmol) at 0° C. and the reaction was allowed to warm to room temperature. Stirring continued for 2 h under argon during which TLC revealed a quantitative conversion into a higher Rf product. Ice cold water was added into the reaction mixture and extracted with Et$_2$O (200 ml). The organic layer was washed with 1N HCL (70 ml), H$_2$O (100 ml), aqueous NaHCO$_3$ (70 ml), and finally H$_2$O (100 ml); and then dried over Na$_2$SO$_4$. Solvent was evaporated off and dried in vacuo to give 7.0 g of compound 3 as brownish oil which was used without further purification.

4'-Ethynylbenzylclarithromycin (4)

To a solution of 4'-desmethylclarithromycin 2 (2.4 g, 3.34 mmol) in anhydrous DMSO (4 ml), was added Hunig's base (3 ml), and 4-ethynylbenzyl methanesulfonate 2 (0.92 g, 4.34 mmol). The reaction mixture was heated at 85° C. for 2.5 h. The reaction was cooled and diluted with EtOAc (30 ml), then washed with saturated NaHCO$_3$ (3×10 ml) and saturated brine (10 ml). The organic layer was dried over Na$_2$SO$_4$ and the solvent evaporated. The crude product was purified on silica column using 12:1 CH$_2$Cl$_2$/C$_2$H$_6$CO gradually increasing the solvent polarity to 10:1 and 8:1 to afford 1.8 g (63%) of the title compound.
$^1$H-NMR (CDCl$_3$, 400 MHz) δ 0.82 (3H, t, J=7.2 Hz), 1.03-1.28 (18H, m), 1.37 (3H, s), 1.40-1.55 (3H, m), 1.65-1.90 (6H, m), 2.03 (1H, d, J=10.0 Hz), 2.22 (3H, s), 2.30 (1H, d, J=15.2 Hz), 2.40-2.60 (2H, m), 2.80-2.90 (2H, m), 294-3.00 (6H, m), 3.04 (1H, s), 3.09 (3H, s), 3.16 (1H, s), 3.24-3.29 (1H, m), 3.38-3.46 (3H, m), 3.59 (1H, d, J=6.8 Hz), 3.70-3.75 (3H, m), 3.88-3.95 (1H, m), 4.37 (1H, d, J=7.2 Hz), 4.88 (1H, d, J=4.4 Hz), 5.02 (1H, dd, J=11.6, 2.4 Hz), 7.23 (2H, d, J=12.0 Hz), 7.42 (2H, d, J=8.0 Hz); $^{13}$C NMR (CDCl$_3$, 100 MHz) δ 9.2, 10.7, 12.4, 16.1, 18.1, 18.7, 19.9, 21.1, 21.5, 29.3, 32.4, 34.8, 36.9, 37.2, 39.2, 45.0, 45.2, 49.3, 50.6, 53.4, 57.6, 63.3, 65.6, 68.5, 69.0, 70.6, 72.5, 74.2, 76.5, 77.8, 78.1, 78.2, 80.8, 95.8, 102.5, 120.9, 128.6, 132.0, 133.5, 139.4, 175.4; HRMS (ESI) talc for [C46H73NO13+H]+ 848.5155. found 848.5181

Descladinose-4'-Ethynylbenzylclarithromycin (5)

A solution of 4'-Ethynylbenzylclarithromycin 4 (27.3 g, 31.2 mmol) in EtOH (200 ml) and 1N HCL (200 ml) was stirred at room temperature for 17 h after which TLC analysis indicated the absence of starting material. The reaction mixture was basified with NH4OH to about pH 9, added H$_2$O (250 ml) and EtOAc (350 ml) and separated the two layers. The aqueous layer was washed with EtOAc (250 ml) and the two organic layers combined and washed with saturated brine, then dried over Na$_2$SO$_4$. The crude product was purified on silica column using gradient elution (12:1, 10:1 and 8:1 CH2Cl/2/C$_2$H$_6$CO) to isolate 77% (17.1 g) of 5 as off-white foam.

$^1$H-NMR (CDCl$_3$, 400 MHz) δ 0.82 (3H, t, J=7.6 Hz), 1.09-1.28 (12H, m), 1.34 (3H, s), 1.40-1.55 (3H, m), 1.70-1.74 (2H, m), 1.87-1.94 (3H, m), 2.08-2.15 (6H, m), 2.54-2.66 (2H, m), 2.94-2.98 (3H, m), 3.05 (1H, s), 3.25 (1H, s), 3.31-3.42 (2H, m), 3.48-3.56 (2H, m), 3.66 (2H, d, J=10.0 Hz), 3.82 (1H, s), 3.90 (1H, s), 4.35 (1H, d, J=7.6 Hz), 5.14 (1H, dd, J=10.8, 2.0 Hz), 7.18 (2H, d, J=8.0 Hz), 7.42 (2H, d, J=8.4 Hz); $^{13}$C NMR (CDCl$_3$, 100 MHz) δ 8.4, 10.5, 12.7, 15.3, 16.3, 17.8, 18.8, 21.4, 29.2, 35.9, 36.6, 37.5, 38.7, 44.5, 45.5, 49.6, 57.8, 65.0, 69.7, 70.1, 70.6, 74.1, 77.9, 78.9, 83.3, 88.5, 106.5, 121.0, 128.4, 132.1, 139.1, 174.7; HRMS (ESI) calc for [C38H59NO10+H]+ 690.4212. found 690.4259

Synthesis of compound (6) (Acetylation)

To a solution of descladinose-4'-ethynylbenzylclarithromycin 5 (3.8 g, 5.5 mmol) in acetone (20 ml), Ac$_2$O (0.62 g, 6.0 mmol) was added and stirred at 40° C. for 36 h. The reaction mixture was diluted with EtOAc (100 ml) and washed with aqueous NaHCO$_3$ (70 ml) and saturated brine (70 ml). Purification on silica column (6:1 CH$_2$Cl$_2$/acetone) afforded 2.8 g (70%) of the title compound as a yellowish solid.

$^1$H NMR (CDCl$_3$, 400 MHz) δ 0.80 (3H, t, J=7.2 Hz), 0.90 (3H, d, J=7.2 Hz), 1.08-1.47 (12H, m), 1.58 (6H, s), 1.63-2.05 (7H, m), 2.08 (3H, s), 2.16 (3H, s), 2.42-2.80 (3H, m), 2.92 (3H, s), 2.94-3.00 (1H, m), 3.03-3.68 (3H, m), 3.79 (2H, s), 3.94 (1H, s), 4.08 (1H, m), 4.54 (1H, d, J=8.0 Hz), 4.80 (1H, m), 5.15 (1H, dd, J=11.6, 2.4 Hz), 7.17 (2H, d, J=8.4 Hz), 7.38 (2H, d, J=8.0 Hz); $^{13}$C NMR (CDCl$_3$, 100 MHz) δ 8.0, 10.7, 12.8, 15.5, 16.4, 18.1, 19.5, 21.3, 21.5, 21.6, 31.1, 31.9, 36.0, 37.0, 37.5, 38.7, 44.3, 45.7, 50.0, 58.4, 62.5, 68.9, 69.8, 71.6, 74.4, 76.9, 77.0, 77.8, 78.1, 81.3, 83.9, 99.9, 120.7, 128.4, 132.2, 141.1, 170.1, 174.9, 221.2; HRMS (FAB, mnba) calc for [C40H61NO11+H]+ 732.43229. found 732.43105

Synthesis of Compound (7) (Oxidation)

Methyl sulfide (1.42 g, 22.8 mmol), was added to a mixture of N-chlorosuccinimide (2.61 g, 19.5 mmol) and CH$_2$Cl$_2$ (10 ml) while maintaining the temperature at −15° C. Compound 6 (10.0 g, 13.7 mmol) dissolved in CH$_2$Cl$_2$ (50 ml) was added to the reaction flask, followed by Et$_3$N (1.56 g, 15.4 mmol) and stirred at −15° C. for 4.5 h. The reaction mixture was poured into EtOAc (350 ml) and 0.5 N aqueous NaOH (250 ml). The organic layer was separated and washed with saturated brine (250 ml), dried over Na$_2$SO$_4$, evaporated solvent and purified on silica column (2:3:0.1 EtOAc/Hexane/Et$_3$N) to afford 9.54 g (96%) of the title compound as off-white solid.

$^1$H NMR (CDCl$_3$, 400 MHz) δ 0.80-0.86 (6H, m), 1.09-1.57 (12H, m), 1.58 (6H, s), 1.62-2.02 (7H, m), 2.05 (3H, s), 2.15 (3H, s), 2.44-2.80 (2H, m), 2.92 (3H, s), 2.95-3.00 (1H, m), 3.05-3.66 (4H, m), 3.80 (1H, q, J=14.0, 6.8 Hz), 3.89 (1H, s), 4.12 (1H, m), 4.38 (1H, d, J=8.0 Hz), 4.79-4.83 (1H, m), 5.14 (1H, dd, J=11.2, 2.0 Hz), 7.16 (2H, d, J=7.6 Hz), 7.38 (2H, d, J=7.6 Hz); $^{13}$C NMR (CDCl$_3$, 100 MHz) δ 10.8, 12.4, 14.4, 14.5, 16.5, 17.9, 19.6, 21.3, 21.5, 31.3, 36.9, 37.6, 39.2, 45.1, 46.3, 49.7, 51.1, 58.5, 62.5, 69.2, 69.6, 71.5, 74.1, 77.0, 77.1, 77.2, 78.1, 83.9, 101.1, 120.7, 128.5, 132.2, 140.9, 169.6, 170.0, 205.7, 221.1; HRMS (FAB, mnba) talc for [C40H59NO11+H]+ 730.41664. found 730.41321

Carbamate Ketolide (8)

To a suspension of 7 (1.5 g, 2.06 mmol) in a mixture of anhydrous THF (20 ml) and anhydrous DMF (7 ml), was added CDI (1.3 g, 8.20 mmol) followed by a solution of NaN(TMS)$_2$ 1.0 M in THF (2.6 ml, 2.6 mmol) over 75 min and stirred at RT for 24 h. The reaction mixture was diluted with EtOAc (50 ml), washed with aqueous NaHCO$_3$ (20 ml) and saturated brine (20 ml) and dried over Na$_2$SO$_4$. The solvent was evaporated and purified on silica column (3:2:0.1 EtOAc/Hexane/Et3N) to yield 42% (0.7 g) of the title compound. NMR (CDCl$_3$, 400 MHz) δ 0.91 (3H, t, 7.6 Hz), 1.09 (3H, d, J=7.2 Hz), 1.14-1.50 (9H, m), 1.80 (3H, s), 1.83 (3H, s), 1.56-1.94 (7H, m), 2.00 (3H, s), 2.05 (3H, s), 2.12 (3H, s), 2.64-2.80 (1H, m), 3.02 (3H, s), 2.95-3.70 (4H, m), 3.73 (1H, q, J=14.0, 6.8 Hz), 4.10-4.06 (2H, m), 4.30 (1H, d, J=7.6 Hz), 4.77-4.80 (1H, m), 5.68 (1H, dd, J=11.2, 2.0 Hz), 6.77 (1H, s), 7.03 (1H, s), 7.16 (2H, d, J=7.6 Hz), 7.36 (3H, m), 8.06 (1H, s); $^{13}$C NMR (CDCl$_3$, 100 MHz) δ 10.7, 13.5, 14.4, 15.2, 19.1, 20.4, 21.1, 21.2, 21.5, 22.8, 31.2, 36.8, 47.6, 50.5, 51.2, 58.5, 60.6, 62.8, 69.3, 71.6, 78.7, 83.9, 84.7, 117.3, 120.7, 128.4, 131.1, 132.2, 137.3, 138.8, 140.9, 146.2, 169.1, 169.8; HRMS (FAB, mnba) calc for [C44H59N3O11+H]+ 806.42279. found 806.42103

Tricyclic Ketolide (9)

To a solution of 8 (0.6 g, 0.74 mmol) in CH$_3$CN (10 ml) and H$_2$O (1 ml), was added ethylenediamine (0.44 g, 7.40 mmol) and heated in a sealed tube at 50-55° C. for 24 h. The solvent was evaporated off and the reaction mixture partitioned between H$_2$O (15 ml) and CH$_2$Cl$_2$ (20 ml) and separated. The organic layer was washed with saturated brine (20 ml), dried over Na$_2$SO$_4$, and the solvent evaporated. The crude product was dissolved in anhydrous MeOH (15 ml) and heated at 90° C. in a sealed tube for 24 h. MeOH was evaporated and the product purified on silica column (EtOAc/Et$_3$N 12:0.1). EtOH (6 ml) followed by AcOH (0.043 g, 0.71 mmol) were added to the pure product (0.27 g, 0.34 mmol) and heated at 95° C. in a sealed tube for 20 h. The reaction mixture was suspended in dilute NH$_4$OH (10 ml) and CH$_2$Cl$_2$ (15 ml) and separated the organic layer, washed with saturated brine (10 ml), and dried over Na$_2$SO$_4$. Purification on silica column (EtOAc/MeOH/Et$_3$N 10:0.5:0.05) afforded 0.24 g (57%) of compound 9.

$^1$H NMR (CDCl$_3$, 400 MHz) δ 0.80 (3H, t, J=7.2 Hz), 1.00 (3H, d, J=6.8 Hz), 1.14-1.55 (12H, m), 1.30 (3H, s), 1.43 (3H, s), 1.60-1.96 (6H, m), 2.12 (3H, s), 2.45-2.95 (6H, m), 3.03 (3H, s) 3.23-3.43 (4H, m), 3.64-3.78 (4H, m), 3.94 (1H, m), 4.16 (1H, d, J=8.4 Hz), 4.25 (1H, d, J=7.6 Hz), 4.90 (1H, d, J=10.0 Hz), 7.18 (2H, d, J=8.0 Hz), 7.39 (2H, d, J=7.2 Hz); $^{13}$C NMR (CDCl$_3$, 100 MHz) δ 10.6, 11.1, 13.0, 14.6, 16.6, 19.3, 19.8, 21.4, 22.3, 29.7, 36.5, 37.1, 38.7, 42.5, 43.0, 48.3, 49.3, 49.7, 51.4, 57.6, 60.1, 65.6, 69.7, 70.5, 76.7, 78.7, 79.4, 81.7, 83.6, 104.0, 121.0, 128.8, 132.4, 140.0, 156.3, 169.8, 181.5, 204.4; HRMS (FAB, mnba) talc for [C41H59N3O9+H]+ 738.43296. found 738.43318

Azidoalkyl-O-trityl Hydroxamate Derivatives (10a-e)

Method A

Tricyclic Ketolide-N-benzyltriazolylhexa-N-Otrityl (11a)

General Procedure: 4'-Ethynylbenzyl tricyclic ketolide 9 (0.105 g, 0.142 mmol) and 6-azidohexa-o-trityl hydroxamic acid 10a (0.058 g, 0.142 mmol) were dissolved in anhydrous THF (7 mL) and stirred under argon at room temperature. Copper (I) iodide (0.012 g, 0.063 mmol) and Hunig's base (0.6 mL) were added to the reaction mixture, and stirring continued for 24 h. The reaction mixture was diluted with 1:4 NH$_4$OH/saturated NH$_4$Cl (50 mL) and extracted with 10% MeOH/CH$_2$Cl$_2$ (3×30 mL). The organic layers were combined, dried over Na$_2$SO$_4$ and concentrated in vacuo. The crude product was purified by prep TLC (silica, 12:1:0.1 CH$_2$Cl$_2$/MeOH/conc. NH$_4$OH) to give 127 mg (78%) of 11a as a yellowish solid.

$^1$H NMR (CDCl$_3$, 400 MHz) δ 0.85 (3H, t, J=7.6 Hz), 1.1 (3H, d, J=6.8 Hz), 1.20-1.39 (17H, m), 1.46-2.00 (15H, m), 2.19 (3H, s), 2.58-2.80 (6H, m), 2.84-3.00 (1H, m), 3.02-3.17 (1H, m), 3.31-3.60 (3H, m), 3.64-3.87 (5H, m), 3.96-4.0 (1H, m), 4.22 (1H, d, J=8.4 Hz), 4.29-4.32 (3H, m), 4.93 (1H, dd, J=10.0, 1.6 Hz), 7.23-7.45 (17H, m), 7.71 (1H, s), 7.79 (2H, d, J=8.0 Hz); $^{13}$C NMR (CDCl$_3$, 100 MHz) δ 10.7, 11.1, 13.1, 14.6, 16.7, 19.3, 19.9, 21.4, 22.3, 22.8, 26.0, 29.6, 30.2, 31.0, 36.5, 37.0, 38.8, 42.5, 43.0, 48.3, 49.3, 49.7, 50.2, 51.4, 53.7, 57.7, 60.1, 65.6, 69.8, 70.5, 76.7, 78.7, 79.4, 81.8, 93.1, 104.1, 119.7, 126.0, 128.2, 128.4, 129.2, 129.4, 130.0, 138.9, 141.2, 147.6, 156.3, 169.8, 177.0, 181.5, 204.5; HRMS (ESI) talc for [C66H85N7O11+H]+ 1152.6379. found 1152.6367

Tricyclic Ketolide-N-benzyltriazolylhepta-N-Otrityl (11b)

Reaction of 4'-ethynylbenzyl tricyclic ketolide 9 (0.102 g, 0.138 mmol) and 6-azidohepta-o-trityl hydroxamic acid 10b (0.059 g, 0.138 mmol) within 24 h as described for the synthesis and purification of 11a gave 133 mg (83%) of 11b as a yellowish solid.

$^1$H NMR (CDCl$_3$, 400 MHz) δ 0.85 (3H, t, J=7.6 Hz), 1.06 (3H, d, J=6.8 Hz), 1.20-1.42 (19H, m), 1.45-1.98 (15H, m), 2.20 (3H, s), 2.57-2.79 (6H, m), 2.85-3.00 (1H, m), 3.03-3.13 (1H, m), 3.30-3.57 (3H, m), 3.72-3.83 (5H, m), 3.96-4.00 (1H, m), 4.22 (1H, d, J=8.8 Hz), 4.29-4.35 (3H, m), 4.95 (1H, dd, J=10.4, 2.4 Hz), 7.22-7.45 (17H, m), 7.71 (1H, s), 7.78 (2H, d, J=8.4 Hz); $^{13}$C NMR (CDCl$_3$, 100 MHz) δ 10.7, 11.1, 13.1, 14.6, 16.6, 19.3, 19.9, 21.4, 22.3, 26.3, 29.6, 30.2, 36.5, 37.0, 38.8, 42.5, 43.0, 48.3, 49.3, 49.7, 50.4, 51.4, 53.7, 57.7, 60.1, 65.5, 69.7, 70.5, 76.7, 78.7, 79.4, 81.8, 92.8, 104.1, 119.7, 126.0, 128.4, 129.2, 129.4, 130.0, 132.3, 138.9, 141.3, 147.6, 156.3, 169.8, 177.6, 182.5, 204.5; HRMS (ESI) calc for [C67H87N7O11+H]+ 1166.6536. found 1166.6478

Tricyclic Ketolide-N-benzyltriazolylocta-N-Otrityl (11c)

Reaction of 4'-ethynylbenzyl tricyclic ketolide 9 (0.075 g, 0.102 mmol) and 6-azidoocta-o-trityl hydroxamic acid 10c (0.045 g, 0.102 mmol) in anhydrous THF (5 ml) within 22 h as described for the synthesis and purification of 11a gave 94 mg (79%) of 11c as a yellowish solid. $^1$H NMR (CDCl$_3$, 400 MHz) δ 0.83 (3H, t, J=7.2 Hz), 1.04 (3H, d, J=7.2 Hz), 1.15-1.41 (21H, m), 1.45-1.95 (15H, m), 2.18 (3H, s), 2.55-2.73 (6H, m), 2.87-2.97 (1H, m), 3.03-3.10 (1H, m), 3.28-3.57 (3H, m), 3.70-3.82 (5H, m), 3.93-3.97 (1H, m), 4.21 (1H, d, J=8.4 Hz), 4.27-4.34 (3H, m), 4.94 (1H, dd, J=12.8, 2.4 Hz), 7.25-7.42 (17H, m), 7.71 (1H, s), 7.76 (2H, d, J=8.0 Hz); $^{13}$C NMR (CDCl$_3$, 100 MHz) δ 10.7, 11.1, 13.1, 14.6, 16.6, 19.3, 19.9, 21.4, 22.3, 26.4, 28.8, 29.6, 30.4, 36.6, 37.0, 38.8, 42.5, 42.9, 48.3, 49.3, 49.7, 50.6, 51.4, 53.7, 57.7, 60.1, 65.5, 69.8, 70.5, 76.7, 78.7, 79.4, 81.8, 93.8, 104.1, 119.6, 126.0, 127.7, 128.3, 128.8, 129.2, 129.4, 130.0, 132.7, 138.9, 141.3, 147.7, 156.3, 169.8, 177.0, 182.4, 204.4; HRMS (ESI) calc for [C68H89N7O11+H]+ 1180.6692. found 1180.6637

Tricyclic Ketolide-N-benzyltriazolylnona-N-Otrityl (11d)

Reaction of 4'-ethynylbenzyl tricyclic ketolide 9 (0.075 g, 0.102 mmol) and 6-azidonona-o-trityl hydroxamic acid 10d (0.046 g, 0.102 mmol) in anhydrous THF (5 ml) within 20 h as described for the synthesis and purification of 11a gave 93 mg (76%) of 11d as a yellowish solid. $^1$H NMR (CDCl$_3$, 400 MHz) δ 0.85 (3H, t, J=8.0 Hz), 1.05 (3H, d, J=6.8 Hz), 1.16-1.44 (23H, m), 1.45-1.96 (15H, m), 2.20 (3H, m), 2.57-2.78 (6H, m), 2.90-2.99 (1H, m), 3.02-3.12 (1H, m), 3.30-3.57 (3H, m), 3.72-3.84 (5H, m), 3.96-4.00 (1H, m), 4.29 (1H, d, J=8.4 Hz), 4.31 (1H, d, J=7.2 Hz), 4.37 (2H, J=7.2 Hz), 4.95 (1H, dd, J=12.8, 2.4 Hz), 7.19-7.45 (17H, m), 7.72 (1H, s), 7.78 (2H, d, J=8.0 Hz); $^{13}$C NMR (CDCl$_3$, 100 MHz) δ 10.7, 11.1, 13.1, 14.6, 16.6, 19.3, 19.9, 21.4, 22.3, 26.6, 28.9, 29.2, 29.6, 29.9, 30.5, 36.5, 37.0, 37.1, 38.8, 42.5, 43.0, 48.3, 49.3, 49.7, 50.6, 51.4, 57.7, 60.1, 65.5, 65.6, 69.7, 70.5, 76.7, 78.7, 79.4, 81.8, 94.3, 104.1, 119.6, 126.0, 128.3, 128.8, 129.0, 129.2, 129.4, 130.0, 132.3, 138.9, 141.3, 147.6, 156.3, 169.8, 178.0, 181.5, 204.5; HRMS (ESI) calc for [C69H91N7O11+H]+ 1194.6849. found 1194.6838

Tricyclic Ketolide-N-benzyltriazolyldeca-N-Otrityl (11e)

Reaction of 4'-ethynylbenzyl tricyclic ketolide 9 (0.075 g, 0.102 mmol) and 6-azidodeca-o-trityl hydroxamic acid 10e (0.048 g, 0.102 mmol) in anhydrous THF (5 ml) within 20 h as described for the synthesis and purification of 11a gave 98 mg (80%) of 11e as a yellowish solid. $^1$H NMR (CDCl$_3$, 400 MHz) δ 0.83 (3H, t, J=6.8 Hz), 1.03 (3H, d, J=7.2 Hz), 1.15-1.40 (25H, m), 1.44-1.96 (15H, m), 2.17 (3H, s), 2.57-2.78 (6H, m), 2.87-2.95 (1H, m), 3.03-3.08 (1H, m), 3.28-3.53 (3H, m), 3.70-3.82 (5H, m), 3.92-3.96 (1H, m), 4.20 (1H, d, J=8.4 Hz), 4.29 (1H, d, J=6.8 Hz), 4.33 (2H, t, J=7.2 Hz), 4.93 (1H, d, J=10.0 Hz), 7.26-7.43 (17H, m), 7.73 (1H, s), 7.76 (2H, d, J=8.0 Hz); $^{13}$C NMR (CDCl$_3$, 100 MHz) δ 10.7, 11.1, 13.1, 14.6, 16.6, 19.3, 19.8, 21.4, 22.3, 26.6, 29.1, 29.3, 29.6, 29.9, 30.5, 36.6, 37.0, 38.8, 42.5, 43.0, 48.3, 49.3, 49.7, 50.6, 51.4, 57.7, 60.1, 65.5, 69.7, 70.5, 76.7, 78.7, 79.4, 81.8, 93.4, 104.1, 199.6, 126.0, 128.3, 129.2, 129.4, 130.0, 138.9, 147.6, 156.3, 169.8, 177.6, 182.0, 204.5; HRMS (ESI) calc for [C70H93N7O11+H]+ 1208.7005. found 1208.6888

Tricyclic Ketolide-N-benzyltriazolylhexahydroxamic acid (56a)

Protocol B: To a solution of tricyclic ketolide-N-benzyltriazolylhexa-N-Otrityl 11a (0.120 g, 0.105 mmol) in methylene chloride (1 ml) at 0° C., was added thioanisole (0.2 ml) and TFA (0.2 ml) dropwise. Stirring was continued at 0° C. for 2 h after which TLC analysis indicated completion of reaction. Excess TFA and solvent were evaporated off and immediately placed back in the ice-bath followed by addition of PBS buffer (10 ml). Saturated NaHCO₃ was added dropwise until the pH was neutral. Extraction with 20% MeOH/CH₂Cl₂ (10 ml×3), drying over Na₂SO₄, and evaporation of solvent afforded liquid crude product which was then purified by prep TLC (silica, 12:1:0.1 CH₂Cl₂/MeOH/conc. NH₄OH) to afford 47 mg (50%) of 56a as a yellowish solid.

Protocol C: To a mixture of tricyclic ketolide-N-benzyltriazolylhexa-N-Otrityl 11a (0.136 g, 0.118 mmol) in CH₂Cl₂/MeOH (2 ml: 2 ml) was added BF₃.OEt₂ (0.033 g, 0.236 mmol) and stirred at room temperature for 45 min. Dilute NaHCO₃ (20 ml) was added until pH=8, and then extracted with 10% MeOH/CH₂Cl₂ (10 ml×4), dried over Na₂SO₄ and concentrated in vacuo. The crude product was purified by prep TLC (silica, 12:1:0.1 CH₂Cl₂/MeOH/conc. NH₄OH) to give 64 mg (60%) of 56a as a yellowish solid.

Protocol D: 4'-Ethynylbenzyl tricyclic ketolide 9 (0.050 g, 0.065 mmol) and 6-azidohexahydroxamic acid 13a (0.025 g, 0.145 mmol) were dissolved in anhydrous THF (7 mL) and stirred under argon at room temperature. Copper (I) iodide (0.007 g, 0.036 mmol) and Hunig's base (0.5 mL) were added to the reaction mixture, and stirring continued for 12 h. The reaction mixture was diluted with 10% MeOH/CH2Cl2 (20 mL) and washed with 1:4 NH4OH/saturated NH4Cl (3×10 mL) and saturated NH4Cl (10 mL). The organic layer was dried over Na2SO4 and concentrated in vacuo. The crude product was purified by prep TLC (silica, 12:1:0.1 CH2Cl2/MeOH/conc. NH4OH) to give 20 mg (34%) of 56a as a brown solid.

$^1$H NMR (CDCl₃, 400 MHz) δ 0.85 (3H, t, J=8.0 Hz), 1.05 (3H, d, J=7.2 Hz), 1.20-2.00 (30H, m), 2.13-2.18 (2H, m), 2.20 (3H, s), 2.58-2.72 (6H, m), 2.92-2.98 (1H, m), 3.05-3.09 (1H, m), 3.30-3.55 (3H, m), 3.70-3.84 (5H, m), 3.95-3.98 (1H, m), 4.22 (1H, d, J=8.0 Hz), 4.31-4.38 (3H, m), 4.95 (1H, d, J=8.8 Hz), 7.33 (2H, d, J=8.0 Hz), 7.77 (3H, m); $^{13}$C NMR (CDCl₃, 100 MHz) δ 10.6, 11.1, 13.1, 14.6, 16.5, 19.3, 19.8, 21.4, 22.3, 24.7, 25.9, 29.7, 29.9, 30.0, 36.6, 37.1, 38.8, 42.5, 42.8, 49.4, 49.6, 50.3, 51.4, 53.7, 57.7, 60.1, 65.5, 69.7, 70.5, 76.7, 78.7, 79.3, 81.8, 104.1, 120.1, 126.0, 129.5, 129.7, 139.1, 147.7, 156.3, 169.8, 171.1, 182.3, 204.5; HRMS (EST) talc for [C47H71N7O11+H]+ 910.5284. found 910.5279; Melting point 127-130° C.

Tricyclic Ketolide-N-benzyltriazolylheptahydroxamic acid (56b)

According to protocol B, reaction of 11b (0.132 g, 0.113 mmol) in CH₂Cl₂ (1 ml), thioanisole (0.3 ml) and TFA (0.3 ml) for 3 h afforded 56 mg (55%) of 56b as a yellowish solid.

According to protocol C, reaction of 11b (0.15 g, 0.127 mmol) and BF₃.OEt₂ (0.037 g, 0.257 mmol) afforded 65 mg (55%) of 56b as a yellowish solid.

Reaction of 4'-ethynylbenzyl tricyclic ketolide 9 (0.048 g, 0.063 mmol) and 7-azidoheptahydroxamic acid 13b (0.020 g, 0.107 mmol) within 12 h, according to the protocol D described for the synthesis of compound 56a, gave 22 mg (38%) of 56b as a brown solid.

$^1$H NMR (CDCl₃, 400 MHz) δ 0.83 (3H, t, J=7.6 Hz), 1.03 (3H, d, J=6.4 Hz), 1.18-1.90 (32H, m), 2.10-2.13 (2H, m), 2.17 (3H, s), 2.58-2.73 (6H, m), 2.93-2.98 (1H, m), 3.03-3.07 (1H, m), 3.28-3.60 (3H, m), 3.70-3.81 (5H, m), 3.98 (1H, m), 4.20 (1H, d, J=8.4 Hz), 4.29-4.38 (3H, m), 4.93 (1H, d, J=10.4 Hz), 7.30 (2H, d, J=7.6 Hz), 7.75 (2H, d, J=7.6 Hz), 7.78 (1H, s); $^{13}$C NMR (CDCl₃, 100 MHz) δ 10.6, 11.1, 13.1, 14.6, 16.5, 19.3, 19.8, 21.4, 22.3, 25.2, 26.0, 28.2, 29.7, 29.9, 30.1, 36.6, 37.0, 38.8, 42.5, 42.7, 48.2, 49.3, 49.5, 50.4, 51.4, 53.7, 57.7, 60.1, 65.5, 69.7, 70.5, 76.7, 78.7, 79.3, 81.8, 104.0, 120.0, 126.0, 129.4, 129.8, 139.1, 147.7, 156.3, 169.8, 171.2, 182.4, 204.5; HRMS (ESI) calc for [C48H73N7O11+H]+ 924.5440. found 924.5422; Melting point 128-131° C.

Tricyclic Ketolide-N-benzyltriazolyloctahydroxamic acid (56c)

Reaction of 11c (0.092 mg, 0.079 mmol) in CH₂Cl₂ (1 ml), thioanisole (0.2 ml) and TFA (0.2 ml) according to protocol B afforded 37 mg (51%) of 56c as a yellowish solid.

$^1$H NMR (CDCl₃, 400 MHz) δ 0.83 (3H, t, J=6.4 Hz), 1.03 (3H, d, J=5.6 Hz), 1.18-1.60 (21H, m), 1.66-2.1 (15H, m), 2.18 (3H, s), 2.56-2.70 (6H, m), 290-2.98 (1H, m), 3.02-3.07 (1H, m), 3.28-3.58 (3H, m), 3.70-3.81 (5H, m), 3.94-3.97 (1H, m), 4.20 (1H, d, J=7.2 Hz), 4.28 (1H, d, J=6.0 Hz), 4.35 (2H, m), 4.93 (1H, d, J=10.4 Hz), 7.30 (2H, d, J=7.2 Hz), 7.73-7.76 (3H, m); $^{13}$C NMR (CDCl₃, 100 MHz) δ 10.6, 11.1, 13.1, 14.4, 14.6, 16.5, 19.3, 19.8, 21.3, 21.4, 22.3, 25.2, 26.1, 28.3, 29.7, 29.9, 30.2, 32.9, 36.6, 37.1, 38.8, 42.5, 42.7, 48.2, 49.4, 49.5, 50.5, 51.4, 57.7, 60.1, 60.6, 65.5, 69.7, 70.5, 76.7, 78.7, 79.3, 81.8, 104.0, 119.9, 126.0, 129.5, 129.8, 139.0, 147.7, 156.3, 169.8, 171.7, 182.4, 204.5; HRMS (ESI) calc for [C49H75N7O11+H]+ 938.5597. found 938.5556; Melting point 113-115° C.

Tricyclic Ketolide-N-benzyltriazolylnonahydroxamic acid (56d)

Reaction of 11d (0.091 mg, 0.077 mmol) in CH₂Cl₂ (1 ml), thioanisole (0.2 ml) and TFA (0.2 ml) according to protocol B afforded 43 mg (60%) of 56d as a yellowish solid.

$^1$H NMR (CDCl₃, 400 MHz) δ 0.83 (3H, t, J=7.2 Hz), 1.03 (3H, d, J=7.2 Hz), 1.17-1.60 (23H, m), 1.66-2.14 (15H, m), 2.17 (3H, s), 2.58-2.73 (6H, m), 2.87-2.95 (1H, m), 3.00-3.07 (1H, m), 3.27-3.55 (3H, m), 3.70-3.82 (5H, m), 3.93-3.97 (1H, m), 4.20 (1H, d, J=8.8 Hz), 4.28 (1H, d, 7.2 Hz), 4.35 (2H, t, J=6.8 Hz), 4.92 (1H, dd, J=10.0, 1.2 Hz), 7.30 (2H, d, J=8.0 Hz), 7.75 (3H, m); $^{13}$C NMR (CDCl₃, 100 MHz) δ 10.7, 11.1, 13.1, 14.6, 16.5, 19.3, 19.8, 21.4, 22.3, 25.4, 26.3, 28.6, 28.8, 28.9, 29.6, 29.9, 30.3, 32.9, 36.6, 37.1, 38.8, 42.5, 42.8, 48.2, 49.3, 49.6, 50.6, 51.4, 57.7, 60.1, 65.5, 69.7, 70.5, 76.7, 78.7, 79.3, 81.8, 104.1, 119.8, 126.0, 129.5, 129.8, 139.0, 147.7, 156.3, 169.8, 171.3, 182.9, 204.5; HRMS (ESI) calc for [C50H77N7O11+H]+ 952.5753. found 952.5728; Melting point 112-115° C.

Tricyclic Ketolide-N-benzyltriazolyldecahydroxamic acid (56e)

Reaction of 11e (0.097 mg, 0.081 mmol) in CH₂Cl₂ (1 ml), thioanisole (0.2 ml) and TFA (0.2 ml) according to protocol B afforded 42 mg (55%) of 56e as a yellowish solid.

$^1$H NMR (CDCl₃, 400 MHz) δ 0.83 (3H, t, J=7.2 Hz), 1.03 (3H, d, J=6.4 Hz), 1.18-1.61 (25H, m), 1.66-2.14 (15H, m), 2.18 (3H, s), 2.59-2.73 (6H, m), 2.89-2.94 (1H, m), 3.01-3.07 (1H, m), 3.28-3.54 (3H, m), 3.70-8.83 (5H, m), 3.93-3.97 (1H, m), 4.20 (1H, d, J=8.4 Hz), 4.28 (1H, d, J=6.8 Hz), 4.36 (2H, t, J=7.2 Hz), 4.92 (1H, dd, J=10.4, 1.6 Hz), 7.30 (2H, d, J=8.0 Hz), 7.76 (3H, m); $^{13}$C NMR (CDCl₃, 100 MHz) δ 10.7, 11.1, 13.1, 14.4, 14.6, 16.5, 19.3, 19.9, 21.4, 22.3, 25.5, 26.3, 28.7, 28.9, 29.0, 29.6, 29.9, 30.3, 33.1, 36.6, 37.1, 38.8, 42.5, 42.7, 48.2, 49.4, 49.5, 50.6, 51.4, 57.7, 60.1, 60.6, 65.5, 69.7, 70.5, 76.7, 78.7, 79.3, 81.8, 104.0, 119.8, 126.0, 129.5, 129.8, 139.0, 147.7, 156.3, 169.8, 171.7, 182.9, 204.5; HRMS (ESI) calc for [C51H79N7O11+H]+ 966.5910. found 966.5919; Melting point 123-126° C.

Example 5

Anti-HDAC Activity of Nonpeptide Macrocyclic HDAC Inhibitors

Inhibition of HeLa nuclear extract HDAC1/2 and HDAC8 by compounds 7-14, 23-30, 36, and 38 was evaluated in a Fluor de Lys assay according to the manufacture's protocol. Each $IC_{50}$ value was obtained by averaging three independent experiments. This data is shown in Table 4. The compounds displayed both linker-length and macrolide-type dependent HDAC inhibition activities with $IC_{50}$ in low nanomolar range.

TABLE 4

Inhibitory activity of HDAC inhibitors

| Compound | HDAC ½ (nM) | HDAC 8 (nM) |
| --- | --- | --- |
| 7 | 91.6 | 4,730 |
| 8 | 88.8 | 3,740 |
| 9 | 13.85 | 994 |
| 10 | 10.56 | 1,020 |
| 11 | 58.88 | 7,130 |
| 12 | 72.44 | 6,780 |
| 13 | 145.50 | 11,050 |
| 14 | 226.73 | N.D. |
| 23 | 36.98 | 3,990 |
| 24 | 44.26 | 4,750 |
| 25 | 4.09 | 1,890 |
| 26 | 1.87 | 1,390 |
| 27 | 55.59 | 5,880 |
| 28 | 123.03 | 4,420 |
| 29 | 169.80 | 10,550 |
| 30 | 223.36 | N.D |
| 36 | 107.1 | 6,680 |
| 38 | 109.8 | 2,320 |

The ketolides 56 were also evaluated for their HDAC inhibitory activity against HDACs 1 and 2 from HeLa cell nuclear extract, HDAC6, and HDAC8 using the Fluor de Lys assay. The results are shown in Table 5.

TABLE 5

HDAC inhibition activity ($IC_{50}$) and Isoform Selectivity of tricyclic ketolide-based HDAC inhibitors

| Compd | n | Nuclear Extract (nM) | HDAC 8 (nM) | HDAC8: Nuclear Extract Isoform Selectivity | HDAC 6 (nM) | HDAC6: Nuclear Extract Isoform Selectivity |
| --- | --- | --- | --- | --- | --- | --- |
| 56a | 1 | 7.77 | 796.2 | 102.5 | 1180.1 | 151.9 |
| 56b | 2 | 1.03 | 544.6 | 528.7 | 728.7 | 707.5 |
| 56c | 3 | 104.2 | 1909.3 | 18.3 | 1709.8 | 16.4 |
| 56d | 4 | 163.6 | 2859.9 | 17.5 | 1916.9 | 11.7 |
| 56e | 5 | 208.2 | 4557.8 | 21.9 | 3203.1 | 15.4 |

Results show a linker-dependent anti-HDAC activity which peaked with compound 56b, an analog having 6 methylene spacers separating the triazole ring from the zinc binding hydroxamic acid group (Table 5). Compound 56b potently inhibits the deacetylase activity of HDACs 1 and 2 with a single digit nanomolar $IC_{50}$. Compounds 56c-e, analogs having longer methylene spacers than those of 56b, show a progressive reduction in anti-HDAC activity with increase in methylene spacer length. The HDAC inhibition profiles of these triketolide-derived HDACi paralleled those we previously reported for the macrolide-derived HDACi.

To obtain evidence for the HDAC isoform selectivity, the triketolide HDAC inhibitors were tested against HDAC6 and HDAC8. Compared to SAHA, compounds 56a and 56b are more selective for HDAC1/2 with selectivity indices comparable to those of their 14-membered macrolide congeners. Compounds 56c-e are less selective for either HDAC isoform compared to 56a-b. However, 56c-e have improved HDAC6 and comparable HDAC8 isoform selectivity relative to SAHA (Table 5).

Example 6

Evaluating in Vitro Anti-Cancer Activity of HDAC Inhibitors

The potency of compounds in Table 5 were investigated by determining the drug concentrations necessary for 50% inhibition of cell viability ($IC_{50}$) in SKMES 1, NCI-1169, DU 145 cells, lung fibroblasts, and HMEC. Drug concentrations necessary for 50% inhibition of cell viability ($EC_{50}$) were quantitatively measured using trypan blue exclusion according to literature protocol (Mosmann, T. (1983). *J. Immunol. Methods* 65: 55; Chen et al. (2008) Bioorg. Med. Chem. 16: 4839). Table 6 shows the $EC_{50}$ values for each compound. All compounds inhibit the proliferation of the transformed cells studied with $EC_{50}$ in low micromolar range. Most importantly, these compounds are less toxic to untransformed cell-lines (lung fibroblast and HMEC) that we have studied to date.

TABLE 6

Cell growth inhibitory data

| Compound | SKMES 1 (uM) | NCI-H69 (uM) | DU-145 (uM) | Lung fibroblast (uM) | HMEC (uM) |
| --- | --- | --- | --- | --- | --- |
| 7 | 1.79 | 1.92 | 1.45 | >10 | >10 |
| 8 | 1.68 | 1.77 | 1.24 | >10 | >10 |
| 9 | 2.33 | 3.45 | 1.88 | >10 | >10 |
| 10 | 2.56 | 3.01 | 1.97 | >10 | >10 |
| 11 | 4.89 | 4.56 | 5.89 | >10 | >10 |
| 12 | 4.67 | 3.99 | 5.68 | >10 | >10 |
| 13 | 7.54 | 8.45 | >10 | >10 | >10 |
| 23 | 2.15 | 2.67 | 2.98 | >10 | >10 |
| 24 | 1.95 | 1.92 | 3.29 | >10 | >10 |
| 25 | 1.33 | 1.45 | 1.12 | >10 | >10 |
| 26 | 1.28 | 1.49 | 1.05 | >10 | >10 |
| 27 | 4.89 | 5.67 | 6.97 | >10 | >10 |
| 28 | 4.45 | 5.09 | 5.78 | >10 | >10 |
| 29 | 7.12 | 7.29 | 8.14 | >10 | >10 |

The effect of compounds 56a-e on cancer cell lines: prostate (DU-145), lung (A549), and breast cancer (MCF-7) and a non-transformed cell, human lung fibroblast cell (Hs1.Lu) were also evaluated. Drug concentrations necessary for 50% inhibition of cell viability ($EC_{50}$) were quantitatively measured using MTS colorimetric assay as described above. Table 7 shows the $EC_{50}$ values of each compound.

TABLE 7

Anti-proliferative activity (μM) of tricyclic ketolide-based HDAC inhibitors

| Compd | n | DU-145 (μM) | A549 (μM) | MCF-7 (μM) | Hs1.Lu Normal Lung Fibroblast (μM) |
| --- | --- | --- | --- | --- | --- |
| 56a | 1 | 1.64 | 1.17 | 1.26 | N.D. |
| 56b | 2 | 0.82 | 0.66 | 0.75 | N.D. |
| 56c | 3 | 3.70 | 1.64 | 1.35 | N.D. |
| 56d | 4 | 3.89 | 2.48 | 2.56 | N.D. |
| 56e | 5 | 4.83 | 2.81 | 3.68 | N.D. |

Compounds 56a-e inhibit the proliferation of all transformed cells studied with anti-proliferative activity that closely matched their in vitro ant-HDAC activity. Specifically, compound 56b has the most potent anti-proliferative activity with high nanomolar efficacy against all three cancer cell lines. Moreover, none of the compound shows any discernible toxicity against normal Hs1.Lu cells at drug concentrations in excess of 10 µM (Table 7). These data showed that the triketolide hydroxamates reported here are selectively toxic to the transformed cells.

Example 7

Antiparasitic Activity of Non-Peptide Macrocyclic Histone Deacetylase Inhibitors Macrocyclic histone deacetylase inhibitors were evaluated for parasitic activity against *Plasmodium falciparum* and *Leismania donovani*. *P. falciparum* and *L. donovani* are the causative parasites of malaria and leishmaniasis, two human diseases which constitute a serious threat to public health in tropical and sub-tropical countries. Antimalarial activity was evaluated in vitro using chloroquine-sensitive (D6, Sierra Leone) and chloroquine-resistant (W2, Indochina) strains of *P. falciparum*. Antileishmanial activity was evaluated in vitro against the promastigote stage of *L. donovani*.

*Plasmodium* growth inhibition was determined by a parasite lactate dehydrogenase assay using Malstat reagent. Inhibition of viability of the promastigote stage of *L. donovani* was determined using standard Alamar blue assay, modified to a fluorometric assay. Amphotericin B and pentamidine, standard antileishmanial agents; chloroquine and artimisinin, standard antimalarial; and suberoylanilide hydroxamic acid (SAHA), standard HDACi were all used as positive controls. To determine selective toxicity index, all compounds were tested against nontransformed mammalian cell lines namely, monkey kidney fibroblasts (Vero) and murine macrophages (J774.1) using Neutral Red assay. The results are shown in Table 8.

TABLE 8

Antiparasitic activity of non-peptide HDAC inhibitors

| Compd | R | n | HDAC Inhibition IC$_{50}$ (nM)$^a$ | Antileshmanial activity IC$_{50}$ (µg/ml) | Antileshmanial activity IC$_{90}$ (µg/ml) | Antimalarial Activity Plasmodium falciparum (D6 clone) IC$_{50}$ (µg/ml) | Antimalarial Activity Plasmodium falciparum (W2 clone) IC$_{50}$ (µg/ml) | Cytotoxicity (VERO) IC$_{50}$ (µg/ml) | S.I. D6 (W2) |
|---|---|---|---|---|---|---|---|---|---|
| 1 | [structure] | 5 | 37.0 | NA | NA | 0.90 | 0.93 | NC | >5.3 (>5.1) |
| 2 | [structure] | 5 | 44.3 | NA | NA | 1.20 | 1.40 | NC | >4.0 (>3.4) |
| 3 | [structure] | 5 | 91.6 | NA | NA | 1.20 | 1.60 | NC | >4.0 (>3.0) |

TABLE 8-continued

Antiparasitic activity of non-peptide HDAC inhibitors

| Compd | R | n | HDAC Inhibition IC$_{50}$ (nM)$^a$ | Antileshmanial activity IC$_{50}$ (μg/ml) | | Antimalarial Activity | | Cytotoxicity (VERO) IC$_{50}$ (μg/ml) | S.I. D6 (W2) |
|---|---|---|---|---|---|---|---|---|---|
| | | | | | IC$_{90}$ (μg/ml) | Plasmodium falciparum (D6 clone) IC$_{50}$ (μg/ml) | Plasmodium falciparum (W2 clone) IC$_{50}$ (μg/ml) | | |
| 4 | *structure* | 5 | 88.8 | NA | NA | 1.30 | 1.70 | NC | >3.7 (>2.8) |
| 5 | *structure* | 6 | 4.1 | 18 | NA | 0.27 | 0.31 | NC | >17.6 (>15.4) |
| 6 | *structure* | 6 | 1.9 | NA | NA | 0.18 | 0.25 | NC | >26.4 (>19.0) |
| 7 | *structure* | 6 | 13.9 | NA | NA | 0.23 | 0.10 | NC | >20.7 (>47.6) |
| 8 | *structure* | 6 | 10.6 | NA | NA | 0.16 | 0.17 | NC | >29.8 (>28.0 |

TABLE 8-continued

Antiparasitic activity of non-peptide HDAC inhibitors

| Compd | R | n | HDAC Inhibition IC$_{50}$ (nM)$^a$ | Antileshmanial activity | | Antimalarial Activity | | Cytotoxicity (VERO) IC$_{50}$ (μg/ml) | S.I. D6 (W2) |
|---|---|---|---|---|---|---|---|---|---|
| | | | | IC$_{50}$ (μg/ml) | IC$_{90}$ (μg/ml) | Plasmodium falciparum (D6 clone) IC$_{50}$ (μg/ml) | Plasmodium falciparum (W2 clone) IC$_{50}$ (μg/ml) | | |
| 9 | [structure] | 7 | 55.6 | 20 | 34 | 2.50 | 2.00 | NC | >1.9 (>2.4) |
| 10 | [structure] | 7 | 123.0 | NA | NA | 3.00 | 2.70 | NC | >1.6 (>1.8) |
| 11 | [structure] | 7 | 58.9 | NA | NA | 2.40 | 2.30 | NC | >2.0 (>2.1) |
| 12 | [structure] | 7 | 72.4 | NA | NA | 3.50 | 3.20 | NC | >1.4 (>1.5) |

TABLE 8-continued

Antiparasitic activity of non-peptide HDAC inhibitors

| Compd | R | n | HDAC Inhibition IC$_{50}$ (nM)$^a$ | Antileshmanial activity IC$_{50}$ (μg/ml) | | Antimalarial Activity | | Cyto-toxicity (VERO) IC$_{50}$ (μg/ml) | S.I. D6 (W2) |
|---|---|---|---|---|---|---|---|---|---|
| | | | | | IC$_{90}$ (μg/ml) | Plasmodium falciparum (D6 clone) IC$_{50}$ (μg/ml) | Plasmodium falciparum (W2 clone) IC$_{50}$ (μg/ml) | | |
| 13 | (structure) | 8 | 169.8 | 3.40 | 7.00 | 1.70 | 1.00 | NC | >2.8 (>4.8) |
| 14 | (structure) | 8 | 145.5 | 20 | 35 | 1.10 | 0.83 | NC | >4.3 (>5.7) |
| 15 | (structure) | 9 | 223.4 | 3.40 | 7.00 | 1.40 | 0.80 | NC | >3.4 (6.0) |

TABLE 8-continued

Antiparasitic activity of non-peptide HDAC inhibitors

| Compd | R | n | HDAC Inhibition IC$_{50}$ (nM)$^a$ | Antileshmanial activity | | Antimalarial Activity | | Cytotoxicity (VERO) | S.I. |
|---|---|---|---|---|---|---|---|---|---|
| | | | | IC$_{50}$ (μg/ml) | IC$_{90}$ (μg/ml) | Plasmodium falciparum (D6 clone) IC$_{50}$ (μg/ml) | Plasmodium falciparum (W2 clone) IC$_{50}$ (μg/ml) | IC$_{50}$ (μg/ml) | D6 (W2) |
| 16 | *structure* | 9 | 226.7 | 3.50 | 7.00 | 0.84 | 0.88 | NC | >5.7 (>5.4) |
| Chloroquine | | — | NT | NT | NT | 0.017 | 0.125 | NT | NT |
| Artetnisinin | | — | NT | NT | NT | 0.004 | 0.006 | NT | NT |
| Pentamidine | | — | NT | 0.90 | 1.70 | NT | NT | NT | NT |
| Amphotericine B | | — | NT | 0.18 | 0.32 | NT | NT | NT | NT |
| SAHA | | — | 65 | 22 | 50 | 0.25 | 0.47 | 1.20 | 4.8 (2.5) |

NA = Not active up to the highest concentration tested
NC = Not cytotoxic up to the highest concentration tested
NT = Not tested The non-peptide macrocyclic HDAC inhibitors potently inhibited the proliferation of both the sensitive and resistant strains of *P. falciparum* with IC50 ranging from 0.1 μg/mL to 3.5 μg/mL (Table 1). In particular, compounds 5-8 in Table 8, derived from either the 14- or 15-membered macrolide analogs macrolides and having 6 methylene spacers separating the triazole ring from the zinc-binding hydroxamic acid group (n=6), have the most potent antimalarial activities in this series. These compounds are equipotent or >4-fold more potent than the control compound SAHA. Moreover, they are several folds more selectively toxic to either strains of *P. falciparum* compared to SAHA. The antimalarial activities of these macrocyclic HDACi followed a similar trend as their anti-HDAC activity against HDAC1/2 from HeLa nuclear extract, suggesting that parasite HDACs could be an intracellular target of the these compounds.

Compounds 5 and 9 exhibited modest activity against the promastigote stage of *L. donovani*. This result is contrary to previous data on simple aryltriazolylhydroxamates which have antimalarial and antileishmanial activities that followed a similar trend.

A comparison of the antileishmanial activities of compounds 13 and 14, analogs with n=8, revealed an interesting disparity between the activity of 14- and 15-membered macrocyclic rings. 14-Membered compound 13 is 5- to 6-fold more potent than its 15-membered congener 14. However, this disparity dissipates after a single methylene group extension (n=9), as compounds 15 and 16 have virtually indistinguishable antileishmanial activities. Comparatively, compounds 13, 15 and 16, analogs with the most potent antileishmanial activities, are about 7- to 10-fold more potent than SAHA and approximately 3-fold less potent than pentamidine.

Since these non-peptide macrocyclic HDACi have nanomolar anti-HDAC activities, the observed disparity in the trend of their antimalarial and antileishmanial activities may have implication in the organization of the active sites of the relevant *P. falciparum* and *L. donovani* HDAC isozymes. These observations provide additional evidence of the suitability of HDAC inhibition as a viable therapeutic option to curb infections caused by apicomplexan protozoans and trypanosomatids (1, 5, 6, 14) and could facilitate the identification of other HDACi that are more selective for either parasite.

The antiparasitic activity of ketolides 56 were also evaluated against *P. falciparum* and *L. donovani*. The results are shown in Table 9.

TABLE 9

Antiparasitic activity of ketolide non-peptide HDAC inhibitors

| Compound | n | Antileishmanial Activity | | Antimalarial Activity | | Cytotoxicity (VERO) | S.I. |
|---|---|---|---|---|---|---|---|
| | | $IC_{50}$ (µg/ml) | $IC_{90}$ (µg/ml) | *Plasmodium falciparum* (D6 clone) $IC_{50}$ (µg/ml) | *Plasmodium falciparum* (W2 clone) $IC_{50}$ (µg/ml) | $IC_{50}$ (µg/ml)$^a$ | D6 (W2) |
| 56a | 1 | NA | NA | 0.96 | 1.80 | NC | >5.0 (no value) |
| 56b | 2 | NA | NA | 0.14 | 0.12 | NC | >34 (>39.7) |
| 56c | 3 | 19 | 36 | 1.20 | 1.50 | NC | >4.0 (>3.2) |
| 56d | 4 | 14 | 32 | 1.20 | 1.30 | NC | >4.0 (>3.7) |
| 56e | 5 | 4.8 | 23 | 1.20 | 0.84 | NC | >4.0 (>5.7) |
| Chloroquine | — | NT | NT | 0.011 | 0.14 | NT | NT |
| Artemisinin | — | NT | NT | 0.006 | 0.009 | NT | NT |
| Pentamidine | — | 1.4 | 6.0 | NT | NT | NT | NT |
| Amphotericine B | — | 0.08 | 0.3 | NT | NT | NT | NT |
| SAHA | — | 22 | 50 | 0.25 | 0.47 | 1.20 | 4.8 (2.5) |

Compounds 56a-e potently inhibit the proliferation of both the sensitive and resistant strains of *P. falciparum* with $IC_{50}$ ranging from 0.12 µg/mL to 1.5 µg/mL (Table 9). 56b has the most potent antimalarial activity which is between 2- to 4-fold more potent than the control compound SAHA. Moreover, 56b is several folds more selectively toxic to either strains of *P. falciparum* compared to SAHA. Compounds 56c-e have a moderate to good antileishmanial activity against the promastigote stage of *L. donovani* activity which peaks with 56e, the analog with the longest methylene spacers in the series. This result is in contrast to the antimalarial activity that mirrors compound anti-HDAC activity and it may have implications in the organization of the active sites of the relevant *P. falciparum* and *L. donovani* HDAC isozymes. We have observed a similar methylene spacer-length dependence in the antileishmanial activity of macrocyclic HDACi 14- and 15-membered macrolides as shown in Table 8. The foregoing observations further support the suitability of HDAC inhibition as a viable therapeutic strategy to curb infections caused by apicomplexan protozoans and trypanosomatids.

Example 8

3-Hydroxypyridine-2-thiones as Zinc Binding Groups for HDAC Inhibition

In Silico Analysis of Pyridinone Zinc Binding Groups

To evaluate the feasibility of pyridinone fragments in HDACi design, fragments were docked against HDAC crystal structures using validated molecular dock program (AutoDock 4.2). Three representative pyridinone fragments—3-hydroxypyridine-2-thione (3-HPT), 3-hydroxypyridine-4-thiones, and 1-hydroxypyridine-2-thione, the structures of which are shown below, were docked against HDAC macromolecules. It is noted that the N-1 position of 3-hydroxypyridine-2-thione and 3-hydroxypyridine-4-thione could be modified, as required, to include a prototypical HDACi linker region coupled to a surface recognition cap group. Small fragments tend to have lower binding energy and non-specific interaction at the surface. These problems were addressed by: i) selecting compact grid size around the $Zn^{2+}$ active site; and ii) selecting thione analogs of pyridinone fragments which are expected to bind more tightly with $Zn^{2+}$ metal ion than their carbonyl counterparts, thereby improving binding energy.

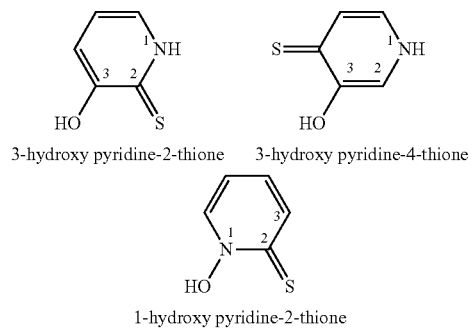

3-hydroxy pyridine-2-thione   3-hydroxy pyridine-4-thione 1-hydroxy pyridine-2-thione These fragments were docked against class I HDAC enzymes HDAC1 and HDAC8 and structurally distinct HDAC6 which belongs to class II. These isoforms have distinct structural differences at the $Zn^{2+}$ active site. Any evidence of isoform selectivity against any one of them should establish a broader isoform profile. The HDAC8 crystal structure (PDB code: 1VKG) has been solved, while HDAC1 and HDAC6 homology model were built from human HDAC2 (PDB code: 3MAX) and HDAC8 (PDB code: 3FOR) X-ray structure coordinates respectively. These were used to obtain in silico data for fragment interaction at the active sites. Preliminary docking analysis against HDAC isoforms revealed that 3-hydroxypyridine-2-thione (3-HPT), 3-hydroxypyridine-4-thiones, and 1-hydroxypyridine-2-thione bind to the vicinity of $Zn^{2+}$ ion at the active sites of HDAC1, HDAC6 and HDAC8. This suggests that pyridinones can serve as effective ZBGs in HDACi design.

Closer analyses of the docked structures revealed that the orientation of N-1 position of 3-hydroxypyridine-4-thione is pointing towards the base of the active site pocket instead of pointing toward the surface as seen with 3-HPT. In order to evaluate ZBGs other than hydroxamic acid, 3-hydroxypyridine-2-ones were selected for further investigation.

In vitro analysis of 3-hydroxypyridine-2-ones as ZBGs

To verify the in silico findings, an HDAC inhibition assay using 3-hydroxypyridine-2-ones was performed to determine their effect on enzyme activity. HDAC inhibition was assayed initially using cell free assay (Fluor de Lys) as described above.

There is precedence that fluorescently labeled substrates can perturb enzyme activity and the effect of inhibitors. Indeed, many recommended Fluor de Lys substrates have been shown not to be active toward their corresponding enzymes, including HDAC8, in the absence of fluorophore. Additionally, 3-hydroxypyridine-2-ones are highly colored solids and might lead to false positive signals. Mindful of these facts, a label-free SAMDI (self-assembled monolayers for MALDI) mass spectrometry assay was also used to assess HDAC inhibition.

The SAMDI technique, wherein self-assembled monolayers (SAM) of alkanethiolates on gold are analyzed by matrix assisted laser desorption/ionization (MALDI) mass spectrometry, has been widely used to characterize many biochemical activities, including the deacetylase enzyme family. The SAMDI assay was used to measure the inhibition constant ($K_I$) of fragments against HDAC1, HDAC6 and HDAC8 using a previously identified preferred HDAC substrate. 3-hydroxypyridine-2-one was found to be inactive against the three HDAC isoforms. However, the thione derivative (3-HPT) showed low micromolar $IC_{50}$ values against the HDAC6 and HDAC8 isoform and inactive against HDAC1 (Table 10).

TABLE 10

Activity of 3-hydroxypyridine-2-one and 3-hydroxypyridine-2-thione as determined by SAMDI analysis.

| Compounds | $IC_{50}$ (nM) | | |
|---|---|---|---|
| | HDAC1 | HDAC6 | HDAC8 |
| 3-hydroxypyridine-2-one | NI | NI | NI |
| 3-hydroxypyridine-2-thione | NI | 681 ± 110 | 3675 ± 1201 |

NI — No significant Inhibition (below 20% Inhibition);
% inhibitions of the compounds at 10 μM are given if the $IC_{50}$ was above 10 μM.

Analysis of substituted 3-hydroxypyridine-2-thiones

After promising results which demonstrated the activity of 3-hydroxypyridine-2-thione and suggested potential isoform selectivity, 3-HPT analogues substituted at the N-1 nitrogen were investigated to determine if linker substitution at this position can be tolerated. Accordingly, 1-methyl-3-hydroxypyridine-2-thione was docked against HDAC6 and HDAC8.

Substitution with N-methyl group didn't alter the docked pose of 3-HPT fragment. The amino acid residues surrounding the docked structure of 1-methyl-3-hydroxypyridine-2-thiones were analyzed to further refine the design of the linker region. The hydrophobic tunnel which joins the ZBG active site of HDAC6 to the surface consists of amino acid (AA) residues Leu74, Pro501, Asp567, Gly619, Phe620, Phe680, Pro748, Tyr782. Hydrophobic aromatic Phe620, Phe680, Tyr782 AA residues are in close proximity to the N-methyl group of docked 1-methyl-3-hydroxypyridine-2-thione's structure. Similarly, the hydrophobic tunnel which joins the ZBG active site of HDAC8 to the surface consists of amino acid (AA) residues Phe152, Phe208, Tyr306, Trp141, His180, Asp267. Hydrophobic aromatic AA residues Phe152, Phe208, Tyr306, Trp141 are in close proximity of N-methyl group of docked 1-methyl-3-hydroxypyridine-2-thione's structure. As a consequence, aromatic linkers containing, for example, phenyl, biphenyl or triazole rings, might contribute to pi-stacking interactions with aromatic AA, thereby enhancing binding energy and improve compounds' affinity for HDAC6 and HDAC8.

Compounds 138-140, 3-hydroxypyridine-2-thiones containing aromatic substituents attached to the N-1 nitrogen, were investigated in silico.

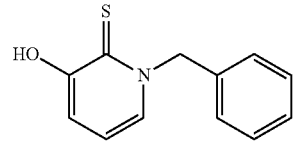

138

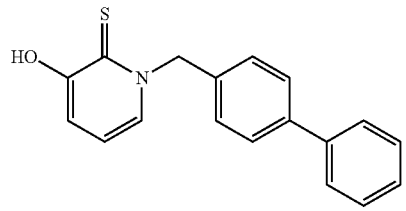

139

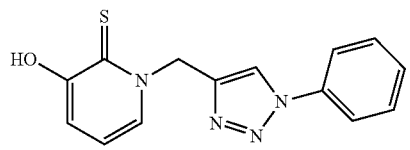

140

Analysis of HDAC6 docking with compound 138 reveals hydrophobic interaction between the compound 138 phenyl ring and AA residues Phe620 and Pro501. However, upon addition of a $2^{nd}$ phenyl ring, as in compound 139, the compound adopts a higher energy confirmation which loses hydrophobic interaction as seen in compound 138.

In the case of HDAC8 docking, analysis of compounds 138, 139, and 140 revealed that the phenyl ring and the triazole group participated in pi-stacking interactions with aromatic AA Trp141 in HDAC8. In compound 139, containing a biphenyl substitution, the $1^{st}$ phenyl ring adjacent to ZBG maintained its pi-stacking interaction with Trp141 and the $2^{nd}$ phenyl ring orients in deep subpocket near the active site, albeit without any significant interaction. However, it is interesting to note that the $2^{nd}$ phenyl ring of compound 139 is surrounded by amino acids which can potentially contribute to a low energy conformation by exploiting hydrogen bonding and hydrophobic interaction surrounding it. Similarly, Pro74 and Leu749 surround the $2^{nd}$ phenyl ring of compound 139 in HDAC6 docked conformation. This suggests that substitution of the $2^{nd}$ phenyl ring with hydrogen bonding or hydrophobic groups will potentially lower binding energy and improve potency.

To investigate the effect of incorporation of functional groups on the $2^{nd}$ phenyl group of the 3-hydroxypyridine-2-thiones, compounds possessing varied substituents on the second phenyl ring were evaluated. The proposed modifications allow the 3-hydroxypyridine-2-thiones to participate in hydrogen bonding as well as hydrophobic interactions with AA residues surrounding the $2^{nd}$ phenyl group of 139. The compounds chosen for initial investigation are shown below

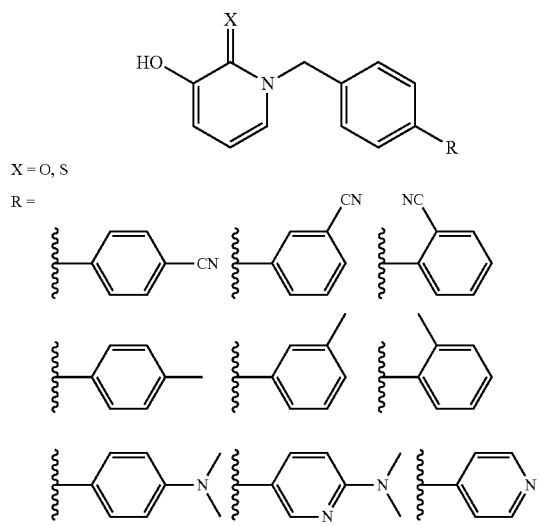

X = O, S

R =

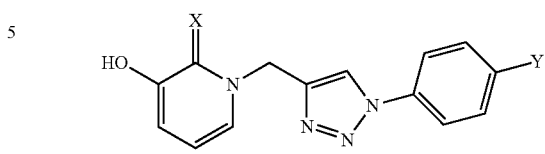

X = O, S
Y = H,
Y = dimethyamino

Initial fragments 142a-142c and 144a-144c were synthesized in 2 to 3 steps as indicated in Scheme 17. Synthesis involved coupling of methyl iodide and corresponding benzyl bromides with commercially available 3-methoxypyridine-2-one to give the O-methyl protected intermediates 141a-141c. Thione intermediates were synthesized from their carbonyl precursors using Lawesson's reagent chemistry. Finally, deprotection of O-methyl group by lewis acid $BBr_3$ gave the desired products 142a-142c and 144a-144c.

Scheme 17. Synthesis of 142a-142c and 144a-144c.

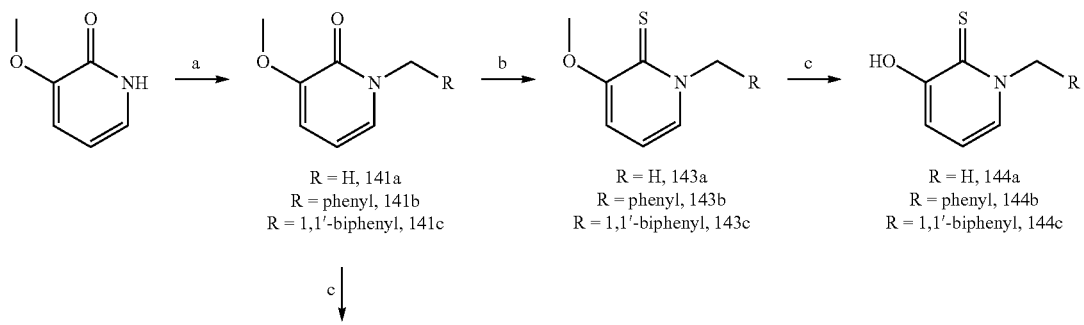

R = H, 141a
R = phenyl, 141b
R = 1,1'-biphenyl, 141c

R = H, 143a
R = phenyl, 143b
R = 1,1'-biphenyl, 143c

R = H, 144a
R = phenyl, 144b
R = 1,1'-biphenyl, 144c

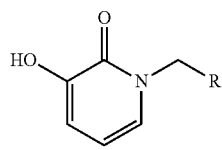

R = H, 142a
R = phenyl, 142b
R = 1,1'-biphenyl, 142c

For 141a a) MeI, KOH, MeOH; For 141b, 141c; a) R—$CH_2Br$, $K_2CO_3$, DMF, 100° C. b) Lawesson's reagent, toluene, reflux. c) $BBr_3$, $CH_2Cl_2$.

The proposed routes to the biphenyl fragments require crucial intermediate 145 which was obtained by coupling of 4-bromobenzylbromide with 3-methoxypyridine-2-ones (Scheme 18). Standard Suzuki coupling with corresponding boronic acids gave intermediates 146a-146i. Similarly, Lawesson's chemistry was used to prepare thione intermediates. Deprotection of the O-methyl group yielded the final biphenyl compounds 148a-148i and 149a-149i (Scheme 18).

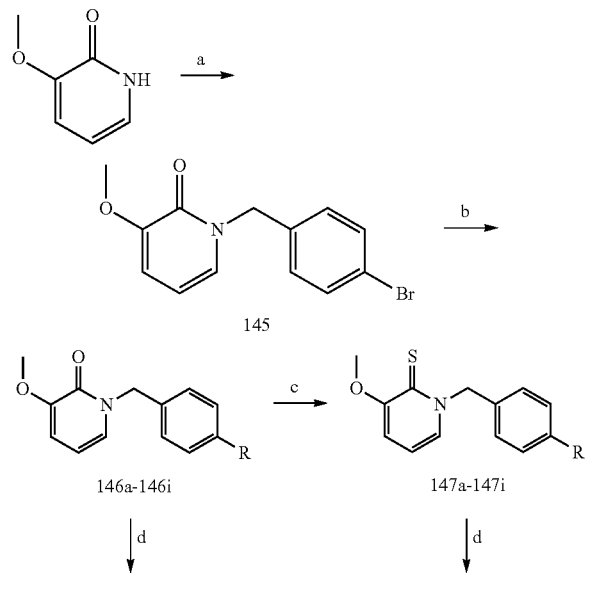

Scheme 18. Synthesis of 148a-148i and 149a-149i.

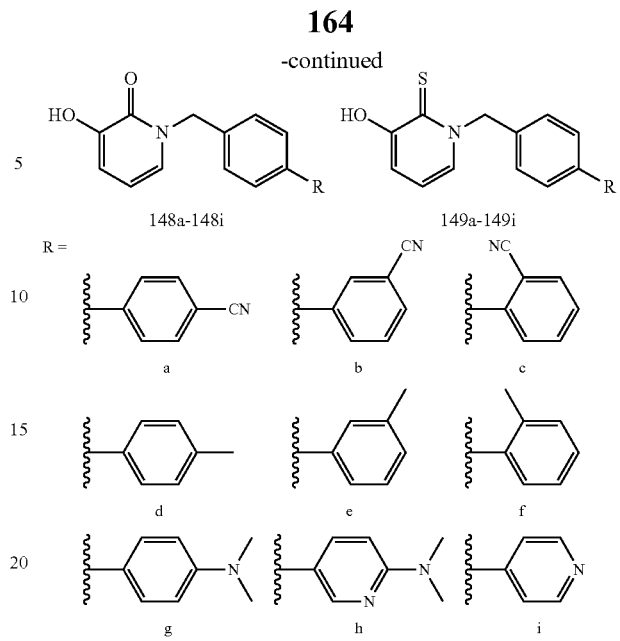

a) 4-bromobenzylbromide, K$_2$CO$_3$, THF, reflux, b) R—B(OH)$_2$, Pd(PPh$_3$)$_4$, K$_2$CO$_3$, toluene:ethanol:H$_2$O; 80° C. c) Lawesson's reaget, toluene, reflux; d) BBr$_3$, CH$_2$Cl$_2$ Synthesis of triazole based compounds 153a-153b and 154a-154b is shown in Scheme 18. It involves the intermediacy of terminal alkyne 150, by N-alkylation reaction of 3-methoxypyridine-2-one with propargyl bromide. Cu(I)-catalyzed Huisgen cycloaddition gave the cyclized product 151a-151b. Lawesson's chemistry was again used to gain access to thiolated analogs. Deprotection of O-methyl group was achieved by reaction with BBr$_3$ (Scheme 19).

Scheme 19. Synthesis of 153a-153b and 154a-154b.

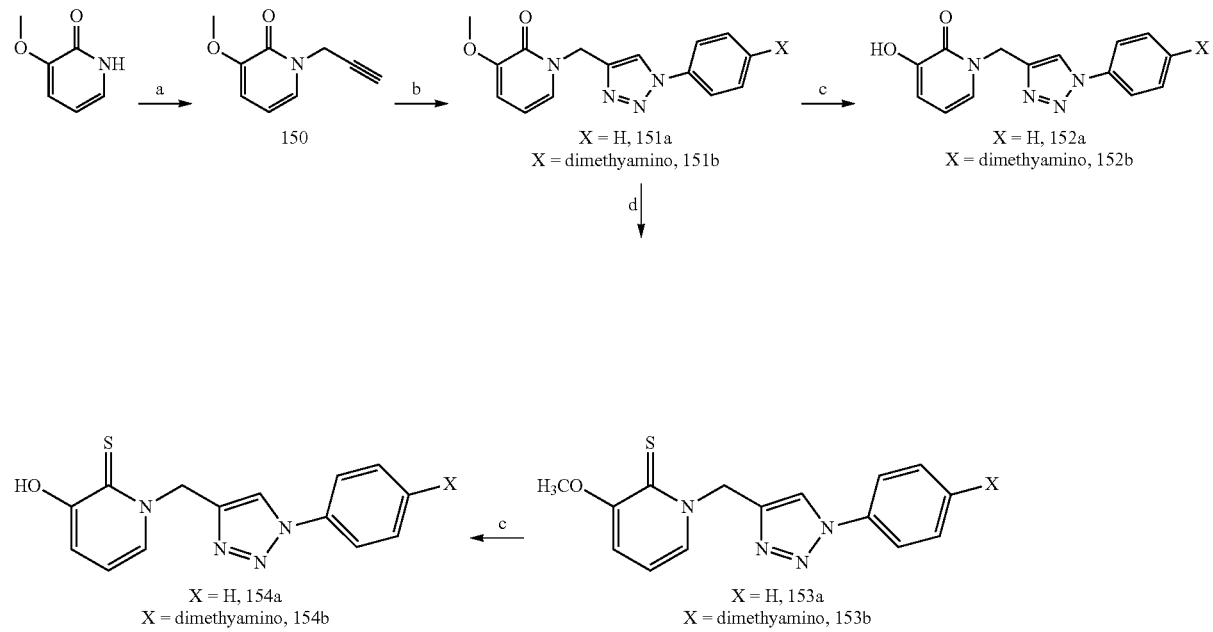

a) propargyl bromide, K$_2$CO$_3$, THF, reflux
b) azido intermediates (phenyl azide, 4-azido-N, N-dimethylaniline), CuI, DIPEA, THF;
c) BBr$_3$, CH$_2$Cl$_2$;
d) Lawessons' reagent, Toluene, reflux The activity of these compounds was evaluated using SAMDI analysis as described above. There is clear distinction in the HDAC inhibition activities of the carbonyl and thione analogs with the latter showing higher potency (Table 11). The enhanced anti-HDAC activity of the thione analogs could be attributed to thiophilicity which favors $Zn^{2+}$ binding. Most of the compounds in this series showed more selectivity towards HDAC6 and HDAC8 compared to HDAC1. A head to head comparison of HDAC6 inhibition showed that compound 144b which contains one phenyl ring has better activity than biphenyl compound 144e. Similarly, for HDAC8 compound 144b showed 2 fold superior activity when compared to 144e. This observation is consistent with the docking result as the $2^{nd}$ phenyl ring doesn't take part in any meaningful interactions with residues on HDAC6 and HDAC8 outer rims. However, replacement of the $2^{nd}$ phenyl ring of compound 144c with a 4-pyridyl ring results in slightly better activity against HDAC8, however this substitution wasn't tolerated very well against HDAC6 resulting in 4-fold diminished activity when compared to 144b.

Substitution of $2^{nd}$ phenyl ring with electron donating N,N-dimethylamino group at para position (149g) has similar effect as 4-pyridyl substitution (149i) for HDAC8. Importantly, it resulted in loss of activity against HDAC6, making it distinctively selective for HDAC8 (Table 11). On the contrary, combination of pyridine and N,N-dimethylamine substitutions as seen in compound 149h resulted in HDAC6 selectivity as compared to HDAC1 and HDAC8. Incorporation of methyl group, another electron donating group, revealed an interesting paradigm of selectivity for HDAC6 and HDAC8. In case of HDAC6, ortho-substitution found to be more favored, followed by meta and then para. Conversely, for HDAC8, trend for potency was reversed with para-substitution showing the best $IC_{50}$ values (comparing compounds 149d, 149e, 149f in Table 11). Ortho-cyano substitution was also tolerated very well for electron withdrawing cyano group in case of HDAC6 with $IC_{50}$ value of 372 nM, followed by para-substitution. Meta-cyano substitution was least tolerated. In case of HDAC8, changing substitution pattern didn't change $IC_{50}$ values significantly showing approximately 2 µM activity (comparing compounds 149a, 149b, 149c in Table 11). Interestingly, triazole substituted compounds 154a was found to be more active than corresponding biphenyl compound 144c for HDAC8 inhibition. However, a para-N,N-dimethylamino substitution of 154a which resulted in compound 154b was not beneficial. This is contrary to the effect of a similar substitution on the biphenyl compound (Table 11, comparing 144c and 149g; 154a and 154b) where para-N,N-dimethylamino substitution showed enhancement of activity. In case of HDAC6 inhibition, biphenyl compound 144c showed superior activity when compared to triazole compound 154a which was also not surpassed by a para-N,N-dimethylamino substitution as seen in 154b. This SAR provided selective inhibitors of HDAC6 and HDAC8, albeit with lower micromolar activity.

TABLE 11

In-vitro HDAC inhibition of 3-hydroxypyridine-2-thiones

| COMPOUNDS | $IC_{50}$ (nM)* | | |
|---|---|---|---|
| | HDAC1 | HDAC6 | HDAC8 |
| 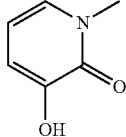<br>142a | NI | NI | 8% |
| 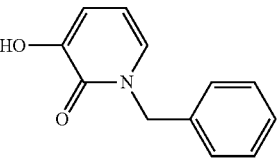 [SMILES: O=c1c(O)cccn1Cc1ccccc1]<br>142b | NI | NI | 8% |
| 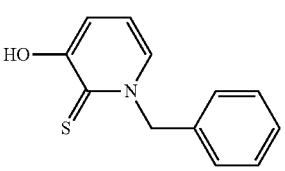 [SMILES: Oc1cccn(Cc2ccccc2)c1=S]<br>144b | NI | 457 ± 27 | 1272 ± 200 |

TABLE 11-continued
In-vitro HDAC inhibition of 3-hydroxypyridine-2-thiones
| COMPOUNDS | IC$_{50}$ (nM)* | | |
|---|---|---|---|
| | HDAC1 | HDAC6 | HDAC8 |
| 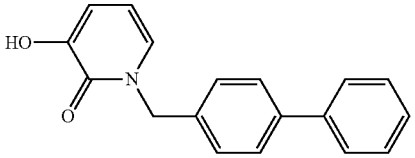 [SMILES: O=c1c(O)cccn1Cc1ccc(-c2ccccc2)cc1] 142c | NI | NI | 8% |
| 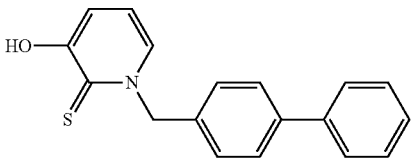 [SMILES: Oc1cccn(Cc2ccc(-c3ccccc3)cc2)c1=S] 144c | NI | 847 ± 188 | 4283 ± 1548 |
| 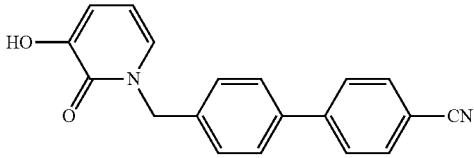 [SMILES: N#Cc1ccc(-c2ccc(Cn3cccc(O)c3=O)cc2)cc1] 148a | NI | NI | 16% |
| 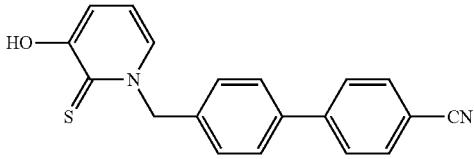 [SMILES: N#Cc1ccc(-c2ccc(Cn3cccc(O)c3=S)cc2)cc1] 149a | NI | 957 ± 159 | 2075 ± 459 |
| 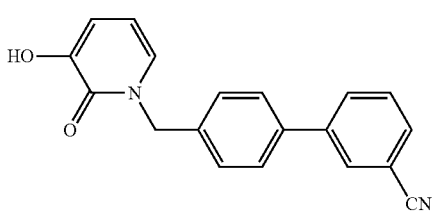 [SMILES: N#Cc1cccc(-c2ccc(Cn3cccc(O)c3=O)cc2)c1] 148b | NI | NI | 9% |
| 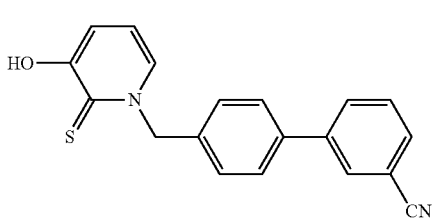 [SMILES: N#Cc1cccc(-c2ccc(Cn3cccc(O)c3=S)cc2)c1] 149b | NI | 44% | 1701 ± 717 |

TABLE 11-continued
In-vitro HDAC inhibition of 3-hydroxypyridine-2-thiones
| COMPOUNDS | IC$_{50}$ (nM)* | | |
|---|---|---|---|
| | HDAC1 | HDAC6 | HDAC8 |
| 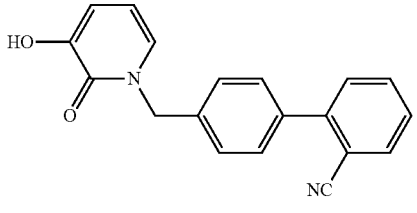 [SMILES: N#Cc1ccccc1-c1ccc(Cn2cccc(O)c2=O)cc1] 148c | NI | 5% | 9% |
| 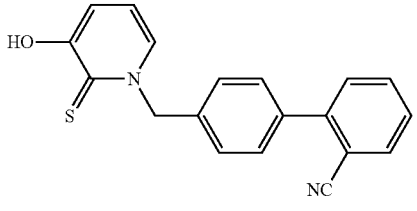 [SMILES: N#Cc1ccccc1-c1ccc(Cn2cccc(O)c2=S)cc1] 149c | NI | 372 ± 35 | 1907 ± 771 |
| 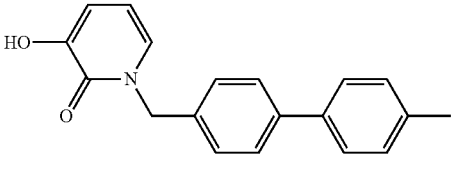 [SMILES: Cc1ccc(-c2ccc(Cn3cccc(O)c3=O)cc2)cc1] 148d | NI | NI | 25% |
| 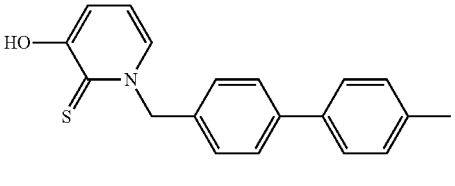 [SMILES: Cc1ccc(-c2ccc(Cn3cccc(O)c3=S)cc2)cc1] 149d | NI | 454 ± 42 | 800 ± 304 |
| 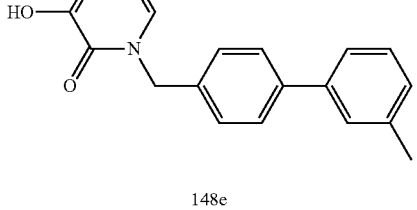 148e | NI | NI | NI |
| 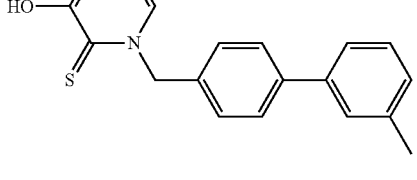 149e | NI | 812 ± 286 | 2496 ± 1180 |

TABLE 11-continued

In-vitro HDAC inhibition of 3-hydroxypyridine-2-thiones

| COMPOUNDS | IC$_{50}$ (nM)* | | |
|---|---|---|---|
| | HDAC1 | HDAC6 | HDAC8 |
| 148f | NI | NI | 9% |
| 149f | NI | 306 ± 69 | 3105 ± 1649 |
| 148g | NI | 11% | 35% |
| 149g | NI | NI | 2858 ± 944 |
| 148h | NI | NI | 37% |
| 149h | NI | 2390 ± 458 | 34% |

TABLE 11-continued

In-vitro HDAC inhibition of 3-hydroxypyridine-2-thiones

| COMPOUNDS | IC$_{50}$ (nM)* | | |
|---|---|---|---|
| | HDAC1 | HDAC6 | HDAC8 |
| 148i | NI | NI | 16% |
| 149i | NI | 2204 ± 355 | 2780 ± 323 |
| 152a | NI | NI | 17% |
| 154a | NI | 41% | 1570 ± 1067 |
| 152b | NI | NI | 8% |

TABLE 11-continued

In-vitro HDAC inhibition of 3-hydroxypyridine-2-thiones

| COMPOUNDS | IC$_{50}$ (nM)* | | |
|---|---|---|---|
| | HDAC1 | HDAC6 | HDAC8 |
| 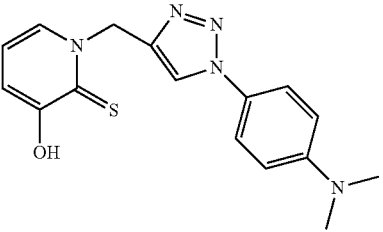 [SMILES: CN(C)c1ccc(-n2cc(Cn3cccc(O)c3=S)nn2)cc1]<br>154b | NI | 1023 ± 99 | 1868 ± 723 |
| SAHA | 38 +/− 2 | 95% | 232 ± 19 |

SAHA wass used for a positive control;
NI — No significant Inhibition (below 20% Inhibition);
% inhibitions of the compounds at 10 μM are given if the IC$_{50}$ was above 10 μM.

Synthetic Procedures

Bromoalkanoic acid, benzyl bromide, 4-bromobenzylbromide, 4-(bromomethyl)-1,1'-biphenyl, 3-methoxy-2(1H)-pyridone, propargyl bromide, phenylacetylene and representative boronic acids were purchased from either Sigma-Aldrich or Alfa-Aesar. Anhydrous solvents and other reagents were purchased and used without further purification. Analtech silica gel plates (60 F$_{254}$) were used for analytical TLC, and Analtech preparative TLC plates (UV 254, 2000 μm) were used for purification. UV light was used to examine the spots. Silica gel (200-400 Mesh) was used in column chromatography. NMR spectra were recorded on a Varian-Gemini 400 magnetic resonance spectrometer. $^1$H NMR spectra were recorded in parts per million (ppm) relative to the peak of CDCl$_3$, (7.24 ppm), CD$_3$OD (3.31 ppm), or DMSO-d$_6$ (2.49 ppm). $^{13}$C spectra were recorded relative to the central peak of the CDCl$_3$ triplet (77.0 ppm), CD$_3$OD (49.0 ppm), or the DMSO-d$_6$ septet (39.7 ppm), and were recorded with complete heterodecoupling. Multiplicities are described using the abbreviation s, singlet; d, doublet, t, triplet; q, quartet; m, multiplet; and app, apparent. High-resolution mass spectra were recorded at the Georgia Institute of Technology mass spectrometry facility in Atlanta. Synthesis of 138a was adapted from literature protocol. Azidoalkanols (138a-138f) were prepared according to literature protocols and was used without further purification. Synthesis of phenyl azide and 4-azido-N,N-dimethylaniline were adapted from literature protocols.

Synthesis of 1-methyl-3-methoxypyridine-2-one (141a)

To a stirring reaction mixture of 3-methoxypyridine-2-one (0.2 g, 1.6 mmol) and KOH (0.18 g, 3.2 mmol) in methanol was added MeI (0.68 g, 4.8 mmol) dropwise in condenser equipped round bottom flask. After overnight stirring at room temperature revealed quantitative formation of product. Reaction mixture was then diluted with water (35 mL) and CHCl$_3$ (40 mL). Organic layer was washed with water (1×35 mL), brine (1×30 mL) and dried over Na$_2$SO$_4$ and solvent was evaporated in vacua to yield pure 141a (0.20 g, 89%) as a colorless oil. $^1$H NMR (400 MHz, CDCl$_3$) δ 6.66 (m, 1H), 6.35 (d, J=7.4 Hz, 1H), 5.83 (t, J=7.1 Hz, 1H), 3.52 (s, 3H), 3.28 (s, 3H). $^{13}$C NMR (100 MHz, CDCl$_3$) δ 158.01, 149.56, 128.81, 111.91, 104.31, 55.44, 37.10.

1-Benzyl-3-methoxypyridine-2-one (141b)

To a stirring reaction mixture of 3-methoxypyridine-2-one (0.2 g, 1.6 mmol) and K$_2$CO$_3$ (0.66 g, 4.8 mmol) in DMF (8 mL) was added benzyl bromide (0.33 g, 1.92 mmol) dropwise in a condenser equipped round bottom flask. Reaction mixture was then heated to 100° C. After overnight stirring, reaction mixture was cooled down and diluted with water (40 mL) and CHCl$_3$ (50 mL). Organic layer was washed with water (3×40 mL), brine (1×30 mL) and dried over Na$_2$SO$_4$ and solvent was evaporated in vacuo to yield pure 141b (0.26 g, 75%) as a colorless oil without any further purification needed. $^1$H NMR (400 MHz, CDCl$_3$) δ 7.26 (m, 5H), 6.85 (dd, J=6.9, 1.7 Hz, 1H), 6.54 (dd, J=7.5, 1.6 Hz, 1H), 6.03 (m, 1H), 5.13 (s, 2H), 3.76 (s, 3H). $^{13}$C NMR (100 MHz, CDCl$_3$) δ 157.94, 150.05, 136.31, 128.56, 128.01, 127.74, 127.70, 111.82, 104.83, 104.81, 55.64, 51.64.

1-(1,1'-Biphenylmethyl)-3-methoxypyridine-2-one (141c)

Reaction of 3-methoxypyridine-2-one (0.2 g, 1.6 mmol), K$_2$CO$_3$ (0.66 g, 4.8 mmol), (4-bromomethyl)-1,1'-biphenyl (0.47 g, 1.92 mmol) in DMF (8 mL) according to method described for synthesis of 141b followed by column chromatography with CH$_2$Cl$_2$, acetone (0-15% gradient), MeOH (0-5% gradient) afforded pure 14 k (0.35 g, 76%) as a colorless oil. $^1$H NMR (400 MHz, CDCl$_3$) 7.48 (dd, J=25.9, 20.6 Hz, 4H), 7.32 (m, 5H), 6.88 (m, 1H), 6.54 (d, J=7.2 Hz, 1H), 6.04 (t, J=7.1 Hz, 1H), 5.16 (s, 2H), 3.76 (s, 3H). $^{13}$C NMR (100 MHz, CDCl$_3$) δ 157.86, 149.97, 140.51, 140.24, 135.28, 128.51, 128.40, 127.71, 127.16, 127.13, 126.74, 111.82, 104.80, 55.56, 51.36.

1-Methyl-3-hydroxypyridine-2-one (142a)

To a solution of 141a (0.1 g, 0.68 mmol) in dry CH$_2$Cl$_2$ (8 mL) was slowly added 1M BBr$_3$ (0.82 mL) at −30° C. under inert atmosphere. The reaction mixture was stirred for 48 h at room temperature. The mixture was again cooled to −30° C.

& then MeOH (5 mL) was slowly added to the mixture. After evaporation of solvent, the residue was adjusted to pH 7 with 1M NaOH and then extracted with CHCl$_3$ (3×30 mL). The combined organic layer dried over Na$_2$SO$_4$. After evaporation of solvent, the residue was purified by prep-TLC with CH$_2$Cl$_2$:Acetone:MeOH (10:1:0.2) to give 61 mg (72%) of pure off white solid. $^1$H NMR (400 MHz, CDCl$_3$) δ 7.92 (s, 1H), 6.78 (dd, J=11.1, 7.1 Hz, 2H), 6.10 (t, J=7.0 Hz, 1H), 3.57 (s, 3H). $^{13}$C NMR (100 MHz, CDCl$_3$) δ 158.82, 146.67, 127.63, 114.36, 106.68, 37.28. HRMS (EI) calcd for C$_6$H$_7$NO$_2$ [M]$^+$ 125.0477. found 125.0477.

1-Benzyl-3-hydroxypyridine-2-one (142b)

Reaction of 141b (0.15 g, 0.55 mmol) with 1M BBr$_3$ (0.66 mL) in dry CH$_2$Cl$_2$ (5 mL) within 48 h according to procedure 142a afforded pure 142b (0.13 g, 90%) as slightly brownish solid. $^1$H NMR (400 MHz, CDCl$_3$) δ 7.3.1 (m, 5H), 6.83 (m, 3H), 6.14 (t, J=7.1 Hz, 1H), 5.19 (s, 2H). $^{13}$C NMR (100 MHz, CDCl$_3$) δ 158.62, 146.78, 135.82, 128.74, 127.97, 126.53, 113.94, 106.95, 52.18. HRMS (EI) calcd for C$_{12}$H$_{11}$NO$_2$ [M]$^+$ 201.0792. found 201.0790.

1-(1,1'-Biphenylmethyl)-3-hydroxypyridine-2-one (142c)

Reaction of 14 k (0.13 g, 0.43 mmol) with 1M BBr$_3$ (0.51 mL) in dry CH$_2$Cl$_2$ (7 mL) within 48 h according to procedure 142a afforded pure 142c (0.1 g, 82%) as slightly brownish solid. $^1$H NMR (400 MHz, DMSO-d$_6$) δ 9.06 (s, 1H), 7.61 (d, J=7.5 Hz, 4H), 7.36 (m, 6H), 6.70 (d, J=6.5 Hz, 1H), 6.12 (t, J=6.9 Hz, 1H), 5.16 (s, 2H). $^{13}$C NMR (100 MHz, DMSO-d$_6$) δ 147.02, 139.77, 139.46, 136.58, 128.93, 128.35, 128.15, 127.49, 126.86, 126.66, 114.75, 105.64, 51.07. HRMS (EI) calcd for C$_{18}$H$_{15}$NO$_2$ [M]$^+$ 277.1101. found 277.1103.

1-Benzyl-3-methoxypyridine-2-thione (143b)

A suspension of 141b (0.060 g, 0.28 mmol) and Lawesson's reagent (0.067 g, 0.17 mmol) in toluene (10 mL) was heated to reflux overnight. Reaction mixture was then cooled to room temperature. Toluene was evaporated in vacuo and resulting crude solid was directly loaded on prep-TLC. Elution with CH$_2$Cl$_2$:Acetone:MeOH (5:1:0.2) gave 143b 53 mg (82%) of yellow solid.

$^1$H NMR (400 MHz, CDCl$_3$) δ 7.30 (m, 6H), 6.65 (d, J=7.7 Hz, 1H), 6.54 (t, J=7.0 Hz, 1H), 5.89 (s, 2H), 3.88 (s, 3H). $^{13}$C NMR (100 MHz, CDCl$_3$) δ 173.18, 159.01, 135.18, 131.70, 128.72, 128.03, 127.98, 111.57, 109.63, 58.79, 56.61. HRMS (EI) calcd for C$_{13}$H$_{13}$NOS [M]$^+$ 231.0718. found 231.0716.

1-(1,1'-Biphenylmethyl)-3-methoxypyridine-2-thione (143c)

Reaction of 141c (0.13 g, 0.44 mmol) and Lawesson's reagent (0.11 g, 0.27 mmol) in toluene according to method described for synthesis of 143b afforded 122 mg of 143c (88%) of yellow solid. $^1$H NMR (400 MHz, CDCl$_3$) 7.52 (m, 1H), 7.35 (m, 2H), 6.66 (dd, J=7.8, 1.3 Hz, 1H), 6.55 (dd, J=7.8, 6.6 Hz, 1H), 5.93 (s, 1H), 3.89 (s, 1H). $^{13}$C NMR (100 MHz, CDCl$_3$) δ 173.08, 158.99, 140.81, 140.20, 134.14, 131.72, 128.61, 128.42, 127.35, 127.28, 126.83, 111.62, 109.67, 104.80, 58.52, 56.58. HRMS (EI) calcd for C$_{19}$H$_{17}$NOS [M]$^+$ 307.1031. found 307.1029.

1-Benzyl-3-hydroxypyridine-2-thione (144b)

Reaction of 143b (0.050 g, 0.21 mmol) with 1M BBr$_3$ (0.66 mL) in dry CH$_2$Cl$_2$ (5 mL) within 48 h according to procedure 142a afforded pure 144b (0.034 g, 72%) as olive green solid. $^1$H NMR (400 MHz, cd$_3$od) δ 7.34 (m, 3H), 6.84 (m, 1H), 5.83 (d, J=49.5 Hz, 1H). $^{13}$C NMR (100 MHz, CD$_3$OD) δ 128.12, 127.61, 127.27, 126.94, 113.77. HRMS (EI) calcd for C$_{12}$H$_{11}$NOS [M]$^+$ 217.0561. found 217.0762.

1-(1,1'-Biphenylmethyl)-3-hydroxypyridine-2-thione (144c)

Reaction of 143c (0.10 g, 0.32 mmol) with 1M BBr$_3$ (0.48 mL) in dry CH$_2$Cl$_2$ (5 mL) within 48 h according to procedure 142a afforded pure 144c (0.074 g, 90%) as olive green solid. $^1$H NMR (400 MHz, cd$_3$od) δ 7.39 (m, 9H), 6.88 (m, 3H), 5.86 (s, 2H). $^{13}$C NMR (101 MHz, cd$_3$od) δ 141.33, 140.21, 128.71, 128.52, 127.49, 127.45, 126.89. HRMS (EI) calcd for C$_{18}$H$_{15}$NOS [M]$^+$ 293.0874. found 293.0873.

1-(4-Bromobenzyl)-3-methoxypyridine-2 (1H)-one (145)

To a stirring reaction mixture of 3-methoxypyridine-2-one (2.00 g, 16 mmol) and K$_2$CO$_3$ (4.42 g, 32 mmol) in THF was added 4-bromobenzyl bromide (5.20 g, 20.8 mmol) slowly. Reaction mixture was the heated to reflux and stirring continued overnight. Reaction mixture was then cooled down and separated into organic and aqueous layer by adding CH$_2$Cl$_2$ (120 mL) and water (60 mL). Organic layer was separated and subsequently washed with water (2×60 mL), brine (1×40 mL). Organic layer was dried on Na$_2$SO$_4$ and solvent was evaporated in vacuo. Crude yellowish solid was triturated with hexanes to give pure white solid 145 (3.49 g, 74%) without further purification. $^1$H NMR (400 MHz, CDCl$_3$) δ 7.25 (m, 2H), 7.04 (m, 2H), 6.78 (dd, J=6.8, 1.2 Hz, 1H), 6.45 (dd, J=7.2, 1.6 Hz, 1H), 5.94 (t, J=7.2 Hz, 1H), 4.95 (s, 2H), 3.64 (s, 3H). $^{13}$C NMR (100 MHz, CDCl$_3$) δ 157.71, 149.91, 135.29, 131.49, 129.59, 127.53, 121.57, 111.82, 104.98, 55.54, 51.10. HRMS (EI) calcd for C$_{13}$H$_{12}$BrNO$_2$ [M]$^+$ 293.0051. found 293.0051.

1-(4-Cyano-(1,1'-biphenylmethyl))-3-methoxyoxy-pyridine-2-one (146a)

145 (0.26 g, 0.86 mmol), (4-cyanophenyl)boronic acid (0.14 g, 0.95 mmol), 2M aq. K$_2$CO$_3$ (0.24 g, 1.73 mmol), toluene (8 mL), EtOH (4 mL) and water (4 mL) were added into reaction flask equipped with magnetic stirrer and water condenser. The resulting suspension was degassed for 10 min by sparging with argon gas. Pd(PPh$_3$)$_4$ (2.5 mol %) was added and the reaction mixture was heated to reflux overnight under argon atmosphere. After cooling to room temperature, CH$_2$Cl$_2$ was added (50 mL) & washed with water (1×40 mL), brine (1×20 mL) and dried on Na$_2$SO$_4$. Column chromatography using gradient CHCl$_3$:Acetone:MeOH (with 5%-20% of acetone and 1%-8% MeOH gradual increase) gave pure off white solid 146a (0.42 g, 78%). $^1$H NMR (CDCl$_3$, 400 MHz) δ 7.60 (m, 4H), 7.40 (m, 4H), 6.90 (dd, J=6.8, 1.6 Hz, 1H), 6.55 (dd, J=7.6, 1.6 Hz, 1H), 6.07 (t, J=7.2 Hz, 1H), 5.16 (s, 2H), 3.75 (s, 3H). $^{13}$C NMR (100 MHz, CDCl$_3$) δ 158.08, 150.28, 144.96, 138.62, 137.13, 132.56, 131.96, 128.85, 128.55, 128.43, 127.96, 127.60, 127.53, 118.88, 112.11, 110.88, 105.24, 56.20, 51.80. HRMS (EI) calcd for C$_2$OH$_6$N$_2$O$_2$ [M]$^+$ 316.1212. found 316.1210.

1-(3-Cyano-(1,1'-biphenylmethyl))-3-methoxyoxy-pyridine-2-one (146b)

Reaction of 140 (0.25 g, 0.85 mmol), (3-cyanophenyl) boronic acid (0.14 g, 0.93 mmol), 2M aq. K$_2$CO$_3$ (0.23 g, 1.69 mmol) and Pd(PPh$_3$)$_4$ (2.5 mol %) according to method described for synthesis of 146a within 18 h afforded 175 mg of 146b (66%) of white solid. $^1$H NMR (400 MHz, CDCl$_3$) δ 7.70 (m, 2H), 7.48 (m, 6H), 6.92 (dd, J=6.9, 1.6 Hz, 1H), 6.57 (dd, J=7.4, 1.4 Hz, 1H), 6.08 (t, J=7.2 Hz, 1H), 5.16 (s, 2H), 3.76 (s, 3H). $^{13}$C NMR (100 MHz, CDCl$_3$) δ 158.09, 150.24, 141.70, 138.33, 136.81, 131.38, 130.76, 130.45, 129.66, 128.87, 127.96, 127.36, 118.76, 112.82, 112.14, 105.26, 55.84, 51.66. HRMS (EI) calcd for C$_{20}$H$_{16}$N$_2$O$_2$ [M]$^+$ 316.1212. found 332.1216.

1-(2-Cyano-(1,1'-biphenylmethyl)-3-methoxyoxypyridine-2-one (146c)

Reaction of 140 (0.15 g, 0.50 mmol), (2-cyanophenyl) boronic acid (0.09 g, 0.60 mmol), 2M aq. K$_2$CO$_3$ (0.14 g, 1.69 mmol) and Pd(PPh$_3$)$_4$ (2.5 mol %) according to method described for synthesis of 146a within 18 h afforded 118 mg of 146c (75%) of white solid. $^1$H NMR (400 MHz, cdcl$_3$) δ 7.72 (m, 1H), 7.60 (m, 1H), 7.45 (m, 2H), 6.94 (dd, J=6.9, 1.7 Hz, 1H), 6.60 (dd, J=7.4, 1.6 Hz, 1H), 6.10 (t, J=7.2 Hz, 1H), 5.21 (s, 1H), 3.80 (s, 1H). $^{13}$C NMR (100 MHz, cdcl$_3$) δ 158.01, 150.18, 144.70, 137.56, 136.94, 133.61, 132.78, 129.91, 129.01, 128.31, 127.92, 127.55, 118.54, 112.01, 110.94, 105.13, 55.74, 51.60. HRMS (EI) calcd for C$_{20}$H$_{16}$N$_2$O$_2$ [M]$^+$ 316.1212. found 316.1201.

1-(4-Methyl-(1,1'-biphenylmethyl))-3-methoxyoxypyridine-2-one (146d)

Reaction of 145 (0.25 g, 0.85 mmol), p-tolylboronic acid (0.14 g, 1.02 mmol), 2M aq. K$_2$CO$_3$ (0.23 g, 1.69 mmol), Pd(PPh$_3$)$_4$ (2.5 mol %) according to method described for synthesis of 146a within 18 h afforded 259 mg of 146d (quantitative) of white solid. $^1$H NMR (400 MHz, CDCl$_3$) δ 7.49 (d, J=8.1 Hz, 2H), 7.42 (d, J=8.1 Hz, 2H), 7.33 (d, J=8.1 Hz, 2H), 7.19 (d, J=8.0 Hz, 2H), 6.88 (dd, J=6.9, 1.6 Hz, 1H), 6.54 (dd, J=7.4, 1.4 Hz, 1H), 6.03 (t, J=7.2 Hz, 1H), 5.15 (s, 2H), 3.76 (s, 3H), 2.34 (s, 3H). $^{13}$C NMR (100 MHz, CDCl$_3$) δ 157.81, 149.88, 140.39, 137.29, 136.87, 134.93, 129.21, 128.35, 127.66, 126.91, 126.53, 111.75, 104.78, 55.51, 51.31, 20.80. HRMS (EI) calcd for C$_{20}$H$_{19}$NO$_2$ [M]$^+$ 305.1416. found 305.1422.

1-(3-Methyl-(1,1'-biphenylmethyl))-3-methoxyoxypyridine-2-one (146e)

Reaction of 140 (0.20 g, 0.68 mmol), m-tolylboronic acid (0.11 g, 0.82 mmol), 2M aq. K$_2$CO$_3$ (0.19 g, 1.36 mmol) and Pd(PPh$_3$)$_4$ (2.5 mol %) according to method described for synthesis of 146a within 18 h afforded 259 mg of 146e (quantitative) of white solid. $^1$H NMR (400 MHz, cdcl$_3$) δ 7.49 (m, 1H), 7.29 (m, 2H), 7.11 (d, J=7.2 Hz, 1H), 6.88 (dd, J=6.9, 1.7 Hz, 1H), 6.53 (dd, J=7.4, 1.6 Hz, 1H), 6.03 (t, J=7.2 Hz, 1H), 5.15 (s, 11H), 3.75 (s, 1H), 2.35 (s, 1H). $^{13}$C NMR (100 MHz, cdcl$_3$) δ 157.81, 149.86, 140.58, 140.16, 137.99, 135.11, 128.37, 128.29, 127.83, 127.66, 127.46, 127.10, 123.80, 111.81, 104.80, 55.48, 51.30, 21.19. HRMS (EI) calcd for C$_{20}$H$_{19}$NO$_2$ [M]$^+$ 305.1416. found 305.1415.

1-(2-Methyl-(1,1'-biphenylmethyl))-3-methoxyoxypyridine-2-one (146f)

Reaction of 140 (0.20 g, 0.68 mmol), O-tolylboronic acid (0.11 g, 0.82 mmol), 2M aq. K$_2$CO$_3$ (0.19 g, 1.36 mmol) and Pd(PPh$_3$)$_4$ (2.5 mol %) according to method described for synthesis of 146a within 18 h afforded 243 mg of 146f (98%) of white solid. $^1$H NMR (400 MHz, cdcl$_3$) δ 7.31 (d, J=7.9 Hz, 1H), 7.17 (m, 2H), 6.93 (m, 1H), 6.56 (dd, J=7.4, 1.6 Hz, 1H), 6.06 (t, J=7.2 Hz, 1H), 5.18 (s, 1H), 3.76 (s, 1H), 2.20 (s, 1H). $^{13}$C NMR (101 MHz, cdcl$_3$) δ 158.13, 150.23, 141.51, 141.26, 135.23, 135.00, 130.33, 129.68, 129.51, 128.13, 127.85, 127.34, 125.77, 112.13, 105.07, 55.82, 51.79, 20.45. HRMS (EI) calcd for C$_{20}$H$_{19}$NO$_2$ [M]$^+$ 305.1416. found 305.1419.

1-(4-Dimethylamino-(1,1'-biphenylmethyl))-3-methoxyoxypyridine-2-one (146g)

Reaction of 145 (0.25 g, 0.85 mmol), (4-(dimethylamino) phenyl)boronic acid (0.17 g, 1.02 mmol), 2M aq. K$_2$CO$_3$ (0.23 g, 1.69 mmol), Pd(PPh$_3$)$_4$ (2.5 mol %) according to method described for synthesis of 146a within 18 h afforded 230 mg of 146 g (81%) as white solid. $^1$H NMR (400 MHz, CDCl$_3$) δ 7.46 (m, 4H), 7.29 (m, 2H), 6.86 (dd, J=7.2, 2.0 Hz, 1H), 7.73 (m, 2H), 6.52 (dd, J=7.2, 1.6 Hz, 1H), 6.01 (t, J=7.2 Hz, 1H), 5.13 (s, 2H), 3.76 (s, 3H), 2.93 (s, 6H). $^{13}$C NMR (100 MHz, CDCl$_3$) δ 157.86, 149.90, 149.73, 140.55, 133.81, 128.43, 128.04, 127.68, 127.28, 126.16, 112.40, 111.77, 104.69, 55.53, 51.31, 40.18. HRMS (EI) calcd for C$_{21}$H$_{22}$N$_2$O$_2$ [M]$^+$ 334.1681. found 334.1684.

1-(4-(6-(Dimethylamino)pyridine-3-yl)benzyl))-3-methoxyoxypyridine-2-one (146h)

Reaction of 145 (0.43 g, 1.44 mmol), (6-(dimethylamino) pyridine-3-yl)boronic acid (0.2 g, 1.20 mmol), 2M aq. K$_2$CO$_3$ (0.33 g, 2.41 mmol), Pd(PPh$_3$)$_4$ (2.5 mol %) according to method described for synthesis of 146a within 18 h afforded 335 mg of 146h (83%) of white solid. $^1$H NMR (400 MHz, CDCl$_3$) δ 8.28 (d, J=2.3 Hz, 1H), 7.51 (dd, J=8.8, 2.5 Hz, 1H), 7.33 (d, J=8.2 Hz, 2H), 7.22 (d, J=8.2 Hz, 2H), 6.80 (dd, J=6.9, 1.6 Hz, 1H), 6.44 (m, 2H), 5.94 (t, J=7.2 Hz, 1H), 5.04 (s, 2H), 3.66 (s, 3H), 2.97 (s, 6H). $^{13}$C NMR (100 MHz, CDCl$_3$) δ 158.12, 157.61, 149.68, 145.49, 137.75, 135.14, 134.20, 128.35, 127.54, 125.69, 123.15, 111.62, 105.23, 104.62, 55.36, 51.16, 37.66. HRMS (EI) calcd for C$_{20}$H$_{21}$N$_3$O$_2$ [M]$^+$ 335.1634. found 335.1635.

1-(4-(Pyridin-4-yl)benzyl)-3-methoxy-pyridine-2-one (146i)

Reaction of 145 (0.25 g, 0.85 mmol), pyrdin-4-ylboronic acid (0.12 g, 1.02 mmol), 2M aq. K$_2$CO$_3$ (0.23 g, 1.69 mmol), Pd(PPh$_3$)$_4$ (2.5 mol %) according to method described for synthesis of 146a within 18 h afforded 203 mg of 146i (82%) of white solid. $^1$H NMR (400 MHz, CDCl$_3$) δ 8.54 (dd, J=4.5, 1.6 Hz, 2H), 7.48 (m, 2H), 7.36 (m, 4H), 6.87 (dd, J=6.9, 1.7 Hz, 1H), 6.53 (dd, J=7.4, 1.6 Hz, 1H), 6.03 (t, J=7.2 Hz, 1H), 5.13 (s, 2H), 3.72 (s, 3H). $^{13}$C NMR (100 MHz, CDCl$_3$) δ 157.82, 150.32, 150.01, 149.90, 147.40, 137.31, 137.28, 128.57, 127.68, 127.04, 121.22, 111.90, 104.98, 55.57, 51.42. HRMS (EI) calcd for C$_{18}$H$_{16}$N$_2$O$_2$ [M]$^+$ 292.1212. found 292.1205.

1-(4-Cyano-(1,1'-biphenylmethyl))-3-methoxyoxypyridine-2-thione (147a)

A suspension of 146a (0.13 g, 0.42 mmol) and Lawesson's reagent (0.10 g, 0.25 mmol) in toluene (10 mL) was heated to reflux overnight. Reaction mixture was then cooled to room temperature. Toluene was evaporated off under vacuo and resulting crude solid was directly loaded on prep-TLC. Elution with CHCl$_3$:Acetone:EtOH (12:1:0.2) gave 147a 123 mg (88%) of yellow solid. $^1$H NMR (CDCl$_3$, 400 MHz) δ 7.60 (m, 4H), 7.40 (m, 4H), 6.90 (dd, J=6.8, 1.6 Hz, 1H), 6.55 (dd, J=7.6, 1.6 Hz, 1H), 6.07 (t, J=7.2 Hz, 1H), 5.16 (s, 2H), 3.75 (s, 3H). $^{13}$C NMR (100 MHz, CDCl$_3$) δ 158.08, 150.28, 144.96, 138.62, 137.13, 132.56, 131.96, 128.85, 128.55, 128.43, 127.96, 127.60, 127.53, 118.88, 112.11, 110.88, 105.24, 56.20, 51.80 HRMS (EI) calcd for C$_{20}$H$_{16}$N$_2$OS [M]$^+$ 332.0983. found 332.0987.

1-(3-Cyano-(1,1'-biphenylmethyl))-3-methoxypyridine-2-thione (147b)

Reaction of 146b (0.11 g, 0.36 mmol) and Lawesson's reagent (0.09 g, 0.22 mmol) in toluene according to method described for synthesis of 147a afforded 113 mg of 147b (95%) of yellow solid. $^1$H NMR (400 MHz, DMSO-d$_6$) δ 7.92 (m, 3H), 7.84 (m, 2H), 7.71 (d, J=8.4 Hz, 2H), 7.36 (d, J=8.8 Hz, 2H), 7.00 (m, 1H), 6.80 (m, 1H), 5.95 (s, 2H), 3.78 (s, 3H). $^{13}$C NMR (100 MHz, CDCl$_3$) δ 173.39, 159.26, 144.82, 138.81, 135.79, 132.55, 131.81, 128.65, 127.58, 127.50, 118.77, 111.80, 110.98, 109.69, 58.63, 56.74. HRMS (EI) calcd for C$_{20}$H$_{16}$N$_2$OS [M]$^+$ 332.0983. found 332.0984.

1-(2-Cyano-(1,1'-biphenylmethyl)-3-methoxyoxypyridine-2-thione (147c)

Reaction of 146c (0.09 g, 0.28 mmol) and Lawesson's reagent (0.07 g, 0.17 mmol) in toluene according to method described for synthesis of 147a afforded 72 mg of 147c (77%) of yellow solid. $^1$H NMR (400 MHz, cdcl$_3$) δ 7.74 (m, 1H), 7.63 (td, J=7.7, 1.4 Hz, 1H), 7.45 (m, 2H), 6.71 (dd, J=7.8, 1.3 Hz, 1H), 6.62 (dd, J=7.8, 6.6 Hz, 1H), 6.00 (s, 1H), 5.28 (s, 1H), 3.93 (s, 1H). $^{13}$C NMR (101 MHz, cdcl$_3$) δ 173.38, 159.22, 144.68, 137.79, 135.80, 133.67, 132.86, 131.95, 129.97, 129.17, 128.25, 127.66, 118.59, 111.84, 111.01, 109.76, 58.63, 56.74. HRMS (EI) calcd for C$_{20}$H$_{16}$N$_2$OS [M]$^+$ 332.0983. found 332.0981.

1-(4-Methyl-(1,1'-biphenylmethyl))-3-methoxyoxypyridine-2-thione (147d)

Reaction of 146d (0.12 g, 0.39 mmol) and Lawesson's reagent (0.09 g, 0.23 mmol) in toluene according to method described for synthesis of 147a afforded 117 mg of 147d (94%) as yellow solid. $^1$H NMR (400 MHz, CDCl$_3$) δ 7.51 (m, 2H), 7.42 (m, 2H), 7.34 (m, 3H), 7.21 (dd, J=8.4, 0.6 Hz, 2H), 6.66 (dd, J=7.8, 1.2 Hz, 1H), 6.55 (dd, J=7.8, 6.6 Hz, 1H), 5.92 (s, 2H), 3.89 (s, 3H), 2.36 (s, 3H). $^{13}$C NMR (100 MHz, CDCl$_3$) δ 173.05, 158.97, 140.74, 137.30, 137.08, 133.81, 131.70, 129.33, 128.42, 127.12, 126,64, 111.59, 109.65, 58.52, 56.57, 20.91. HRMS (EI) calcd for C$_{20}$H$_{19}$NOS [M]$^+$ 321.1187. found 321.1192.

1-(3-Methyl-(1,1'-biphenylmethyl))-3-methoxyoxypyridine-2-thione (147e)

Reaction of 146e (0.12 g, 0.37 mmol) and Lawesson's reagent (0.09 g, 0.23 mmol) in toluene according to method described for synthesis of 147a afforded 112 mg of 147e (93%) as yellow solid. $^1$H NMR (400 MHz, cdcl$_3$) δ 7.53 (m, 1H), 7.33 (m, 2H), 7.14 (dd, J=7.1, 0.6 Hz, 1H), 6.67 (dd, J=7.8, 1.2 Hz, 1H), 6.56 (m, 1H), 5.94 (s, 1H), 3.91 (s, 1H), 2.39 (s, 1H). $^{13}$C NMR (101 MHz, cdcl$_3$) δ 173.21, 159.07, 141.06, 140.28, 138.24, 134.07, 131.72, 128.57, 128.48, 128.09, 127.69, 127.44, 124.01, 111.62, 109.66, 58.60, 56.63, 21.39. HRMS (EI) calcd for C$_{20}$H$_{19}$NOS [M]$^+$ 305.1187. found 321.1188.

1-(2-Methyl-(1,1'-biphenylmethyl)-3-methoxyoxypyridine-2-thione (147f)

Reaction of 146f (0.14 g, 0.45 mmol) and Lawesson's reagent (0.11 g, 0.27 mmol) in toluene according to method described for synthesis of 147a afforded 118 mg of 147f (86%) as yellow solid. $^1$H NMR (400 MHz, cdcl$_3$) δ 7.42 (dd, J=6.6, 1.0 Hz, 1H), 7.22 (m, 3H), 6.68 (d, J=7.3 Hz, 1H), 6.59 (m, 1H), 5.96 (s, 1H), 3.90 (s, 1H), 2.22 (s, 1H). $^{13}$C NMR (101 MHz, cdcl$_3$) δ 158.97, 141.54, 140.93, 135.02, 133.59, 131.79, 130.13, 129.46, 129.42, 127.65, 127.18, 125.57, 111.62, 109.67, 58.56, 56.57, 20.25. HRMS (EI) calcd for C$_{20}$H$_{19}$NOS [M]$^+$ 305.1187. found 321.1189.

1-(4-Dimethylamino-(1,1'-biphenylmethyl))-3-methoxyoxypyridine-2-thione (147g)

Reaction of 146 g (0.22 g, 0.67 mmol) and Lawesson's reagent (0.16 g, 0.40 mmol) in toluene according to method described for synthesis of 147a afforded 172 mg of 147 g (73%) as yellow solid. $^1$H NMR (400 MHz, CDCl$_3$) 7.39 (m, 5H), 7.22 (m, 2H), 6.69 (m, 3H), 6.65 (m, 1H), 5.82 (s, 2H), 3.82 (s, 3H), 2.88 (s, 6H). $^{13}$C NMR (100 MHz, CDCl$_3$) δ 172.36, 158.73, 149.92, 140.89, 132.48, 131.84, 128.44, 128.20, 127.29, 126.32, 112.69, 112.02, 110.17, 58.68, 56.31, 40.24. HRMS (EI) calcd for C$_{21}$H$_{22}$N$_2$OS [M]$^+$ 350.1453. found 350.1451.

1-(4-(6-(Dimethylamino)pyridin-3-yl)benzyl))-3-methoxyoxypyridine-2-thione (147h)

Reaction of 146h (0.14 g, 0.42 mmol) and Lawesson's reagent (0.10 g, 0.25 mmol) in toluene according to method described for synthesis of 147a afforded 130 mg of 147h (88%) of yellow solid. $^1$H NMR (400 MHz, CDCl$_3$) δ 8.32 (d, J=2.3 Hz, 1H), 7.56 (dd, J=8.6, 2.1 Hz, 1H), 7.36 (dd, J=19.8, 7.3 Hz, 3H), 7.26 (d, J=8.0 Hz, 2H), 6.61 (d, J=7.8 Hz, 1H), 6.50 (m, 2H), 5.85 (s, 2H), 3.83 (s, 3H), 3.03 (s, 6H). $^{13}$C NMR (100 MHz, CDCl$_3$) δ 172.74, 158.80, 158.31, 145.65, 138.13, 135.32, 133.08, 131.66, 128.46, 125.95, 123.21, 111.57, 109.64, 105.42, 58.42, 56.47, 37.86. HRMS (EI) calcd for C$_{20}$H$_{21}$N$_3$OS [M]$^+$ 351.1405. found 351.1405.

1-(4-(Pyridin-4-yl)benzyl)-3-methoxypyridine-2-thione (147i)

Reaction of 146i (0.13 g, 0.45 mmol) and Lawesson's reagent (0.11 g, 0.27 mmol) in toluene according to method described for synthesis of 147a afforded 104 mg of 147i (76%) as yellow solid with greenish tinge. $^1$H NMR (400 MHz, CDCl$_3$) δ 8.59 (d, J=5.9 Hz, 2H), 7.55 (d, J=8.3 Hz, 2H), 7.39 (m, 5H), 6.67 (dd, J=7.8, 1.1 Hz, 1H), 6.58 (dd, J=73, 6.7 Hz, 1H), 5.95 (s, 2H), 3.89 (s, 3H). $^{13}$C NMR (100 MHz, CDCl$_3$) δ 173.29, 159.15, 150.11, 147.43, 137.67, 136.17, 131.78, 128.58, 127.28, 121.35, 111.72, 109.67, 58.54, 56.66. HRMS (EI) calcd for C$_{18}$H$_{16}$N$_2$OS [M]$^+$ 308.0983. found 308.0975.

1-(4-Cyano-(1,1'-biphenylmethyl)-3-hydroxyoxypyridine-2-one (148a)

To a solution of 146a (0.1 g, 0.32 mmol) in dry CH$_2$Cl$_2$ (8 mL) was slowly added 1M BBr$_3$ (0.35 mL) at −30° C. under argon atmosphere. The reaction mixture was stirred for 32 h at room temperature. The mixture was again cooled to −30 & then MeOH (5 mL) was slowly added to the mixture. After evaporation of solvent, the residue was adjusted to pH 7 with 1M NaOH and then extracted with CHCl$_3$ (3×30 mL). The combined organic layer dried over Na$_2$SO$_4$. After evaporation of solvent, the residue was purified by prep-TLC with CHCl$_3$: Acetone:EtOH (10:1:0.2) to give 89 mg of 148a (94%) as pure slightly brownish solid. $^1$H NMR (400 MHz, DMSO) δ 9.08 (s, 1H), 7.87 (dd, J=24.8, 7.9 Hz, 4H), 7.71 (d, J=7.6 Hz, 2H), 7.40 (d, J=7.7 Hz, 2H), 7.29 (d, J=6.7 Hz, 1H), 6.70 (d, J=6.7 Hz, 1H), 6.13 (t, J=6.8 Hz, 1H), 5.18 (s, 2H). $^{13}$C NMR (100 MHz, CDCl$_3$) δ 147.11, 145.13, 139.24, 136.77, 132.87, 128.95, 127.97, 127.89, 127.06, 119.08, 114.15, 111.35, 107.55, 52.48, 29.93. HRMS (ESI) calcd for C$_{19}$H$_{15}$N$_2$O$_2$ [M+H]$^+$ 303.1128. found 303.1124.

1-(3-Cyano-(1,1'-biphenylmethyl))-3-hydroxyoxypyridine-2-one (148b)

Reaction of 146b (0.05 g, 0.15 mmol) with 1M BBr$_3$ (0.26 mL) in dry CH$_2$Cl$_2$ within 48 h according to procedure 148a afforded pure 148b (44 mg, quantitative) as slightly brownish solid. $^1$H NMR (400 MHz, DMSO-d$_6$) δ 9.08 (s, 1H), 8.11 (s, 1H), 7.98 (d, J=7.8 Hz, 1H), 7.70 (m, 4H), 7.40 (d, J=7.7 Hz, 2H), 7.28 (d, J=6.2 Hz, 1H), 6.70 (d, J=6.8 Hz, 1H), 6.13 (t, J=6.7 Hz, 1H), 5.17 (s, 2H). $^{13}$C NMR (101 MHz, CDCl$_3$) δ 146.78, 141.62, 138.62, 136.13, 131.31, 130.82, 130.51, 129.62, 128.71, 127.49, 126.66, 118.66, 113.90, 112.96, 107.26, 52.25. HRMS (EI) calcd for C$_{19}$H$_{14}$N$_2$O$_2$ [M+H]$^+$ 302.1055. found 302.1055.

1-(2-Cyano-(1,1'-biphenylmethyl))-3-hydroxyoxypyridine-2-one (148c)

Reaction of 146e (0.072 g, 0.15 mmol) with 1M BBr$_3$ (0.34 mL) in dry CH$_2$Cl$_2$ within 48 h according to procedure 148a afforded pure 148c (61 mg, 90%) as slightly brownish solid. $^1$H NMR (400 MHz, cdcl$_3$) δ 7.75 (d, J=7.6 Hz, 1H), 7.63 (t, J=7.7 Hz, 1H), 7.53 (d, J=7.3 Hz, 1H), 7.43 (m, 2H), 7.12 (m, 1H), 6.86 (dd, J=28.2, 6.6 Hz, 1H), 6.19 (t, J=6.1 Hz, 1H), 5.25 (s, 1H). $^{13}$C NMR (101 MHz, cdcl$_3$) δ 144.67, 137.88, 13642, 133.71, 132.85, 129.95, 129.23, 128.20, 127.69, 118.56, 111.08, 107.17, 52.13. HRMS (EI) calcd for C$_{19}$H$_{14}$N$_2$O$_2$ [M+H]$^+$ 302.1055. found 302.1053.

1-(4-Methyl-(1,1'-biphenylmethyl))-3-hydroxyoxypyridine-2-one (148d)

Reaction of 146d (0.06 g, 0.20 mmol) with 1M BBr$_3$ (0.30 mL) in dry CH$_2$Cl$_2$ (5 mL) within 48 h according to procedure 148a afforded pure 148d (57 mg, quantitative) as slightly brownish solid. $^1$H NMR (400 MHz, DMSO-d$_6$) δ 9.07 (s, 1H), 7.57 (m, 2H), 7.50 (d, J=8.1 Hz, 2H), 7.34 (d, J=6.8 Hz, 2H), 7.25 (dd, J=14.8, 7.1 Hz, 3H), 6.69 (d, J=7.4 Hz, 1H), 6.11 (t, J=7.1 Hz, 1H), 5.14 (s, 2H), 2.30 (s, 3H). $^{13}$C NMR (100 MHz, DMSO-d$_6$) δ 139.81, 137.29, 137.22, 136.68, 129.94, 128.77, 127.00, 126.89, 51.69, 21.10. Even after repeated cycles, quaternary carbons couldn't be visualized. (No improvement with relaxation delay of 2 sec). HRMS (EI) calcd for C$_{19}$H$_{17}$NO$_2$ [M]$^+$ 291.1259. found 291.1250.

1-(3-Methyl-(1,1'-biphenylmethyl))-3-hydroxyoxypyridine-2-one (148e)

Reaction of 146e (0.064 g, 0.20 mmol) with 1M BBr$_3$ (0.30 mL) in dry CH$_2$Cl$_2$ (5 mL) within 48 h according to procedure 148a afforded pure 148e (60 mg, quantitative) as slightly brownish solid. $^1$H NMR (400 MHz, cdcl$_3$) δ 7.56 (d, J=7.5 Hz, 1H), 7.33 (m, 2H), 7.17 (d, J=7.2 Hz, 1H), 6.85 (dd, J=22.2, 6.4 Hz, 1H), 6.16 (t, J=6.5 Hz, 1H), 5.23 (s, 1H), 2.42 (s, 1H). $^{13}$C NMR (101 MHz, cdcl$_3$) δ 146.71, 141.19, 140.38, 138.32, 134.70, 128.63, 128.41, 128.16, 127.79, 127.56, 126.60, 124.11, 113.66, 106.98, 52.10, 21.45. HRMS (EI) calcd for C$_{19}$H$_{17}$NO$_2$ [M]$^+$ 291.1259. found 291.1263.

1-(2-Methyl-(1,1'-biphenylmethyl))-3-hydroxyoxypyridine-2-one (148f)

Reaction of 146f (0.077 g, 0.25 mmol) with 1M BBr$_3$ (0.38 mL) in dry CH$_2$Cl$_2$ (5 mL) within 48 h according to procedure 148a afforded pure 148f (65 mg, 90%) as slightly brownish solid. $^1$H NMR (400 MHz, cdcl$_3$) δ 7.28 (m, 3H), 6.87 (dd, J=31.4, 6.8 Hz, 1H), 6.18 (t, J=6.9 Hz, 1H), 5.27 (d, J=16.7 Hz, 1H), 2.26 (s, 1H). $^{13}$C NMR (101 MHz, cdcl$_3$) δ 146.73, 141.81, 141.14, 135.24, 134.30, 130.31, 129.66, 127.68, 127.37, 126.73, 125.75, 113.59, 106.99, 52.21, 20.40. HRMS (EI) calcd for C$_{19}$H$_{17}$NO$_2$ [M]$^+$ 291.1259. found 291.1260.

1-(4-Dimethylamino-(1,1'-biphenylmethyl))-3-hydroxyoxypyridine-2-one (148g)

Reaction of 146g (0.10 g, 0.30 mmol) with 1M BBr$_3$ (0.45 mL) in dry CH$_2$Cl$_2$ (8 mL) within 48 h according to procedure 148a afforded pure 148g (84 mg, 87%) as slightly brownish solid. $^1$H NMR (400 MHz, DMSO-d$_6$) δ 9.06 (s, 1H), 7.52 (d, J=8.0 Hz, 3H), 7.28 (m, 4H), 6.76 (m, 2H), 6.10 (t, J=5.8 Hz, 1H), 5.12 (s, 2H), 2.90 (s, 6H). $^{13}$C NMR (100 MHz, CDCl$_3$) δ 158.71, 149.98, 146.62, 141.07, 135.81, 133.29, 128.83, 128.47, 128.21, 128.07, 127.98, 127.55, 126.57, 113.48, 112.60, 106.89, 52.11, 40.44. HRMS (EI) calcd for C$_{20}$H$_{20}$N$_2$O$_2$ [M]$^+$ 320.1524. found 320.1512.

1-(4-(6-(Dimethylamino)pyridine-3-yl)benzyl))-3-hydroxyoxypyridine-2-one (148h)

Reaction of 146h (0.10 g, 0.29 mmol) with 1M BBr$_3$ (0.45 mL) in dry CH$_2$Cl$_2$ (7 mL) within 48 h according to procedure 148a afforded pure 148h (67 mg, 83%) as slightly brownish solid. $^1$H NMR (400 MHz, CDCl$_3$) δ 8.40 (s, 1H), 7.66 (d, J=8.0 Hz, 1H), 7.49 (d, J=7.7 Hz, 2H), 7.33 (d, J=7.7 Hz, 2H), 6.84 (dd, J=27.3, 6.8 Hz, 3H), 6.57 (d, J=8.7 Hz, 1H), 6.15 (t, J=7.0 Hz, 1H), 5.20 (s, 2H), 3.12 (s, 6H). $^{13}$C NMR (100 MHz, CDCl$_3$) δ 158.47, 146.67, 145.66, 138.31, 135.79, 133.89, 131.95, 128.49, 126.79, 126.28, 123.61, 114.16, 107.19, 105.94, 52.13, 38.15. HRMS (EI) calcd for C$_{19}$H$_{19}$N$_3$O$_2$ [M]$^+$ 321.1477. found 321.1479.

1-(4-(Pyridine-4-yl)benzyl)-3-hydroxypyridine-2-one (148i)

Reaction of 146i (0.10 g, 0.34 mmol) with 1M BBr$_3$ (0.51 mL) in dry CH$_2$Cl$_2$ within 48 h according to procedure 148a afforded pure 148i (79 mg, 83%) as slightly brownish solid. $^1$H NMR (400 MHz, CDCl$_3$) δ 8.65 (s, 2H), 7.46 (s, 2H), 7.39 (d, J=7.9 Hz, 2H), 6.83 (dd, J=22.5, 7.0 Hz, 2H), 6.16 (t, J=7.0 Hz, 1H), 5.22 (s, 2H). $^{13}$C NMR (100 MHz, CDCl$_3$) δ 150.23, 147.62, 146.76, 137.98, 136.87, 128.66, 127.51, 126.64, 121.58, 113.66, 107.13, 52.19. HRMS (FAB) calcd for C$_{17}$H$_{15}$N$_2$O$_2$ [M+H]$^+$ 279.1133. found 279.1147.

1-(4-Cyano-(1,1'-biphenylmethyl))-3-hydroxyoxypyridine-2-thione (149a)

Reaction of 147a (0.10 g, 0.30 mmol) with 1M BBr$_3$ (0.33 mL) in dry CH$_2$Cl$_2$ (8 mL) within 48 h according to procedure 148a afforded pure 149a (84 mg, 88%) as olive green color solid. $^1$H NMR (400 MHz, DMSO-d$_6$) δ 7.87 (m, 5H), 7.74

(d, J=8.1 Hz, 2H), 7.37 (d, J=8.1 Hz, 2H), 7.04 (m, 1H), 6.90 (d, J=8.1 Hz, 1H), 5.87 (s, 2H). $^{13}$C NMR (100 MHz, CDCl$_3$) δ 164.47, 144.66, 139.24, 134.64, 132.60, 128.56, 127.74, 127.62, 118.75, 111.15, 61.79, 29.64. HRMS (EI) calcd for C$_{19}$H$_{15}$N$_2$OS [M]$^+$ 318.0827. found 318.0828.

1-(3-Cyano-(1,1'-biphenylmethyl))-3-hydroxyoxypyridine-2-thione (149b)

Reaction of 147b (0.07 g, 0.21 mmol) with 1M BBr$_3$ (0.32 mL) in dry CH$_2$Cl$_2$ (5 mL) within 48 h according to procedure 148a afforded pure 149b (53 mg, 79%) as olive green color solid. $^1$H NMR (400 MHz, CD$_3$OD) δ 7.89 (m, 2H), 7.65 (m, 5H), 7.44 (d, J=8.2 Hz, 2H), 7.02 (d, J=7.7 Hz, 2H), 6.77 (m, 1H), 5.90 (s, 2H). $^{13}$C NMR (100 MHz, CD$_3$OD) δ 142.99, 140.04, 132.82, 132.18, 131.69, 131.12, 130.03, 129.97, 129.89, 128.69, 128.59, 119.83, 113.94, 106.40, 54.78. HRMS (EI) calcd for C$_{19}$H$_{14}$N$_2$O$_2$ [M+H]$^+$ 318.0827. found 318.0827

1-(2-Cyano-(1,1'-biphenylmethyl))-3-hydroxyoxypyridine-2-thione (149c)

Reaction of 147c (0.042 g, 0.21 mmol) with 1M BBr$_3$ (0.19 mL) in dry CH$_2$Cl$_2$ (5 mL) within 48 h according to procedure 148a afforded pure 149c (31 mg, 78%) as olive green color solid. $^1$H NMR (400 MHz, cd$_3$od) δ 7.77 (dd, J=7.7, 0.9 Hz, 1H), 7.67 (m, 2H), 7.48 (m, 4H), 7.01 (d, J=13.1 Hz, 1H), 6.70 (m, 11.1), 5.90 (s, 1H). $^{13}$C NMR (101 MHz, cd$_3$od) δ 145.34, 138.90, 134.40, 133.88, 130.75, 129.88, 128.90, 128.62, 119.17, 115.12, 111.38. HRMS (EI) calcd for C$_{19}$H$_{14}$N$_2$O$_2$ [M+H]$^+$ 318.0821. found 318.0827

1-(4-Methyl-(1,1'-biphenylmethyl))-3-hydroxyoxypyridine-2-thione (149d)

Reaction of 147d (0.06 g, 0.20 mmol) with 1M BBr$_3$ (0.30 mL) in dry CH$_2$Cl$_2$ (5 mL) within 48 h according to procedure 148a afforded pure 149d (45 mg, 73%) as olive green color solid. $^1$H —NMR (400 MHz, CD$_3$OD) δ 7.70 (d, J=1.1 Hz, 1H), 7.63 (d, J=6.3 Hz, 1H), 7.55 (d, J=8.2 Hz, 2H), 7.40 (m, 3H), 7.21 (d, J=8.1 Hz, 2H), 7.03 (dd, J=14.9, 7.8 Hz, 2H), 6.75 (t, J=7.0 Hz, 1H), 5.87 (s, 2H), 2.35 (s, 3H). Even after repeated cycles, quaternary carbons couldn't be visualized. (No improvement with relaxation delay of 2 see). HRMS (EI) calcd for C$_{19}$H$_{17}$NOS [M]$^+$ 307.1031. found 307.1022.

1-(3-Methyl-(1,1'-biphenylmethyl))-3-hydroxyoxypyridine-2-thione (149e)

Reaction of 147e (0.08 g, 0.20 mmol) with 1M BBr$_3$ (0.36 mL) in dry CH$_2$Cl$_2$ (5 mL) within 48 h according to procedure 148a afforded pure 149e (51 mg, 70%) as olive green color solid. $^1$H NMR (400 MHz, cd$_3$od) δ 7.53 (m, 1H), 7.30 (m, 2H), 7.12 (d, J=7.2 Hz, 1H), 6.97 (m, 1H), 6.68 (m, 1H), 5.81 (s, 1H), 2.36 (s, 1H). $^{13}$C NMR (101 MHz, cd$_3$od) δ 141.53, 140.21, 138.34, 128.62, 128.48, 128.21, 127.69, 127.54, 124.03, 21.19. HRMS (EI) calcd for C$_{19}$H$_{17}$NOS [M]$^+$ 307.1031. found 307.1031.

1-(2-Methyl-(1,1'-biphenylmethyl))-3-hydroxyoxypyridine-2-thione (149f)

Reaction of 147f (0.08 g, 0.20 mmol) with 1M BBr$_3$ (0.36 mL) in dry CH$_2$Cl$_2$ (5 mL) within 48 h according to procedure 148a afforded pure 149f (49 mg, 67%) as olive green color solid. $^1$H NMR (400 MHz, cd$_3$od) δ 7.54 (m, 1H), 7.19 (m, 3H), 6.98 (m, 1H), 6.70 (m, 1H), 5.83 (s, 1H), 2.19 (s, 1H). $^{13}$C NMR (101 MHz, cd$_3$od) δ 142.14, 140.99, 135.05, 130.21, 129.58, 129.48, 127.76, 127.33, 125.66, 20.02. HRMS (EI) calcd for C$_{19}$H$_{17}$NOS [M]$^+$ 307.1031. found 307.1034.

1-(4-Dimethylamino-(1,1'-biphenylmethyl))-3-hydroxyoxypyridine-2-thione (149g)

Reaction of 147g (0.11 g, 0.33 mmol) with 1M BBr$_3$ (0.39 mL) in dry CH$_2$Cl$_2$ (5 mL) within 48 h according to procedure 148a afforded pure 149g (68 mg, 62%) as olive green color solid. $^1$H NMR (400 MHz, CDCl$_3$) δ 8.57 (d, J=8.5 Hz, 1H), 7.53 (d, J=8.2 Hz, 2H), 7.46 (m, 2H), 7.33 (d, J=8.0 Hz, 3H), 6.97 (d, J=6.8 Hz, 1H), 6.77 (d, J=8.8 Hz, 2H), 6.62 (m, 1H), 5.79 (s, 2H), 2.98 (s, 6H). $^{13}$C NMR (100 MHz, CDCl$_3$) δ 169.71, 155.14, 150.08, 141.51, 131.92, 130.80, 129.00, 128.83, 127.99, 127.58, 126.68, 113.58, 112.62, 111.90, 60.11, 40.45. HRMS (EI) calcd for C$_{20}$H$_{20}$N$_2$OS [M]$^+$ 336.1296. found 336.1295.

1-(4-(6-(Dimethylamino)pyridin-3-yl)benzyl))-3-hydroxyoxypyridine-2-thione (149h)

Reaction of 147h (0.064 g, 0.18 mmol) with 1M BBr$_3$ (0.27 mL) in dry CH$_2$Cl$_2$ (5 mL) within 48 h according to procedure 148a afforded pure 149h (48 mg, 79%) as olive green color solid. $^1$H NMR (400 MHz, CDCl$_3$) δ 8.30 (s, 1H), 7.70 (d, J=8.9 Hz, 1H), 7.46 (s, 2H), 7.31 (t, J=7.6 Hz, 3H), 6.98 (d, J=7.8 Hz, 1H), 6.67 (m, 2H), 5.75 (s, 2H), 3.11 (s, 8H). $^{13}$C NMR (100 MHz, CDCl$_3$) δ 157.02, 143.45, 142.18, 137.74, 136.98, 132.81, 128.75, 127.56, 126.37, 123.70, 114.43, 107.03, 38.48, 29.54. HRMS (EI) calcd for C$_{19}$H$_{19}$N$_3$OS [M]$^+$ 337.1249. found 337.1251.

1-(4-(Pyridin-4-yl)benzyl)-3-hydroxypyridine-2-thione (149i)

Reaction of 147i (0.08 g, 0.25 mmol) with 1M BBr$_3$ (0.38 mL) in dry CH$_2$Cl$_2$ (5 mL) within 48 h according to procedure 148a afforded pure 149i (65 mg, 88%) as olive green color solid. $^1$H NMR (400 MHz, CDCl$_3$) δ 8.65 (d, J=5.3 Hz, 2H), 8.55 (s, 1H), 7.62 (d, J=8.0 Hz, 2H), 7.42 (m, 5H), 6.99 (d, J=7.5 Hz, 1H), 6.67 (t, J=7.0 Hz, 1H), 5.85 (s, 2H). $^{13}$C NMR (100 MHz, CDCl$_3$) δ 170.05, 155.32, 150.25, 147.44, 138.22, 135.48, 130.91, 128.80, 127.55, 121.48, 113.73, 111.94, 59.91. HRMS (EI) calcd for C$_{17}$H$_{14}$N$_2$OS [M]$^+$ 294.0827. found 294.0823.

1-Propargyl-3-methoxypyridine-2-one (150)

To a stirring solution of 3-methoxy-2-pyridinone (1.00 g, 8.00 mmol) in DMF (25 mL), was added propargyl bromide (80 wt % solution in toluene, 1.5 equiv) and K$_2$CO$_3$ (3.313 g, 24 mmol). Reaction mixture was heated to 100° C. After overnight reaction, reaction mixture was partitioned between EtOAc (120 mL) and water (100 mL). Organic layer was separated and washed repeatedly with water (7×100 mL) and brine (1×60 mL). Organic layer was dried on Na$_2$SO$_4$ and evaporated under vacuo to yield dark brown crude product. Column chromatography using gradient CH$_2$Cl$_2$:Acetone (max 20%) gave pure 150 (0.79 g, 60%) as a slightly brownish solid. $^1$H NMR (CDCl$_3$, 400 MHz) δ 2.36 (1H, t, J=2.8), 3.67 (3H, m), 4.66 (1H, d, J=2.8), 6.05 (1H, t, J=7.2), 6.50 (1H, dd, J=1.6, 7.2), 7.11 (1H, dd, J=1.6, 6.8); $^{13}$C NMR (CDCl$_3$, 100

MHz) δ 37.2, 55.5, 74.6, 77.3, 104.8, 112.0, 126.3, 149.4, 157.1. HRMS (EI) calcd for $C_9H_9NO_2$ [M]$^+$ 163.0633. found 163.0636

1-Phenyltriazolylmethyl-3-methoxypyridine-2-one (151a)

150 (0.32 g, 1.951 mmol) and phenylazide (0.348 g, 2.926 mmol) were dissolved in anhydrous THF (10 mL) and stirred under argon at room temperature. Copper (I) iodide (0.011 g, 0.07 mmol) and Hunig's base (0.1 mL) were then added to the reaction mixture, and stirring continued for 4 h. The reaction mixture was diluted with $CH_2Cl_2$ (40 mL) and washed with 1:4 $NH_4OH$/saturated $NH_4Cl$ (3×30 mL) and saturated $NH_4Cl$ (30 mL). The organic layer was dried over $Na_2SO_4$ and concentrated in vacuo. The crude product was triturated with hexanes to give 510 mg (92%) of white solid 151a. $^1$H NMR (CDCl$_3$, 400 MHz) δ 3.58 (3H, s), 5.11 (2H, s), 5.93 (1H, t, J=7.6), 6.42 (1H, d, J=7.2), 7.07 (1H, d, J=6.4), 7.16-7.20 (1H, m), 7.26 (2H, t, J=7.6), 7.49 (2H, d, J=8.0); $^{13}$C NMR (CDCl$_3$, 100 MHz) δ 44.2, 55.2, 104.7, 112.0, 119.7, 121.8, 127.9, 128.1, 129.0, 136.2, 142.8, 149.3, 157.2. HRMS (EI) calcd for $C_{15}H_{14}N_4O_2$ [M]$^+$ 282.1117. found 282.1115.

1-(4-Dimethylamino)phenyltriazolylmethyl-3-methoxypyridine-2-one (151b)

Reaction of 4-azido-N,N-dimethylaniline (0.09 g, 0.61 mmol) and 150 (0.10 g, 0.61 mmol) within 4 h as described for synthesis of 151a gave compound 151b (0.13 g, 68%) as a white solid. $^1$H NMR (400 MHz, cdcl$_3$) δ 8.04 (s, 1H), 7.41 (m, 2H), 7.15 (dd, J=6.9, 1.7 Hz, 1H), 6.62 (m, 2H), 6.51 (dd, J=7.5, 1.6 Hz, 1H), 6.03 (m, 1H), 5.19 (s, 2H), 3.70 (s, 3H), 2.89 (s, 6H). $^{13}$C NMR (100 MHz, CDCl$_3$) δ 157.54, 150.18, 149.65, 142.60, 128.17, 126.18, 121.90, 121.43, 112.20, 111.84, 104.93, 55.55, 44.54, 40.08. HRMS (EI) calcd for $C_{17}H_{19}N_5O_2$ [M]$^+$ 325.1539. found 325.1544.

1-Phenyltriazolylmethyl-3-hydroxypyridine-2-one (152a)

Reaction of 151a (0.212 g, 0.75 mmol) and 1M BBr$_3$ in $CH_2Cl_2$ (1.5 equiv) within 48 h as described for the synthesis of 148a gave compound 152a (0.123 g, 61%) as light brown solid. $^1$H NMR (DMSO-d$_6$, 400 MHz) δ 5.27 (2H, s), 6.13 (1H, t, J=6.4), 6.67 (1H, d, J=7.2), 7.30 (1H, d, J=5.6), 7.45-7.49 (1H, m), 7.57 (2H, t, J=7.6), 7.87 (2H, d, J=8.0), 8.73 (1H, s), 9.08 (1H, s); $^{13}$C NMR (101 MHz, CDCl$_3$) δ 136.59, 129.60, 128.94, 122.29, 120.62, 107.99, 29.29. (quaternary carbons were not seen). HRMS (EI) calcd for $C_{14}H_{12}N_4O_2$ [M]$^+$ 268.0960. found 268.0967.

1-(4-Dimethylamino)phenyltriazolylmethyl-3-hydroxypyridine-2-one (152b)

Reaction of 151b (0.045 g, 0.14 mmol) and 1M BBr$_3$ in $CH_2Cl_2$ (0.22 mL, 1.5 equiv) within 48 h as described for the synthesis of 148a gave compound 152b (0.033 g, 77%) as light brown solid. $^1$H NMR (400 MHz, cdcl$_3$) δ 8.08 (s, 1H), 7.48 (dd, J=19.9, 8.4 Hz, 2H), 7.18 (d, J=6.7 Hz, 1H), 6.69 (ddd, J=25.8, 24.8, 7.5 Hz, 4H), 6.16 (t, J=6.9 Hz, 1H), 5.31 (s, 2H), 2.98 (m, 6H). $^{13}$C NMR (101 MHz, CDCl$_3$) δ 158.35, 150.52, 146.68, 142.48, 127.10, 126.44, 122.06, 121.88, 121.76, 112.12, 107.14, 44.66, 40.33. HRMS (EI) calcd for $C_{16}H_{17}N_5O_2$ [M]$^+$ 311.1382. found 311.1386.

1-Phenyltriazolylmethyl-3-methoxypyridine-2-thione (153a)

Reaction of 151a (0.295 g, 1.04 mmol) and Lawesson's reagent (0.252 g, 0.624 mmol) in toluene (15 mL) within 12 h as described for the synthesis of 147a gave compound 153a (0.291 g, 94%) as yellow solid. $^1$H NMR (CDCl$_3$, 400 MHz) δ 3.90 (3H, s), 6.04 (2H, s), 6.62-6.68 (2H, m), 7.38-7.42 (1H, m), 7.48 (2H, t, J=7.2), 7.68 (2H, d, J=8.0), 7.82 (1H, d, J=4.8), 8.53 (1H, s); $^{13}$C NMR (CDCl$_3$, 100 MHz) δ 50.9, 56.4, 110.0, 112.0, 120.2, 122.4, 128.5, 129.3, 132.2, 136.4, 141.9, 158.7, 171.5 HRMS (EI) calcd for $C_{15}H_{14}N_4O_2$ [M]$^+$ 282.1117. found 282.1115. HRMS (EI) calcd for $C_{15}H_{14}N_4OS$ [M]$^+$ 298.0888. found 298.0888.

1-(4-Dimethylamino)phenyltriazolylmethyl-3-methoxypyridine-2-thione (153b)

Reaction of 151b (0.078 g, 0.248 mmol) and Lawesson's reagent (0.06 g, 0.15 mmol) in toluene (8 mL) within 12 h as described for the synthesis of 147a gave compound 153b (0.07 g, 84%) as yellow solid. $^1$H NMR (400 MHz, cdcl$_3$) δ 8.36 (s, 1H), 7.81 (dd, J=6.4, 1.5 Hz, 1H), 7.46 (m, 2H), 6.66 (m, 4H), 6.01 (s, 2H), 3.87 (s, 3H), 2.97 (s, 6H). $^{13}$C NMR (100 MHz, CDCl$_3$) δ 171.82, 158.93, 150.44, 141.54, 132.44, 126.29, 122.49, 121.77, 112.10, 112.03, 110.14, 56.65, 51.20, 40.29. HRMS (EI) calcd for $C_{17}H_{19}N_5OS$ [M]$^+$ 314.1310. found 314.1304.

1-Phenyltriazolylmethyl-3-hydroxypyridine-2-thione (154a)

Reaction of 153a (0.28 g, 0.93 mmol) and 1M BBr$_3$ in $CH_2Cl_2$ (1.5 equiv) within 48 h as described for the synthesis of 148a gave compound 154a (0.178 g, 67%) as olive green solid. $^1$H NMR (400 MHz, CDCl$_3$) δ 8.43 (d, J=16.6 Hz, 1H), 8.39 (s, 1H), 7.79 (dd, J=6.6, 1.3 Hz, 1H), 7.69 (m, 2H), 7.46 (m, 3H), 6.97 (dd, J=7.7, 1.2 Hz, 1H), 6.69 (dd, J=7.6, 6.8 Hz, 1H), 5.94 (s, 2H). $^{13}$C NMR (100 MHz, CDC$_3$) δ 168.59, 155.12, 141.60, 136.66, 131.65, 129.69, 128.99, 122.57, 120.60, 114.04, 112.47, 77.30, 76.99, 76.67, 52.08. HRMS (EI) calcd for $C_{14}H_{12}N_4OS$ [M]$^+$ 284.0730. found 284.0732.

1-(4-Dimethylamino)phenyltriazolylmethyl-3-hydroxypyridine-2-thione (154b)

Reaction of 153b (0.07 g, 0.212 mmol) and 1M BBr$_3$ in $CH_2Cl_2$ (0.64 mL, 1.5 equiv) within 48 h as described for the synthesis of 148a gave compound 154b (0.032 g, 48%) as olive green solid. $^1$H NMR (400 MHz, CDCl$_3$) δ 8.42 (s, 1H), 8.29 (d, J=11.5 Hz, 1H), 7.79 (d, J=6.4 Hz, 1H), 7.50 (m, 2H), 6.98 (dd, J=36.5, 28.9 Hz, 2H), 6.72 (m, 3H), 5.94 (s, 2H), 3.01 (d, J=2.7 Hz, 6H). $^{13}$C NMR (100 MHz, CDCl$_3$) δ 155.09, 150.66, 141.13, 131.72, 127.68, 126.27, 122.45, 121.97, 114.04, 112.52, 112.16, 52.21, 40.41. HRMS (EI) calcd for $C_{16}H_{17}N_5OS$ [M]$^+$ 327.1154. found 327.1154.

Example 9

2$^{nd}$ Generation 3-Hydroxypyridine-2-thione-based HDAC Inhibitors

Compounds with variable methylene group linker lengths; from one (as seen in compound 154a) to seven (as seen in SAHA) were synthesized and evaluated for their activity as HDAC inhibitors.

The synthesis of 2$^{nd}$ generation 3-HPT-based compounds is depicted in Scheme 20. The crucial azidoalkyl methanesulfonates are synthesized in two steps. The reaction of corresponding bromoalkanols with sodium azide furnished azidoalkanols 155a-155f which were subsequently mesylated to give methanesulfonate intermediates 156a-156f in almost quantitative yields. As described earlier, N-alkylation of O-methyl or O-benzyl protected 3-hydroxypyridine-2-one with the mesylate intermediates gave azido intermediates 157a-157f in moderate to good yields. Aromatic surface recognition cap group was linked to these azido intermediates via 1,2,3-triazole ring. Cu(I)-catalyzed Huisgen cycloaddition between phenylacetylene and azido intermediates 157a-157f, followed by deprotection of methyl ether by Lewis acid BBr$_3$ furnished the desired compounds in good to excellent yields. All the higher linker thione compounds were synthesized from their carbonyl counterparts by using P$_4$S$_{10}$ chemistry as previously reported. However, methylene linker compound 159a did not tolerate the rigorous temperature conditions and was degraded to complex reaction mixture within 2 hrs. Therefore the synthetic scheme shown in Scheme 20 was modified. Incorporation of O-methyl protected intermediate 158a permitted the use of milder Lawesson's reaction chemistry to access thione compound 161 (Scheme 20).

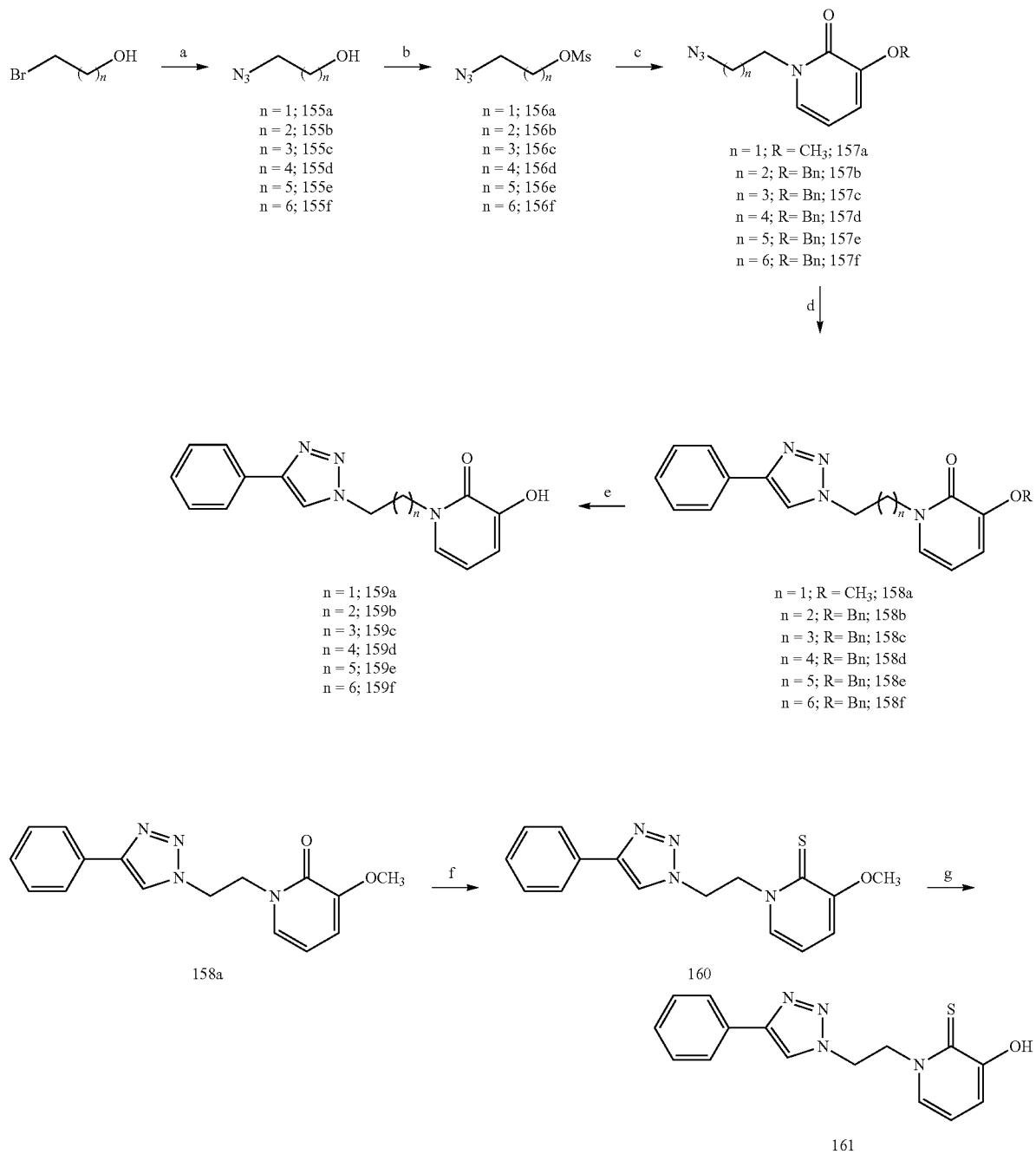

Scheme 20. Synthesis of 2nd generation 3-HPT based HDACis.

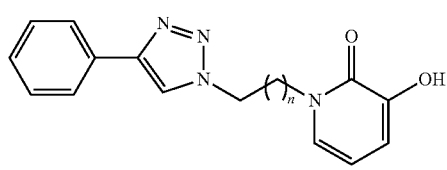 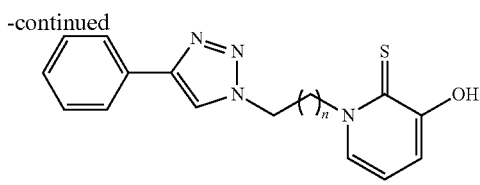

n = 2; 159b
n = 3; 159c
n = 4; 159d
n = 5; 159e
n = 6; 159f n = 2; 162b
n = 3; 162c
n = 4; 162d
n = 5; 162e
n = 6; 162f a) NaN$_3$, DMF, 75° C. (b) methanesulfonyl chloride, Et$_3$N, THF; (c) 3-methocypridine-2-one, K$_2$CO$_3$, THF/DMF, reflux (d) Phenylacetylene, CuI, DIPEA, THF/DMSO; (e) for 22a-BBr$_3$, DCM; for 22b-f-H$_2$, Pd/C, THF; (f) Lawesson's reagent, toluene, reflux; (g) BBr$_3$, DCM; (h) P$_4$S$_{10}$, 175° C., neat.

Activities of 2$^{nd}$ generation compounds also were consistent for HDAC6 and HDAC8 selectivity over HDAC1 and thione compounds always outperformed their corresponding carbonyl compounds. It is interesting to note that very similar trend was observed for HDAC6 and HDAC8 activities according to variation in linker length. For thione analogs, increase in methylene spacer by 1-carbon to compound 154a shows significant loss of activity (comparing 154a and 161 in Table 11 and Table 12). Gradual increase in methylene spacer length from 3-carbon to 5-carbon shows improvement in activity with 5-carbon linker shows optimum activity (compound 162d, IC$_{50}$=911 nM for HDAC6; IC$_{50}$=917 nM for HDA8). However, one additional carbon linker again results in drop of activity (Table 12; comparing 162d and 162e). Interestingly, 7-carbon linker compound 162f showed superior activity than 162e however it still didn't surpass the activity of 162d.

This suggests that 5-carbon methylene chain is optimum linker in HDACi design containing 3-HPT as ZBG. In addition to five methylene spacer, one and seven methylene spacer showed comparable activities and should be viable leads as well.

TABLE 12

In vitro HDAC Inhibition of 2$^{nd}$Generation Compounds

| COMPOUND | IC$_{50}$ (nM) | | |
|---|---|---|---|
| | HDAC1 | HDAC6 | HDAC8 |
| 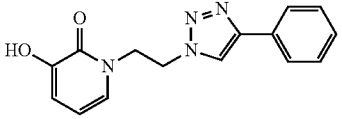 [SMILES: O=c1c(O)cccn1CCn1cc(-c2ccccc2)nn1] 159a | 12% | NI | 15% |
| 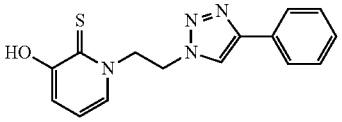 [SMILES: Oc1cccn(CCn2cc(-c3ccccc3)nn2)c1=S] 161 | 21% | 14% | 56% |
| 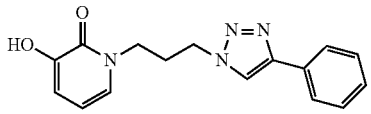 [SMILES: O=c1c(O)cccn1CCCn1cc(-c2ccccc2)nn1] 159b | 8% | 41% | 47% |
| 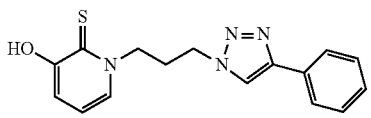 [SMILES: Oc1cccn(CCCn2cc(-c3ccccc3)nn2)c1=S] 162b | 27% | 3628 ± 1363 | 63% |

TABLE 12-continued

In vitro HDAC Inhibition of 2nd Generation Compounds

| COMPOUND | IC$_{50}$ (nM) | | |
|---|---|---|---|
| | HDAC1 | HDAC6 | HDAC8 |
| 159c | 15% | NI | 10% |
| 162c | ND | 1085 ± 333 | 3303 ± 260 |
| 159d | 43% | NI | 30% |
| 162d | 30% | 911 ± 173 | 917 +/− 139 |
| 159e | 12% | NI | 5% |
| 162e | 23% | 22% | 6791 ± 910 |
| 159f | 2% | 34% | 42% |
| 162f | 35% | 955 ± 150 | 232 ± 19 |
| SAHA | 38 +/− 2 | 95% | 232 ± 19 |

SAHA was used for a positive control;
NI — No significant Inhibition (below 20% Inhibition);
% inhibitions of the compounds at 10 μM are given if the IC$_{50}$ was above 10 μM.

Synthetic Procedures

2-Azidoethyl methanesulfonate (156a)

To a solution of compound 2-azidoethanol (1.00 g, 11.49 mmol) in THF (25 mL) and triethylamine ($Et_3N$) (2.418 mL, 17.24 mmol) was added mesyl chloride (1.328 mL, 17.24 mmol) at 0° C., and the mixture was allowed to warm to room temperature. Stirring continued for 3 h, during which TLC revealed a quantitative conversion into a higher $R_f$ product. $CH_2Cl_2$ (70 mL) and saturated sodium bicarbonate (50 mL) were added, and the two layers were separated. The organic layer was washed with sodium bicarbonate (2×50 mL), saturated brine (45 mL) and dried over $Na_2SO_4$. Solvent was evaporated off to give crude compound 156a (1.70 g) as a colorless oil, which was used for next step without further purification.

2-Azidopropyl methanesulfonate (156b)

Reaction of 3-azidopropanol (1.00 g, 9.90 mmol) and mesyl chloride (1.14 mL, 14.85 mmol) within 3 h as described for synthesis of 156a gave compound 156b (1.18 g) as a crude colorless oil.

2-Azidobutyl methanesulfonate (156c)

Reaction of 4-azidobutanol (0.80 g, 6.95 mmol) and mesyl chloride (1.48 mL, 10.43 mmol) within 3 h as described for synthesis of 156a gave compound 156c (1.33 g) as a crude colorless oil.

2-Azidopentyl methanesulfonate (156d)

Reaction of 5-azidopentanol (1.1 g, 8.53 mmol) and mesyl chloride (0.98 mL, 12.79 mmol) within 3 h as described for synthesis of 156a gave compound 156d (1.54 g) as a crude colorless oil.

2-Azidohexyl methanesulfonate (156e)

Reaction of 6-azidohexanol (0.74 g, 5.22 mmol) and mesyl chloride (0.61 mL, 7.83 mmol) within 3 h as described for synthesis of 156a gave compound 156e (0.87 g) as a crude colorless oil.

2-Azidoheptyl methanesulfonate (156f)

Reaction of 7-azidoheptanol (0.55 g, 3.49 mmol) and mesyl chloride (0.41 mL, 5.30 mmol) within 3 h as described for synthesis of 156a gave compound 156l (0.79 g) as a crude colorless oil.

1-(2-Azidoethyl)-3-methoxypyridine-2-one (157a)

3-methoxypyridine-2-one (0.40 g, 3.20 mmol), 156a (0.79 g, 4.80 mmol), and $K_2CO_3$ (1.32 g, 9.60 mmol) stirred overnight in THF at reflux temperature. Reaction mixture was cooled down to room temperature. Reaction mixture was partitioned between $CH_2Cl_2$ (60 mL) and water (50 mL). Organic layer washed with water (2×35 mL), brine (1×30 mL). Organic layer dried on $Na_2SO_4$ and evaporated in vacuo. Crude product was purified by flash chromatography with stepwise gradient of $CH_2Cl_2$ and acetone (max 15%) to give 0.34 mg of 157a (55%) as colorless oil. $^1H$ NMR (400 MHz, $CDCl_3$) δ 6.77 (dd, J=6.9, 1.6 Hz, 1H), 6.48 (dd, J=7.5, 1.6 Hz, 1H), 5.96 (m, 1H), 3.91 (m, 2H), 3.62 (s, 3H), 3.52 (m, 2H). $^{13}C$ NMR (100 MHz, $CDCl_3$) δ 157.39, 149.41, 128.61, 112.16, 104.37, 55.36, 49.00, 48.91. HRMS (EI) calcd for $C_8H_{10}N4O_2$ $[M]^+$ 194.0804. found 194.0816.

(3-Azidopropyl)-3-benzyloxypyridine-2-one (157b)

Reaction of 3-benzyloxypyridine-2-one (0.40 g, 1.99 mmol) and 156b (0.53 g, 2.98 mmol) within 16 h as described for synthesis of 157a gave compound 157b (0.30 g, 53%) as a colorless oil. $^1H$ NMR (300 MHz, $CDCl_3$) 7.28 (m, 5H), 6.84 (dd, J=6.9, 1.6 Hz, 1H), 6.60 (dd, J=7.4, 1.5 Hz, 1H), 5.98 (t, J=7.1 Hz, 1H), 3.97 (t, J=6.8 Hz, 2H), 3.28 (t, J=6.5 Hz, 2H), 1.98 (p, J=6.7 Hz, 2H). $^{13}C$ NMR (75 MHz, $CDCl_3$) δ 157.78, 148.65, 135.93, 128.85, 128.24, 127.69, 127.03, 115.16, 104.53, 70.39, 48.14, 47.06, 27.66. HRMS (EI) calcd for $C_{15}H_{16}N_4O_2$ $[M]^+$ 284.1273. found 284.1271.

1-(4-Azidobutyl)-3-benzyloxypyridine-2-one (157c)

Reaction of 3-benzyloxypyridine-2-one (0.40 g, 1.99 mmol) and 156c (0.58 g, 2.98 mmol) within 16 h as described for synthesis of 157a gave compound 157c (0.36 g, 62%) as a colorless oil. $^1H$ NMR (400 MHz, $CDCl_3$) δ 7.22 (m, 5H), 6.78 (dd, J=6.9, 1.7 Hz, 1H), 6.54 (dd, J=7.4, 1.7 Hz, 1H), 5.91 (m, 1H), 4.96 (s, 2H), 3.85 (t, J=7.2 Hz, 2H), 3.17 (t, J=6.8 Hz, 2H), 1.71 (m, 2H), 1.48 (m, 2H). $^{13}C$ NMR (100 MHz, $CDCl_3$) δ 157.52, 148.27, 135.78, 128.37, 127.98, 127.42, 126.82, 114.92, 104.32, 70.09, 50.43, 48.46, 25.83, 25.42. HRMS (EI) calcd for $C_{16}H_{18}N_4O_2$ $[M]^+$ 298.1430. found 298.1446.

1-(5-Azidopentyl)-3-benzyloxypyridine-2-one (157d)

Reaction of 3-benzyloxypyridine-2-one (0.50 g, 2.49 mmol) and 156d (0.62 g, 2.98 mmol) within 16 h as described for synthesis of 157a gave compound 157d (0.49 g, 63%) as a colorless oil. $^1H$ NMR (400 MHz, $CDCl_3$) δ 7.35 (d, J=8.0 Hz, 2H), 7.23 (m, 3H), 6.81 (m, 1H), 6.56 (m, 1H), 5.94 (m, 1H), 5.01 (s, 2H), 3.85 (m, 2H), 3.18 (m, 2H), 1.71 (m, 2H), 1.54 (m, 2H), 1.32 (m, 2H). $^{13}C$ NMR (100 MHz, $CDCl_3$) δ 157.68, 148.47, 135.98, 128.60, 128.12, 127.53, 126.93, 115.09, 104.32, 70.27, 50.77, 49.21, 28.19, 28.06, 23.37. HRMS (EI) calcd for $C_{17}H_{20}N_4O_2$ $[M]^+$ 312.1586. found 312.1589.

1-(6-Azidohexyl)-3-benzyloxypyridine-2-one (157e)

Reaction of 3-benzyloxypyridine-2-one (0.50 g, 2.49 mmol) and 156d (0.66 g, 2.98 mmol) within 16 h as described for synthesis of 157a gave compound 157e (0.48 g, 60%) as a colorless oil. $^1H$ NMR (400 MHz, $CDCl_3$) δ 7.15 (m, 5H), 6.65 (dd, J=7.4, 1.8 Hz, 1H), 6.45 (dd, J=7.4, 1.8 Hz, 1H), 5.81 (t, J=7.1 Hz, 1H), 4.92 (s, 2H), 3.76 (t, J=6.8 Hz, 2H), 3.05 (t, J=6.8 Hz, 2H), 1.58 (m, 2H), 1.40 (m, 2H), 1.90 (m, 4H). $^{13}C$ NMR (100 MHz, $CDCl_3$) δ 157.55, 148.25, 135.95, 128.60, 128.10, 126.95, 126.50, 115.05, 104.90, 70.50, 51.05, 49.20, 28.65, 28.50, 26.20, 25.80. HRMS (FAB) calcd for $C_{18}H_{23}N_4O_2$ $[M+H]^+$ 327.1821. found 327.1848.

1-(7-Azidoheptyl)-3-benzyloxypyridine-2-one (157f)

Reaction of 3-benzyloxypyridine-2-one (0.79 g, 3.38 mmol) and 156f (0.81 g, 4.05 mmol) within 16 h as described for synthesis of 157a gave compound 157f (0.55 g, 48%) as a colorless oil. $^1H$ NMR (400 MHz, $CDCl_3$) δ 7.42 (dd, J=7.8, 1.0 Hz, 2H), 7.31 (m, 3H), 6.85 (dd, J=6.9, 1.7 Hz, 1H), 6.61

(dd, J=7.4, 1.7 Hz, 1H), 5.99 (m, 1H), 5.09 (s, 2H), 3.93 (m, 2H), 3.23 (t, J=6.9 Hz, 2H), 1.74 (m, 2H), 1.55 (m, 2H), 1.34 (m, 6H). $^{13}$C NMR (100 MHz, CDCl$_3$) δ 158.32, 149.19, 136.63, 129.15, 128.74, 128.13, 127.52, 115.66, 104.69, 94.66, 70.96, 51.62, 50.03, 29.22, 28.98, 26.77, 26.72.

1-Phenyltriazolylethyl-3-methoxypyridine-2-one (158a)

Phenylacetylene (0.167 g, 1.63 mmol) and 157a (0.265 g, 1.36 mmol) were dissolved in anhydrous THF (10 mL) and stirred under argon at room temperature. Copper (I) iodide (0.011 g, 0.07 mmol) and Hunig's base (0.1 mL) were then added to the reaction mixture, and stirring continued for 4 h. The reaction mixture was diluted with CH$_2$Cl$_2$ (40 mL) and washed with 1:4 NH$_4$OH/saturated NH$_4$Cl (3×30 mL) and saturated NH$_4$Cl (30 mL). The organic layer was dried over Na$_2$SO$_4$ and concentrated in vacuo. The crude product was triturated with hexanes to give 366 mg (91%) of white solid 158a. $^1$H NMR (400 MHz, CDCl$_3$) δ 7.68 (s, 1H), 7.47 (d, J=7.5 Hz, 2H), 7.11 (m, 3H), 6.43 (d, J=7.4 Hz, 1H), 6.35 (dd, J=6.8, 0.9 Hz, 1H), 5.78 (t, J=7.2 Hz, 1H), 4.57 (t, J=5.7 Hz, 2H), 4.25 (t, J=5.6 Hz, 2H), 3.53 (s, 3H). $^{13}$C NMR (100 MHz, CDCl$_3$) δ 157.70, 149.08, 147.21, 129.40, 128.30, 128.08, 127.80, 125.00, 120.91, 113.02, 105.44, 55.15, 49.72, 47.44. HRMS (EI) calcd for C$_{16}$H$_{16}$N$_4$O$_2$ [M]$^+$ 296.1273. found 296.1268.

1-Phenyltriazolylpropyl-3-benzyloxypyridine-2-one (158b)

Reaction of phenylacetylene (0.127 g, 1.25 mmol) and 157b (0.295 g, 1.04 mmol) within 4 h as described for synthesis of 158a gave compound 158b (0.31 g, 77%) as a white solid. $^1$H NMR (400 MHz, CDCl$_3$) δ 8.00 (s, 1H), 7.77 (d, J=7.3 Hz, 2H), 7.27 (m, 8H), 6.88 (d, J=5.7 Hz, 1H), 6.57 (d, J=6.4 Hz, 1H), 5.95 (t, J=7.1 Hz, 1H), 4.99 (s, 2H), 4.34 (t, J=6.4 Hz, 2H), 3.94 (t, J=6.4 Hz, 2H), 2.32 (m, 2H). $^{13}$C NMR (100 MHz, CDCl$_3$) δ 157.92, 148.47, 147.30, 135.73, 130.26, 128.81, 128.49, 128.22, 127.76, 127.71, 127.01, 125.33, 120.16, 114.95, 104.83, 70.33, 47.00, 46.48, 29.30. HRMS (EI) calcd for C$_{23}$H$_{22}$N$_4$O$_2$ [M]$^+$ 386.1743. found 386.1734.

1-Phenyltriazolylbutyl-3-benzyloxypyridine-2-one (158c)

Reaction of phenylacetylene (0.124 g, 1.21 mmol) and 157c (0.30 g, 1.01 mmol) within 4 h as described for synthesis of 158a gave compound 158c (0.31 g, 77%) as a white solid. $^1$H NMR (400 MHz, CDCl$_3$) δ 7.83 (s, 1H), 7.76 (m, 2H), 7.26 (m, 8H), 6.76 (dd, J=6.9, 1.5 Hz, 1H), 6.56 (dd, J=7.4, 1.5 Hz, 1H), 5.91 (t, J=7.1 Hz, 1H), 4.99 (s, 2H), 4.31 (m, 2H), 3.89 (t, J=7.1 Hz, 2H), 1.85 (m, 2H), 1.67 (m, 2H). $^{13}$C NMR (100 MHz, CDCl$_3$) δ 157.71, 148.38, 147.20, 135.83, 130.29, 128.45, 128.41, 128.16, 127.68, 127.63, 126.96, 125.25, 119.87, 114.99, 104.60, 70.26, 49.11, 48.02, 26.78, 25.65. HRMS (EI) calcd for C$_{24}$H$_{24}$N$_4$O$_2$ [M]$^+$ 400.1899. found 400.1888.

1-Phenyltriazolylpentyl-3-benzyloxypyridine-2-one (158d)

Reaction of phenylacetylene (0.04 g, 0.32 mmol) and 157d (0.10 g, 0.32 mmol) within 4 h as described for synthesis of 158a gave compound 158d (0.092 g, 72%) as a white solid. $^1$H NMR (400 MHz, CDCl$_3$) δ 7.78 (m, 3H), 7.30 (m, 8H), 6.79 (d, J=6.8 Hz, 1H), 6.57 (d, J=7.3 Hz, 1H), 5.94 (t, J=7.1 Hz, 1H), 5.02 (s, 2H), 4.31 (t, J=7.0 Hz, 2H), 3.87 (t, J=7.2 Hz, 2H), 1.91 (m, 2H), 1.74 (m, 2H), 1.30 (m, 2H). $^{13}$C NMR (100 MHz, CDCl$_3$) δ 157.80, 148.57, 147.39, 136.02, 130.44, 128.64, 128.56, 128.27, 127.81, 127.71, 127.05, 125.40, 119.57, 115.12, 104.49, 70.40, 49.71, 49.06, 29.42, 28.03, 23.05.

1-Phenyltriazolylhexyl-3-benzyloxypyridine-2-one (158e)

Reaction of phenylacetylene (0.80 g, 0.78 mmol) and 157e (0.21 g, 0.65 mmol) within 4 h as described for synthesis of 158a gave compound 158e (0.16 g, 56%) as a white solid. NMR (400 MHz, CDCl$_3$) δ 7.66 (m, 3H), 7.20 (m, 8H), 6.68 (dd, J=6.9, 1.5 Hz, 1H), 6.46 (dd, J=7.4, 1.5 Hz, 1H), 5.82 (t, J=7.1 Hz, 1H), 4.92 (s, 2H), 4.18 (t, J=6.8 Hz, 2H), 3.75 (t, J=6.8 Hz, 2H), 1.76 (m, 2H), 1.56 (m, 2H), 1.19 (m, 4H). $^{13}$C NMR (100 MHz, CDCl$_3$) δ 157.64, 148.46, 147.27, 135.95, 130.36, 128.57, 128.48, 128.19, 127.72, 127.60, 126.96, 125.32, 119.37, 115.02, 104.37 70.45, 50.03, 49.35, 29.90, 28.66, 25.87, 25.78. HRMS (FAB) calcd for C$_{26}$H$_{29}$N$_4$O$_2$ [M+H]$^+$ 429.2290. found 429.2291.

1-Phenyltriazolylheptyl-3-benzyloxypyridine-2-one (158f)

Reaction of phenylacetylene (0.90 g, 0.88 mmol) and 157f (0.25 g, 0.735 mmol) within 4 h as described for synthesis of 158a gave compound 158l (0.23 g, 63%) as a white solid. $^1$H NMR (400 MHz, CDCl$_3$) δ 7.79 (m, 3H), 7.31 (m, 8H), 6.83 (dd, J=6.9, 1.7 Hz, 1H), 6.60 (dd, J=7.4, 1.7 Hz, 1H), 5.97 (t, J=7.1 Hz, 1H), 5.07 (s, 2H), 4.35 (t, J=7.1 Hz, 2H), 3.91 (m, 2H), 1.88 (m, 2H), 1.71 (m, 2H), 1.32 (d, J=10.0 Hz, 6H). $^{13}$C NMR (100 MHz, CDCl$_3$) δ 158.31, 149.13, 147.92, 136.57, 130.93, 129.15, 129.04, 128.74, 128.28, 128.15, 127.51, 125.90, 125.86, 119.75, 115.60, 104.79, 70.92, 50.52, 49.90, 30.42, 29.13, 28.72, 26.53, 26.46. HRMS (FAB) calcd for C$_{27}$H$_{31}$N$_4$O$_2$ [M+H]$^+$ 443.2447. found 443.2494.

1-Phenyltriazolylethyl-3-hydroxypyridine-2-one (159a)

To a solution of 158a (0.10 g, 0.338 mmol) in dry CH$_2$Cl$_2$ (8 mL) was slowly added 1M BBr$_3$ (1.2 equiv) at −30° C. under argon atmosphere. The reaction mixture was stirred for 48 h at room temperature. The mixture was again cooled to −30° C. and the MeOH (5 mL) was slowly added to the mixture. After evaporation of solvent, the residue was adjusted to pH 7 with 1M NaOH and then extracted with CHCl$_3$ (30 mL×3). The combined organic layer dried over Na$_2$SO$_4$ to give 79 mg (83%) of 159a as slightly brownish solid without any further purification required. $^1$H NMR (400 MHz, DMSO) δ 9.11 (s, 1H), 8.51 (s, 1H), 7.78 (d, J=7.3 Hz, 2H), 7.43 (t, J=7.6 Hz, 2H), 7.31 (t, J=7.3 Hz, 1H), 6.75 (d, J=5.9 Hz, 1H), 6.64 (d, J=6.0 Hz, 1H), 5.95 (t, J=7.0 Hz, 1H), 4.76 (t, J=5.5 Hz, 2H), 4.42 (t, J=5.6 Hz, 2H). $^{13}$C NMR (100 MHz, DMSO) δ 158.25, 147.17, 146.77, 131.11, 129.34, 128.41, 128.31, 125.54, 122.23, 115.38, 105.76, 49.42, 48.33. HRMS (EI) calcd for C$_{15}$H$_{14}$N$_4$O$_2$ [M]$^+$ 282.1117. found 282.1120.

1-Phenyltriazolylpropyl-3-hydroxypyridine-2-one (159b)

To a solution of 158b (0.29 g, 1.01 mmol) in CH$_2$Cl$_2$: EtOAc:MeOH (2:2:1, 10 mL) was added 10% Pd on carbon (15 mg). Reaction was stirred under balloon hydrogen pressure for 5 h. Reaction mixture was filtered and solvent was evaporated. Column chromatography using gradient CH$_2$Cl$_2$: Acetone (max 20%) gave pure 159b (0.19 g, 64%) as a slightly brownish solid. $^1$H NMR (400 MHz, DMSO) δ 9.03 (s, 1H), 8.62 (s, 1H), 7.82 (d, J=7.6 Hz, 2H), 7.38 (m, 3H), 7.15 (d, J=6.6 Hz, 1H), 6.68 (d, J=6.4 Hz, 1H), 6.11 (t, J=6.7 Hz, 1H), 4.43 (t, J=6.4 Hz, 2H), 3.99 (m, 2H), 2.27 (m, 2H). $^{13}$C NMR (100 MHz, CDCl$_3$) δ 147.49, 129.71, 128.52, 127.99, 125.29, 120.42, 107.98, 66.61, 47.10, 29.27. (expected aromatic carbons=11; quaternary carbons can't be seen even after repeated cycles) HRMS (EI) calcd for C$_{16}$H$_{16}$N$_4$O$_2$ [M]$^+$ 296.1273. found 296.1274.

1-Phenyltriazolylbutyl-3-hydroxypyridine-2-one (159c)

Reaction of 158c (0.25 g, 0.62 mmol) in anhydrous THF as described for synthesis of 159b gave 159c (0.12 g, 63%) of pure product. $^1$H NMR (400 MHz, CDCl$_3$) δ 7.79 (m, 3H), 7.41 (t, J=7.6 Hz, 2H), 7.32 (t, J=7.4 Hz, 1H), 6.76 (m, 3H), 6.13 (t, J=7.2 Hz, 1H), 4.45 (t, J=6.8 Hz, 2H), 4.02 (t, J=7.1 Hz, 2H), 1.99 (m, 2H), 1.82 (m, 2H). $^{13}$C NMR (100 MHz, CDCl$_3$) δ 158.47, 147.63, 146.62, 130.41, 128.69, 127.99, 126.60, 125.53, 119.80, 114.15, 107.10, 49.38, 48.57, 27.02, 26.01. HRMS (EI) calcd for C$_{17}$H$_{18}$N$_4$O$_2$ [M]$^+$ 310.1430. found 310.1425.

1-Phenyltriazolylpentyl-3-hydroxypyridine-2-one (159d)

Reaction of 158d (0.085 g, 0.20 mmol) in anhydrous THF as described for synthesis of 159b gave 159d (0.045 g, 68%) of pure product. $^1$H NMR (400 MHz, DMSO) δ 8.56 (s, 1H), 7.82 (d, J=8.1 Hz, 2H), 7.43 (t, J=7.7 Hz, 2H), 7.32 (t, J=7.4 Hz, 1H), 7.10 (dd, J=6.8, 1.6 Hz, 1H), 6.65 (dd, J=7.2, 1.5 Hz, 1H), 6.05 (t, J=7.0 Hz, 1H), 4.38 (t, J=7.0 Hz, 2H), 3.89 (t, J=7.2 Hz, 2H), 1.89 (m, 2H), 1.67 (m, 2H), 1.25 (m, 2H). $^{13}$C NMR (100 MHz, CDCl$_3$) δ 158.44, 147.67, 146.61, 130.51, 128.72, 128.01, 126.71, 125.57, 119.54, 113.81, 106.86, 49.86, 49.38, 29.58, 28.31, 23.19. HRMS (FAB) calcd for C$_{18}$H$_{21}$N$_4$O$_2$ [M+H]$^+$ 325.1664. found 325.1683.

1-Phenyltriazolylhexyl-3-hydroxypyridine-2-one (159e)

Reaction of 158e (0.15 g, 0.35 mmol) in anhydrous THF as described for synthesis of 159b gave 159e (0.081 g, 69%) of pure product. $^1$H NMR (400 MHz, CDCl$_3$) δ 7.81 (m, 3H), 7.42 (m, 2H), 7.32 (m, 1H), 6.77 (m, 2H), 6.12 (t, J=7.1 Hz, 1H), 4.38 (t, J=7.1 Hz, 2H), 3.95 (m, 2H), 1.95 (m, 2H), 1.76 (d, J=7.0 Hz, 2H), 1.39 (m, 4H). $^{13}$C NMR (100 MHz, CDCl$_3$) δ 158.20, 147.25, 146.40, 130.30, 128.60, 127.85, 126.65, 125.40, 119.65, 113.90, 106.80, 50.20, 49.60, 30.05, 28.95, 26.00, 25.90. HRMS (FAB) calcd for C$_{19}$H$_{23}$N$_4$O$_2$ [M+H]$^+$ 339.1821. found 339.1814.

1-Phenyltriazolylheptyl-3-hydroxypyridine-2-one (159f)

Reaction of 158f (0.22 g, 0.50 mmol) in anhydrous THF as described for synthesis of 159b gave 159f (0.13 g, 74%) of pure product. $^1$H NMR (400 MHz, DMSO) δ 8.91 (s, 1H), 8.57 (s, 1H), 7.82 (d, J=7.4 Hz, 2H), 7.42 (t, J=7.6 Hz, 2H), 7.31 (t, J=7.3 Hz, 1H), 7.09 (d, J=6.6 Hz, 1H), 6.64 (d, J=7.0 Hz, 1H), 6.04 (t, J=6.9 Hz, 1H), 4.36 (t, J=7.0 Hz, 2H), 3.86 (t, J=7.2 Hz, 2H), 1.83 (m, 2H), 1.61 (m, 2H), 1.26 (m, 6H). $^{13}$C NMR (100 MHz, CDCl$_3$) δ 158.80, 147.89, 147.00, 130.88, 129.05, 128.30, 127.12, 125.87, 119.83, 114.13, 107.10, 50.48, 50.05, 30.37, 29.20, 28.67, 26.46, 26.42. HRMS (FAB) calcd for C$_{20}$H$_{25}$N$_4$O$_2$ [M+H]$^+$ 353.1977. found 353.1992.

1-Phenyltriazolylethyl-3-methoxypyridine-2-thione (160)

To a stirring solution of Lawesson's reagent (0.075 g, 0.185 mmol) in toluene (10 mL), was added starting material 158a (0.10 g, 0.33 mmol). Reaction mixture was heated to reflux temperature. After overnight reaction, solvent was evaporated under reduced pressure. Crude product was dissolved in small amount of CH$_2$Cl$_2$ to load onto preparative-TLC and eluted with CHCl$_3$:Acetone:EtOH (10:1:0.2) to give pure yellow solid 160 (0.07 g, 68%). $^1$H NMR (400 MHz, CDCl$_3$) δ 7.69 (d, J=7.4 Hz, 2H), 7.56 (s, 1H), 7.35 (t, J=7.5 Hz, 2H), 7.28 (m, 1H), 6.97 (d, J=6.6 Hz, 1H), 6.62 (d, J=7.8 Hz, 1H), 6.37 (m, 1H), 5.13 (t, J=5.6 Hz, 2H), 5.03 (t, J=5.6 Hz, 2H), 3.86 (s, 3H). $^{13}$C NMR (100 MHz, CDCl$_3$) δ 171.92, 158.94, 147.52, 132.68, 129.92, 128.69, 128.14, 125.43, 120.96, 111.72, 110.22, 56.72, 56.63, 46.38. HRMS (EI) calcd for C$_{16}$H$_{16}$N$_4$OS [M]$^+$ 312.104. found 312.1039.

1-Phenyltriazolylethyl-3-hydroxypyridine-2-thione (161)

Reaction of 160 (0.062 g, 0.198 mmol) and 1M BBr$_3$ in CH$_2$Cl$_2$ (0.218 mmol) within 48 h as described for synthesis of 148a gave compound 161 (0.055 g, 93%) as a dark violet solid. $^1$H NMR (400 MHz, CDCl$_3$) δ 8.40 (s, 1H), 7.73 (d, J=7.3 Hz, 2H), 7.51 (s, 1H), 7.40 (t, J=7.5 Hz, 2H), 7.33 (t, J=7.3 Hz, 1H), 6.95 (dd, J=9.2, 7.2 Hz, 1H), 6.46 (m, 1H), 5.08 (m, 4H). $^{13}$C NMR (100 MHz, CDCl$_3$) δ 168.47, 155.10, 147.75, 132.00, 129.82, 128.77, 128.30, 125.53, 120.90, 113.66, 112.61, 57.45, 46.41. HRMS (EI) calcd for C$_{15}$H$_{14}$N$_4$OS [M]$^+$ 298.088. found 298.0888.

1-Phenyltriazolylpropyl-3-hydroxypyridine-2-thione (162b)

159b (0.062 g, 0.21 mmol) was ground together with P$_4$S$_{10}$ (0.047 g, 0.105 mmol) in mortar and pestle to form grey powder. The powder was stirred under argon in a flask fitted with condenser and heated to 175° C. for 2 h. The reaction flask was covered with aluminum foil during reaction. After 2 h of reaction, flask was cooled down to room temperature. 25 mL of CH$_2$Cl$_2$:MeOH (10%) mixtures was added and stirred for 15 min. This reaction mixture then washed with water (2×30 mL). Organic layer dried with Na2SO4 and evaporated to yield crude product which was purified by prep-TLC (Eluent —CH$_2$Cl$_2$:MeOH (8%) to give 162b (0.04 g, 60%) as olive green solid. $^1$H NMR (400 MHz, CDCl$_3$) δ 8.47 (s, 1H), 7.82 (m, 3H), 7.50 (d, J=6.5 Hz, 1H), 7.43 (t, J=7.5 Hz, 2H), 7.34 (t, J=7.4 Hz, 1H), 6.97 (m, 1H), 6.66 (m, 1H), 4.62 (t, J=6.9 Hz, 2H), 4.48 (m, 2H). $^{13}$C NMR (100 MHz, CDCl$_3$) δ 168.59, 155.22, 148.03, 131.85, 130.17, 128.84, 128.29, 125.61, 119.84, 113.87, 112.28, 54.99, 46.95, 28.02. HRMS (EI) calcd for C$_{16}$H$_{16}$N$_4$OS [M]$^+$ 312.104. found 312.1060.

1-Phenyltriazolylbutyl-3-hydroxypyridine-2-thione (162c)

Reaction of 159c (0.055 g, 0.18 mmol) and P$_4$S$_{10}$ (0.051 g, 0.115 mmol) under neat conditions as described for synthesis of 162b gave compound 162c (0.032 g, 55%) as a olive green solid. δ 8.50 (s, 1H), 7.81 (m, 3H), 7.36 (m, 4H), 6.94 (d, J=7.6 Hz, 1H), 6.62 (t, J=6.8 Hz, 1H), 4.54 (t, J=7.6 Hz, 2H), 4.46 (t, J=6.4 Hz, 2H), 2.03 (m, 4H). $^{13}$C NMR (100 MHz, CDCl$_3$) δ 168.51, 155.08, 147.73, 131.02, 130.36, 128.79, 128.13, 125.58, 119.91, 113.87, 112.10, 56.96, 49.41, 27.02, 25.08. HRMS (EI) calcd for C$_{17}$H$_{18}$N$_4$OS [M]$^+$ 326.1201. found 326.1200.

1-Phenyltriazolylpentyl-3-hydroxypyridine-2-thione (162d)

Reaction of 159d (0.025 g, 0.077 mmol) and P$_4$S$_{10}$ (0.020 g, 0.046 mmol) under neat conditions as described for synthesis of 162b gave compound 162d (0.019 g, 73%) as a olive green solid. $^1$H NMR (400 MHz, DMSO) δ 8.55 (d, J=2.9 Hz, 2H), 7.83 (t, J=7.8 Hz, 3H), 7.43 (q, J=7.4 Hz, 2H), 7.32 (t, J=6.6 Hz, 1H), 7.08 (m, 1H), 6.92 (dd, J=31.0, 6.8 Hz, 1H), 6.81 (m, 1H), 4.51 (m, 2H), 4.41 (t, J=7.0 Hz, 2H), 1.89 (m, 4H), 1.32 (m, 2H). $^{13}$C NMR (100 MHz, CDCl$_3$) δ 168.37, 155.10, 147.66, 131.04, 130.46, 128.75, 128.05, 125.57, 119.68, 113.69, 111.96, 57.73, 49.73, 29.47, 27.12, 23.04. HRMS (EI) calcd for C$_{18}$H$_{20}$N$_4$OS [M]$^+$ 340.135. found 326.1364.

1-Phenyltriazolylhexyl-3-hydroxypyridine-2-thione (162e)

Reaction of 159e (0.18 g, 0.532 mmol) and P$_4$S$_{10}$ (0.118 g, 0.266 mmol) under neat conditions as described for synthesis of 162b gave compound 162e (0.080 g, 42%) as a olive green semi-solid. $^1$H NMR (400 MHz, CDCl$_3$) δ 8.57 (s, 1H), 7.83 (d, J=7.5 Hz, 2H), 7.76 (s, 1H), 7.41 (t, J=7.5 Hz, 2H), 7.32 (m, 2H), 6.94 (m, 1H), 6.72 (m, 1H), 4.49 (m, 2H), 4.40 (t, J=6.9 Hz, 2H), 1.97 (m, 4H), 1.36 (m, 4H). $^{13}$C NMR (100 MHz, CDCl$_3$) δ 164.38, 162.90, 147.70, 130.54, 128.76, 128.03, 126.64, 125.61, 119.51, 118.75, 118.29, 59.74, 50.10, 29.91, 27.99, 25.82, 25.65. HRMS (ESI) calcd for C$_{19}$H$_{23}$N$_4$OS [M+H]$^+$ 355.158. found 355.1632.

1-Phenyltriazolylheptyl-3-hydroxypyridine-2-thione (162f)

Reaction of 159f (0.12 g, 0.532 mmol) and P$_4$S$_{10}$ (0.076 g, 0.17 mmol) under neat conditions as described for synthesis of 162b gave compound 162f (0.054 g, 43%) as a olive green semi-solid. $^1$H NMR (400 MHz, DMSO) δ 8.55 (m, 1H), 7.81 (d, J=8.2 Hz, 2H), 7.65 (d, J=6.2 Hz, 1H), 7.42 (m, 2H), 7.30 (m, 1H), 7.02 (m, 1H), 6.85 (m, 1H), 4.50 (m, 2H), 4.36 (t, J=7.1 Hz, 2H), 1.85 (d, J=7.0 Hz, 4H), 1.33 (s, 6H). $^{13}$C NMR (100 MHz, CDCl$_3$) δ 147.76, 130.66, 128.76, 130.39, 128.98, 128.80, 128.06, 125.97, 125.67, 119.46, 60.10, 50.25, 30.11, 29.67, 28.33, 26.13, 26.10. HRMS (FAB) calcd for C$_{20}$H$_{25}$N$_4$OS [M+H]$^+$ 369.174. found 369.1762.

Example 10

3$^{rd}$ Generation 3-Hydroxypyridine-2-thione-based HDAC Inhibitors

A 3$^{rd}$ generation of HDAC inhibitors containing 5-carbon methylene spacers were prepared. The synthetic route to the 3$^{rd}$ generation compounds was identical to that described for the 2$^{nd}$ generation compounds. The new surface cap recognition cap groups were coupled to ZBG modified linker using Cu(I)-catalyzed Huisgen cycloaddition to give intermediates in good to excellent yields. As described earlier, Lawessons' chemistry followed by deprotection with BBr$_3$ resulted in desired compounds 166a-166g and 167a-168g. Carbonyl derivatives were also synthesized using similar deprotection chemistry (Scheme 21).

Scheme 21. Synthesis of 3rd generation 3-HPT based HDACis.

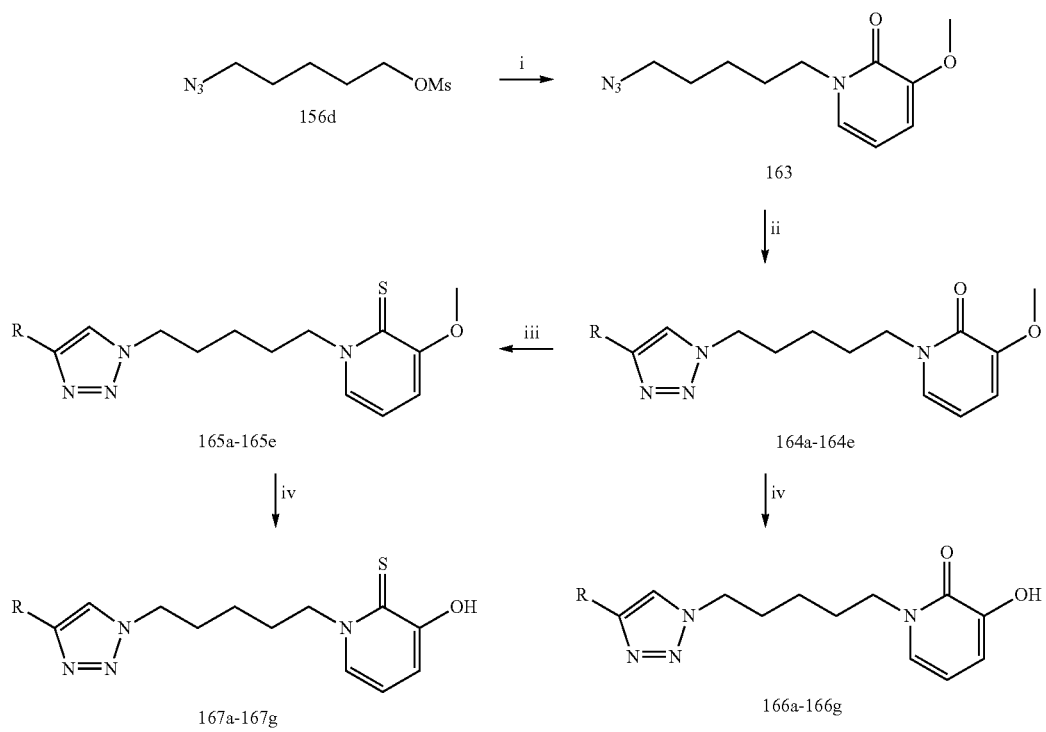

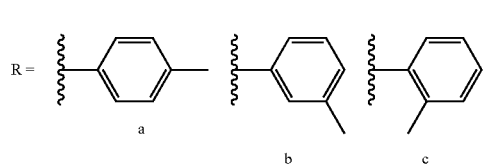
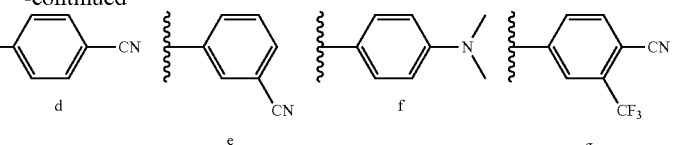

i) 3-methoxypyridine-2-one, K$_2$CO$_3$, THF, reflux; ii)R-alkynes, CuI, DIPEA, DMSO:THF; iii) Lawesson's reagent, Toluene, reflux; iv) BBr$_3$m DCM. Compounds 26, 27a-27e synthesized by Quaovi Sojdi. Included here to show complete synthetic scheme.

The 3$^{rd}$ generation compounds in 3-HPT series were tested against HDAC1, HDAC6 and HDAC8 using the label-free SAMDI mass spectrometry assay as described above. The trend in HDAC inhibition activity was very similar to that observed in the early generation compounds with the thione compounds showing superior activity compared to the carbonyl derivatives. For HDAC8, the results from this study indicate that substitution on the phenyl ring as cap group is not helpful for anti-HDAC activity. Almost all of the cap groups other than simple phenyl ring failed to improve compound potency (compounds 166a-166g; 167a-167g in table 13). However, for HDAC6 docking substitution pattern on phenyl ring yielded improved potency. In case of methyl substitution, para and ortho substitution resulted in more potent drugs than meta substitution. This trend was very similar to 1$^{st}$ generation methyl substituted compounds (comparing compound 149d-149f and 167a-167e). Out of para (compound 167d) and meta (compound 167e) cyano substitution, meta showed superior activity compared to para substitution (compound 167e, IC$_{50}$=356 nM against HDAC6). In addition, substitution with electron donating group N,N-dimethylamino and electron withdrawing group such as shown in compound 167g did not surpass the activity of compound 167e. In order to gain additional insight into binding interactions of 2$^{nd}$ and 3$^{rd}$ generation of compounds at the enzyme active site, docking analyses were performed on the most active compounds in this series against HDAC8.

TABLE 13

In vitro HDAC Inhibition of 3$^{rd}$ Generation Compounds

| COMPOUNDS | HDAC1 | IC$_{50}$ (nM) HDAC6 | HDAC8 |
|---|---|---|---|
| 166a | 66% | NI | 15% |
| 167a | 31% | 807 ± 207 | 2533 +/− 823 |
| 166b | 88% | NI | NI |
| 167b | 19% | 1100 ± 443 | 1660 +/− 416 |
| 166c | NT | NI | 4% |

TABLE 13-continued

In vitro HDAC Inhibition of 3rd Generation Compounds

| COMPOUNDS | IC50 (nM) | | |
|---|---|---|---|
| | HDAC1 | HDAC6 | HDAC8 |
| 167c | NT | 637 ± 160 | 2402 +/− 263 |
| 166d | 70% | NI | 26% |
| 167d | 33% | 905 ± 249 | 1465 +/− 217 |
| 166e | 71% | NI | NI |
| 167e | ND | 356 ± 72 | 2831 +/− 520 |
| 166f | 59% | NI | 28% |
| 167f | 28% | 1006 ± 425 | 1482 +/− 389 |
| 166g | 71% | NI | 14% |

TABLE 13-continued

In vitro HDAC Inhibition of 3rd Generation Compounds

| COMPOUNDS | IC$_{50}$ (nM) | | |
|---|---|---|---|
| | HDAC1 | HDAC6 | HDAC8 |
| 167g | 55% | 661 ± 121 | 2258 +/− 1005 |
| SAHA | 38 +/− 2 | 95% | 232 ± 19 |

SAHA is used for a positive control;
NI — No significant Inhibition (below 20% Inhibition);
% inhibitions of the compounds at 10 μM are given if the IC$_{50}$ was above 10 μM.

Docking of 3$^{rd}$ Generation Compounds

Compound 162d adopts a docked pose at HDAC8 active site which presents the phenyl cap group into a deep, non-solvent exposed hydrophobic pocket, while the 5-carbon methylene spacer optimally fills the connecting the hydrophobic pocket to the Zn$^{2+}$ active site. The ideal spacer length of the 5-carbon methylene group facilitates a proper presentation off the 3-HPT ZBG to the active site Zn$^{2+}$. The deep pocket where the phenyl ring orients consists of Tyr111, Ala112, Leu155, Tyr154 AA residues. Two tyrosine residues are within 3.5 Å of the phenyl cap group of compound 162d and are ideally suited for pi-stacking interaction. Tyr154 is expected to have stronger pi-stacking interaction since plane of its ring is parallel to the phenyl cap group of compound 162d. However, Tyr111 will contribute less to the pi-stacking interaction because the edge of its phenol ring is oriented toward the plane of the cap group 162d. Other AA residues such as Leu115 and Ala112 are within 3.5 Å and contribute to the overall hydrophobicity of the pocket into which the phenyl cap group of compound 162d is bound. This might lead to lower binding energy conformation and hence better IC$_{50}$ value for this 2$^{nd}$ generation compound.

The docked structures of 162d and six methylene linker compound 162e were overlayed. Both compounds bind to the same pocket and adopt almost the similar orientation, except for slight kinks, at the methylene groups. The major difference between the docked poses of 162d and 162e is at their phenyl cap group which is slightly pushed outside of pi-stacking interaction with Tyr154 in compound 162e and thus abolishing this important interaction. This could be the reason that there is almost 7-fold activity difference between 162d and 162e.

Similarly, compound 167d binds to same pocket as discussed earlier. However para-cyano substitution on cap group 167d causes its phenyl ring to be pushed out of the binding pocket seen for compound 162d (Figure 20). Though two tyrosine residues are not far away from the phenyl cap group (~3.2 Å), their orientation is not optimum for pi-stacking interaction with the phenyl group of 167d. Moreover, hydrophobic interactions with Ala112 and Leu155 are completely lost. However, there is a compensatory pi-stacking interaction with Trp141 which may explain the better activity for compound 167d relative to 162e.

The preference for the HDAC8 isoform over HDAC1 was consistent for almost all of the compounds tested in this series. This is an important and interesting observation considering the fact that other aromatic ZBG such as benzamide showed HDAC1 selectivity (250 fold). To obtain information on the structural basis of the observed disparity in the HDAC isoform selectivity, molecular docking analysis was performed on lead compound 149d with two HDAC isoforms. However, HDAC1 docking of 149d revealed that there was no fruitful interaction of compound 149d at HDAC1 enzyme active site. Repeated docking suggested that the ZBG of 149d was unable to deeply penetrate (~14 Å) the Zn$^2$ active site of HDAC1.

Synthetic Procedures 1-(4-Tolyl)triazolylpentyl-3-methoxypyridine-2-thione (165a)

Reaction of 164a (0.235 g, 0.667 mmol) and Lawesson's reagent (0.162 g, 0.40 mmol) in toluene (12 mL) within 12 h as described for the synthesis of 147a gave compound 165a (0.232 g, 95%) as yellow solid. $^1$H NMR (400 MHz, CDCl$_3$) δ 7.77 (s, 1H), 7.73 (d, J=8.2 Hz, 2H), 7.33 (m, 1H), 7.25 (dd, J=11.4, 5.2 Hz, 2H), 6.66 (d, J=7.8 Hz, 1H), 6.59 (dd, J=7.8, 6.5 Hz, 1H), 4.60 (m, 2H), 4.43 (t, J=6.9 Hz, 2H), 3.91 (s, 3H), 2.38 (s, 3H), 2.01 (m, 4H), 1.43 (m, 2H); $^{13}$C NMR (75 MHz, CDCl$_3$) δ 171.03, 158.50, 147.11, 137.37, 131.77, 129.02, 127.33, 125.03, 119.32, 111.60, 109.78, 56.27, 49.28, 30.48, 29.05, 26.51, 22.57, 20.82. HRMS (EI) calcd for C$_{20}$H$_{24}$N$_4$OS [M]$^+$ 368.167. found 368.1667.

1-(3-Tolyl)triazolylpentyl-3-methoxypyridine-2-thione (165b)

Reaction of 164b (0.137 g, 0.389 mmol) and Lawesson's reagent (0.094 g, 0.223 mmol) in toluene (10 mL) within 12 h as described for the synthesis of 147a gave compound 165b (0.104 g, 73%) as yellow solid. $^1$H NMR (400 MHz, CDCl$_3$) δ 7.78 (s, 1H), 7.62 (s, 1H), 7.54 (d, J=7.7 Hz, 1H), 7.26 (m, 2H), 7.07 (d, J=7.6 Hz, 1H), 6.59 (m, 1H), 6.52 (dd, J=7.8, 6.5 Hz, 1H), 4.50 (m, 2H), 4.34 (t, J=7.0 Hz, 2H), 3.81 (s, 3H), 2.32 (s, 3H), 1.90 (m, 4H), 1.33 (m, 2H); $^{13}$C NMR (100 MHz, CDCl$_3$) δ 171.47, 158.81, 147.45, 138.19, 131.83, 130.21, 128.58, 128.46, 126.03, 122.48, 119.68, 111.72, 109.80, 56.55, 56.47, 49.50, 29.24, 26.70, 22.77, 21.18. HRMS (EI) calcd for C$_{20}$H$_{24}$N$_4$OS [M]$^+$ 368.1671. found 368.1682.

1-(2-Tolyl)triazolylpentyl-3-methoxypyridine-2-thione (165c)

Reaction of 164c (0.124 g, 0.351 mmol) and Lawesson's reagent (0.085 g, 0.21 mmol) in toluene (10 mL) within 12 h as described for the synthesis of 147a gave compound 165c (0.093 g, 72%) as yellow solid. $^1$H NMR (400 MHz, CDCl$_3$) δ 7.72 (m, 1H), 7.27 (m, 2H), 6.60 (m, 1H), 4.57 (m, 1H), 4.42 (t, J=7.0 Hz, 1H), 3.86 (s, 1H), 2.44 (s, 1H), 1.99 (m, 2H), 1.41 (dt, J=15.2, 7.6 Hz, 1H). $^{13}$C NMR (100 MHz, CDCl$_3$) δ 171.81, 159.04, 146.84, 135.33, 131.86, 130.74, 129.81, 128.68, 127.94, 125.93, 121.86, 111.78, 109.79, 104.88, 56.75, 56.61, 49.60, 29.45, 26.85, 22.97, 21.36. HRMS (EI) calcd for C$_{20}$H$_{24}$N$_4$OS [M]$^+$ 368.167. found 368.1662.

1-(4-Benzonitrile)triazolylpentyl-3-methoxypyridine-2-thione (165d)

Reaction of 164d (0.210 g, 0.551 mmol) and Lawesson's reagent (0.133 g, 0.330 mmol) in toluene (12 mL) within 12 h as described for the synthesis of 147a gave compound 165d (0.146 g, 67%) as yellow solid. $^1$H NMR (400 MHz, CDCl$_3$) δ 7.64 (m, 3H), 7.28 (m, 1H), 6.73 (d, J=8.3 Hz, 2H), 6.61 (d, J=7.6 Hz, 1H), 6.52 (t, J=7.1 Hz, 1H), 4.50 (m, 2H), 4.31 (t, J=6.7 Hz, 2H), 3.81 (s, 3H), 2.92 (s, 6H), 1.89 (m, 4H), 1.32 (m, 2H); $^{13}$C NMR (100 MHz, CDCl$_3$) δ 171.44, 158.81, 149.78, 147.77, 131.91, 126.37, 119.05, 118.34, 112.52, 111.73, 109.84, 56.60, 56.49, 49.44, 40.45, 29.29, 26.74, 22.81. HRMS (EI) calcd for C$_{21}$H$_{27}$N$_5$OS [M]$^+$ 397.193. found 397.1928.

1-(3-Benzonitrile)triazolylpentyl-3-methoxypyridine-2-thione (165e)

Reaction of 164e (0.190 g, 0.523 mmol) and Lawesson's reagent (0.130 g, 0.314 mmol) in toluene (10 mL) within 12 h as described for the synthesis of 147a gave compound 165e (0.133 g, 67%) as yellow solid. $^1$H NMR (400 MHz, CDCl$_3$) δ 7.98 (s, 1H), 7.84 (d, J=8.4 Hz, 2H), 7.56 (d, J=8.4 Hz, 2H), 7.30 (d, J=6.5 Hz, 1H), 6.60 (d, J=7.0 Hz, 1H), 6.52 (dd, J=7.7, 6.6 Hz, 1H), 4.48 (m, 2H), 4.34 (t, J=6.9 Hz, 2H), 3.76 (s, 3H), 1.88 (m, 4H), 1.31 (m, 2H). $^{13}$C NMR (100 MHz, CDCl$_3$) δ 171.23, 158.70, 145.36, 134.76, 132.30, 131.78, 125.68, 121.20, 118.49, 111.83, 110.73, 109.92, 56.43, 49.50, 29.01, 26.56, 22.56. HRMS (EI) calcd for C$_{20}$H$_{21}$N$_5$OS [M]$^+$ 379.146. found 379.1466.

1-(4-(N,N-dimethylaniline))triazolylpentyl-3-methoxypyridine-2-thione (165f)

Reaction of 1641 (0.145 g, 0.40 mmol) and Lawesson's reagent (0.098 g, 0.241 mmol) in toluene (10 mL) within 12 h as described for the synthesis of 147a gave compound 1651 (0.149 g, 98%) as yellow solid. $^1$H NMR (400 MHz, CDCl$_3$) δ 8.12 (t, J=1.4 Hz, 1H), 8.06 (m, 1H), 7.90 (s, 1H), 7.59 (dt, J=7.7, 1.4 Hz, 1H), 7.52 (t, J=7.8 Hz, 1H), 7.33 (dd, J=6.5, 1.4 Hz, 1H), 6.67 (dd, 7.9, 1.3 Hz, 1H), 6.60 (dd, J=7.8, 6.5 Hz, 1H), 4.59 (m, 2H), 4.46 (t, J=6.9 Hz, 2H), 3.89 (s, 3H), 2.02 (m, 4H), 1.43 (m, 2H); $^{13}$C NMR (100 MHz, CDCl$_3$) δ 171.30, 158.73, 145,13, 131.82, 131.71, 130.97, 129.52, 129.44, 128.64, 120.61, 118.28, 112.49, 111.81, 109.91, 56.44, 49.62, 29.11, 26.64, 22.68. HRMS (EI) calcd for C$_{20}$H$_{21}$N$_5$OS [M]$^+$ 379.146. found 379.1469.

1-(4-(3-Trifluoromethyl)-benzonitrile)triazolylpentyl-3-methoxypyridine-2-thione (165g)

Reaction of 164g (0.090 g, 0.2088 mmol) and Lawesson's reagent (0.051 g, 0.1252 mmol) in toluene (10 mL) within 12 h as described for the synthesis of 147a gave compound 165g (0.075 g, 81%) as yellow solid. $^1$H NMR (400 MHz, CDCl$_3$) δ 8.28 (s, 1H), 8.12 (d, J=6.7 Hz, 2H), 7.86 (d, J=8.1 Hz, 1H), 7.36 (d, J=6.5 Hz, 1H), 6.68 (d, J=7.8 Hz, 1H), 6.61 (t, J=7.2 Hz, 1H), 4.59 (m, 2H), 4.47 (m, 2H), 3.88 (s, 3H), 2.02 (m, 4H), 1.43 (m, 2H); $^{13}$C NMR (100 MHz, CDCl$_3$) δ 171.84, 159.14, 144.54, 135.55, 135.22, 133.51, 133.18, 131.81, 128.59, 121.86, 120.86, 115.46, 112.00, 109.97, 108.47, 77.31, 76.99, 76.67, 56.69, 49.87, 29.19, 26.77, 22.77. HRMS (EI) calcd for C$_{21}$H$_{20}$N$_5$OSF$_3$ [M]$^+$ 447.134. found 447.1341.

1-(4-Tolyl)triazolylpentyl-3-hydroxypyridine-2-one (166a)

Reaction of 164a (0.10 g, 0.284 mmol) and 1M BBr$_3$ (0.34 mL) in CH$_2$Cl$_2$ (8 mL) within 48 h as described for the synthesis of 148a gave compound 166a (0.049 g, 52%) as light brown solid. $^1$H NMR (400 MHz, CDCl$_3$) δ 7.71 (m, 3H), 7.24 (m, 2H), 6.76 (t, J=6.4 Hz, 2H), 6.12 (t, J=7.0 Hz, 1H), 4.40 (t, J=6.9 Hz, 2H), 3.96 (t, J=7.1 Hz, 2H), 2.38 (s, 3H), 2.00 (m, 2H), 1.82 (m, 2H), 1.39 (m, 2H); $^{13}$C NMR (100 MHz, DMSO) δ 171.80, 146.31, 137.02, 129.40, 128.08, 125.02, 120.79, 114.36, 105.20, 49.27, 48.22, 29.17, 28.01, 22.85, 20.82. HRMS (EI) calcd for C$_{19}$H$_{22}$N$_4$O$_2$ [M]$^+$ 338.1743. found 338.1750.

1-(3-Tolyl)triazolylpentyl-3-hydroxypyridine-2-one (166b)

Reaction of 164b (0.073 g, 0.207 mmol) and 1M BBr$_3$ (0.24 mL) in CH$_2$Cl$_2$ (8 mL) within 48 h as described for the synthesis of 148a gave compound 166b (52 mg, 74%) as light brown solid. $^1$H NMR (400 MHz, CDCl$_3$) δ 7.74 (s, 1H), 7.67 (s, 1H), 7.59 (d, J=7.7 Hz, 1H), 7.30 (t, J=7.6 Hz, 1H), 7.14 (d, J=7.4 Hz, 1H), 6.76 (t, J=6.2 Hz, 2H), 6.12 (t, J=7.1 Hz, 1H), 4.39 (t, J=6.9 Hz, 2H), 3.96 (t, J=7.2 Hz, 2H), 2.39 (s, 3H), 1.99 (m, 2H), 1.80 (m, 2H), 1.38 (m, 2H). $^{13}$C NMR (100 MHz, CDCl$_3$) δ 158.58, 147.87, 146.52, 138.46, 130.38, 128.86, 128.67, 126.75, 126.31, 122.72, 119.48, 113.61, 106.85, 49.91, 49.45, 29.65, 28.38, 23.27, 21.38. HRMS (EI) calcd for C$_{19}$H$_{22}$N$_4$O$_2$ [M]$^+$ 338.174. found 338.1741.

1-(2-Tolyl)triazolylpentyl-3-hydroxypyridine-2-one (166c)

Reaction of 164c (0.065 g, 0.18 mmol) and 1M BBr$_3$ (0.27 mL) in CH$_2$Cl$_2$ (8 mL) within 48 h as described for the synthesis of 148a gave compound 166c (54 mg, 87%) as light brown solid. $^1$H NMR (400 MHz, dorso) δ 8.92 (s, 1H), 8.36 (s, 1H), 7.71 (m, 1H), 7.25 (m, 1H), 7.09 (d, J=6.8 Hz, 1H), 6.64 (d, J=6.9 Hz, 1H), 6.04 (t, J=7.0 Hz, 1H), 4.39 (t, J=6.9 Hz, 1H), 3.88 (t, J=7.0 Hz, 1H), 2.41 (s, 1H), 1.90 (m, 1H), 1.67 (m, 1H), 1.25 (m, 1H). $^{13}$C NMR (100 MHz, CD$_3$OD) δ 146.28, 135.00, 130.15, 128.96, 128.21, 127.72, 125.38, 122.09, 106.72, 49.43, 48.98, 29.05, 27.78, 22.69, 20.09. HRMS (EI) calcd for C$_{19}$H$_{22}$N$_4$O$_2$ [M]$^+$ 338.174. found 338.1741.

1-(4-Benzonitrile)triazolylpentyl-3-hydroxypyridine-2-one (166d)

Reaction of 164d (0.075 g, 0.197 mmol) and 1M BBr$_3$ (0.24 mL) in CH$_2$Cl$_2$ (8 mL) within 48 h as described for the synthesis of 148a gave compound 166d (43 mg, 60%) as light brown solid. $^1$H NMR (400 MHz, CDCl$_3$) δ 7.69 (d, J=8.8 Hz, 2H), 7.61 (s, 1H), 6.77 (m, 4H), 6.11 (t, J=7.1 Hz, 1H), 4.37 (t, J=6.9 Hz, 2H), 3.96 (t, J=7.2 Hz, 2H), 2.99 (s, 6H), 1.99 (m, 2H), 1.81 (m, 2H), 1.39 (m, 2H). $^{13}$C NMR (100 MHz, CDCl$_3$) δ 158.57, 150.35, 148.26, 146.61, 126.84, 126.61, 118.87, 118.11, 113.72, 112.49, 106.86, 49.83, 49.52, 40.46, 29.70, 28.41, 23.34. HRMS (EI) calcd for $C_{20}H_{25}N_5O_2$ $[M]^+$ 367.200. found 367.2007.

1-(3-Benzonitrile)triazolylpentyl-3-hydroxypyridine-2-one (166e)

Reaction of 164e (0.09 g, 0.25 mmol) and 1M BBr$_3$ (0.30 mL) in CH$_2$Cl$_2$ (8 mL) within 48 h as described for the synthesis of 148a gave compound 166e (62 mg, 72%) as light brown solid. $^1$H NMR (400 MHz, DMSO) δ 8.93 (s, 1H), 8.76 (s, 1H), 8.01 (d, J=7.7 Hz, 2H), 7.90 (d, J=8.0 Hz, 2H), 7.09 (d, J=6.4 Hz, 1H), 6.64 (d, J=7.1 Hz, 1H), 6.04 (t, J=7.0 Hz, 1H), 4.41 (t, J=6.5 Hz, 2H), 3.88 (t, J=6.9 Hz, 2H), 1.89 (m, 2H), 1.67 (m, 2H), 1.24 (m, 2H). $^{13}$C NMR (100 MHz, CDCl$_3$) δ 146.62, 145.80, 134.92, 132.57, 126.69, 125.93, 120.88, 118.70, 114.06, 111.19, 107.06, 50.00, 49.29, 29.43, 28.28, 23.08. HRMS (EI) calcd for $C_{19}H_{19}N_5O_2$ $[M]^+$ 349.153. found 349.1544.

1-(4-(N,N-dimethylaniline))triazolylpentyl-3-hydroxypyridine-2-one (166f)

Reaction of 164f (0.078 g, 0.22 mmol) and 1M BBr$_3$ (0.26 mL) in CH$_2$Cl$_2$ (6 mL) within 48 h as described for the synthesis of 148a gave compound 166f (48 mg, 64%) as light brown solid. $^1$H NMR (400 MHz, CD$_3$OD) δ 8.39 (s, 1H), 8.16 (s, 1H), 8.12 (d, J=7.5 Hz, 1H), 7.68 (d, J=7.5 Hz, 1H), 7.61 (t, J=7.6 Hz, 1H), 7.04 (m, 1H), 6.76 (m, 1H), 6.21 (m, 1H), 4.45 (m, 2H), 3.99 (m, 2H), 2.01 (m, 2H), 1.78 (m, 2H), 1.33 (m, 2H). $^{13}$C NMR (100 MHz, CDCl$_3$) δ 145.61, 131.97, 131.31, 129.74, 129.65, 129.10, 120.30, 118.49, 112.99, 104.90, 50.07, 49.40, 29.52, 28.37, 23.17. HRMS (EI) calcd for $C_{19}H_{19}N_5O_2$ $[M]^+$ 349.153. found 349.1539.

1-(4-(3-Trifluomethyl)-benzonitrile)triazolylpentyl-3-hydroxypyridine-2-one (166g)

Reaction of 164g (0.042 g, 0.097 mmol) and 1M BBr$_3$ (0.17 mL) in CH$_2$Cl$_2$ (6 mL) within 48 h as described for the synthesis of 148a gave compound 166g (35 mg, 85%) as light brown solid. $^1$H NMR (400 MHz, CDCl$_3$) δ 8.24 (s, 1H), 8.12 (d, J=7.9 Hz, 1H), 8.00 (s, 1H), 7.86 (d, J=7.9 Hz, 1H), 6.75 (t, J=5.8 Hz, 2H), 6.12 (t, J=7.0 Hz, 1H), 4.44 (t, J=6.9 Hz, 2H), 3.96 (t, J=7.1 Hz, 2H), 2.02 (m, 2H), 1.81 (m, 2H), 1.37 (m, 2H). $^{13}$C NMR (100 MHz, CDCl$_3$) δ 158.58, 146.54, 144.71, 135.49, 135.26, 128.57, 126.70, 123.59, 123.54, 121.46, 115.47, 113.82, 108.63, 107.02, 50.19, 49.31, 29.45, 28.30, 23.12. HRMS (EI) calcd for $C_{20}H_{18}N_5O_2F_3$ $[M]^+$ 417.141. found 417.1425. HRMS (EI) calcd for $C_{20}H_{18}N_5O_2F_3$ $[M]^+$ 417.141. found 417.1425.

1-(4-Tolyl)triazolylpentyl-3-hydroxypyridine-2-thione (167a)

Reaction of 165a (0.075 g, 0.203 mmol) and 1M BBr$_3$ (0.24 mL) in CH$_2$Cl$_2$ (8 mL) within 48 h as described for the synthesis of 148a gave compound 167a (0.042 g, 62%) as olive green solid. $^1$H NMR (400 MHz, CD$_3$OD) δ 8.18 (s, 1H), 7.66 (d, J=8.0 Hz, 2H), 7.55 (d, J=5.7 Hz, 1H), 7.20 (d, J=7.7 Hz, 2H), 6.97 (d, J=6.7 Hz, 1H), 4.55 (m, 2H), 4.43 (t, J=6.7 Hz, 2H), 2.34 (s, 3H), 2.01 (m, 4H), 1.39 (t, J=22.5 Hz, 2H). $^{13}$C NMR (100 MHz, CD$_3$OD) δ 149.25, 139.68, 130.93, 129.13, 127.01, 122.27, 51.41, 30.95, 24.51, 21.83. HRMS (EI) calcd for $C_{19}H_{22}N_4OS$ $[M]^+$ 354.151. found 354.1512.

1-(3-Tolyl)triazolylpentyl-3-hydroxypyridine-2-thione (167b)

Reaction of 165b (0.10 g, 0.271 mmol) and 1M BBr$_3$ (0.33 mL) in CH$_2$Cl$_2$ (8 mL) within 48 h as described for the synthesis of 148a gave compound 167b (0.053 g, 56%) as olive green solid. $^1$H NMR (400 MHz, CD$_3$OD) δ 8.20 (s, 1H), 7.61 (s, 1H), 7.55 (m, 2H), 7.26 (t, J=7.6 Hz, 1H), 7.12 (d, J=7.5 Hz, 1H), 6.92 (m, 2H), 4.55 (m, 2H), 4.44 (t, J=6.7 Hz, 2H), 2.36 (s, 3H), 2.01 (m, 4H), 1.41 (m, 2H). $^{13}$C NMR (100 MHz, CD$_3$OD) δ 149.29, 140.05, 131.87, 131.78, 130.38, 130.20, 127.90, 127.63, 124.13, 122.51, 51.40, 31.07, 30.93, 28.97, 24.49, 22.02. HRMS (EI) calcd for $C_{19}H_{22}N_4OS$ $[M]^+$ 354.151. found 354.1523.

1-(2-Tolyl)triazolylpentyl-3-hydroxypyridine-2-thione (167c)

Reaction of 165c (0.072 g, 0.195 mmol) and 1M BBr$_3$ (0.30 mL) in CH$_2$Cl$_2$ (8 mL) within 48 h as described for the synthesis of 148a gave compound 167c (0.046 g, 67%) as olive green solid. $^1$H NMR (400 MHz, CD$_3$OD) δ 7.94 (s, 1H), 7.61 (m, 1H), 7.47 (s, 1H), 7.21 (m, 1H), 6.97 (m, 1H), 6.76 (m, 1H), 4.52 (m, 1H), 4.45 (t, J=6.8 Hz, 1H), 2.38 (s, 1H), 2.01 (m, 2H), 1.43 (m, 1H). $^{13}$C NMR (100 MHz, CD$_3$OD) δ 146.74, 135.53, 130.65, 129.46, 128.69, 128.21, 125.88, 122.79, 53.41, 49.83, 29.42, 27.32, 22.98, 20.55. HRMS (EI) calcd for $C_{19}H_{22}N_4OS$ $[M]^+$ 354.151. found 354.1509.

1-(4-Benzonitrile)triazolylpentyl-3-hydroxypyridine-2-thione (167d)

Reaction of 165d (0.10 g, 0.271 mmol) and 1M BBr$_3$ (0.33 mL) in CH$_2$Cl$_2$ (8 mL) within 48 h as described for the synthesis of 148a gave compound 167d (0.053 g, 56%) as olive green solid. $^1$H NMR (400 MHz, DMSO-d$_6$) δ 8.53 (s, 1H), 8.27 (s, 1H), 7.82 (d, J=7.1 Hz, 1H), 7.62 (d, J=8.8 Hz, 2H), 7.06 (d, J=7.5 Hz, 1H), 6.93 (m, 1H), 6.77 (m, 2H), 4.52 (d, J=6.9 Hz, 2H), 4.36 (t, J=7.0 Hz, 2H), 3.21 (s, 6H), 1.88 (m, 4H), 1.34 (m, 2H). HRMS (EI) calcd for $C_{20}H_{25}N_5OS$ $[M]^+$ 383.178. found 383.1776.

1-(3-Benzonitrile)triazolylpentyl-3-hydroxypyridine-2-thione (167e)

Reaction of 165e (0.095 g, 0.25 mmol) and 1M BBr$_3$ (0.30 mL) in CH$_2$Cl$_2$ (8 mL) within 48 h as described for the synthesis of 148a gave compound 167e (0.055 g, 60%) as olive green solid. $^1$H NMR (400 MHz, DMSO) δ 8.76 (s, 1H), 8.01 (d, J=8.1 Hz, 2H), 7.87 (m, 2H), 7.65 (d, J=6.4 Hz, 1H), 7.00 (m, 1H), 6.87 (d, J=8.2 Hz, 1H), 6.70 (m, 1H), 4.44 (m, 4H), 1.89 (m, 4H), 1.31 (m, 2H). $^{13}$C NMR (100 MHz, CDCl$_3$) δ 168.23, 155.01, 145.75, 134.86, 132.56, 131.00, 125.91, 121.05, 118.68, 113.76, 112.04, 111.17, 57.64, 49.81, 29.31, 27.06, 22.91. HRMS (EI) calcd for $C_{19}H_{19}N_5OS$ $[M]^+$ 365.131. found 365.1313.

1-(4-(N,N-dimethylaniline)triazolylpentyl-3-hydroxypyridine-2-thione (167f)

Reaction of 165f (0.105 g, 0.25 mmol) and 1M BBr$_3$ (0.33 mL) in CH$_2$Cl$_2$ (8 mL) within 48 h as described for the synthesis of 148a gave compound 167f (0.072 g, 66%) as olive green solid. $^1$H NMR (400 MHz, CD$_3$OD) δ 8.38 (s, 1H), 8.15 (s, 1H), 8.10 (d, J=7.9 Hz, 1H), 7.63 (m, 3H), 6.95 (d, J=7.5 Hz, 1H), 6.67 (m, 1H), 4.57 (m, 2H), 4.48 (t, J=7.0

Hz, 2H), 2.03 (m, 4H), 1.43 (m, 2H). $^{13}$C NMR (100 MHz, CD$_3$OD) δ 145.34, 132.04, 131.14, 129.72, 129.58, 128.63, 121.75, 112.74, 104.99, 49.79, 29.08, 27.04, 22.73. HRMS (EI) calcd for C$_{19}$H$_{19}$N$_5$OS [M]$^+$ 365.131. found 365.1310.

1-(4-(3-Trifluomethyl)-benzonitrile)triazolylpentyl-3-hydroxypyridine-2-thione (167g)

Reaction of 165g (0.105 g, 0.25 mmol) and 1M BBr$_3$ (0.33 mL) in CH$_2$Cl$_2$ (8 mL) within 48 h as described for the synthesis of 148a gave compound 167g (0.072 g, 66%) as olive green solid. $^1$H NMR (400 MHz, CD$_3$OD) δ 8.59 (s,

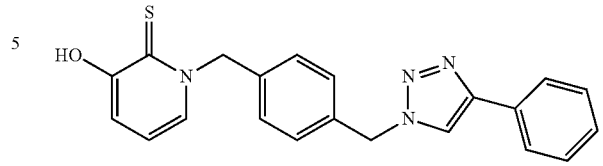

Compound 168

TABLE 14

Anti-cancer activity of selected HDAC inhibitor models.

| | HDAC1 (nm) | HDAC 6 (nm) | HDAC 8 (nm) | DU 145 (μm) | LNCaP (μm) | Jurkat (μm) |
|---|---|---|---|---|---|---|
| 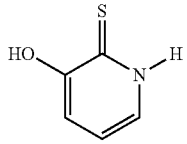 | NI | 681 ± 110 | 3675 ± 1201 | NI | NI | NI |
| 149g | NI | NI | 2858 ± 944 | 22.84 ± 3.8 | 16.23 ± 1.11 | 10.62 ± 0.97 |
| | | | | >20 | | |
| 149c | NI | 372 ± 35 | 1907 ± 771 | 30.0 ± 5.85 | 14.65 ± 0.84 | 8.95 ± 0.69 |
| | | | | >20 | | |
| 149f | NI | 306 ± 69 | 3105 ± 1649 | 13.59 ± 2.91 | 7.75 ± 0.73 | 3.19 ± 0.3 |
| 154a | NI | 41% | 1570 ± 1067 | 24.02 ± 7.47 | 13.11 ± 1.51 | 4.68 ± 0.34 |
| | | | | >20 | | |
| 162d | NI | 911 ± 173 | 917 ± 139 | 9.33 ± 0.96 | 5.43 ± 0.47 | 3.27 ± 0.60 |
| 162f | NI | 955 ± 150 | 1377 ± 205 | 17.72 ± 3.28 | 10.95 ± 1.92 | 9.04 ± 1.31 |
| 167e | NI | 637 ± 160 | 2402 ± 263 | 11.08 ± 2.38 | 4.95 ± 0.43 | 5.18 ± 1.18 |
| 167e | NI | 356 ± 72 | 2831 ± 520 | 5.03 ± 1.13 | 3.49 ± 0.34 | 3.44 ± 0.57 |
| 168 | NI | 534 ± 185 | 5470 ± 1603 | 16.07 ± 2.24 | 7.80 ± 0.55 | 6.55 ± 0.91 |
| SAHA | | | | 2.49 ± 0.2 | 2.31 ± 0.74 | 1.49 ± 0.10 |

1H), 8.35 (s, 1H), 8.21 (d, J=7.8 Hz, 1H), 8.00 (t, J=9.5 Hz, 1H), 7.58 (d, J=6.2 Hz, 1H), 6.96 (d, J=7.5 Hz, 1H), 6.72 (m, 1H), 4.57 (m, 4H), 2.04 (m, 4H), 1.42 (m, 2H). $^{13}$C NMR (100 MHz, CD$_3$OD) δ 146.09, 137.48, 137.24, 134.79, 130.46, 125.55, 124.87, 123.60, 122.77, 116.84, 109.75, 55.10, 51.63, 30.84, 28.90, 24.47. HRMS (EI) calcd for C$_{19}$H$_{19}$N$_5$OS [M]$^+$ 365.131. found 365.1310. HRMS (EI) calcd for C$_{20}$H$_{13}$N$_5$OS [M]$^+$ 433.1184. found 433.1189.

Example 11

Anti-Cancer Activity of Selected 3-Hydroxypyridine-2-thione-based HDAC Inhibitors Selected HDAC model inhibitors, including compound 1.68 (below), were screened for activity against three cancer cell lines: DU 145 (androgen independent prostate cancer known to be responsive to HDAC inhibitors), LNCaP (androgen dependent prostate cancer, sensitive to HDAC6 activity), and Jurkat (T cell leukemia overexpressing HDAC8). The IC$_{50}$ values for the selected compounds are shown in Table 14 below. When calculated IC$_{50}$ was greater than 20 μM (highest concentration tested), it is reported as >20 μM.

Example 12

Synthesis of Macrolide HDAC Inhibitors on a Multi-Gram Scale

Synthetic strategies which permit the synthesis of macrolide HDAC inhibitors one a multi-gram scale were also developed (Scheme 22). Clarithromycin or azithromycin can be N-demethylated to afford des-N-methyl clarithromycin or azithromycin (A). Subsequent alkylation of A with 4-ethynylbenzyl methanesulfonate afforded the modified 4'-ethynylbenzylclarithromycin or 4'-ethynylbenzylazithromycin (B). Copper (I) catalyzed cycloaddition of B containing an azithromycin macrolide with a protected azidohydoxamate analog (route A), afforded the 1,2,3-triazole linked derivatives. Subsequent deprotection with CsF gave the desired azithromycin product (C) in good yield. Copper (I) catalyzed cycloaddition of B containing a clarithromycin macrolide with an unprotected azidohydoxamate analog (route 13), afforded the 1,2,3-triazole linked clarithromycin product (D) in good yield. The yields for each step are shown in Table 15.

TABLE 15

| Compound | Starting material scale | Yield | Comments |
|---|---|---|---|
| A (Azithromycin or Clarithromycin) | 25 g | 55% | Purified by crystallization (4:1 acetone-NH$_4$OH) |
| B (Azithromycin) | 10 g | 60% | Condition: K$_2$CO$_3$, CH$_3$CN, 80° C., 2 h; purified by pH selective (acetate buffer) extraction |
| B (Clarithromycin) | 10 g | 60% | Condition: Hünig's base, DMSO, 80° C., 2 h; purified by pH selective (acetate buffer) extraction followed by crystallization (4:1 hexane-dichloromethane) |
| C (Azithromyoin) | 5 g | 80% | Purified by trituration (2:1 hexane-dichloromethane) |
| D (Clarithromycin) | 5 g | 80% | Purified by trituration (2:1 hexane-dichloromethane) |

To improve the efficiency of the multi-gram synthesis, methods of purifying B which obviate the need for chromatography were developed.

Methods for purifying compound A containing an azithromycin macrolide are shown in Scheme 23.5 g of crude material were dissolved in 70 mL of MeOH. 70 mL of acetate buffer (0.75 M, pH 5.5) was added, forming a colorless suspension. 70 mL of methanol was added, forming a clear solution. The solution was extracted with mixtures of hexanes and ethyl acetate, and organics were discarded. 50% aqueous NH$_4$OH was added to the aqueous phase, raising the pH of the solution to 8.5. The solution was extracted with hexanes and mixtures of hexanes and ethyl acetate, and the organic phases were collected and dried in vacu to obtain B.

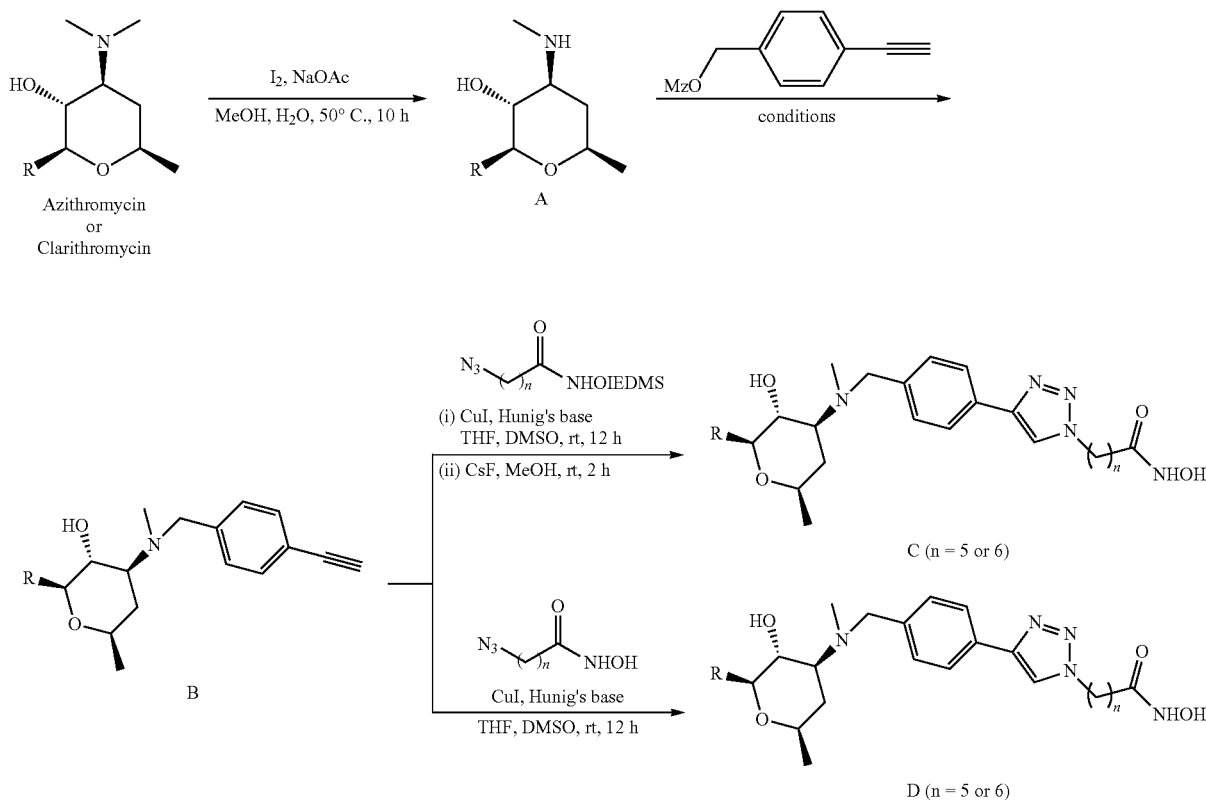

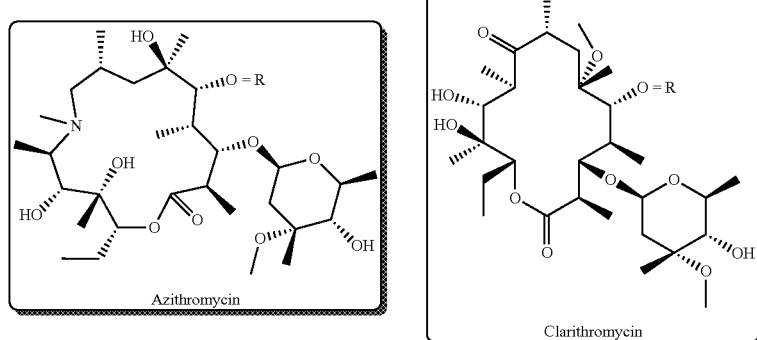

Scheme 23. Purification of compound B (Azithromycin).

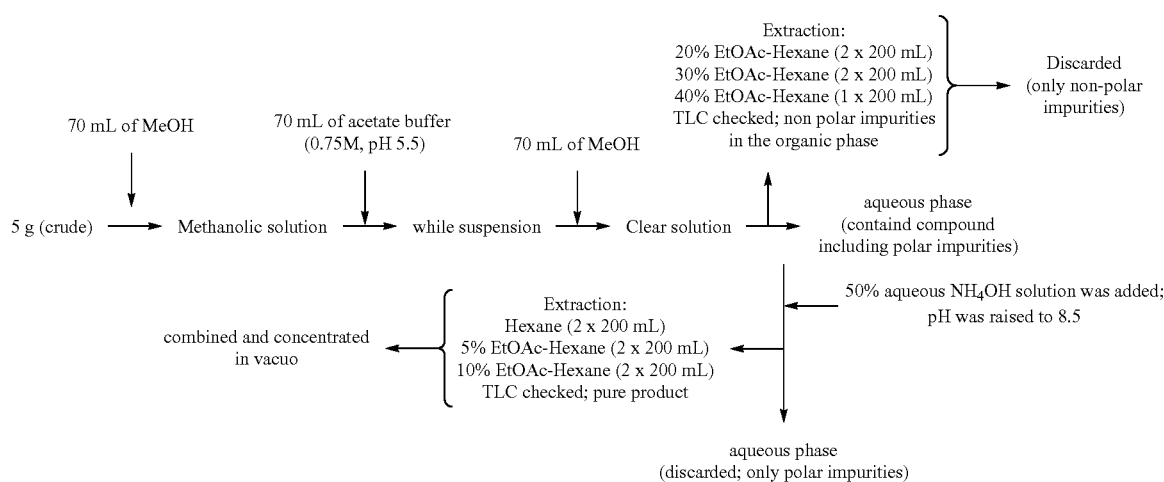

Methods for purifying compound B containing a clarithromycin macrolide are shown in Scheme 24. 4 g of crude material were dissolved in 70 mL of MeOH. 15 mL of acetate buffer (0.75 M, pH 5.5) was added, forming a colorless suspension. 50 mL of methanol was added, forming a clear solution. The solution was extracted with mixtures of hexanes and ethyl acetate, and the organic phases were collected and dried in vacuo. B was then purified by crystallization from a 4:1 mixture of hexanes:dichloromethane.

Scheme 24. Purification of compound B (Clarithromycin).

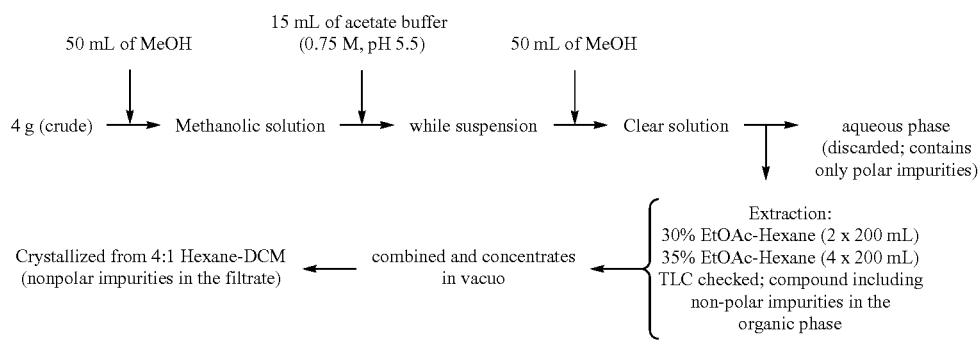

We claim:

1. A compound of Formula I or II:

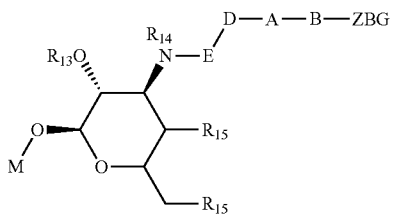

wherein M represents a macrolide subunit,

E is a $C_{1-6}$ group, optionally containing one or more heteroatoms, wherein the carbon atoms and/or heteroatoms are in a linear and/or cyclic arrangement, D is a substituted or unsubstituted alkyl, substituted or unsubstituted heteroalkyl, substituted or unsubstituted aryl, substituted or unsubstituted heteroaryl group, A is a linking group connected to D,
B is an alkyl, heteroalkyl, alkylaryl or alkylheteroaryl spacer group,
ZBG is a Zinc Binding Group comprising a heterocyclic moiety,
$R_{13}$ is selected from hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group,
$R_{14}$ and $R_{16}$ is selected from hydrogen, hydroxyl, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group,
$R_{15}$ is hydrogen or $-OR_{17}$,
$R_{17}$ is selected from a group consisting of hydrogen, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{1-6}$ alkanoate group, a substituted or unsubstituted $C_{2-6}$ carbamate group, a substituted or unsubstituted $C_{2-6}$ carbonate group, a substituted or unsubstituted $C_{2-6}$ carbamate group, or a substituted or unsubstituted $C_{2-6}$ thiocarbamate group.

2. The compound of claim 1, wherein the macrolide subunit is a multi-member lactonic ring structure.

3. The compound of claim 2, wherein the macrolide subunit has the structure:

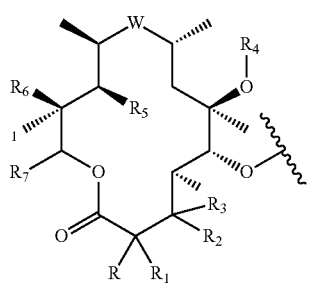

wherein
W is selected from $-C(O)-$, $-C(=NOR_{11})-$, $-CH(-OR_{11})-$, $-NR_{11}CH_2-$, $-CH_2NR_{11}-$, $-CH(NR_{11}R_{11})-$, $-C(=NNR_{11}R_{11})-$, $-NR_{11}C(O)-$, $-C(O)NR_{11}-$, and $-C(=NR_{11})-$;
R is selected from the group consisting of H and $C_{1-6}$ alkyl;
$R_1$ is selected from the group H, halogen, $-NR_{11}R_{11}$, $NR_{11}C(O)R_{11}$, $-OR_{11}$, $-OC(O)R_{11}$, $-OC(O)OR_{11}$, $-OC(O)NR_{11}R_{11}$, $-OC(O)C_{1-6}$ alcyl-$R_{12}$, $-OC(O)C_{1-6}$ alkyl-$R_{12}$, $-OC(O)OC_{1-6}$ alkyl-$R_{12}$, $-OC(O)NR_{11}C_{1-6}$ alkyl-$R_{12}$, $C_{1-6}$ alkyl, $C_{1-6}$ alkenyl, $C_{1-6}$ alkynyl, optionally is substituted with one or more $R_{12}$ groups;

$R_2$ is H;
$R_3$ is selected from H, $-OR_{11}$, $-OC_{1-6}$ alkyl-$R_{12}$, $-OC(O)R_{11}$, $-OC(O)C_{1-6}$ alkyl-$R_{12}$, $-OC(O)OR_{11}$, $-OC(O)OC_{1-6}$ alkyl-$R_{12}$, $-OC(O)NR_{11}R_{11}$, $-OC(O)NR_{11}C_{1-6}$ alkyl-$R_{12}$; alternatively, $R_3$ is a pyran ring which can be substituted as defined above in Formulae I and II;
$R_4$ is selected from H, $R_{11}$, $-C(O)R_{11}$, $-C(O)OR_{11}$, $-C(O)NR_{11}R_{11}$, $-C_{1-6}$ alkyl-T-$R_{11}$, $-C_{2-6}$ alkenyl-T-$R_{11}$, and $-C_{2-6}$ alkynyl-T-$R_{11}$; alternatively $R_3$ and $R_4$ taken together form

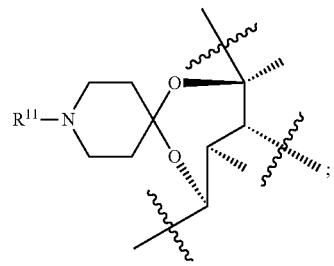

T is selected from $-C(O)-$, $-C(O)O-$, $-C(O)NR_{11}-$, $-C(=NR_{11})-$, $-C(=NR_{11})O-$, $-C(=NR_{11})NR_{11}-$, g) $-OC(O)-$, $-OC(O)O-$, $-OC(O)NR_{11}-$, $-NR_{11}C(O)-$, $-NR_{11}C(O)O-$, $-NR_{11}C(O)NR_{11}-$, $-NR_{11}C(=NR_{11})NR_{11}-$, and $-S(O)_p-$, wherein p 0-2;
$R_5$ is selected from $R_{11}$, $-OR_{11}$, $-NR_{11}R_{11}$, $-OC_{1-6}$ alkyl-$R_{12}$, $-C(O)R_{11}$, $-C(O)C_{1-6}$ alkyl-$R_{12}$, $-OC(O)R_{11}$, $-OC(O)G_{1-6}$ alkyl-$R_{12}$, $-OC(O)OR_{11}$, $-OC(O)OC_{1-6}$ alkyl-$R_{12}$, $-OC(O)NR_{11}R_{11}$, $-OC(O)NR_{11}C_{1-6}$ alkyl-$R_{12}$, $-C(O)C_{2-6}$ alkenyl-$R_{12}$, and $-C(O)C_{2-6}$ alkynyl-$R_{12}$;
alternatively, $R_4$ and $R_5$ taken together with the atoms to which they are bonded, form:

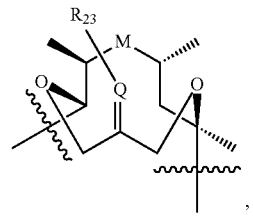

wherein, Q is CH or N, and $R_{23}$ is $-OR_{11}$ or $R_{11}$;
$R_6$ is selected from $-OR_{11}$, $-C_{1-6}$ alkoxy-$R_{12}$, $-C(O)R_{11}$, $-OC(O)R_{11}$, $-OC(O)OR_{11}$, $-OC(O)NR_{11}R_{11}$, $-NR_{11}R_{11}$;
alternatively, $R_5$ and $R_6$ taken together with the atoms to which they are attached form a 5-membered ring by attachment to each other through a linker selected from $-OC(R_{12})_2O-$, $-OC(O)O-$, $-OC(O)NR_{11}-$, d) $-NR_{11}C(O)O-$, $-OC(O)NOR_{11}-$, $-NOR_{11}C(O)O-$, $-OC(O)NNR_{11}R_{11}-$, $-NNR_{11}R_{11}C(O)O-$, $-OC(O)C(R_{12})_2-$, $-C(R_{12})_2C(O)O-$, $-OC(S)O-$, $-OC(S)NR_{11}-$, $-NR_{11}C(S)O-$, n) $-OC(S)NOR_{11}-$, $-NOR_{11}C(S)O-$, $-OC(S)NNR_{11}R_{11}-$, $-NNR_{11}R_{11}C(S)O-$, $-OC(S)C(R_{12})_2-$, $-C(R_{12})_2C(S)O-$;

alternatively, W, $R_5$, and $R_6$ taken together with the atoms to which they are attached form:

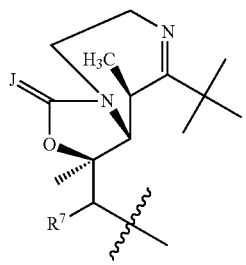

wherein J is selected from the group consisting of O, S, and $NR_{11}$;

$R_{6'}$ is selected from H, unsubstituted or substituted $C_{1-4}$ alkyl, $C_{2-4}$ alkenyl, which can be further substituted with $C_{1-2}$ alkyl or one or more halogens, $C_{2-4}$ alkynyl, which can be further substituted with $C_{1-2}$ alkyl or one or more halogens, aryl or heteroaryl, which can be further substituted with $C_{1-2}$ alkyl or one or more halogens, —C(O)H, —COOH, —CN, —COOR$_{11}$, —C(O)NR$_{11}$R$_{11}$, —C(O)R$_{11}$, —C(O)SR$_{11}$;

alternatively $R_6$ and $R_{6'}$ taken together with the atom to which they are attached to form an epoxide, a carbonyl, an olefin, or a substituted olefin, or a $C_3$-$C_7$ carbocyclic, carbonate, or carbamate, wherein the nitrogen of the carbamate can be further substituted with a $C_1$-$C_6$ alkyl;

$R_7$ is selected from $C_{1-6}$ alkyl, $C_{2-6}$ alkenyl, and $C_{2-6}$ alkynyl, optionally is substituted with one or more $R_{12}$ groups;

$R_{11}$, for each occurrence, is selected from H, $C_{1-6}$ alkyl, $C_{2-6}$ alkenyl, $C_{2-6}$ alkynyl, $C_{6-10}$ saturated, unsaturated, or aromatic carbocycle, 3-12 membered saturated, unsaturated, or aromatic heterocycle containing one or more heteroatoms selected from nitrogen, oxygen, and sulfur, —C(O)—$C_{1-6}$ alkyl, —C(O)—$C_{2-6}$ alkenyl, —C(O)—$C_{2-6}$ alkynyl, —C(O)—$C_{6-10}$ saturated, unsaturated or aromatic carbocycle, —C(O)-3-12 membered saturated, unsaturated, or aromatic heterocycle containing one or more heteroatoms selected from nitrogen, oxygen, and sulfur, —C(O)O—$C_{1-6}$ allyl, —C(O)O—$C_{2-6}$ alkenyl, —C(O)O—$C_{2-6}$ alkynyl, —C(O)O—$C_{6-10}$ saturated, unsaturated, or aromatic carbocycle, —C(O)O-3-12 membered saturated, unsaturated, or aromatic heterocycle containing one or more heteroatoms selected from the group consisting of nitrogen, oxygen, and sulfur, and —C(O)NR$_{13}$R$_{13}$, optionally is substituted with one or more $R_{12}$ groups; and $R_{12}$ is selected from $R_{14}$, $C_{1-8}$ alkyl, $C_{2-8}$ alkenyl, $C_{2-8}$ alkynyl, $C_{3-12}$ saturated, unsaturated, or aromatic carbocycle, 3-12 membered saturated, unsaturated, or aromatic heterocycle containing one or more heteroatoms selected from nitrogen, oxygen, and sulfur, optionally substituted with one or more substituents.

4. The compound of claim 1, wherein D is a phenyl, biphenyl, or naphthyl group.

5. The compound of claim 1, wherein A is an amide, —O—, or 1,2,3-triazolyl group.

6. The compound claim 1, wherein B is an alkyl group having from 4-9 carbon atoms.

7. The compound claim 1, wherein the zinc binding group is 3-hydroxypyridine-2-thione.

8. The compound claim 1, wherein the compound is defined by the following formula

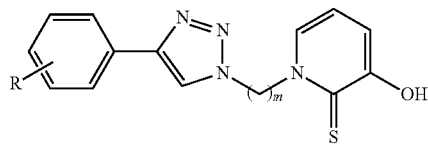

wherein R is:

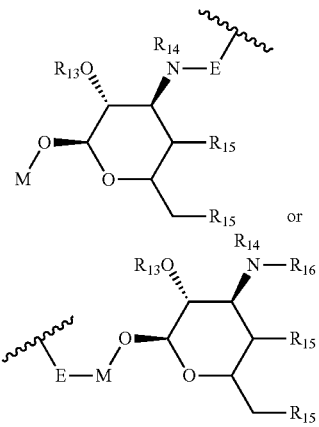

and m is an integer from 1-12 inclusive.

9. The compound of claim 8, wherein m is an integer from 5-9 inclusive.

10. A pharmaceutical composition comprising an effective amount of the compound of claim 1 in combination with a pharmaceutically acceptable diluent, excipient, or carrier.

11. The composition of claim 10, wherein the composition is formulated for enteral or parenteral administration.

12. The composition of claim 10, wherein the composition is formulated for immediate release, modified release, and combinations thereof.

13. The composition of claim 12, wherein the formulation is selected from the group consisting of delayed release, extended release, pulsatile release, and combinations thereof.

14. A method of treating a disease or disorder in a human or animal subject in need thereof comprising administering an effective amount of a compound claim 1 to the subject, wherein the disease or disorder is selected from the group consisting of cancer, inflammation, and parasitic infections.

15. The method of claim 14, wherein the disease or disorder to be treated is cancer.

16. The method of claim 15, wherein the cancer is selected from the group consisting of lung cancer, myeloma, leukemia, lymphoma, breast cancer, prostate cancer, pancreatic cancer, cervical cancer, ovarian cancer, and liver cancer.

17. The method of claim 14, wherein the parasitic infection is selected from the group consisting of malaria and leishmaniasis.

\* \* \* \* \*